US005972984A

United States Patent [19]
Anthony et al.

[11] Patent Number: 5,972,984
[45] Date of Patent: Oct. 26, 1999

[54] INHIBITORS OF FARNESYL-PROTEIN TRANSFERASE

[75] Inventors: Neville J. Anthony, Hatfield; Jeffrey M. Bergman, Telford; S. Jane deSolms, Norristown; Chrisopher J. Dinsmore, North Wales; Robert P. Gomez, Perkasie; Suzanne C. MacTough, Chalfont; Kelly M. Solinsky, Lansdale; Theresa M. Williams, Harleysville, all of Pa.

[73] Assignee: Merck & Co., Inc., Rahway, N.J.

[21] Appl. No.: 08/960,248

[22] Filed: Oct. 29, 1997

Related U.S. Application Data

[60] Division of application No. 08/652,055, May 23, 1996, Pat. No. 5,756,528, which is a continuation-in-part of application No. 08/468,180, Jun. 6, 1995, abandoned.

[51] Int. Cl.⁶ ...................... C07D 403/02; A61K 31/415; A61K 31/40
[52] U.S. Cl. .......................................... 514/397; 548/314.7
[58] Field of Search ............................................... 514/397

[56] References Cited

U.S. PATENT DOCUMENTS

| | | | |
|---|---|---|---|
| 3,280,098 | 10/1966 | Otsuka et al. | 514/357 |
| 3,399,193 | 8/1968 | Giraldi et al. | 544/139 |
| 3,737,422 | 6/1973 | Fluoret | 514/18 |
| 3,996,366 | 12/1976 | Baker et al. | 514/213 |
| 4,241,060 | 12/1980 | Smithen | 514/18 |
| 4,324,792 | 4/1982 | Bradshaw et al. | 514/212 |
| 4,472,305 | 9/1984 | Hansen et al. | 514/18 |
| 4,591,648 | 5/1986 | Jones et al. | 514/336 |
| 5,019,572 | 5/1991 | Claremon et al. | 514/213 |
| 5,043,268 | 8/1991 | Stock | 435/15 |
| 5,071,837 | 12/1991 | Doherty et al. | 514/18 |
| 5,141,851 | 8/1992 | Brown et al. | 435/15 |
| 5,238,922 | 8/1993 | Graham et al. | 514/18 |
| 5,326,773 | 7/1994 | de Solms et al. | 514/336 |
| 5,340,828 | 8/1994 | Graham et al. | 514/357 |
| 5,352,705 | 10/1994 | Deana et al. | 514/630 |
| 5,401,851 | 3/1995 | Boyd et al. | 546/336 |
| 5,420,245 | 5/1995 | Brown et al. | 540/328 |
| 5,439,918 | 8/1995 | de Solms et al. | 514/18 |
| 5,478,934 | 12/1995 | Yuan et al. | 540/546 |
| 5,504,212 | 4/1996 | de Solms et al. | 546/336 |
| 5,534,537 | 7/1996 | Ciccarone et al. | 514/397 |
| 5,686,472 | 11/1997 | Anthony et al. | 514/357 |

FOREIGN PATENT DOCUMENTS

| | | |
|---|---|---|
| 0 437 103 | 7/1991 | European Pat. Off. . |
| 0 456 180 A1 | 11/1991 | European Pat. Off. . |
| 0 618 221 A2 | 10/1994 | European Pat. Off. . |
| H7-112930 | 5/1995 | Japan . |
| WO 90/15599 | 12/1990 | WIPO . |
| WO 91/16340 | 10/1991 | WIPO . |
| WO 95/11917 | 5/1994 | WIPO . |
| WO 95/09000 | 4/1995 | WIPO . |
| WO 95/09001 | 4/1995 | WIPO . |
| WO 95/12612 | 5/1995 | WIPO . |
| WO 96/00736 | 1/1996 | WIPO . |
| WO 96/03374 | 2/1996 | WIPO . |

OTHER PUBLICATIONS

James, G.L. et al., "Benzodiazepine Peptidomimetics: Potent Inhibitors of Ras Farnesylation in Animal Cells", Science, vol. 260, pp. 1937–1942 (1993).

Kohl, N.E. et al., "Selective Inhibition of ras–Dependent Transformation by a Farnesyltransferase Inhibitor", Science, vol. 260, pp. 1934–1937 (1993).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Pompliano, D.L., "Steady–State Kinetic Mechanism of Ras Farnesyl:Protein Transferase", Biochemistry, vol. 31, pp. 3800–3807 (1992).

James, G., et al., Polylysine and CVIM Sequences of K–RasB Dictate Specificity of Prenylation and Confer Resistance to Benzodiazepine Peptidomimetic in Vitro, The Journal of Biological Chemistry, vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8, pp. 792–797 (1995).

Arrang, J.–M., et al., "Highly potent and selective ligands for histamine H3–receptors," Nature, vol. 327, No. 6118, pp. 117–123 (1987).

Giraldi, P.N., et al., Arzneimettel–Forschu NG Drug Res., vol. 20, No. 1, pp. 52–55 (1970).

Shafiee, A., et al., "Nitroimidazoles VIII [1.] Syntheses, Antibacterial and Antifungal Activities of 2–Pyridyl–Nitroimidazoles," J. Sci., I.R. Iran, vol. 1, No. 3, pp. 197–201 (1990).

Giraldi, P.N., et al., "Studies on Antiprotozoans. Synthesis and Biological Activity of Some Styrylimidazole Derivatives," J. Med. Chem., vol. 11, No. 1, pp. 66–70 (1967).

Kukkola, Paivi J. et al., "Optimization of Retro–Thiorphan for Inhibition of Endothelin Converting Enzyme," Biorg. Med. Chem. Lett., vol. 6, No. 6, pp. 619–624 (1996).

(List continued on next page.)

*Primary Examiner*—Zinna Northington Davis
*Attorney, Agent, or Firm*—Dianne Pecoraro; David A. Muthard; Mark R. Daniel

[57] ABSTRACT

The present invention comprises low molecular weight peptidyl compounds that inhibit the farnesyl-protein transferase. Furthermore, these compounds differ from the mono- or dipeptidyl analogs previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

22 Claims, No Drawings

OTHER PUBLICATIONS

Brown, T., et al., "Protection of Histidine Side–chains with n–Benzyloxymethyl–or n–Bromobenzyloxymethyl–groups," J. Chem. Soc. Chem. Commun., vol. 13, pp. 648–649 (1981).

Prior, K. J., et al., Synthesis, vol. 25, No. 3, pp. 247–255 (1988).

Colombo, R., et al., "Acid–labile Histidine Side–chain Protection: the N(n)–t–Butoxymethyl Group," Acid–Labile, vol. 5, pp. 292–293 (1984).

Patel, D. V., et al., "Retro Inverso Tripeptide Renin Inhibitors," Bioorganic and Medicinal Chemistry Letters, vol. 2, No. 9, pp. 1089–1092 (1992).

Colombo, R., et al., Pept. Proc. Eur. Pept. Symp, 17th, pp. 251–256 (1983).

Bolton, G.L., et al., "Modified Peptide Inhibitors of Ras Farnesyl Protein Transferase," Handout from Poster Session, 209th ACS Meeting, Apr. 2–7, 1995.

Bolton, G.L., et al., "The SAR of Tripeptide Inhibitors of Ras Farnesyl Protein Transferase," Handout from Poster Session, 209th ACS Meeting, Apr. 2–7, 1995.

Sepp–Lorenzino, L., et al., "A Peptidomimetic Inhibitor of Farnesyl:Protein Transferase Blocks the Anchorage–dependent and–independent Growth of Human Tumor Cell Lines," Cancer Research, vol. 55, pp. 5302–5309 (1995).

Krontiris, T.G., "Molecular and Cellular Biology of Cancer," Int. Med., 4th ed., pp. 699–715 (1995).

INHIBITORS OF FARNESYL-PROTEIN TRANSFERASE

RELATED U.S. APPLICATION DATA

This application is a divisional of U.S. Ser. No. 08/652,055, filed on May 23, 1996, now issued as U.S. Pat. No. 5,756,528, which is a continuation-in-part of U.S. Ser. No. 08/468,180, filed Jun. 6, 1995, now abandoned.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995). It has also been reported that a farnesyl-protein transferase inhibitor inhibits the growth of a broad range of human tumor cell lines, including those that do not have mutant forms of ras (L. Sepp-Lorenzino et al., *Cancer Research*, 55:5302–5309 (1995)).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001, WO 96/00736 and EP 0 675 112 A1). Substituted di-, tri- tetra- and pentapeptide inhibitors of farnesyl-protein transferase have also recently been disclosed (WO 95/12612 and WO 95/11917).

It is, therefore, an object of this invention to develop small molecules that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises low molecular weight peptidyl compounds that inhibit the farnesyl-protein transferase. Furthermore, these compounds differ from the mono- or dipeptidyl analogs previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formula:

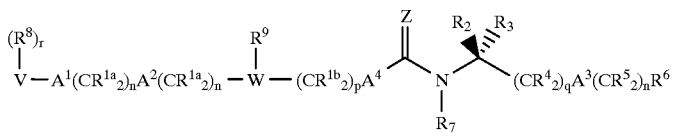

I

DETAILED DESCRIPTION OF THE INVENTION

The compounds of this invention inhibit the farnesyl-protein transferase. In a first embodiment of this invention, the farnesyl-protein transferase inhibitors are illustrated by the formula I:

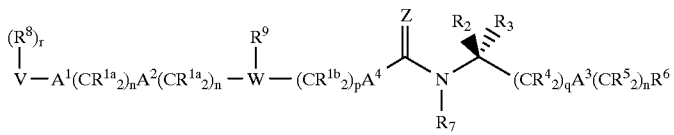

I wherein:
$R^{1a}$ is independently selected from:
  a) hydrogen,
  b) aryl, heterocycle, $C_3$–$C_{10}$ cycloalkyl, $C_2$–$C_{20}$ alkenyl, $C_2$–$C_{20}$ alkynyl, $R^{10}O$-, $R^{11}S(O)_m$-, $R^{10}C(O)NR^{10}$-, CN, NO$_2$, $(R^{10})_2$N-C(NR$^{10}$)-, $R^{10}C(O)$-, $R^{10}OC(O)$-, N$_3$, -N(R$^{10}$)$_2$, or $R^{11}OC(O)NR^{10}$-,
  c) $C_1$–$C_6$ alkyl unsubstituted or substituted by aryl, heterocyclic, $C_3$–$C_{10}$ cycloalkyl, $C_2$–$C_{20}$ alkenyl, $C_2$–$C_{20}$ alkynyl, $R^{10}O$-, $R^{11}S(O)_m$-, $R^{10}C(O)NR^{10}$-, CN, $(R^{10})_2$N-C(NR$^{10}$)-, $R^{10}C(O)$-, $R^{10}OC(O)$-, N$_3$, -N(R$^{10}$)$_2$, or $R^{11}OC(O)$-NR$^{10}$-;
$R^{1b}$ is independently selected from:
  a) hydrogen,
  b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $R^{10}O$-, $R^{11}S(O)_m$-, CN, NO$_2$, $(R^{10})_2$N-C(NR$^{10}$)-, $R^{10}C(O)$-, $R^{10}OC(O)$-, N$_3$ or -N(R$^{10}$)$_2$,
  c) $C_1$–$C_6$ alkyl unsubstituted or substituted by substituted or unsubstituted aryl, substituted or unsubstituted heterocyclic, $C_3$–$C_{10}$ cycloalkyl, $C_2$–$C_{20}$ alkenyl, $C_2$–$C_{20}$ alkynyl, $R^{10}O$-, $R^{11}S(O)_m$-, CN, $(R^{10})_2$N-C(NR$^{10}$)-, $R^{10}C(O)$-, $R^{10}OC(O)$-, N$_3$ or -N(R$^{10}$)$_2$;
$R^2$ and $R^3$ are independently selected from:
  a) a side chain of a naturally occurring amino acid,
  b) an oxidized form of a side chain of a naturally occurring amino acid which is:
    i) methionine sulfoxide, or
    ii) methionine sulfone, and
  c) substituted or unsubstituted $C_1$–$C_{20}$ alkyl, substituted or unsubstituted $C_2$–$C_{20}$ alkenyl, substituted or unsubstituted $C_3$–$C_{10}$ cycloalkyl, substituted or unsubstituted aryl or substituted or unsubstituted heterocyclic group, wherein the substituent is selected from F, Cl, Br, N(R$^{10}$)$_2$, NO$_2$, R$^{10}$O-, R$^{11}$S(O)$_m$-, R$^{10}$C(O)NR$^{10}$-, CN, (R$^{10}$)$_2$N-C(NR$^{10}$)-, R$^{10}$OC(O)-, R$^{10}$OC(O)-, N$_3$, -N(R$^{10}$)$_2$, R$^{11}$OC(O)NR$^{10}$- and $C_3$–$C_{20}$ alkyl, and
  d) $C_1$–$C_6$ alkyl substituted with an unsubstituted or substituted group selected from aryl, heterocycle and $C_3$–$C_{10}$ cycloalkyl; or
$R^2$ and $R^3$ are combined to form -(CH$_2$)$_s$-; or $R^2$ or $R^3$ are combined with $R^7$ to form a ring such that

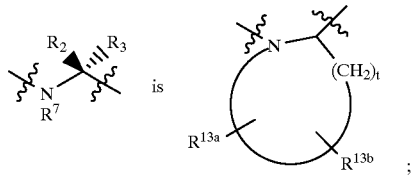

;

$R^4$ and $R^5$ are independently selected from:
  a) hydrogen,
  b) $C_1$–$C_6$ alkyl unsubstituted or substituted by $C_2$–$C_{20}$ alkenyl, $R^{10}O$-, $R^{11}S(O)_m$-, $R^{10}C(O)NR^{10}$-, CN, N$_3$, (R$^{10}$)$_2$N-C(NR$^{10}$)-, $R^{10}C(O)$-, -N(R$^{10}$)$_2$, or $R^{11}OC(O)NR^{10}$-,
  c) unsubstituted or substituted aryl, unsubstituted or substituted heterocycle, $C_3$–$C_{10}$ cycloalkyl, $C_2$–$C_{20}$ alkenyl, halogen, $R^{10}O$-, $R^{11}S(O)_m$-, $R^{10}C(O)NR^{10}$-, CN, NO$_2$, (R$^{10}$)$_2$N-C(NR$^{10}$)-, $R^{10}C(O)$-, N$_3$, -N(R$^{10}$)$_2$, or $R^{11}OC(O)NR^{10}$-, and
  d) $C_1$–$C_6$ alkyl substituted with an unsubstituted or substituted group selected from aryl, heterocyclic and $C_3$–$C_{10}$ cycloalkyl;
$R^{13a}$ and $R^{13b}$ are independently selected from:
  a) hydrogen,
  b) $C_1$–$C_6$ alkyl unsubstituted or substituted by $C_2$–$C_{20}$ alkenyl, $R^{10}O$-, $R^{11}S(O)_m$-, $R^{10}C(O)NR^{10}$-, CN, N$_3$, (R$^{10}$)$_2$N-C(NR$^{10}$)-, $R^{10}C(O)$-, -N(R$^{10}$)$_2$, or $R^{11}OC(O)NR^{10}$-, c) unsubstituted or substituted aryl, unsubstituted or substituted heterocycle, $C_3$–$C_{10}$ cycloalkyl, $C_2$–$C_{20}$ alkenyl, halogen, $R^{14}O$-, $R^{11}S(O)_m$-, $R^{10}C(O)NR^{10}$-, CN, $NO_2$, $(R^{10})_2N$-$C(NR^{10})$-, $R^{10}C(O)$-, $N_3$, -$N(R^{10})_2$, or $R^{11}OC(O)NR^{10}$-, and d) $C_1$–$C_6$ alkyl substituted with an unsubstituted or substituted group selected from aryl, heterocyclic and $C_3$–$C_{10}$ cycloalkyl;

$R^6$ is selected from:
a) hydrogen,
b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^{10}O$-, $R^{11}S(O)_m$-, $R^{10}C(O)NR^{10}$-, CN, $NO_2$, $R^{10}{}_2N$-$C(NR^{10})$-, $R^{10}C(O)$-, $N_3$, -$N(R^{10})_2$, $(R^{12})_2NC(O)$- or $R^{11}OC(O)NR^{10}$-, and
c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^{10}O$-, $R^{11}S(O)_m$-, $R^{10}C(O)NH$-, CN, $H_2N$-$C(NH)$-, $R^{10}C(O)$-, $N_3$, -$N(R^{10})_2$, or $R^{10}OC(O)NH$-;

$R^7$ is independently selected from
a) hydrogen,
b) unsubstituted or substituted aryl,
c) unsubstituted or substituted heterocycle,
d) unsubstituted or substituted $C_3$–$C_{10}$ cycloalkyl, and
e) $C_1$–$C_6$ alkyl substituted with hydrogen or an unsubstituted or substituted group selected from aryl, heterocycle and $C_3$–$C_{10}$ -cycloalkyl;

$R^8$ is selected from:
a) hydrogen,
b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^{10}O$-, $R^{11}S(O)_m$-, $R^{10}C(O)NR^{10}$-, -$S(O)_2NR^{10}{}_2$, CN, $NO_2$, $R^{10}{}_2N$-$C(NR^{10})$-, $R^{10}C(O)$-, $R^{10}OC(O)$-, $N_3$, -$N(R^{10})_2$, or $R^{11}OC(O)NR^{10}$-, and
c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^{10}O$-, $R^{11}S(O)_m$-, $R^{10}C(O)NH$-, CN, $H_2N$-$C(NH)$-, $R^{10}C(O)$-, $R^{10}OC(O)$-, $N_3$, -$N(R^{10})_2$, or $R^{10}OC(O)NH$-;

$R^9$ is selected from:
a) hydrogen,
b) $C_2$–$C_{20}$ alkenyl, $C_2$–$C_{20}$ alkynyl, $C_2$–$C_{20}$ perfluoroalkyl, F, Cl, Br, $R^{10}O$-, $R^{11}S(O)_m$-, $R^{10}C(O)NR^{10}$-, CN, $NO_2$, $(R^{10})_2N$-$C$-$(NR^{10})$-, $R^{10}C(O)$-, $R^{10}OC(O)$-, $N_3$, -$N(R^{10})_2$, or $R^{11}OC(O)NR^{10}$-, and
c) $C_1$–$C_6$ alkyl unsubstituted or substituted by $C_2$–$C_{20}$ perfluoroalkyl, F, Cl, Br, $R^{10}O$-, $R^{11}S(O)_m$-, $R^{10}C(O)$ $NR^{10}$-, CN, $(R^{10})_2N$-$C(NR^{10})$-, $R^{10}C(O)$-, $R^{10}OC(O)$-, $N_3$, -$N(R^{10})_2$, or $R^{11}OC(O)NR^{10}$-;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl and aryl, or $(R^{12})_2$ forms -$(CH_2)_s$-;

$R^{14}$ is independently selected from hydrogen, $C_1$–$C_6$ alkyl, $C_1$–$C_6$ alkyl substituted with $CO_2R^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;

$A^1$, $A^2$ and $A^3$ are independently selected from: a bond, -CH=CH-, -C≡C-, -C(O)-, -C(O)$NR^7$-, -$NR^7C(O)$-, O, -$N(R^7)$-, -$S(O)_2N(R^7)$-, -$N(R^7)S(O)_2$-, or $S(O)_m$;

$A^4$ is selected from: a bond, O, -$N(R^7)$- or S;

V is selected from:
a) hydrogen,
b) heterocycle,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Z is independently $R^{1a}{}_2$ or O;

| | |
|---|---|
| m is | 0, 1 or 2; |
| n is | 0, 1, 2, 3, or 4; |
| p is | 0, 1, 2, 3, or 4; |
| q is | 0, 1, 2, 3, or 4; |
| r is | 0 to 5, provided that r is 0 when V is hydrogen; |
| s is | 4 or 5; and |
| t is | 3, 4 or 5. |

I

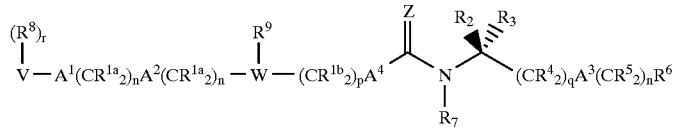

wherein:

$R^{1a}$ is independently selected from: hydrogen or $C_1$–$C_6$ alkyl;

$R^{1b}$ is independently selected from:
a) hydrogen,
b) substituted or unsubstituted aryl, substituted or unsubstituted heterocycle, $C_3$–$C_{10}$ cycloalkyl, $R^{10}O$-, -$N(R^{10})_2$ or $C_2$–$C_6$ alkenyl, and
c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_6$ alkenyl, $R^{10}O$-, or -$N(R^{10})_2$;

$R^2$ and $R^3$ are independently selected from:
a) a side chain of a naturally occurring amino acid,
b) an oxidized form of a side chain of a naturally occurring amino acid which is:
  i) methionine sulfoxide, or
  ii) methionine sulfone,
c) substituted or unsubstituted $C_1$–$C_{10}$ alkyl, substituted or unsubstituted $C_2$–$C_{10}$ alkenyl, substituted or unsubstituted $C_3$–$C_{10}$ cycloalkyl, substituted or unsubstituted aryl or substituted or unsubstituted heterocyclic group, wherein the substituent is selected from F, Cl, Br, $NO_2$, $R^{10}O$-, $R^{11}S(O)_m$-, $R^{10}C(O)NR^{10}$-, CN, $(R^{10})_2$N-C$(NR^{10})$-, $R^{10}C(O)$-, $R^{10}OC(O)$-, $N_3$, -N$(R^{10})_2$, $R^{11}OC(O)NR^{10}$- and $C_1$–$C_{20}$ alkyl, and d) $C_1$–$C_6$ alkyl substituted with an unsubstituted or substituted group selected from aryl, heterocycle and $C_3$–$C_{10}$ cycloalkyl;

wherein said substituted group is substituted with 1 or 2 substitutents selected from: F, Cl, Br, $CF_3$, $NH_2$, N$(C_1$–$C_6$ alkyl$)_2$, $NO_2$, CN, $(C_1$–$C_6$ alkyl)O-, -OH, $(C_1$–$C_6$ alkyl)S(O)$_m$-, $(C_1$–$C_6$ alkyl)C(O)NH-, $H_2$N-C(NH)-, $(C_1$–$C_6$ alkyl)C(O)-, $(C_1$–$C_6$ alkyl)OC(O)-, $N_3$, $(C_1$–$C_6$ alkyl)OC(O)NH- and $C_1$–$C_{20}$ alkyl; or $R^2$ or $R^3$ are combined with $R^7$ to form a ring such that:

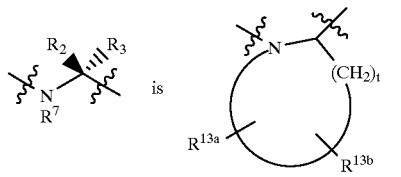

$R^4$ and $R^5$ are independently selected from:

a) hydrogen, b) $C_1$–$C_6$ alkyl unsubstituted or substituted by $C_2$–$C_6$ alkenyl, $R^{10}O$-, $R^{11}S(O)_m$-, $R^{10}C(O)NR^{10}$-, CN, $N_3$, $(R^{10})_2$N-C$(NR^{10})$-, $R^{10}C(O)$-, -N$(R^{10})_2$, or $R^{11}OC(O)NR^{10}$-, c) substituted or unsubstituted aryl, substituted or unsubstituted heterocycle, $C_3$–$C_{10}$ cycloalkyl, $C_2$–$C_6$ alkenyl, halogen, $R^{10}O$-, $R^{11}S(O)_m$-, $R^{10}C(O)NR^{10}$-, CN, $NO_2$, $(R^{10})_2$N-$(NR^{10})$-, $R^{10}C(O)$-, $N_3$, -N$(R^{10})_2$, or $R^{11}OC(O)NR^{10}$-, and d) $C_1$–$C_6$ alkyl substituted with an unsubstituted or substituted group selected from aryl, heterocyclic and $C_3$–$C_{10}$ cycloalkyl;

$R^{13a}$ and $R^{13b}$ are independently selected from:

a) hydrogen, b) $C_1$–$C_6$ alkyl unsubstituted or substituted by $C_2$–$C_6$ alkenyl, $R^{10}O$-, $R^{11}S(O)_m$-, $R^{10}C(O)NR^{10}$-, CN, $N_3$, $(R^{10})_2$N-C$(NR^{10})$-, $R^{10}C(O)$-, -N$(R^{10})_2$, or $R^{11}OC(O)NR^{10}$-, c) substituted or unsubstituted aryl, substituted or unsubstituted heterocycle, $C_3$–$C_{10}$ cycloalkyl, $C_2$–$C_6$ alkenyl, halogen, $R^{14}O$-, $R^{11}S(O)_m$-, $R^{10}C(O)NR^{10}$-, CN, $NO_2$, $(R^{10})_2$N-$(NR^{10})$-, $R^{10}C(O)$-, $N_3$, -N$(R^{10})_2$, or $R^{11}OC(O)NR^{10}$-, and d) $C_1$–$C_6$ alkyl substituted with an unsubstituted or substituted group selected from aryl, heterocyclic and $C_3$–$C_{10}$ cycloalkyl;

$R^6$ is independently selected from:

a) hydrogen, b) substituted or unsubstituted aryl, substituted or unsubstituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$-, allyloxy, $R^{10}C(O)NR^{10}$-, CN, $NO_2$, $(R^{10})_2$N-C$(NR^{10})$-, $R^{10}C(O)$-, -N$(R^{10})_2$, $(R^{12})_2$NC(O)- or $R^{11}OC(O)NR^{10}$-, and c) $C_1$–$C_6$ alkyl substituted by $C_1$–$C_6$ perfluoroalkyl, $R^{10}O$-, $R^{10}C(O)NR^{10}$-, $(R^{10})_2$N-C$(NR^{10})$-, $R^{10}C(O)$-, -N$(R^{10})_2$, or $R^{11}OC(O)NR^{10}$-;

$R^7$ is independently selected from a) hydrogen, b) unsubstituted or substituted aryl, c) unsubstituted or substituted heterocycle, d) unsubstituted or substituted $C_3$–$C_{10}$ cycloalkyl, and e) $C_1$–$C_6$ alkyl substituted with hydrogen or an unsubstituted or substituted group selected from aryl, heterocycle and $C_3$–$C_{10}$ cycloalkyl;

wherein heterocycle is selected from pyrrolidinyl, imidazolyl, pyridinyl, thiazolyl, pyridonyl, indolyl, quinolinyl, isoquinolinyl, and thienyl;

$R^8$ is selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$-, $R^{10}C(O)NR^{10}$-, CN, $NO_2$, $(R^{10})_2$N-C$(NR^{10})$-, $R^{10}C(O)$-, $R^{10}OC(O)$-, -N$(R^{10})_2$, or $R^{11}OC(O)NR^{10}$-, and c) $C_1$–$C_6$ alkyl substituted by $C_1$–$C_6$ perfluoroalkyl, $R^{10}O$-, $R^{10}C(O)NR^{10}$-, $(R^{10})_2$N-C$(NR^{10})$-, $R^{10}C(O)$-, $R^{10}OC(O)$-, -N$(R^{10})_2$, or $R^{11}OC(O)NR^{10}$-;

$R^9$ is selected from:

a) hydrogen, b) $C_2$–$C_6$ alkenyl, $C_2$–$C_6$ alkynyl, $C_1$–$C_6$ perfluoroalkyl, F, Cl, $R^{10}O$-, $R^{11}S(O)_m$-, $R^{10}C(O)NR^{10}$-, CN, $NO_2$, $(R^{10})_2$N-C$(NR^{10})$-, $R^{10}C(O)$-, $R^{10}OC(O)$-, -N$(R^{10})_2$, or $R^{11}OC(O)NR^{10}$-, and c) $C_1$–$C_6$ alkyl unsubstituted or substituted by $C_1$–$C_6$ perfluoroalkyl, F, Cl, $R^{10}O$-, $R^{11}S(O)_m$-, $R^{10}C(O)NR^{10}$-, CN, $(R^{10})_2$N-C$(NR^{10})$-, $R^{10}C(O)$-, $R^{10}OC(O)$-, -N$(R^{10})_2$, or $R^{11}OC(O)NR^{10}$-;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl and aryl, or $(R^{12})_2$ forms -$(CH_2)_s$-;

$R^{14}$ is independently selected from hydrogen, $C_1$–$C_6$ alkyl, $C_1$–$C_6$ alkyl substituted with $CO_2R^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;

$A^1$, $A^2$ and $A^3$ are independently selected from: a bond, -CH=CH-, -C≡C-, -C(O)-, -C(O)NR$^7$-, -NR$^7$C(O)-, -S(O)$_2$NR$^7$-, -NR$^7$S(O)$_2$-, O, -N(R$^7$)-, or S(O)$_m$;

$A^4$ is selected from: a bond, O, -N(R$^7$)- or S;

V is selected from:

a) hydrogen, b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl, d) $C_1$–$C_{20}$ alkyl wherein from 0 to 4 carbon atoms are replaced with a heteroatom selected from O, S, and N, and e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, oxazolyl, isoxazolyl, indolyl, quinolinyl, or isoquinolinyl;

Z is independently $R^{1a}{}_2$ or O;

| | |
|---|---|
| m is | 0, 1 or 2; |
| n is | 0, 1, 2, 3 or 4; |
| p is | 0, 1, 2, 3 or 4; |
| q is | 0, 1, 2, 3 or 4; |
| r is | 0 to 5, provided that r is 0 when V is hydrogen; and |
| t is | 3, 4 or 5; | or the pharmaceutically acceptable salts thereof.

In a further preferred embodiment of this invention, the Ras farnesyl transferase inhibitors are illustrated by the Formula I:

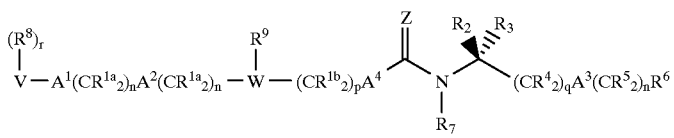

I wherein:

$R^{1a}$ is independently selected from: hydrogen or $C_1$–$C_6$ alkyl;

$R^{1b}$ is independently selected from:
a) hydrogen,
b) substituted or unsubstituted aryl, substituted or unsubstituted heterocycle, $C_3$–$C_{10}$ cycloalkyl, $R^{10}$O- or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}$O-, or -N($R^{10}$)$_2$;

$R^2$ and $R^3$ are independently selected from:
a) a side chain of a naturally occurring amino acid,
b) an oxidized form of a side chain of a naturally occurring amino acid which is:
  i) methionine sulfoxide, or
  ii) methionine sulfone, and
c) substituted or unsubstituted $C_1$–$C_{10}$ alkyl, substituted or unsubstituted $C_2$–$C_{10}$ alkenyl, substituted or unsubstituted $C_3$–$C_{10}$ cycloalkyl, substituted or unsubstituted aryl or substituted or unsubstituted heterocyclic group, wherein the substituent is selected from F, Cl, Br, $NO_2$, $R^{10}$O-, $R^{11}$S(O)$_m$-, $R^{10}$C(O)N$R^{10}$-, CN, $(R^{10})_2$N-C(N$R^{10}$)-, $R^{10}$C(O)-, $R^{10}$OC(O)-, $N_3$, -N($R^{10}$)$_2$, $R^{11}$OC(O)N$R^{10}$- and $C_1$–$C_{20}$ alkyl; or $R^2$ or $R^3$ are combined with $R^7$ to form a ring such that:

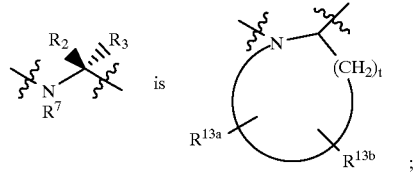

$R^4$ and $R^5$ are independently selected from:
a) hydrogen,
b) $C_1$–$C_6$ alkyl unsubstituted or substituted by $C_2$–$C_6$ alkenyl, $R^{10}$O-, $R^{11}$S(O)$_m$-, $R^{10}$C(O)N$R^{10}$-, CN, $N_3$, $(R^{10})_2$N-C(N$R^{10}$)-, $R^{10}$C(O)-, -N($R^{10}$)$_2$, or $R^{11}$OC(O)N$R^{10}$-,
c) substituted or unsubstituted aryl, substituted or unsubstituted heterocycle, $C_3$–$C_{10}$ cycloalkyl, $C_2$–$C_6$ alkenyl, fluoro, chloro, $R^{10}$O-, $R^{11}$S(O)$_m$-, $R^{10}$C(O)N$R^{10}$-, CN, $NO_2$, $(R^{10})_2$N-C(N$R^{10}$)-, $R^{10}$C(O)-, $N_3$, -N($R^{10}$)$_2$, or $R^{11}$OC(O)N$R^{10}$-, and
d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^{13a}$ and $R^{13b}$ are independently selected from:
a) hydrogen,
b) $C_1$–$C_6$ alkyl unsubstituted or substituted by $C_2$–$C_6$ alkenyl, $R^{10}$O-, $R^{11}$S(O)$_m$-, $R^{10}$C(O)N$R^{10}$-, CN, $N_3$, $(R^{10})_2$N-C(N$R^{10}$)-, $R^{10}$C(O)-, -N($R^{10}$)$_2$, or $R^{11}$OC(O)N$R^{10}$-,
c) substituted or unsubstituted aryl, substituted or unsubstituted heterocycle, $C_3$–$C_{10}$ cycloalkyl, $C_2$–$C_6$ alkenyl, fluoro, chloro, $R^{14}$O-, $R^{11}$S(O)$_m$-, $R^{10}$C(O)N$R^{10}$-, CN, $NO_2$, $(R^{10})_2$N-C(N$R^{10}$)-, $R^{10}$C(O)-, $N_3$, -N($R^{10}$)$_2$, or $R^{11}$OC(O)N$R^{10}$-, and
d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^6$ is independently selected from:
a) hydrogen,
b) substituted or unsubstituted aryl, substituted or unsubstituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}$O-, allyloxy, $R^{10}$C(O)N$R^{10}$-, CN, $NO_2$, $(R^{10})_2$N-C(N$R^{10}$)-, $R^{10}$C(O)-, -N($R^{10}$)$_2$, $(R^{12})_2$NC(O)- or $R^{11}$OC(O)N$R^{10}$-, and
c) $C_1$–$C_6$ alkyl substituted by $C_1$–$C_6$ perfluoroalkyl, $R^{10}$O-, $R^{10}$C(O)N$R^{10}$-, $(R^{10})_2$N-C(N$R^{10}$)-, $R^{10}$C(O)-, -N($R^{10}$)$_2$, or $R^{11}$OC(O)N$R^{10}$-;

$R^7$ is independently selected from
a) hydrogen,
b) unsubstituted or substituted aryl,
c) unsubstituted or substituted heterocycle,
d) unsubstituted or substituted cycloalkyl, and
e) $C_1$–$C_6$ alkyl substituted with hydrogen or an unsubstituted or substituted group selected from aryl, heterocycle and cycloalkyl;
  wherein heterocycle is selected from pyrrolidinyl, imidazolyl, pyridinyl, thiazolyl, pyridonyl, indolyl, quinolinyl, isoquinolinyl, and thienyl;

$R^8$ is selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}$O-, $R^{10}$C(O)N$R^{10}$-, CN, $NO_2$, $(R^{10})_2$N-C(N$R^{10}$)-, $R^{10}$C(O)-, $R^{10}$OC(O)-, -N($R^{10}$)$_2$, or $R^{11}$OC(O)N$R^{10}$-, and
c) $C_1$–$C_6$ alkyl substituted by $C_1$–$C_6$ perfluoroalkyl, $R^{10}$O-, $R^{10}$C(O)N$R^{10}$-, $(R^{10})_2$N-C(N$R^{10}$)-, $R^{10}$C(O)-, $R^{10}$OC(O)-, -N($R^{10}$)$_2$, or $R^{11}$OC(O)N$R^{10}$-;

$R^9$ is selected from:
a) hydrogen, b) $C_2$–$C_6$ alkenyl, $C_2$–$C_6$ alkynyl, $C_1$–$C_6$ perfluoroalkyl, F, Cl, $R^{10}$O-, $R^{11}$S(O)$_m$-, $R^{10}$C(O)NR$^{10}$-, CN, NO$_2$, $(R^{10})_2$N-C(NR$^{10}$)-, $R^{10}$C(O)-, $R^{10}$OC(O)-, -N(R$^{10}$)$_2$, or $R^{11}$OC(O)NR$^{10}$-, and c) $C_1$–$C_6$ alkyl unsubstituted or substituted by $C_1$–$C_6$ perfluoroalkyl, F, Cl, $R^{10}$O-, $R^{11}$S(O)$_m$-, $R^{10}$C(O)NR$^{10}$-, CN, $(R^{10})_2$N-C(NR$^{10}$)-, $R^{10}$C(O)-, $R^{10}$OC(O)-, -N(R$^{10}$)$_2$, or $R^{11}$OC(O)NR$^{10}$-;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl and aryl, or $(R^{12})_2$ forms -(CH$_2$)$_s$-;

$R^{14}$ is independently selected from hydrogen, $C_1$–$C_6$ alkyl, $C_1$–$C_6$ alkyl substituted with CO$_2$R$^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;

$A^1$ and $A^2$ are independently selected from: a bond, -CH=CH-, -C≡C-, -C(O)-, -C(O)NR$^7$-, -NR$^7$C(O)-, -S(O)$_2$NR$^7$-, -NR$^7$S(O)$_2$-, O, -N(R$^7$)-, or S(O)$_m$;

$A^4$ is selected from: a bond, O, -N(R$^7$)- or S;

$A^3$ is selected from: a bond, -C(O)NR$^7$-, -NR$^7$C(O)-, -S(O)$_2$NR$^7$-, -NR$^7$S(O)$_2$- or -N(R$^7$)-;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

| m is | 0, 1 or 2; |
| n is | 0, 1, 2, 3, or 4; |
| p is | 0, 1, 2, 3, or 4; |
| q is | 0 or 1; |
| r is | 0 to 5, provided that r is 0 when V is hydrogen; and |
| t is | 3, 4 or 5; | or the pharmaceutically acceptable salts thereof.

In another preferred embodiment of this invention, the Ras farnesyl transferase inhibitors are illustrated by the Formula Ia:

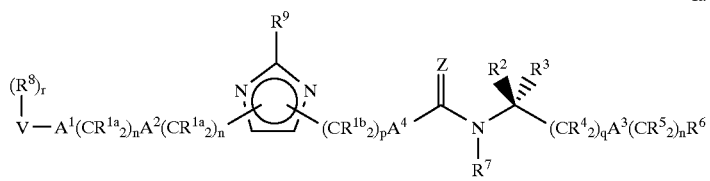

Ia wherein:
$R^{1a}$ is independently selected from: hydrogen or $C_1$–$C_6$ alkyl;

$R^{1b}$ is independently selected from:
a) hydrogen,
b) substituted or unsubstituted aryl, substituted or unsubstituted heterocycle, $C_3$–$C_{10}$ cycloalkyl, $R^{10}$O- or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}$O-, or -N(R$^{10}$)$_2$;

$R^2$ and $R^3$ are independently selected from:
a) a side chain of a naturally occurring amino acid,
b) an oxidized form of a side chain of a naturally occurring amino acid which is:
  i) methionine sulfoxide, or
  ii) methionine sulfone, and
c) substituted or unsubstituted $C_1$–$C_{10}$ alkyl, substituted or unsubstituted $C_2$–$C_{10}$ alkenyl, substituted or unsubstituted $C_3$–$C_{10}$ cycloalkyl, substituted or unsubstituted aryl or substituted or unsubstituted heterocyclic group, wherein the substituent is selected from F, Cl, Br, NO$_2$, $R^{10}$O-, $R^{11}$S(O)$_m$-, $R^{10}$C(O)NR$^{10}$-, CN, $(R^{10})_2$N-C(NR$^{10}$)-, $R^{10}$C(O)-, $R^{10}$OC(O)-, N$_3$, -N(R$^{10}$)$_2$, $R^{11}$OC(O)NR$^{10}$- and $C_1$–$C_{20}$ alkyl; or $R^2$ or $R^3$ are combined with $R^7$ to form a ring such that:

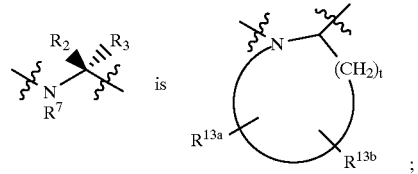

$R^4$ and $R^5$ are independently selected from:
a) hydrogen,
b) $C_1$–$C_6$ alkyl unsubstituted or substituted by $C_2$–$C_6$ alkenyl, $R^{10}$O-, $R^{11}$S(O)$_m$-, $R^{10}$C(O)NR$^{10}$-, CN, N$_3$, $(R^{10})_2$N-C(NR$^{10}$)-, $R^{10}$C(O)-, -N(R$^{10}$)$_2$, or $R^{11}$OC(O)NR$^{10}$-,
c) substituted or unsubstituted aryl, substituted or unsubstituted heterocycle, $C_3$–$C_{10}$ cycloalkyl, $C_2$–$C_6$ alkenyl, fluoro, chloro, $R^{10}$O-, $R^{11}$S(O)$_m$-, $R^{10}$C(O)NR$^{10}$-, CN, NO$_2$, $(R^{10})_2$N-C(NR$^{10}$)-, $R^{10}$C(O)-, N$_3$, -N(R$^{10}$)$_2$, or $R^{11}$OC(O)NR$^{10}$-, and
d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^{13a}$ and $R^{13b}$ are independently selected from:
a) hydrogen, b) $C_1$–$C_6$ alkyl unsubstituted or substituted by $C_2$–$C_6$ alkenyl, $R^{10}O$-, $R^{11}S(O)_m$-, $R^{10}C(O)NR^{10}$-, CN, $N_3$, $(R^{10})_2N$-$C(NR^{10})$-, $R^{10}C(O)$-, -$N(R^{10})_2$, or $R^{11}OC(O)NR^{10}$-, c) substituted or unsubstituted aryl, substituted or unsubstituted heterocycle, $C_3$–$C_{10}$ cycloalkyl, $C_2$–$C_6$ alkenyl, fluoro, chloro, $R^{14}O$-, $R^{11}S(O)_m$-, $R^{10}C(O)NR^{10}$-, CN, $NO_2$, $(R^{10})_2N$-$C(NR^{10})$-, $R^{10}C(O)$-, $N_3$, -$N(R^{10})_2$, or $R^{11}OC(O)NR^{10}$-, and d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^6$ is independently selected from:

a) hydrogen, b) substituted or unsubstituted aryl, substituted or unsubstituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$-, allyloxy, $R^{10}C(O)NR^{10}$-, CN, $NO_2$, $(R^{10})_2N$-$C(NR^{10})$-, $R^{10}C(O)$-, -$N(R^{10})_2$, $(R^{12})_2NC(O)$- or $R^{11}OC(O)NR^{10}$-, and c) $C_1$–$C_6$ alkyl substituted by $C_1$–$C_6$ perfluoroalkyl, $R^{10}O$-, $R^{10}C(O)NR^{10}$-, $(R^{10})_2N$-$C(NR^{10})$-, $R^{10}C(O)$-, -$N(R^{10})_2$, or $R^{11}OC(O)NR^{10}$-;

$R^7$ is independently selected from a) hydrogen, b) unsubstituted or substituted aryl, c) unsubstituted or substituted heterocycle, d) unsubstituted or substituted cycloalkyl, and e) $C_1$–$C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, indolyl, quinolinyl, isoquinolinyl, and thienyl;

$R^8$ is selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$-, $R^{10}C(O)NR^{10}$-, CN, $NO_2$, $(R^{10})_2N$-$C(NR^{10})$-, $R^{10}C(O)$-, $R^{10}OC(O)$-, -$N(R^{10})_2$, or $R^{11}OC(O)NR^{10}$-, and c) $C_1$–$C_6$ alkyl substituted by $C_1$–$C_6$ perfluoroalkyl, $R^{10}O$-, $R^{10}C(O)NR^{10}$-, $(R^{10})_2N$-$C(NR^{10})$-, $R^{10}C(O)$-, $R^{10}OC(O)$-, -$N(R^{10})_2$, or $R^{11}OC(O)NR^{10}$-;

$R^9$ is selected from:

a) hydrogen, b) $C_2$–$C_6$ alkenyl, $C_2$–$C_6$ alkynyl, $C_1$–$C_6$ perfluoroalkyl, F, Cl, $R^{10}O$-, $R^{11}S(O)_m$-, $R^{10}C(O)NR^{10}$-, CN, $NO_2$, $(R^{10})_2N$-$C(NR^{10})$-, $R^{10}C(O)$-, $R^{10}OC(O)$-, -$N(R^{10})_2$, or $R^{11}OC(O)NR^{10}$-, and c) $C_1$–$C_6$ alkyl unsubstituted or substituted by $C_1$–$C_6$ perfluoroalkyl, F, C, $R^{10}O$-, $R^{11}S(O)_m$-, $R^{10}C(O)NR^{10}$-, CN, $(R^{10})_2N$-$C(NR^{10})$-, $R^{10}C(O)$-, $R^{10}OC(O)$-, -$N(R^{10})_2$, or $R^{11}OC(O)NR^{10}$-;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl and aryl, or $(R^{12})_2$ forms -$(CH_2)_s$-;

$R^{14}$ is independently selected from hydrogen, $C_1$–$C_6$ alkyl, $C_1$–$C_6$ alkyl substituted with $CO_2R^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;

$A^1$ and $A^2$ are independently selected from: a bond, -CH=CH-, -C≡C-, -C(O)-, -C(O)NR$^7$-, -NR$^7$C(O)-, -S(O)$_2$NR$^7$-, -NR$^7$S(O)$_2$-, O, -N(R$^7$)-, or S(O)$_m$;

$A^4$ is selected from: a bond, O, -N(R$^7$)- or S;

$A^3$ is selected from: a bond, -(O)NR$^7$-, -NR$^7$C(O)-, -S(O)$_2$NR$^7$-, -NR$^7$S(O)$_2$- or -N(R$^7$)-;

V is selected from:

a) hydrogen, b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl, d) $C_1$–$C_{20}$ alkyl wherein from 0 to 4 carbon atoms are replaced with a heteroatom selected from O, S, and N, and e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

Z is independently $R^{1a}_2$ or O;

| | |
|---|---|
| m is | 0, 1 or 2; |
| n is | 0, 1, 2, 3 or 4; |
| p is | 0, 1, 2, 3 or 4; |
| q is | 0 or 1; |
| r is | 0 to 5, provided that r is 0 when V is hydrogen; and |
| t is | 3, 4 or 5; | or the pharmaceutically acceptable salts thereof.

The preferred compounds of this invention are as follows:

N-Allyloxycarbonyl-N-naphth-1-ylmethyl-2(S)-{1-(4-cyanobenzyl)-1H-imidazol-5-yl)acetyl}amino-3(S)-methylpentanamine N-Naphth-1-ylmethyl-2(S)-{(1-(4-cyanobenzyl)-1H-imidazol-5-yl)acetyl}amino-3(S)- methyl pentanamine N-Methoxycarbonyl-N-naphth-1-ylmethyl-2(S)-{(1-(4-cyanobenzyl)-1H-imidazol-5-yl)acetyl}amino-3(S)-methyl pentanamine N-Acetyl-N-naphth-1-ylmethyl-2(S)-{(1-(4-cyanobenzyl)-1H-imidazol-5-yl)acetyl}amino-3(S)-methylpentanamine N-Propionyl-N-naphth-1-ylmethyl-2(S)-{ (1-(4-cyanobenzyl)-1H-imidazol-5-yl)acetyl}amino-3(S)-methylpentanamine N-Methylsulfonyl-N-naphth-1-ylmethyl-2(S)-{(1-(4-cyanobenzyl)-1H-imidazol-5-yl)acetyl}amino-3(S)-methylpentanamine N-Ethylsulfonyl-N-naphth-1-ylmethyl-2(S)-{(1-(4-cyanobenzyl)- 1H-imidazol-5-yl)acetyl}amino-3(S)-methylpentanamine N-Methylaminocarbonyl-N-naphth-1-ylmethyl-2(S)-{(1-(4-cyanobenzyl)-1H-imidazol-5-yl)acetyl}amino-3(S)-methylpentanamine N-Propyl-N-naphth-1-ylmethyl-2(S)-{(1-(4-cyanobenzyl)-1H-imidazol-5-yl)acetyl}amino-3(S)-methylpentanamine N-3-Chlorobenzyl-N-naphth-1-ylmethyl-2(S)-{(1-(4-cyanobenzyl)-1H-imidazol-5-yl)acetyl}amino-3(S)-methylpentanamine N-(2-Imidazolylmethyl)-N-naphth-1-ylmethyl-2(S)-{(1-(4-cyanobenzyl)-1H-imidazol-5-yl)acetyl}amino-3(S)-methylpentanamine 2(RS)-{[1-(Naphth-2-ylmethyl)-1H-imidazol-5-yl)]acetyl}amino-3-(t-butoxycarbonyl)amino- N-(naphth-1-ylmethyl)propionamide 2(RS)-{[1-(Naphth-2-ylmethyl)-1H-imidazol-5-yl)]acetyl}amino-3-(t-butoxycarbonyl)amino-N-methyl-N-benzyl propionamide 2(RS)-{[1-(Naphth-2-ylmethyl)-1H-imidazol-5-yl)]acetyl}amino-3-(t-butoxycarbonyl)amino-N-(2-methylbenzyl) propionamide 2(RS)-{[1-(Naphth-2-ylmethyl)-1H-imidazol-5-yl] acetyl}amino-3-(t-butoxycarbonyl)amino-N-(3-methylbenzyl) propionamide
2(RS)-{[1-(Naphth-2-ylmethyl)-1H-imidazol-5-yl] acetyl}amino-3-amino-N-(naphth-1-ylmethyl) propionamide
2(RS)-{[1-(Naphth-2-ylmethyl)-1H-imidazol-5-yl] acetyl}amino-3-amino-N-methyl-N-benzyl propionamide
2(RS)-{[1-(Naphth-2-ylmethyl)-1H-imidazol-5-yl] acetyl}amino-3-amino-N-(2-methylbenzyl)propionamide
2(RS)-{[1-(Naphth-2-ylmethyl)-1H-imidazol-5-yl] acetyl}amino-3-amino-N-(3-methylbenzyl)propionamide
2(RS)-{[1-(Naphth-2-ylmethyl)-1H-imidazol-5-yl] acetyl}amino-3-acetylamino-N-(3-methylbenzyl) propionamide
2(RS)-{[1-(Naphth-2-ylmethyl)-1H-imidazol-5-yl] acetyl}amino-3-acetylamino-N-(naphth-1-ylmethyl) propionamide
2(RS)-{[1-(Naphth-2-ylmethyl)-1H-imidazol-5-yl] acetyl}amino-3-(2-methylpropionyl)amino-N-(naphth-1-ylmethyl)propionamide
2(RS)-{[1-(Naphth-2-ylmethyl)-1H-imidazol-5-yl] acetyl}amino-3-(phenylacetyl)amino-N-(naphth-1-ylmethyl)propionamide
2(RS)-{[1-(Naphth-2-ylmethyl)-1H-imidazol-5-yl] acetyl}amino-3-(phenylacetyl)amino-N-methyl-N-benzyl) propionamide
[1-(Naphth-2-ylmethyl)-1H-imidazol-5-yl)]-N-butylacetamide
[1-(Naphth-2-ylmethyl)-1H-imidazol-5-yl)]-N-methyl-N-(3,3-diphenylpropyl)acetamide
2(RS)-{[1-(4-Cyanobenzyl)-1H-imidazol-5-yl] acetyl}amino-3-(t-butoxycarbonyl)amino- N-methyl-N-benzyl propionamide
2(RS)-{[1-(4-Cyanobenzyl)-1H-imidazol-5-yl] acetyl}amino-3-(t-butoxycarbonyl)amino- N-(3-methylbenzyl) propionamide
2(RS)-{[1-(4-Cyanobenzyl)-1H-imidazol-5-yl] acetyl}amino-3-(t-butoxycarbonyl)amino-N-(naphth-1-ylmethyl) propionamide
2(RS)-{[1-(4-Cyanobenzyl)-1H-imidazol-5-yl] acetyl}amino-3-amino-N-methyl-N-benzyl- propionamide
2(RS)-{[1-(4-Cyanobenzyl)-1H-imidazol-5-yl] acetyl}amino-3-amino-N-(3-methylbenzyl) propionamide
2(RS)-{[1-(4-Cyanobenzyl)-1H-imidazol-5-yl] acetyl}amino-3-amino-N-(naphth-1-ylmethyl) propionamide
2(RS)-{[1-(4-Cyanobenzyl)-1H-imidazol-5-yl] acetyl}amino-3-(phenylacetyl)amino-N-methyl-N-benzyl) propionamide
2(RS)-{[1-(4-Cyanobenzyl)-1H-imidazol-5-yl] acetyl}amino-3-(acetyl)amino- N-(naphth-1-yl methyl) propionamide
2(RS)-{[1-(4-Cyanobenzyl)-1H-imidazol-5-yl] acetyl}amino-3-(2-methylpropionyl)amino-N-(naphth-1-ylmethyl) propionamide
2(RS)-{[1-(4-Cyanobenzyl)-1H-imidazol-5-yl] acetyl}amino-3-(2-methylpropionyl)amino-N-(naphth-1-ylmethyl) propionamide
N-[2(S)-([1-(4-Cyanobenzyl)-1H-imidazol-5-yl] acetylamino)-3(S)-methylpentyl]-N-(1-naphthylmethyl) glycine isopropylamide
N-[2(S)-([1-(4-Cyanobenzyl)-1H-imidazol-5-yl] acetylamino)-3(S)-methylpentyl]-N-(1-naphthylmethyl) glycine piperidinylamide
2(RS)-{[1-(4-Cyanobenzyl)-1H-imidazol-5-yl] acetyl}amino-3-(t-butoxycarbonyl)amino-N-methyl-N-(naphth-1-ylmethyl) propionamide
N-{1-(4-Cyanobenzyl)-1H-imidazol-5-yl)acetyl}-2(S){N'-methanesulfonyl-N'-(naphth-1-ylmethyl)aminomethyl}-pyrrolidine
N-{1-(4-Cyanobenzyl)-1H-imidazol-5-yl)acetyl}-2(S)-{N'-acetyl-N'-naphth-1-ylmethyl-aminomethyl}-pyrrolidine
N-{5-(4-Cyanobenzyl)-1H-imidazol-1-yl)acetyl}-2(S)-[1(R)-1-(3-chlorophenyl)-1-hydroxy]methylpyrrolidine
N-{5-(4-Cyanobenzyl)-1H-imidazol-1-yl)acetyl}-2(S)-[1(S)-1-(3-chlorophenyl)-1-hydroxy]methylpyrrolidine
N-{5-(4-Cyanobenzyl)-1H-imidazol-1-yl)ethyl}-2(S)-[1(R)-1-(3-chlorophenyl)-1-hydroxy]methylpyrrolidine
N-{5-(4-Cyanobenzyl)-1H-imidazol-1-yl)ethyl}-2(S)-[1(S)-1-(3-chlorophenyl)-1-hydroxy]methylpyrrolidine
N-{1-(4-Cyanobenzyl)-1H-imidazol-5-yl)methyl}-2(S)-[1(R)-1-(3-chlorophenyl)-1-hydroxy] methylpyrrolidine
N-{1-(4-Cyanobenzyl)-1H-imidazol-5-yl)methyl}-2(S)-[1(S)-1-(3-chlorophenyl)-1-hydroxy]methylpyrrolidine
N-{5-(4-Cyanobenzyl)-1H-imidazol-1-yl)acetyl}-4(R)-hydroxy-2(S)-[1(R)-1-(3-chlorophenyl)-1-hydroxy] methylpyrrolidine
N-{5-(4-Cyanobenzyl)-1H-imidazol-1-yl)acetyl}-4(R)-hydroxy-2(S)-[1(S)-1-(3-chlorophenyl)-1-hydroxy] methylpyrrolidine
N-{1-(4-Cyanobenzyl)-1H-imidazol-1-ylethyl}-4(R)-hydroxy-2(S)-[1(R)-1-(3-chlorophenyl)-1-hydroxy] methylpyrrolidine
N-{1-(4-Cyanobenzyl)-1H-imidazol-1-ylethyl}-4(R)-hydroxy-2(S)-[1(S)-1-(3-chlorophenyl)-1-hydroxy] methylpyrrolidine
N-[5-(4-Cyanobenzyl)-1H-imidazol-1-ylethyl]-4(R)-hydroxy-2(S)-[1(R)-1-(3-chlorophenyl)-1-hydroxy] methylpyrrolidine
N-[5-(4-Cyanobenzyl)-1H-imidazol-1-ylethyl]-4(R)-hydroxy-2(S)-[1(S)-1-(3-chlorophenyl)-1-hydroxy] methylpyrrolidine
N-[1-(4-Cyanobenzyl)-1-imidazol-5-ylmethyl]-4(R)-hydroxy-2(S)- [1(R)-1-(3-chlorophenyl)-1-hydroxy] methylpyrrolidine
N-{1-(4-Cyanobenzyl)-1H-imidazol-5-yl-methyl-4(R)-hydroxy-2(S)-{N'-acetyl-N'-3-chlorobenzyl}aminomethylpyrrolidine
N-{1-(4-Cyanobenzyl)-1H-imidazol-5-ylacetyl}-4(R)-hydroxy-2(S)-{N'-acetyl-N'-3-chlorobenzyl}aminomethylpyrrolidine
N-{1-(4-Cyanobenzyl)-1H-imidazol-5-yl-methyl-4(R)-hydroxy-2(S)-{N'-acetyl-N'-3-chlorobenzyl}aminomethylpyrrolidine
N-{1-(4-Cyanophenethyl)-1H-imidazol-5-yl-methyl-4(R)-hydroxy-2(S)-{N'-acetyl-N'-3-chlorobenzyl}aminomethylpyrrolidine
N-{1-(4-Cyanobenzyl)-1H-imidazol-5-yl-acetyl}-4(R)-methoxy-2(S)-{N'-acetyl-N'-3-chlorobenzyl}aminomethylpyrrolidine
N-{1-(4-Cyanopheneth-1-yl)-1H-imidazol-5-yl-acetyl-4(R)-methoxy-2(S)-{N'-acetyl-N'-3-chlorobenzyl}aminomethylpyrrolidine
N-{1-(4-Cyanobenzyl)-1H-imidazol-5-yl-ethyl}-4(R)-methoxy-2(S)-{N'-acetyl-N'-3-chlorobenzyl}aminomethylpyrrolidine
N-{1-(4-Cyanobenzyl)-1H-imidazol-5-ylethyl}-2(S)-{N'-acetyl-N'-3-chlorobenzyl-aminomethyl}pyrrolidine
N-1-(4-Cyanophenethyl)-1H-imidazol-5-yl-ethyl}-4(R)-methoxy-2(S)-{N'-acetyl-N'-3-chlorobenzyl}aminomethyl pyrrolidine N-{1-(4-Cyanobenzyl)-1H-imidazol-5-ylmethyl}-4(R)-benzyloxy-2(S)-{N'-acetyl-N'-3-chlorobenzyl}aminomethylpyrrolidine N-{1-(4-Cyanobenzyl)-1H-imidazol-5-ylethyl}-4(R)-benzyloxy-2(S)-{N'-acetyl-N'-3-chlorobenzyl}aminomethyl pyrrolidine N-{1-(4-Cyanobenzyl)-5-imidazolacetyl}-4(R)-benzyloxy-2(S)-{N'-acetyl-N'-3-chlorobenzyl}aminomethylpyrrolidine N-1-(4-Cyanobenzyl)-5-imidazol-5-ylmethyl}-4(R)-(2-henylbenzyloxy)-2(S)-{N'-acetyl-N'-3-chlorobenzyl}aminomethylpyrrolidine N-{1-(4-Cyanobenzyl)-1H-imidazol-5-ylmethyl}-4(R)-(4-chlorobenzyloxy)-2(S)-{N'-acetyl-N'-3-chlorobenzyl}aminomethylpyrrolidine N-{1-(4-Cyanobenzyl)-5-imidazolemethyl}-4(R)-(4-cyanobenzyloxy)-2(S)-{N'-acetyl-N'-3-chlorobenzyl}aminomethylpyrrolidine N-{1-(4-Cyanobenzyl)-5-imidazol-5-ylmethyl}-4(R)-(3-pyridylmethoxy)-2(S)-{N'-acetyl-N'-3-chlorobenzyl}aminomethylpyrrolidine N-{1-(4-Cyanobenzyl)-1H-imidazol-5-ylmethyl}-4(R)-(phenoxy)-2(S)-{N'-acetyl-N'-3-chlorobenzyl}aminomethylpyrrolidine N-{1-(4-Cyanobenzyl)-1H-imidazol-5-ylmethyl}-4(R)-(2-methylacetyloxy)-2(S)-{N'-acetyl-N'-3-chlorobenzyl}aminomethylpyrrolidine N-{1-(4-Cyanobenzyl)-1H-imidazol-5-ylmethyl}-4(R)-(acetyloxy)-2(S)-{N'-acetyl-N'-3-chlorobenzyl}aminomethylpyrrolidine N-{1-(4-Cyanobenzyl)-1H-imidazol-5-ylacetyl}-4(R)-(2-methylacetyloxy)-2(S)-{N'-acetyl-N'-3-chlorobenzyl}aminomethylpyrrolidine N-{1-(4-Cyanobenzyl)-1H-imidazol-5-ylacetyl}-4(R)-(acetyloxy)-2(S)-{N'-3-chlorobenzyl-N'-acetyl}aminomethylpyrrolidine N-{1-(4-Cyanobenzyl)-1H-imidazol-5-ylmethyl}-4(S)-(phenoxy)-2(S)-{N'-acetyl-N'-3-chlorobenzyl}aminomethylpyrrolidine N-{1-(4-Cyanobenzyl)-5-imidazolethyl}-4(S)-(phenoxy)-2(S)-{N'-acetyl-N'-3-chlorobenzyl}aminomethylpyrrolidine N-{1-(4-Cyanobenzyl)-1H-imidazol-5-ylethyl}-4(S)-fluoro-2(S)-{N'-acetyl-N'-3-chlorobenzyl}aminomethylpyrrolidine N-{1-(4-Cyanobenzyl)-1H-imidazol-5ylethyl-4(R)-(2-phenylbenzyloxy)-2(S)-{N'-acetyl-N'-3-chlorobenzyl}aminomethylpyrrolidine N-{1-(4-Cyanobenzyl)-1H-imidazol-5-ylethyl}-4(R)-(4-chlorobenzyloxy)-2(S)-{N'-acetyl-N'-3-chlorobenzyl}aminomethylpyrrolidine N-{1-(4-Cyanobenzyl)-1H-imidazol-5-ylethyl -4(R)-(4-cyanobenzyloxy)-2(S)-{N'-acetyl-N'-3-chlorobenzyl}aminomethylpyrrolidine N-{1-(4-Cyanobenzyl)-1H-imidazol-5-ylethyl}-4(R)-(3-pyridylmethoxy)-2(S)-{N'-acetyl-N'-3-chlorobenzyl}aminomethyl-pyrrolidine N-{1-(4-Cyanobenzyl)-1H-imidazol-5-ylacetyl}-2(S)-{N'-acetyl-N'-3-cyanobenzyl}aminomethylpyrrolidine N-{1-(4-Cyanobenzyl)-1H-imidazol-5-yl)acetyl}- 2(S)-[N'-acetyl-N'-3-methoxybenzyl}aminomethylpyrrolidine.

N-{1-(4-Cyanobenzyl)-1H-imidazol-5-yl)acetyl}-2(S)-{N'-acetyl-N'-3-trifluoromethylbenzyl}aminomethylpyrrolidine N-{1-(4-Cyanobenzyl)-1H-imidazol-5-yl)acetyl}-2(S)-{N'-acetyl-N'-2-methoxybenzyl}aminomethylpyrrolidine N-{1-(4-Cyanobenzyl)-1H-imidazol-5-yl)acetyl}-2(S)-{N'-acetyl-N'-2-trifluoromethylbenzyl}aminomethylpyrrolidine N-{1-(4-Cyanobenzyl)-1H-imidazol-5-yl)acetyl}-2(S)-{N'-acetyl-N'-(2,2-diphenylethyl)}aminomethylpyrrolidine N-{1-(4-Cyanobenzyl)-1H-imidazol-5-yl)acetyl}-2(S)-{N'-acetyl-N'-diphenylmethyl}aminomethylpyrrolidine N-{1-(4-Cyanobenzyl)-1H-imidazol-5-yl)acetyl}-2(S)-{N'-acetyl-N'-2-chlorobenzyl}aminomethylpyrrolidine N-{2(R)-Methyl-2-(1-(4-Cyanobenzyl)-1H-imidazol-5-yl))acetyl}-2(S)-{N'-acetyl-N'-3-chlorobenzyl}aminomethylpyrrolidine N-{2(S)-Methyl-2-(1-(4-Cyanobenzyl)-1H-imidazol-5-yl))acetyl}-2(S)-{N'-acetyl-N'-3-chlorobenzyl}aminomethylpyrrolidine N-{1-(4-Cyanobenzyl)-1H-imidazol-5-yl)acetyl}-2(S)-{N'-acetyl-N'-3-chlorobenzyl}aminomethylpyrrolidine N-{1-(4-Cyanobenzyl)-1H-imidazol-5-yl)acetyl}-2(S)-{N'-acetyl-N'-4-chlorobenzyl}aminomethylpyrrolidine N-{1-(4-Cyanobenzyl)-1H-imidazol-5-yl)acetyl}-2(S)-{N'-acetyl-N'-2,3-dichlorobenzyl}aminomethylpyrrolidine N-[1-(4-Cyanobenzyl)-1H-imidazol-5-yl]acetyl-4(R)-benzyloxy-2(S)-{N'-acetyl-N'-naphth-1-ylmethyl}aminomethylpyrrolidine N-[1-(4-Cyanobenzyl)-1H-imidazol-5-yl]acetyl-4(R)-benzyloxy-proline naphth-1-ylmethylamide N-[1-(4-Cyanobenzyl)-1H-imidazol-5-yl]acetylproline naphth-1-ylmethylamide N-{1-(4-cyanobenzyl)-1H-imidazol-5-yl)acetyl-4(R)-methoxy-2(S)-{N'-acetyl-N'-5,6,7,8-tetrahydronaphth-1-ylmethyl}aminomethylpyrrolidine N-{1-(4-cyanobenzyl)-1H-imidazol-5-yl)acetyl-4(R)-benzyloxy-2(S)-{N'-acetyl-N'-5,56,7,8-tetrahydronaphth-1-ylmethyl}aminomethyl-pyrrolidine 1-(4-Cyanobenzyl)-1H-imidazol-5-ylmethyl-2(S)-{N'-acetyl-N'-3-chlorobenzyl}aminomethylpyrrolidine N-Allyloxycarbonyl-2(S)-{(1-(4-Cyanobenzyl)-1H-imidazol-5-yl)acetyl}amino-3(S)-methyl-pentanamine 2(S)-{(1-(4-Cyanobenzyl)-1H-imidazol-5-yl)acetyl}amino-3(S)-methyl-N-(naphth-2-ylsulfonyl)-pentanamine N-Acetyl-N-2-chlorobenzyl-2(S)-{(1-(4-cyanobenzyl)-1H-imidazol-5-yl)acetyl}amino-3(S)-methyl-pentanamine N-Acetyl-N-3-chlorobenzyl-2(S)-{(1-(4-cyanobenzyl)-1H-imidazol-5-yl)acetyl}amino-3(S)-methyl-pentanamine N-Acetyl-N-4-chlorobenzyl-2(S)-{(1-(4-cyanobenzyl)-1H-imidazol-5-yl)acetyl}amino-3 (S)-methyl-pentanamine N-Acetyl-N-2,3-dichlorobenzyl-2(S)-{(1-(4-cyanobenzyl)-1H-imidazol-5-yl)acetyl}amino-3 (S)-methyl-pentanamine N-Allyloxycarbonyl-N-naphth-1-ylmethyl-2(S)-{2(R,S)-methyl-2-(1-(4-cyanobenzyl)-1H-imidazol-5-yl)acetyl}amino-3(S)-methyl-pentanamine N-t-Butoxycarbonylaminoacetyl-N-naphth-1-ylmethyl-2(S)-{1-(4-cyanobenzyl)-1H-imidazol-5-ylacetyl}amino-3(S)-methylpentanamine N-Aminoacetyl-N-naphth-1-ylmethyl-2(S)-{1-(4-cyanobenzyl)-1H-imidazol-5-ylacetyl}amino-3(S)-methylpentanamine N-{5-(4-Cyanobenzyl)-1H-imidazol-1-yl)ethyl}-2(S)-{N'-acetyl-N'-3-chlorobenzyl}aminomethylpyrrolidine N-{5-(4-Cyanobenzyl)-1H-imidazol-1-yl)ethoxycarbonyl}-2(S)-{N'-acetyl-N'-3-chlorobenzyl}aminomethylpyrrolidine N-{5-(4-Cyanobenzyl)-1H-imidazol-1-ylacetyl}-2(S)-{N'-acetyl-N'-3-chlorobenzyl}aminomethylpyrrolidine N-{1-(4-Cyanobenzyl)-1H-imidazol-5-yl)ethyl}-2(S)-{N'-acetyl-N'-3-chlorophenyl}aminomethylpyrrolidine N-{1-(4-Cyanobenzyl)-1H-imidazol-5-yl)methyl}-2(S)-{N'-acetyl-N'-3-chlorophenyl}aminomethylpyrrolidine hydrochloride N-{1-(4-Cyanobenzyl)-1H-imidazol-5-yl)acetyl}-2(S)-{N'-acetyl-N'-3-chlorophenyl}aminomethylpyrrolidine N-[1-(3-[1H-Imidazol-4-yl]propionyl)-pyrrolidin-2(S)-ylmethyl]-(N-2-methylbenzyl)glycine N'-(3-chlorophenyl)amide 1-[1-(4-Cyanobenzyl)-1H-imidazol-5-ylacetyl]pyrrolidin-2(S)-ylmethyl]-(N-2-methylbenzyl)-glycine N'-(3-chlorophenylmethyl) amide N-[1-(3-[1H-Imidazol-4-yl]propionyl)-pyrrolidin-2(S)-ylmethyl]-(N-2-methylbenzyl)-glycine N'-methyl-N'-(3-chlorophenyl) amide 1-[1-(4-Cyanobenzyl)-1H-imidazol-5-ylacetyl]pyrrolidin-2(S)-ylmethyl]-(N-2-methylbenzyl)-glycine N'-methyl-N'-(3-chlorophenylmethyl) amide (S)-2-[(1-(4-cyanobenzyl)-5-imidazolylmethyl)amino]-1-[N-(2,3-dimethylphenyl)acetamido]hexane (S)-2-[N-(1-(4-cyanobenzyl)-5-imidazolylmethyl)-N-(methyl)amino]-1-[N-(2,3-dimethylphenyl)acetamido]hexane N-[1-(4-cyanobenzyl)-5-imidazolylmethyl]-N'-(3-chlorophenyl)ethylenediamine 1-(4-Cyanobenzyl)-5-[N-(3-phenylpropyl)aminomethyl]imidazole and (S)-2-[(1-(4-Cyanobenzyl)-5-imidazolylmethyl)amino]-N-(benzyloxycarbonyl)-N-(3-chlorobenzyl)-4-(methanesulfonyl)butanamine or the pharmaceutically acceptable salts thereof.

Specific examples of the compounds of the invention are:

N-Allyloxycarbonyl-N-1-naphthylmethyl-2(S)-{1-(4-cyanobenzyl)-1H-imidazol-5-yl)acetyl}amino-3(S)-methylpentanamine

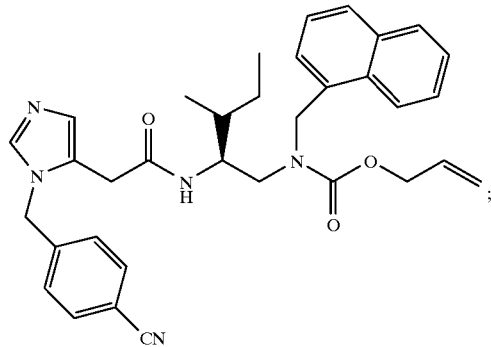

N-1-Acetyl-N-naphthylmethyl-2(S )-{(1-(4-cyanobenzyl)-1H-imidazol-5-yl)acetyl}amino-3(S)-methylpentanamine

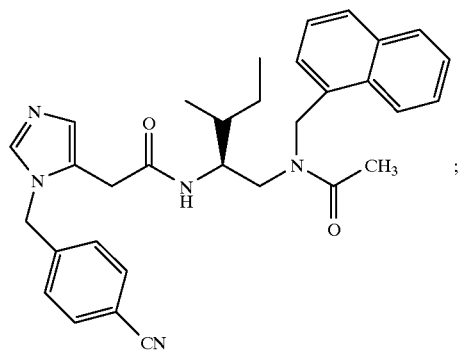

N-Propionyl-N-1-naphthylmethyl-2(S)-{(1-(4-cyanobenzyl)-1H-imidazol-5-yl)acetyl}amino-3(S)-methylpentanamine

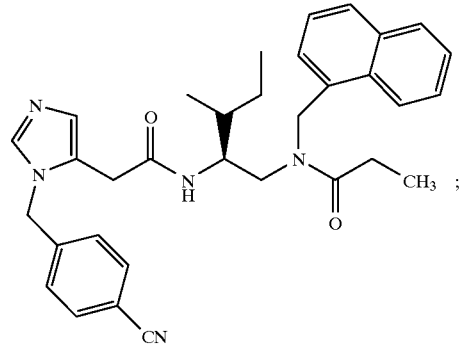

N-Methylsulfonyl-N-1-naphthylmethyl-2(S)-{(1-(4-cyanobenzyl)-1H-imidazol-5-yl)acetyl}amino-3(S)-methylpentanamine

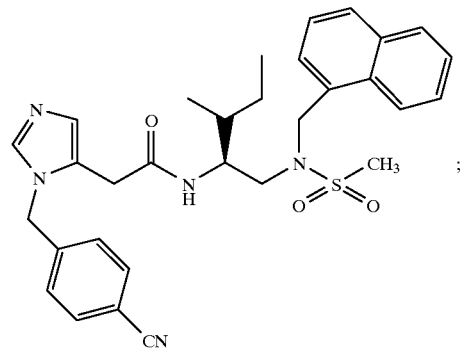

N-Ethylsulfonyl-N-1-naphthylmethyl-2(S)-{(1-(4-cyanobenzyl)-1H-imidazol-5-yl)acetyl}amino-3(S)-methylpentanamine

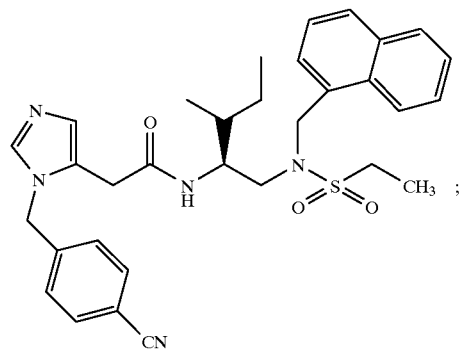

2(RS)-{[1-(Naphth-2-ylmethyl)-1H-imidazol-5-yl)]acetyl}amino-3-(phenylacetyl)amino-N-methyl-N-benzyl) propionamide

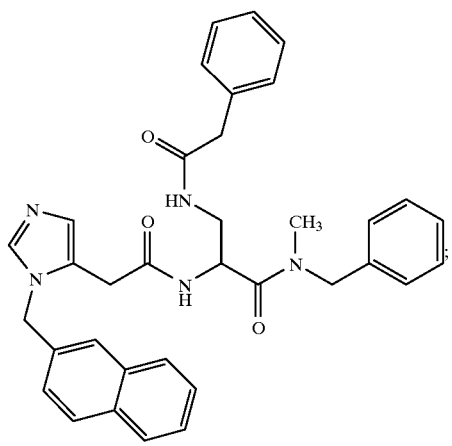

N-[2(S)-([1-(4-cyanobenzyl)-1H-imidazol-5-yl]
acetylamino)-3(S)-methylpentyl]-N-(1-naphthylmethyl)
glycine piperidinylamide

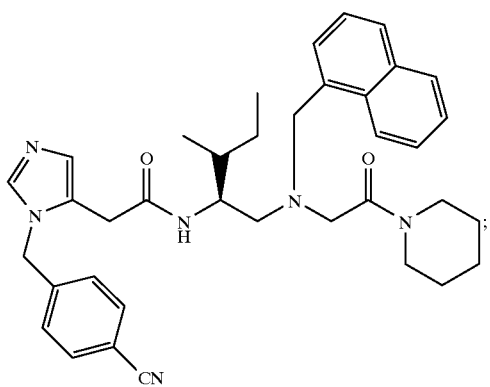

N-{1-(4-cyanobenzyl)-1H-imidazol-5-yl)acetyl}-2(S)-{N'-
acetyl-N'-(naphth-1-ylmethyl)aminomethyl}-pyrrolidine

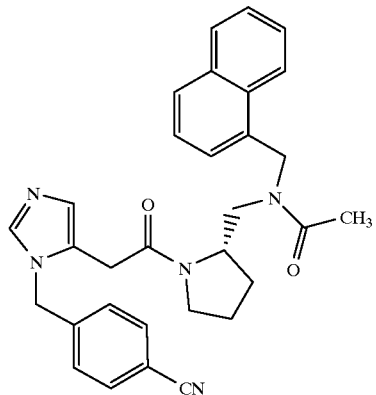

N-(2,3-Dimethylphenyl)-N-methoxycarbonyl-2(S)-[4-
cyanobenzyl-4-(imidazolylmethyl)amino]-3(S)-
methylpentamine

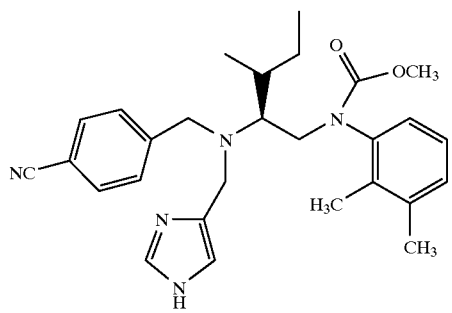

N-{5-(4-Cyanobenzyl)-1H-imidazol-1-yl)ethyl}-2(S)-[1
(R)-1-(3-chlorophenyl)-1-hydroxy]methylpyrrolidine

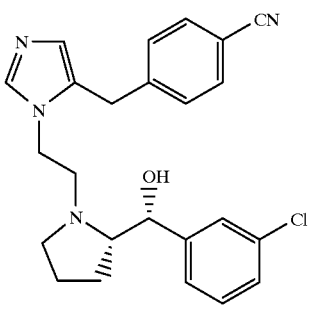

N-{1-(4-Cyanobenzyl)-1H-imidazol-1-ylethyl}-4(R)-
hydroxy-2(S)-[1(R)-1-(3-chlorophenyl)-1-hydroxy]
methylpyrrolidine

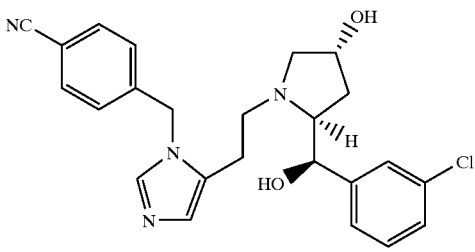

N-[5-(4-Cyanobenzyl)-1H-imidazol-1-ylethyl]-4(R)-
hydroxy-2(S)-[1(R)-1-(3-chlorophenyl)-1-hydroxy]
methylpyrrolidine

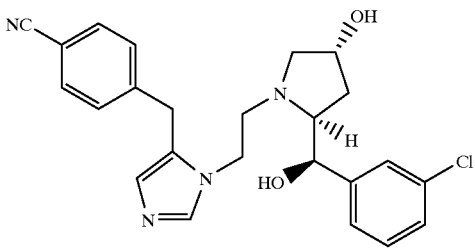

N{1-(4-Cyanobenzyl)-1H-imidazol-5-ylethyl}-2(S)-{N'-
acetyl-N'-3-chlorobenzyl}aminomethylpyrrolidine

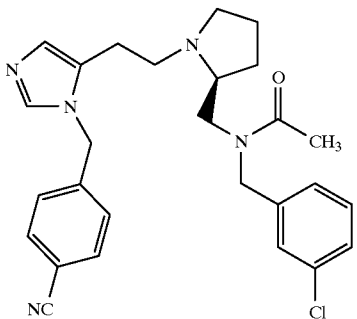

N-{1-(4-Cyanobenzyl)-1H-imidazol-5-yl)methyl}-2(S)-{N'-acetyl-N'-3-chlorophenyl}aminomethylpyrrolidine

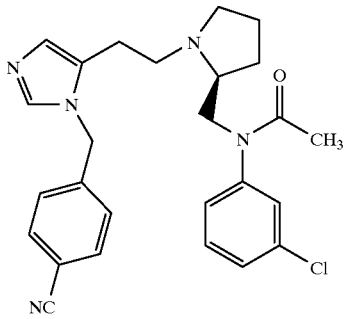

N-{5-(4-Cyanobenzyl)-1H-imidazol-1-yl)ethyl}-2(S)-{N'-acetyl-N'-3-chlorobenzyl}aminomethylpyrrolidine

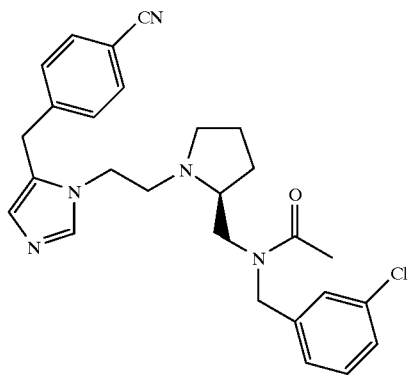

or the pharmaceutically acceptable salts or optical isomers thereof.

In the present invention, the amino acids which are disclosed are identified both by conventional 3 letter and single letter abbreviations as indicated below:

| Alanine | Ala | A |
|---|---|---|
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention. It is also understood that when a bond is drawn from a substituent into a ring, such as the bonds drawn into the imidazolyl ring in formula Ia hereinabove, that attachment of that substituent is at any carbon or heteroatom of the ring as long as a stable compound is formed.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5-to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, oxazolyl, isoxazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl)O-, -OH, $(C_1-C_6$ alkyl)S(O)$_m$-, $(C_1-C_6$ alkyl)C(O)NH-, $H_2$N-C(NH)-, $(C_1-C_6$ alkyl)C(O)-, $(C_1-C_6$ alkyl)OC(O)-, $N_3$, $(C_1-C_6$ alkyl)OC(O)NH- and $C_1-C_{20}$ alkyl.

The following structure:

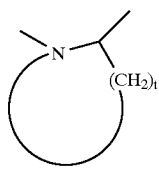

represents a cyclic amine moiety having 5 or 6 members in the ring, such a cyclic amine which may be optionally fused to a phenyl or cyclohexyl ring. Examples of such a cyclic amine moiety include, but are not limited to, the following specific structures:

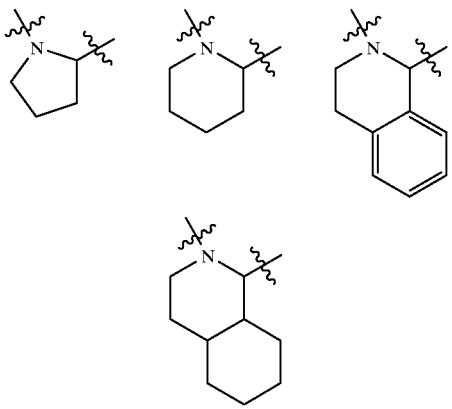

It is also understood that substitution on the cyclic amine moiety by $R^{13a}$ and $R^{13b}$ may be on different carbon atoms or on the same carbon atom.

When $R^2$ and $R^3$ are combined to form $-(CH_2)_s$-, cyclic moieties are formed. Examples of such cyclic moieties include, but are not limited to:

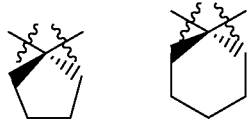

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, $-N(R^{10})_2$ represents -NHH, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

Preferably, $R^{1a}$ and $R^{1b}$ are independently selected from: hydrogen, $-N(R^{10})_2$, $R^{10}C(O)NR^{10}$- or unsubstituted or substituted $C_1-C_6$ alkyl wherein the substituent on the substituted $C_1-C_6$ alkyl is selected from unsubstituted or substituted phenyl, $-N(R^{10})_2$, $R^{10}O$- and $R^{10}C(O)NR^{10}$-. More preferably, $R^{1a}$ and $R^{1b}$ are independently selected from: hydrogen or unsubstituted or substituted $C_1-C_6$ alkyl. Further preferably, $R^{1b}$ is not $-N(R^{10})_2$ or $C_1-C_6$ alkyl substituted with $-N(R^{10})_2$.

Preferably, $R^2$ and $R^3$ are independently selected from: a side chain of a naturally occurring amino acid, methionine sulfoxide, methionine sulfone, $C_1-C_6$ alkyl and $C_1-C_6$ alkyl substituted by a group selected from aryl, heterocycle and $C_3-C_{10}$ cycloalkyl; or $R^2$ or $R^3$ are combined with $R^7$ to form a ring such that

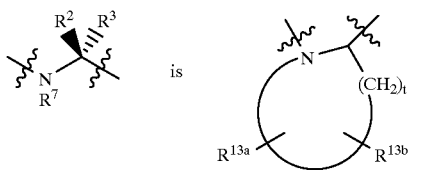

Most preferably, $R^2$ or $R^3$ are combined with $R^7$ to form a ring such that

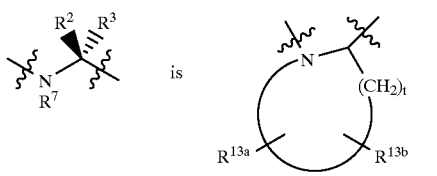

Preferably, $R^4$ and $R^5$ are independently selected from: H, unsubstituted or substituted $C_1-C_6$ alkyl, $R^{10}O$- and halogen.

Preferably, $R^{13a}$ and $R^{13b}$ are independently selected from: H, unsubstituted or substituted $C_1-C_6$ alkyl, $R^{14}O$- and halogen.

Preferably, $R^6$ is not hydrogen or $C_1-C_6$ alkyl when $A^3$ is $-N(R^7)$-.

Preferably, $R^7$ is hydrogen, unsubstituted aryl, substituted aryl, or $C_1-C_6$ alkyl substituted with an unsubstituted aryl or a substituted aryl. Most preferably, $R^7$ is substituted aryl or $C_1-C_6$ alkyl substituted with a substituted aryl.

Preferably, $R^8$ is selected from: hydrogen, perfluoroalkyl, F, Cl, Br, $R^{10}O$-, $R^{11}S(O)_m$-, CN, $NO_2$, $R^{10}_2$N-C(NR$^{10}$)-, $R^{10}C(O)$-, $R^{10}OC(O)$-, $N_3$, $-N(R^{10})_2$, or $R^{11}OC(O)NR^{10}$- and $C_1-C_6$ alkyl.

Preferably, R⁹ is hydrogen.

Preferably, R¹⁰ is selected from H, $C_1$–$C_6$ alkyl and benzyl.

Preferably, $A^1$ and $A^2$ are independently selected from: a bond, -C(O)NR⁷-, -NR⁷C(O)-, O, -N(R⁷)-, -S(O)₂N(R⁷)- and -N(R⁷)S(O)₂-.

Preferably, $A^4$ is selected from a bond and O.

Preferably, V is selected from hydrogen, heterocycle and aryl. More preferably, V is phenyl.

Preferably, W is selected from imidazolinyl, imidazolyl, oxazolyl, pyrazolyl, pyrrolidinyl, thiazolyl and pyridyl. More preferably, W is selected from imidazolyl and pyridyl.

Preferably, Z is O or $H_2$. Most preferably, Z is $H_2$.

Preferably, n and p are independently 0, 1, or 2.

Preferably r is 1, 2 or 3.

Preferably t is 3 or 4.

Preferably q is 1.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from readily available amino acids by conventional peptide synthesis techniques, and the additional methods, well known in the art, described below. Standard methods of peptide synthesis are disclosed, for example, in the following works: Schroeder et al., "*The Peptides*", Vol. 1, Academic Press 1965, or Bodanszky et al., "*Peptide Synthesis*", Interscience Publishers, 1966, or McOmie (ed.) "*Protective Groups in Organic Chemistry*", Plenum Press, 1973, or Barany et al., "*The Peptides: Analysis, Synthesis, Biology*" 2, Chapter 1, Academic Press, 1980, or Stewart et al., "*Solid Phase Peptide Synthesis*", Second Edition, Pierce Chemical Company, 1984. Also useful in exemplifying syntheses of specific unnatural amino acid residues are European Pat. Appl. No. 0 350 163 A2 (particularly page 51–52) and J. E. Baldwin et al. *Tetrahedron*, 50:5049–5066 (1994). The teachings of these works are hereby incorporated by reference.

Abbreviations used in the description of the chemistry and in the Examples that follow are:

| | |
|---|---|
| Ac₂O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| HOBT | 1-Hydroxybenzotriazole hydrate; |
| Et₃N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in the following Reaction Schemes A-J, in addition to other standard manipulations such as ester hydrolysis, cleavage of protecting groups, etc., as may be known in the literature or exemplified in the experimental procedures. Some key bond-forming and peptide modifying reactions are:

Reaction A Amide bond formation and protecting group cleavage using standard solution or solid phase methodologies.

Reaction B Preparation of a reduced peptide subunit by reductive alkylation of an amine by an aldehyde using sodium cyanoborohydride or other reducing agents.

Reaction C Alkylation of a reduced peptide subunit with an alkyl or aralkyl halide or, alternatively, reductive alkylation of a reduced peptide subunit with an aldehyde using sodium cyanoborohydride or other reducing agents.

Reaction D Peptide bond formation and protecting group cleavage using standard solution or solid phase methodologies.

Reaction E Preparation of a reduced subunit by borane reduction of the amide moiety.

These reactions may be employed in a linear sequence to provide the compounds of the invention or they may be used to synthesize fragments which are subsequently joined by the alkylation reactions described in the Reaction Schemes and in Reaction Schemes 1–5 hereinbelow.

REACTION SCHEME A
Reaction A.
Coupling of residues to form an amide bond

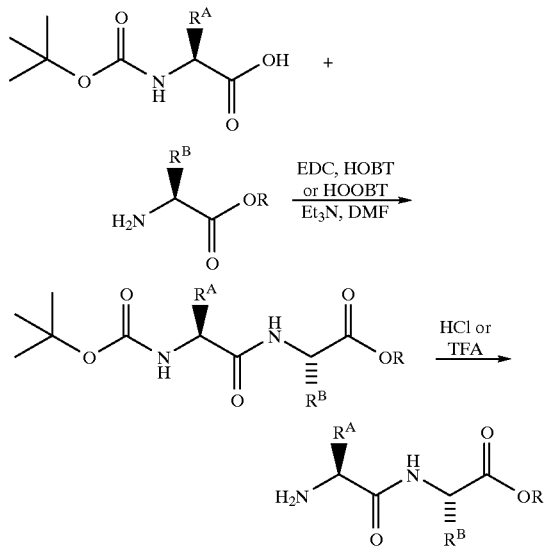

REACTION SCHEME B
Reaction B.
Preparation of reduced peptide subunits by reductive alkylation

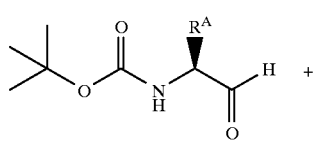

-continued

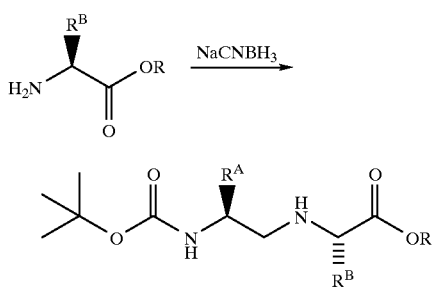

REACTION SCHEME C
Reaction C.
Alkylation/reductive alkylation of reduced peptide subunits

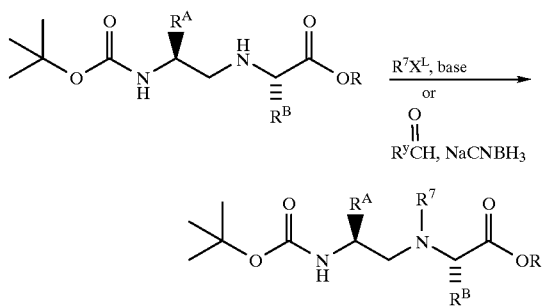

REACTION SCHEME D
Reaction D.
Coupling of residues to form an amide bond

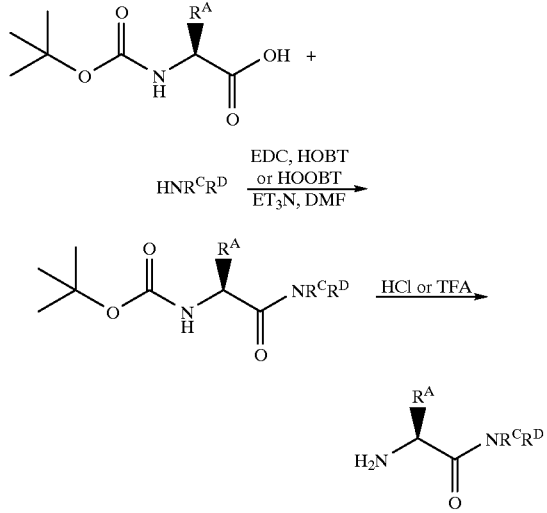

REACTION SCHEME E
Reaction E.
Preparation of reduced dipeptides from peptides

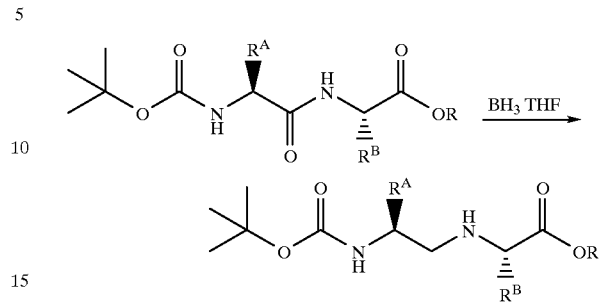

where $R^A$ and $R^B$ are $R^2$, $R^3$ or $R^5$ as previously defined; $R^C$ and $R^D$ are $R^7$ or $R^{12}$; $X^L$ is a leaving group, e.g., Br-, I- or MsO-; and $R^y$ is defined such that $R^7$ is generated by the reductive alkylation process.

In addition to the reactions described in Reaction Schemes A–E, other reactions used to generate the compounds of this invention are shown in the Reaction Schemes 1–20. All of the substituents shown in the Reaction Schemes, represent the same substituents as defined hereinabove. The substituent "Ar" in the Reaction Schemes represents a carbocyclic or heterocyclic, substituted or unsubstituted aromatic ring.

These reactions may be employed in a linear sequence to provide the compounds of the invention or they may be used to synthesize fragments which are subsequently joined by the alkylation reactions described in the Reaction Schemes. The sequential order whereby substituents are incorporated into the compounds is often not critical and thus the order of reactions described in the Reaction Schemes are illustrative only and are not limiting.

Synopsis of Reaction Schemes 1–20:
The requisite intermediates are in some cases commercially available, or can be readily prepared according to known literature procedures, including those described in Reaction Schemes A-E hereinabove. Thus, the intermediate II, generally prepared from the appropriate amino acid by the above noted methods with the suitable substituents fully incorporated, (Scheme 3), can be reductively alkylated with a variety of aldehydes, such as III. The aldehydes can be prepared by standard procedures, such as that described by O. P. Goel, U. Krolls, M. Stier and S. Kesten in *Organic Syntheses*, 1988, 67, 69–75. The reductive alkylation can be accomplished at pH 5–7 with a variety of reducing agents, such as sodium triacetoxyborohydride or sodium cyanoborohydride in a solvent such as dichloroethane, methanol or dimethylformamide. The product IV can be deprotected to give the compounds V with trifluoroacetic acid in methylene chloride. The intermediate V is isolated in the salt form, for example, as a trifluoroacetate, hydrochloride or acetate salt, among others. The product diamine V can further be selectively protected to obtain VI, which can subsequently be reductively alkylated with a second aldehyde to obtain VII. Removal of the protecting group, and conversion to cyclized products such as the dihydroimidazole VIII can be accomplished by literature procedures.

Alternatively, the protected intermediate II can be reductively alkylated with other aldehydes (which may be suitably protected if necessary), many of which are readily commercially available, such as 4-bromo-2-thiophenecarboxaldehyde, 5-methoxyindole-3-carboxaldehyde, 6-methyl-2-pyridinecarboxaldehyde, 3-pyridinecarboxaldehyde, 4-imidazolyl-acetaldehyde and the like, to give products such as IX (Reaction Scheme 2). The trityl protecting group can be removed from IX to give X, or alternatively, IX can first be treated with an alkyl halide then subsequently deprotected to give the alkylated imidazole XI.

As shown in Reaction Scheme 3, related carboxylic acids, such as the imidazole acetic acid XII, can be converted to the acetate XIII by standard procedures and incorporation of a protecting group, and XIII can be first reacted with an alkyl halide, then treated with refluxing methanol to provide the regiospecifically alkylated imidazole acetic acid ester XIV. Hydrolysis and reaction with the fully functionalized peptidyl portion of the molecule II in the presence of condensing reagents such as 1-(3-dimethylaminopropyl)-3-ethylcarbodiimide (EDC) leads to acylated products such as XVI.

It is also understood that the reactions illustrated in Reaction Schemes 1–3 can be utilized to prepare an intermediate that can subsequently be treated as described in Reaction Schemes A-E. Thus, as shown in Reaction Schemes 4 and 5, suitably protected amino acids XVII and XVIII, can be reacted with the acetic acid XV to provide intermediates XIX and XX, which can then undergo further functionalization by standard techniques.

Reaction Schemes 6 and 7 illustrate synthetic routes to the instant compounds in which the sequential order that the substituents are incorporated is shuffled. Thus in Reaction Scheme 6 the suitably protected aldehyde XXI can be reductively aminated to provide compound XXII. The amine group of XXII can be blocked and the BOC protecting group removed. Coupling with the substituted acetic acid provides XXIV, which can then be deblocked with $Pd(PPh_3)_4$ and further functionalized. Alternatively, compound XXII can first be functionalized on the amine to provide, for example, amide XXV. Deprotection and reaction with intermediate XV as before provides the instant compound XXVI.

In Reaction Scheme 7, the primary amine XXVIII is prepared from the alcohol XXVII and blocked with an allyloxycarbonyl group. Deprotection and reaction with intermediate XV as before provides the blocked amine XXIX which, after removal of the allyloxycarbonyl protecting moiety by standard procedures, may be mono- or di-substituted using techniques described above.

Reaction Scheme 8 illustrates incorporation of a cyclic amine moiety, such as a reduced prolyl moiety, into the compounds of the instant invention. Reduction of the azide XXX provides the amine XXXI, which may be mono- or di-substituted using techniques described above. As an example, incorporation of a naphthylmethyl group and an acetyl group is illustrated.

As shown in Reaction Scheme 9, direct attachment of a aromatic ring to a substituted amine such as XXXII is accomplished by coupling with a triarylbismuth reagent, such as tris(3-chlorophenyl)bismuth.

Reaction Scheme 10 illustrates the use of protecting groups to prepare compounds of the instant invention wherein the cyclic amine contains an alkoxy moiety. The hydroxy moiety of key intermediate XXXIV may be further converted to a fluoro or phenoxy moiety, as shown in Reaction Scheme 11. Intermediates XXXV and XXXVI may then be further elaborated to provide the instant compounds.

Reaction Scheme 12 illustrates syntheses of instant compounds wherein the variable $-(CR^4{}_2)_qA^3(CR^5{}_2)_nR^6$ is a suitably substituted α-hydroxybenzyl moiety. Thus the protected intermediate aldehyde XXXVII is treated with a suitably substituted phenyl Grignard reagent to provide the enantiomeric mixture XXXVIII. Treatment of the mixture with 2-picolinyl chloride allows chromatographic resolution of compounds IXL and XL. Removal of the picolinoyl group followed by deprotection provides the optically pure intermediate XLI which can be futher processed as described hereinabove to yield the instant compounds.

Syntheses of imidazole-containing intermediates useful in synthesis of instant compounds wherein the variable p is 0 or 1 and Z is $H_2$ are shown in Reaction Scheme 13 and 14. Thus the mesylate XLII can be utilized to alkylate a suitably substituted amine or cyclic amine, while aldehyde XLIII can be used to similarly reductively alkylate such an amine.

Reaction Scheme 15 illustrates te syntheses of imidazole-containing intermediates wherein the attachment point of the $-(CR^{1b}{}_2)_p-C(Z)-$ moiety to W (imidazolyl) is through a ring nitrogen. Reaction Scheme 16 illustrates the synthesis of an intermediate wherein a $R^{1b}$ substitutent is a methyl.

Reaction Schemes 17–20 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

REACTION SCHEME 1

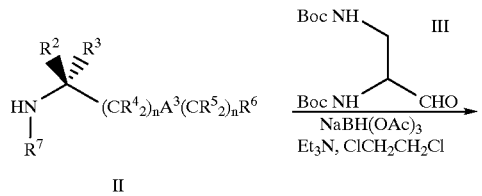

-continued
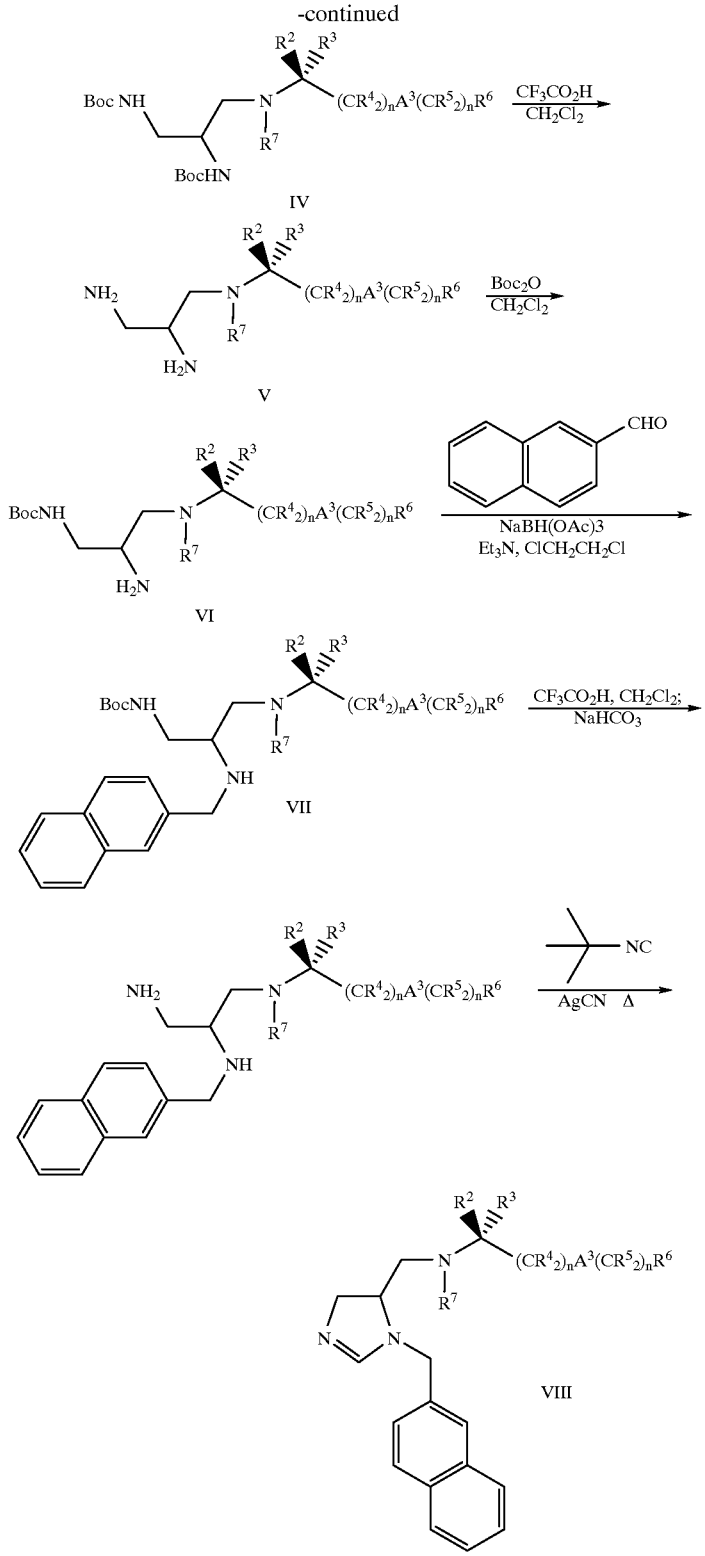

REACTION SCHEME 3
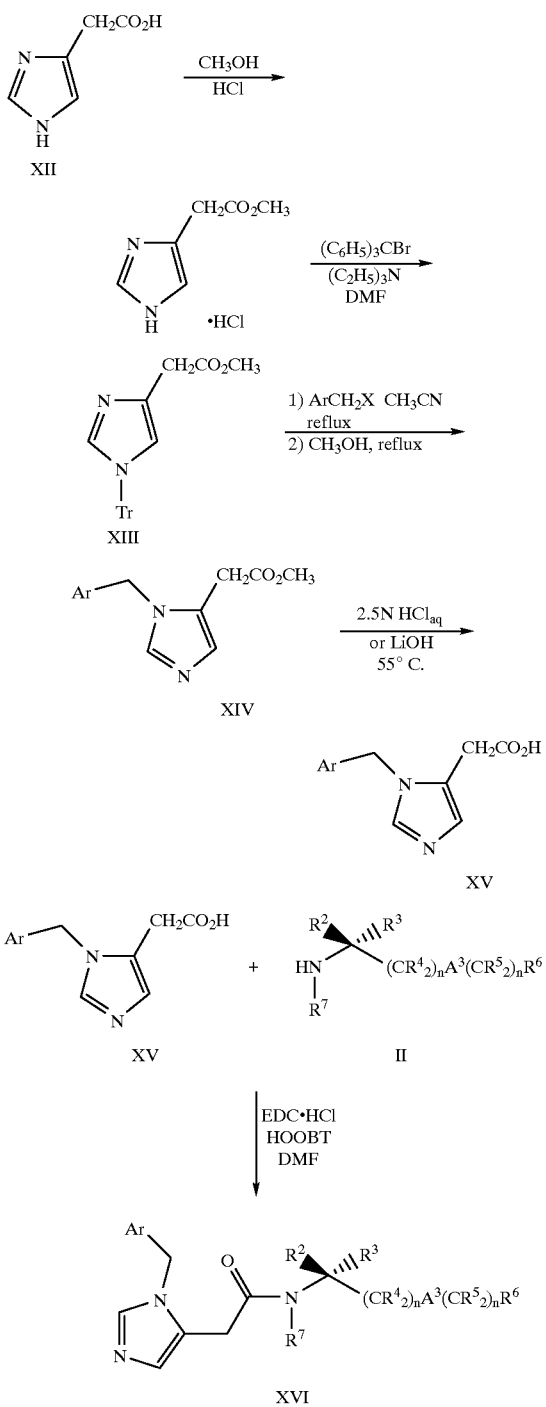
REACTION SCHEME 4
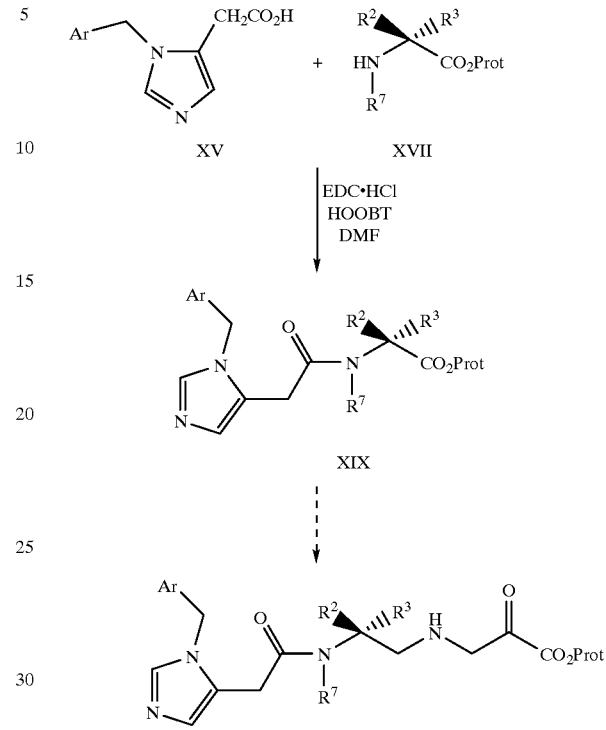
wherein Prot=carboxylic acid protecting group
REACTION SCHEME 5
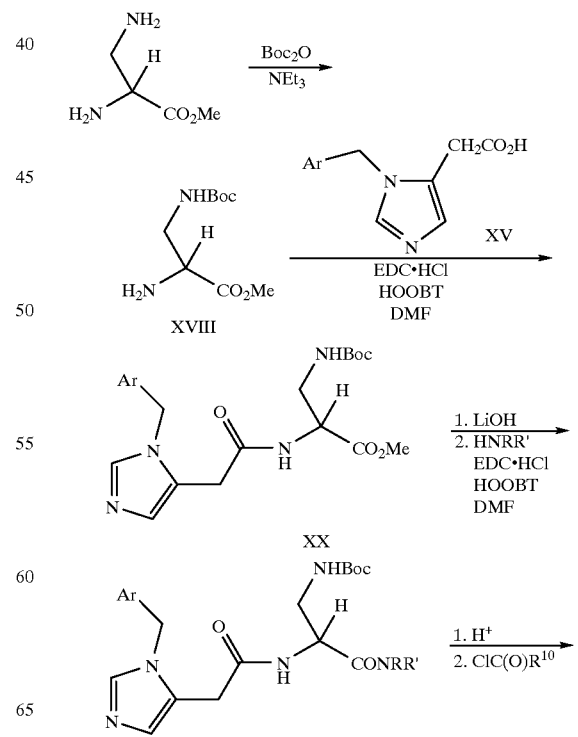

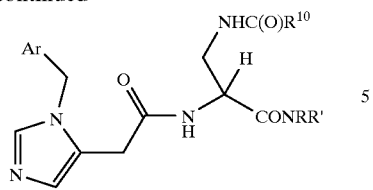
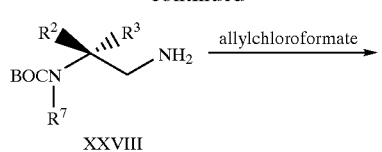
REACTION SCHEME 6
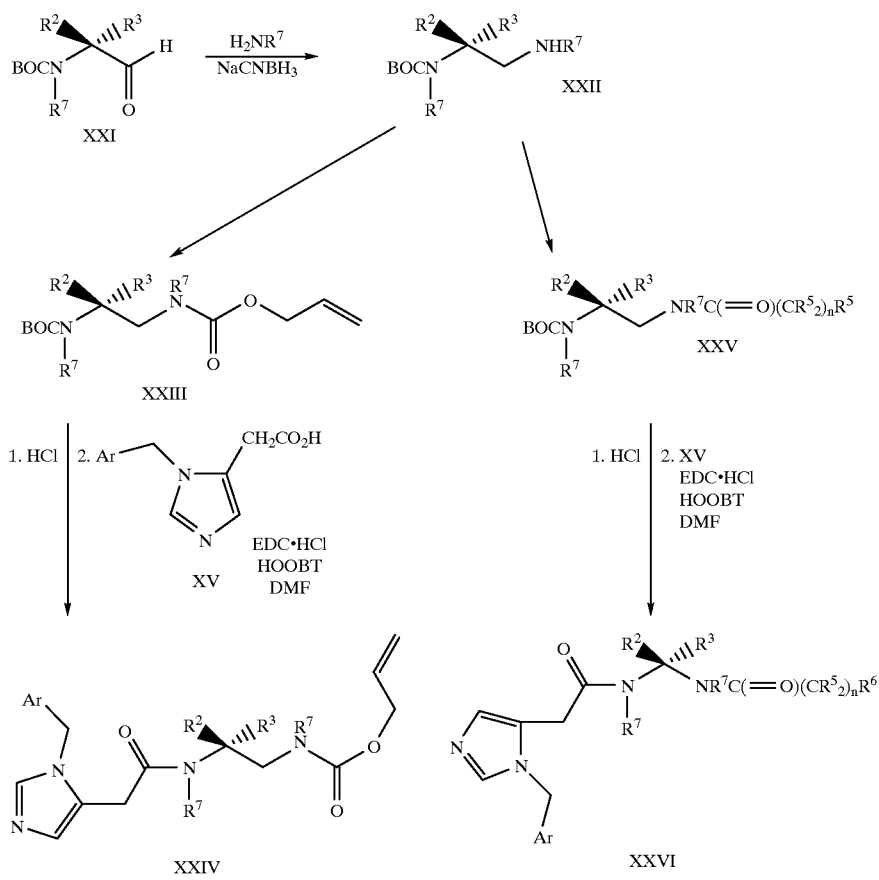
REACTION SCHEME 7
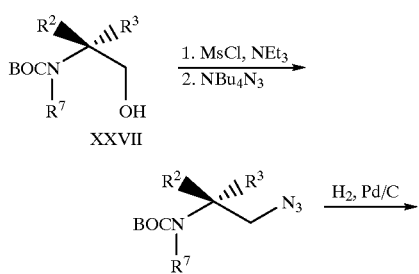
-continued
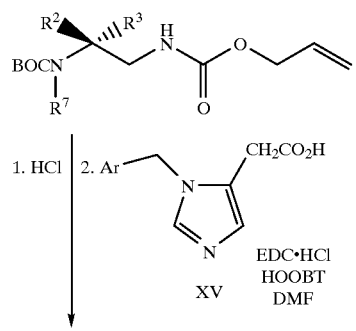

39
-continued
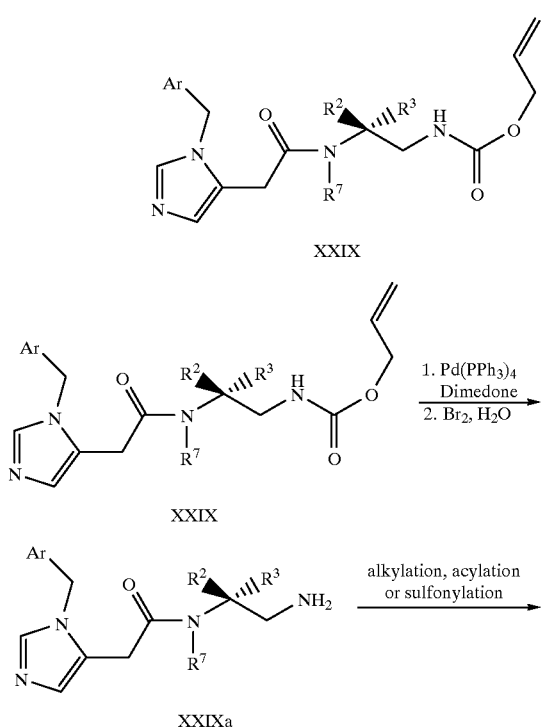
REACTION SCHEME 8
40
-continued
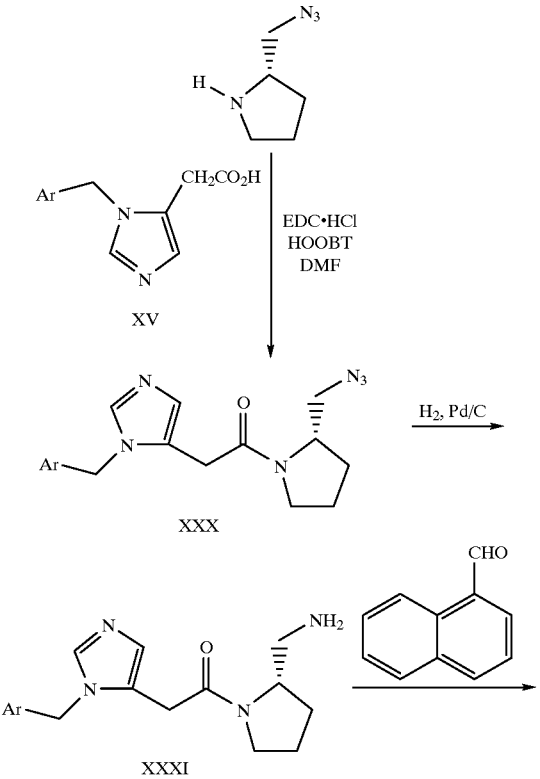
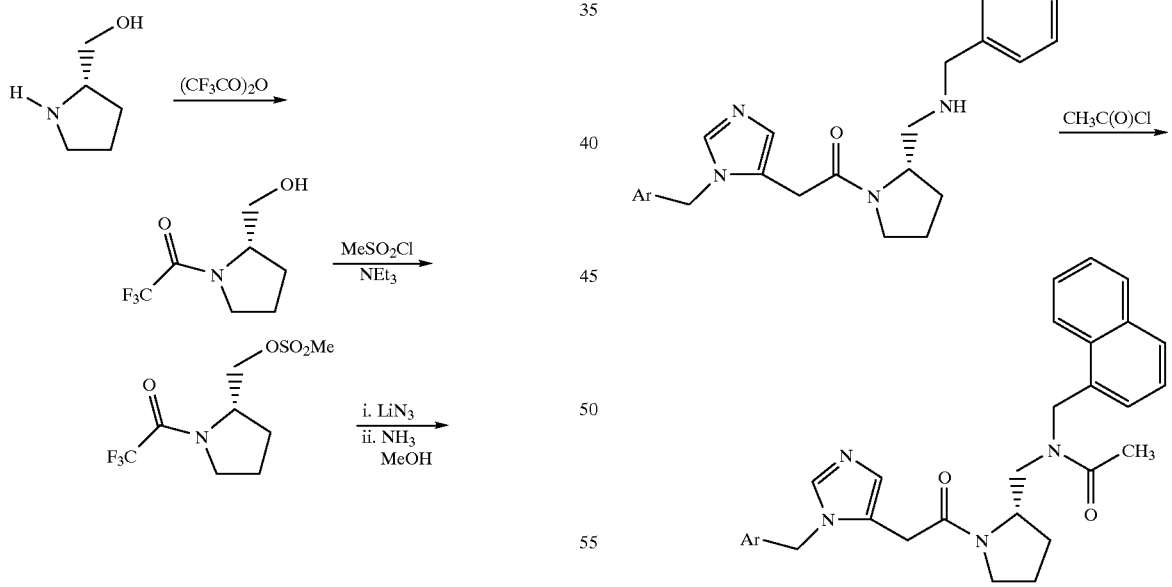

REACTION SCHEME 9
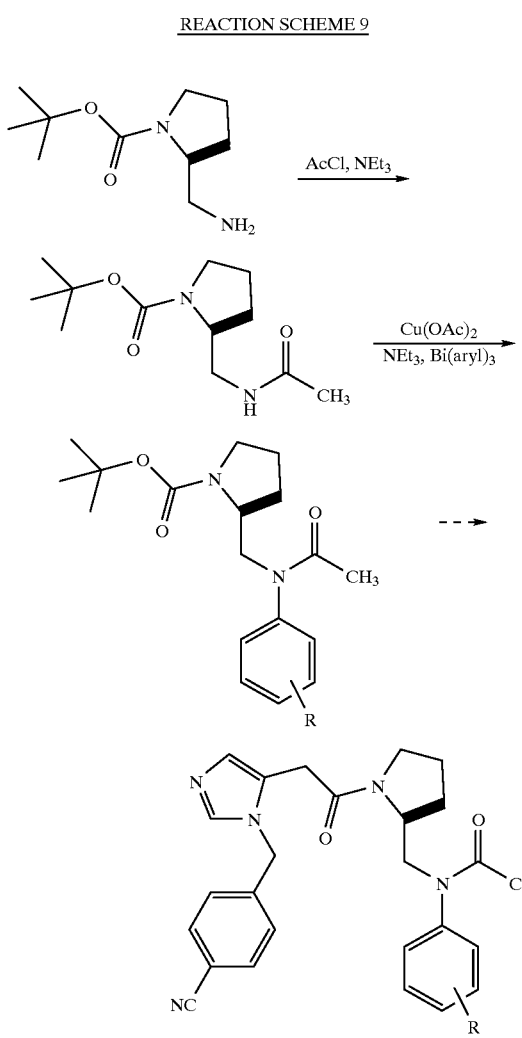
REACTION SCHEME 10
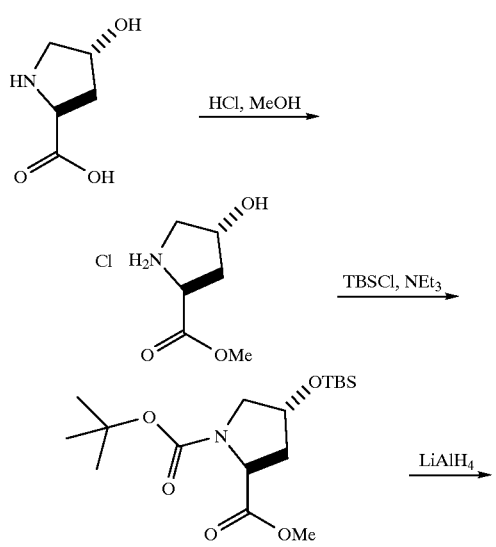
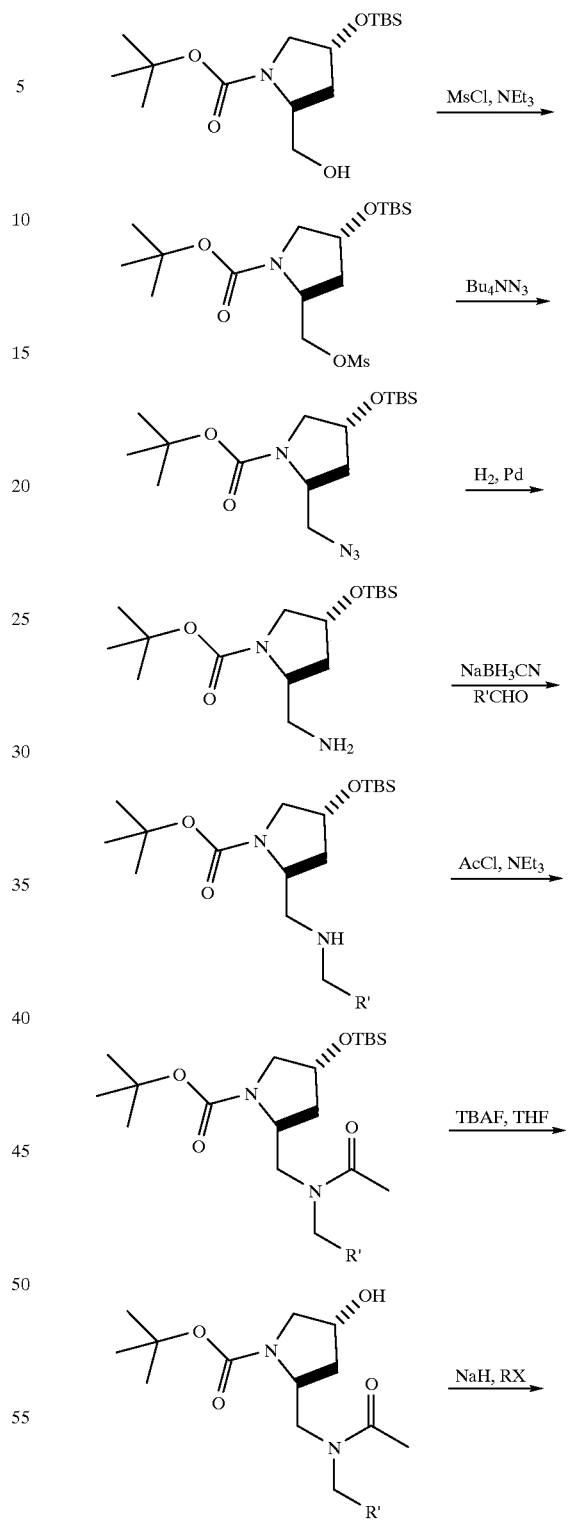
XXXIV -continued
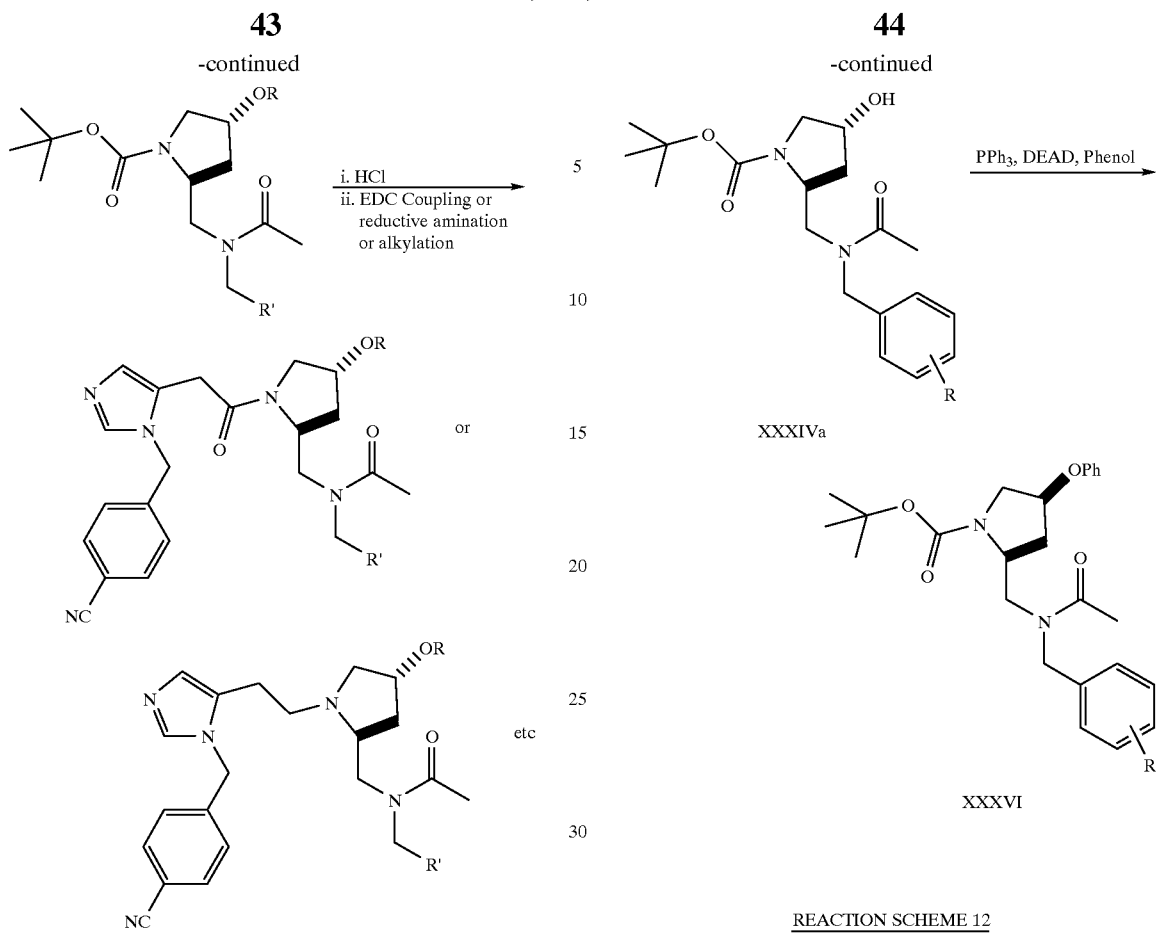
REACTION SCHEME 11
REACTION SCHEME 12
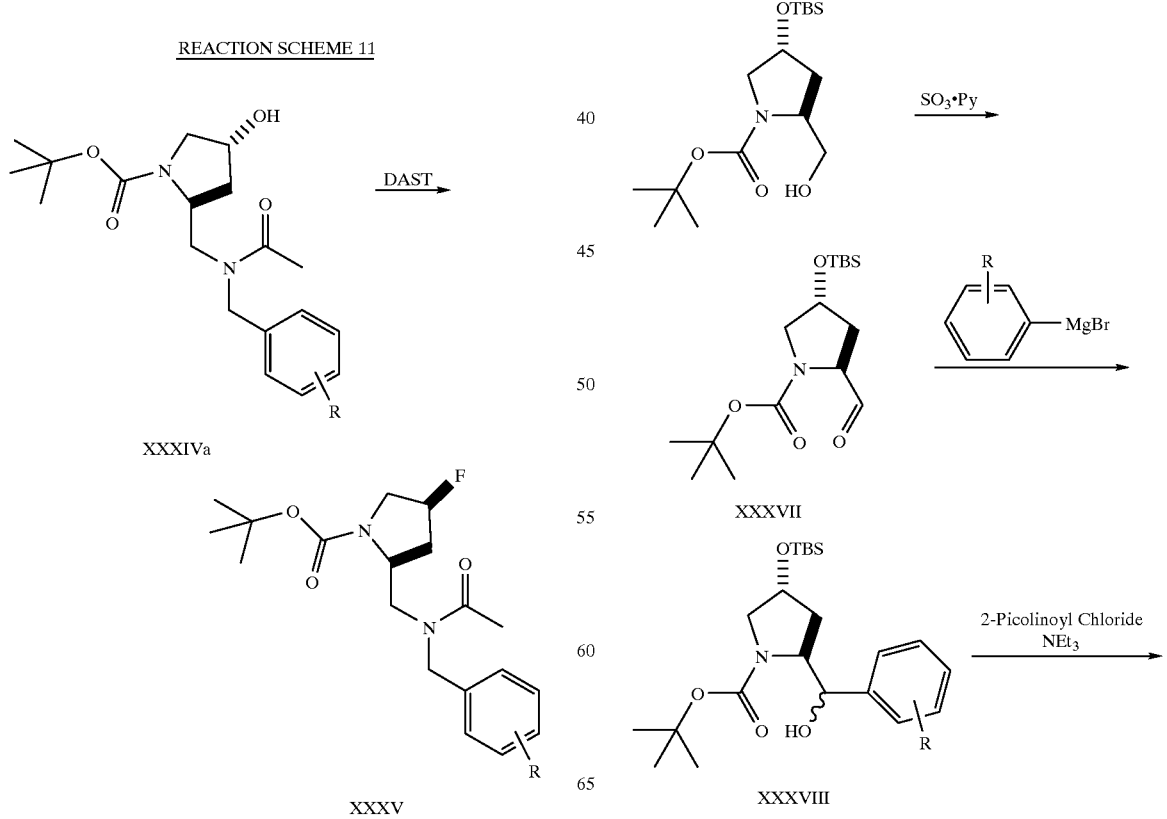

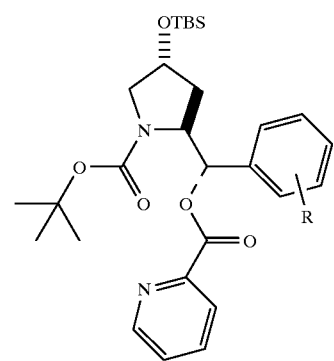
IXL
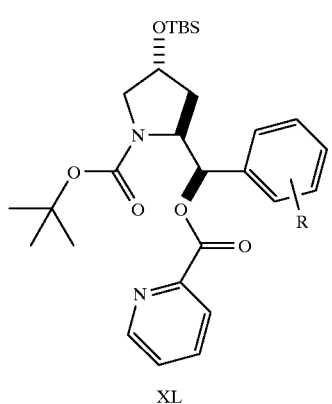
XL
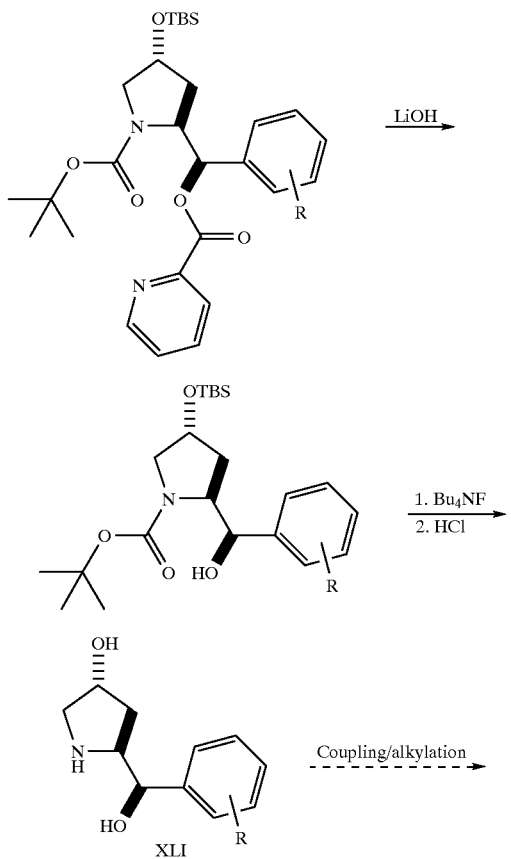
XLI
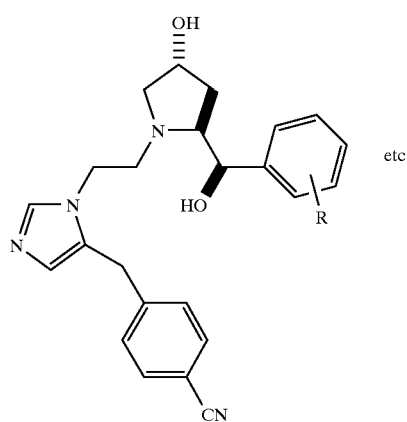
etc
REACTION SCHEME 13
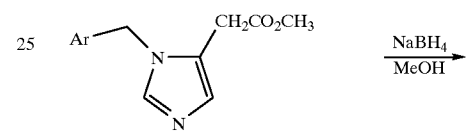
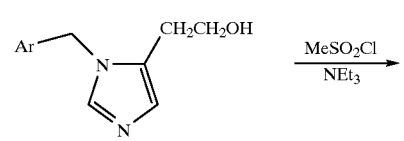
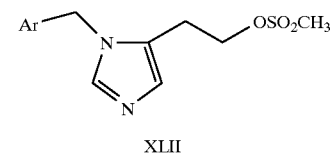
XLII
REACTION SCHEME 14
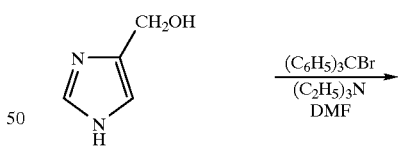
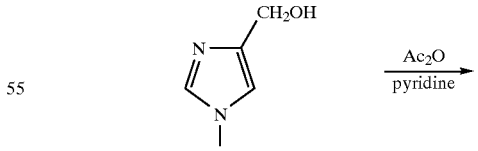
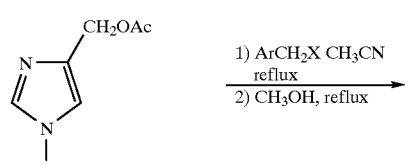

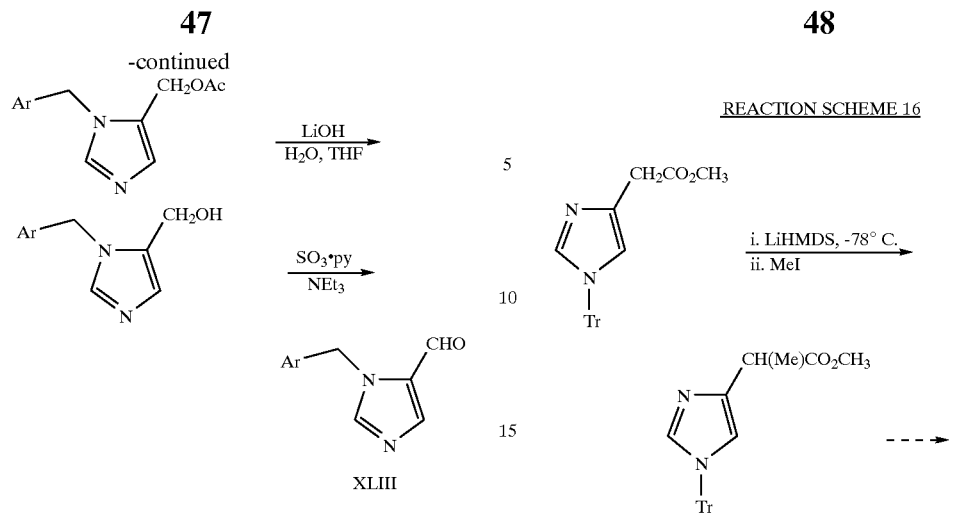
REACTION SCHEME 16
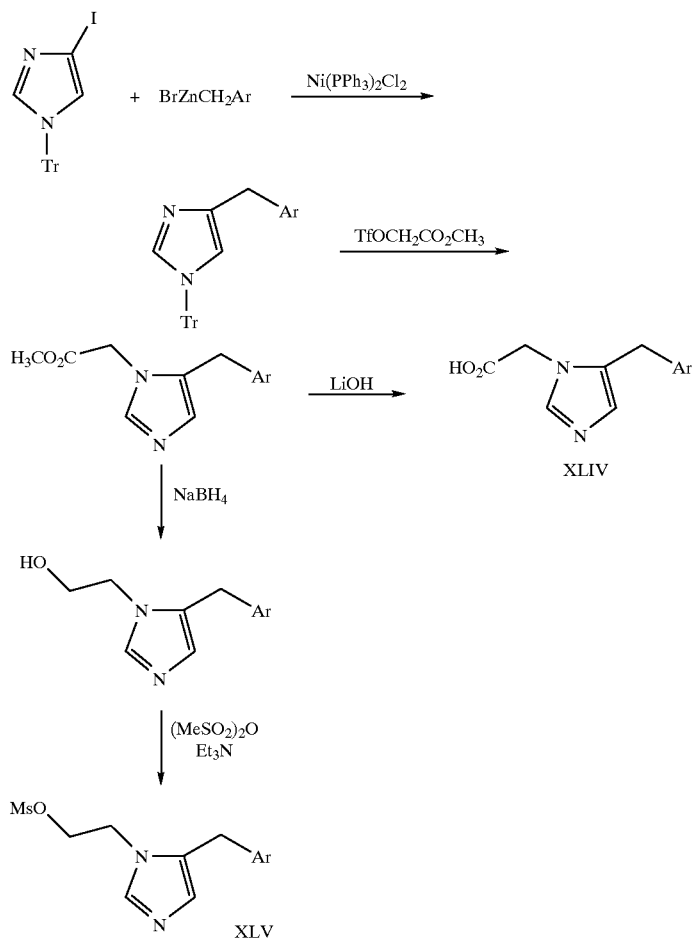
REACTION SCHEME 15

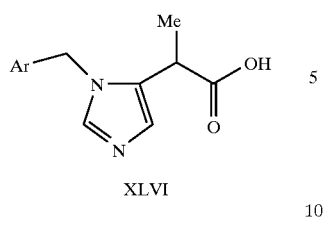
XLVI
REACTION SCHEME 17
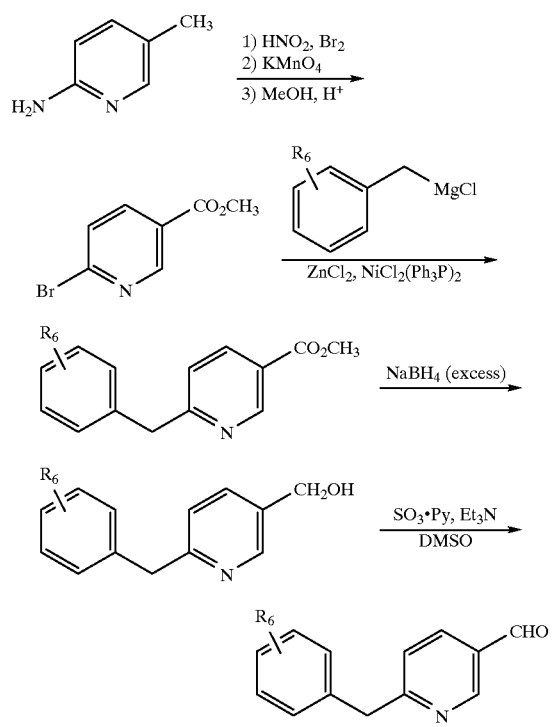
REACTION SCHEME 18
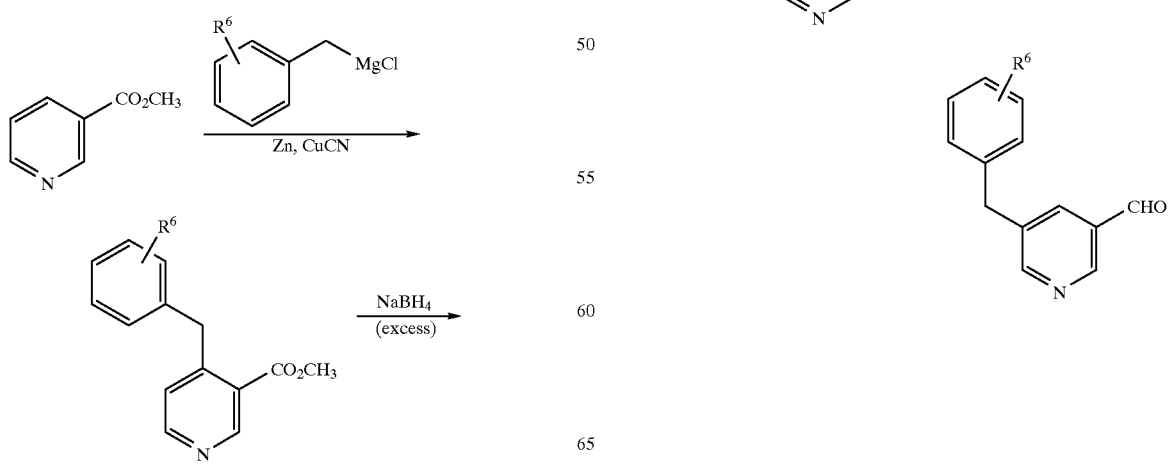

REACTION SCHEME 19

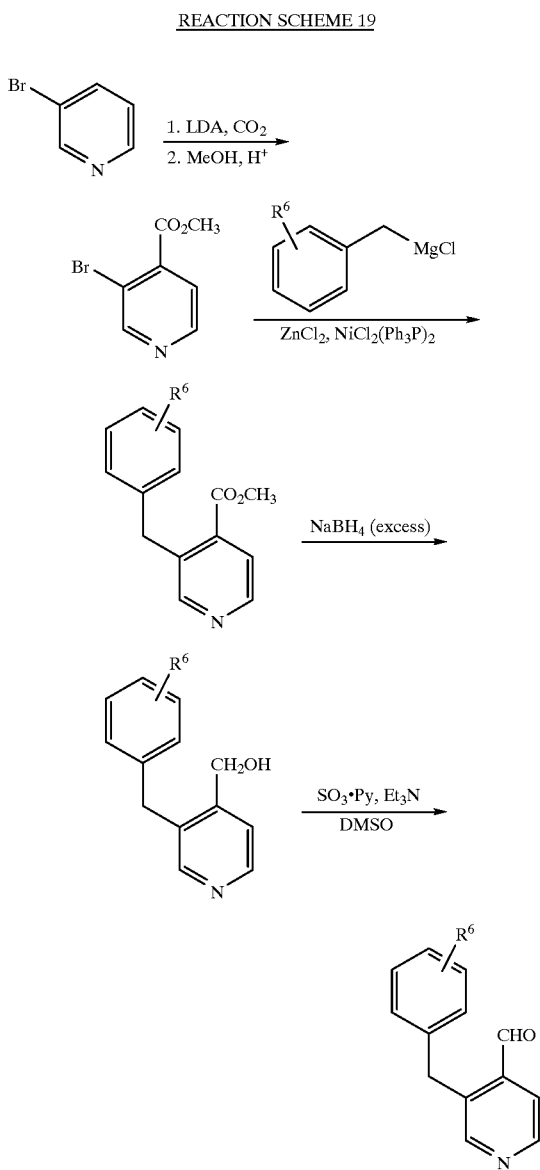

REACTION SCHEME 20

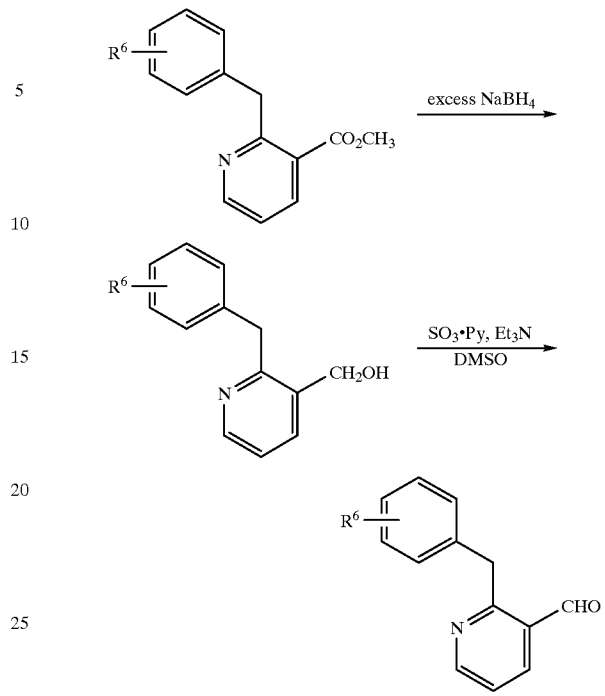

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research,* 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science,* 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

EXAMPLE 1

N-Allyloxycarbonyl-N-naphth-1-ylmethyl-2(S)-{1-(4-cyanobenzyl)-1H-imidazol-5-yl)acetyl}amino-3 (S)- methylpentanamine Step A: Preparation of 1H-Imidazole-4- acetic acid methyl ester hydrochloride.

A solution of 1H-imidazole-4-acetic acid hydrochloride (4.00 g, 24.6 mmol) in methanol (100 ml) was saturated with gaseous hydrogen chloride. The resulting solution was allowed to stand at room temperature (RT) for 18 hr. The solvent was evaporated in vacuo to afford the title compound as a white solid.

¹H NMR(CDCl₃, 400 MHz) δ 8.85(1H, s),7.45(1H, s), 3.89(2H, s) and 3.75(3H, s) ppm.

Step B: Preparation of 1-(Triphenylmethyl)-1H-imidazol-4-ylacetic acid methyl ester.

To a solution of the product from Step A (24.85 g, 0.141 mol) in dimethyl formamide (DMF) (115 ml) was added triethylamine (57.2 ml, 0.412 mol) and triphenylmethyl bromide(55.3 g, 0.171 mol) and the suspension was stirred for 24 hr. After this time, the reaction mixture was diluted with ethyl acetate (EtOAc) (1 l) and water (350 ml). The organic phase was washed with sat. aq. NaHCO₃ (350 ml), dried (Na₂SO₄) and evaporated in vacuo. The residue was purified by flash chromatography (SiO₂, 0–100% ethyl acetate in hexanes; gradient elution) to provide the title compound as a white solid.

¹H NMR (CDCl₃, 400 MHz) δ 7.35(1H, s), 7.31(9H, m), 7.22(6H, m), 6.76(1H, s), 3.68(3H, s) and 3.60(2H, s) ppm.

Step C: Preparation of [1-(4-cyanobenzyl)-1H-imidazol-5-yl]acetic acid methyl ester.

To a solution of the product from Step B (8.00 g, 20.9 mmol) in acetonitrile (70 ml) was added bromo-p-tolunitrile (4. 10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hr. The reaction mixture was cooled to room temperature and evaporated in vacuo. To the residue was added EtOAc (70 ml) and the resulting white precipitate collected by filtration. The precipitated imidazolium salts were combined, suspended in methanol (100 ml) and heated to reflux for 30 min. After this time, the solvent was removed in vacuo, the resulting residue was suspended in EtOAc (75 ml) and the solid isolated by filtration and washed (EtOAc). The solid was treated with sat aq NaHCO₃ (300 ml) and CH₂Cl₂ (300 ml) and stirred at room temperature for 2 hr. The organic layer was separated, dried (MgSO₄) and evaporated in vacuo to afford the title compound as a white solid:

¹HNMR(CDCl₃, 400 MHz) δ7.65(1H, d, J=8 Hz), 7.53 (1H, s), 7.15(1H, d, J=8 Hz), 7.04(1H, s), 5.24(2H, s), 3.62(3H, s) and 3.45(2H, s) ppm.

Step D: Preparation of [1-(4-cyanobenzyl)-1H-imidazol-5-yl]acetic acid.

A solution of [1-(4-cyanobenzyl)-1H-imidazol-5-yl] acetic acid methyl ester (4.44 g, 17.4 mmol ) in THF (100 ml) and 1 M lithium hydoxide (17.4 ml, 17.4 mmol) was stirred at RT for 18 hr. 1 M HCl (17.4 ml) was added and the THF was removed by evaporation in vacuo. The aqueous solution was lyophilised to afford the title compound containing lithium chloride as a white solid.

¹H NMR(CD₃OD, 400 MHz) δ 8.22(1H, s), 7.74(1H, d, J=8.4 Hz), 7.36(1H, d, J=8.4 Hz ), 7.15(1H , s), 5.43(2H, s) and 3.49(2H, s) ppm.

Step E: Preparation of N-Naphth-1-ylmethyl-2(S)-(t-butoxycarbonyl)amino-3(S )-methylpentanamine To a slurry of 1-naphthylmethylamine (5.84 g, 37.2 mmol), crushed 3A molecular sieves (10 g), and N-t-butoxycarbonyl-isoleucinal (8.0 g, 37.2 mmol) in 1,2-dichloroethane (50 ml) was added sodium triacetoxyborohydride (15.8 g, 74.3 mmol) at 0° C. The reaction was allowed to warm slowly to RT and stirred for 48 hrs. The reaction was cooled to 0° C. and quenched with sat. aq. NaHCO₃ and stirred for 30 min. The organic layer was separated, washed with saturated brine, dried (MgSO₄) and evaporated in vacuo. The residue was purified by flash chromatography (SiO₂, 25% ethyl acetate in hexanes) to provide the title compound as an oil.

¹HNMR(CDCl₃, 400 MHz) δ 8.16(1H, d, J=7.9 Hz), 7.87(1H, d, J=7.9 Hz), 7.78(1H, d, J=7.7 Hz), 7.60-7.40 (4H, m), 4.62(1H, m), 4.25(1H, d, J=13.2 Hz), 4.19(1H, d, J=13.2 Hz), 3.68(1H, m), 2.90-2.70(2H, m), 1.70-1.35(3H, m) and 1.45(9H, s) 1.12(1H, m) and 1.00-0.80 (6H, m) ppm.

Step F: Preparation of N-Allyoxycarbonyl-N-naphth-1-ylmethyl-2(S)-(t-butoxycarbonyl)amino-3 (S)-methylpentanamine To a solution of the amine from step E (4.62 g, 13.0 mmol), and triethylamine (4.40 ml, 31.6 mmol) at 0° C., allylchloroformate (1.85 ml, 17.4 mmol) was added dropwise. The reaction was allowed to warm slowly to RT and stirring was continued for 18 hrs. The solvent was evaporated in vacuo and the residue was chromatographed (SiO₂, 10% EtOAc in hexanes) to afford the title compound as an oil.

¹HNMR(CDCl₃, 400 MHz) δ 8.10(0.4H, d, J=7.9 Hz), 8.00(0.6H, d, J=7.9 Hz), 7.88(1H, m), 7.80(1H, m), 7.60-7.30 (4H, m), 6.10-5.85(1H, m), 5.50-5.10(3H, m), 4.90-4.40(4H,m), 3.90(1H,m), 3.71(0.6H, t, J=12.6 Hz), 3.36 (0.4H,t, J=12.6 Hz), 2.90-2.70(1H,m), 1.47(9H,s), 1.50-1.20 (2H,m), 1.05(1H,m) and 0.95-0.70 (6H, m) ppm.

FAB HRMS exact mass calc'd for $C_{26}H_{37}N_2O_4$ 441.275333 (MH⁺), found 441.275084.

Step G: Preparation of N-Allyoxycarbonyl-N-naphth-1-ylmethyl-2(S)-amino-3(S)-methylpentanamine hydrochloride A solution of the product from step F (4.75 g, 10.8 mmol) in EtOAc (200 ml) at 0° C. was saturated with gaseous hydrogen chloride. The resulting solution was allowed to stand at room temperature (RT) for 30 min. The solvent was evaporated in vacuo to afford the title compound as a white solid.

¹H NMR(CD₃OD, 400 MHz) δ 8.06(1H, m), 7.93(1H, m), 7.88(1H,d, J=8.2 Hz), 7.60-7.45(3H,m), 7.38(1H,m), 6.01 (1H,m), 5.40-5.19(2H,m), 5.10(2H,m), 4.80-4.60(2H,m), 3.62(1H,m), 3.50-3.20(1H,m), 3.11 (1H,m), 1.57(1H,m), 1.23(1H,m), 1.03(1H,m) and 0.90-0.75(6H,m) ppm.

FAB HRMS exact mass calc'd for $C_{21}H_{29}N_2O_2$ 341.222903 (MH⁺), found 341.223321

Step H: Preparation of N-Allyoxycarbonyl-N-naphth-1-ylmethyl-2(S)-[1-(4-cyanobenzyl)-1H-imidazol-5-yl]acetylamino-3(S)-methylpentanamine hydrochloride To a solution of the acid from step D (1.47 g, 3.32 mmol), the amine hydrochloride salt from step G (1.252 g, 3.32 mmol), HOOBT (650 mg, 3.98 mmol), and triethylamine (1.60 ml, 11 mmol) in DMF was added EDC (764 mg, 3.99 mmol). The reaction was stirred at room temperature for 48 hrs, diluted with EtOAc and the organic layer washed with sat. aq NaHCO₃, brine, dried (Na₂SO₄). and evaporated in vacuo. The residue was chromatographed (SiO₂, 3.5% MeOH in CH₂Cl₂) to afford the title compound as an oil.

¹H NMR(CD₃OD, 400 MHz) δ 8.00-7.70 (6H, m), 7.52 (2H, m), 7.44(1H,t, J=7.6 Hz), 7.38-7.25(3H,m), 6.96(1H,s), 6.10-5.90(1H,m), 5.43(2H,m), 5.40-4.80(5H,m), 4.60(2H, m), 4.18(1 H,m), 3.60-3.10(4H,m), 1.40(2H,m), 1.06(1H, m), 0.85(3H, t, J=7.5 Hz), and 0.77(3H, d, J=7.5 Hz) ppm.

Anal. calc'd for $C_{34}H_{37}N_5O_3$ 0.65 $H_2O$: C, 70.97; H, 6.71; N, 12.17.

Found: C, 70.59; H, 6.59; N, 12.56.

FAB HRMS exact mass calc'd for $C_{34}H_{38}N_5O_3$ 564.297465 (MH$^+$), found 564.296221.

EXAMPLE 2

N-Naphth-1-ylmethyl-2(S)-{(1-(4-cyanobenzyl)-1H-imidazol-5-yl)acetyl}amino-3(S)- methyl pentanamine The product of Example I (1.67 g, 2.96 mmol), and 5,5-dimethyl-1,3- cyclohexandione (3.31 g, 23.6 mmol) were combined, the flask was purged with argon and tetrakis (triphenylphosphine) palladium (O) (585 mg, 0.506 mmol) was added and the flask purged with argon again. The flask was wrapped with foil, THF (36 ml) was added and the reaction was stirred in the dark, at room temperature for 90 min. The solvent was evaporated in vacuo and the residue was chromatographed (SiO$_2$, 2% NH$_4$OH in 98% CH$_3$CN –5% NH$_4$OH in 95% CH$_3$CN and then 5% MeOH,5% NH$_4$OH in 90% CH$_3$CN; gradient elution) to afford the title compound as a pale yellow solid.

$^1$H NMR(CD$_3$OD, 400 MHz) δ 8.10(1H, m),7.98(1H,m), 7.84(1H,d, J=7.5 Hz), 7.68(1H,s), 7.63(2H, d, J=8.3 Hz), 7.53(2H,m), 7.48-7.40(2H, m), 7.16(2H,d, J=8.3 Hz), 6.91 (1H, s), 5.30(2H, s), 4.35(1H, d, J=13.3 Hz), 4.22(1H, d, J=13.3 Hz), 3.96(1H, m), 3.40(1H, dd, J=15.7 and 7.0 Hz), 3.36-3.28(1H,m), 2.96(1H, dd, J=11.9 and 3.6 Hz), 2.75(1H, dd, J=11.9 and 9.5 Hz), 1.60-1.35(2H,m), 1.20-1.05(1H,m), 0.95-0.84(6H,m) ppm.

Anal. calc'd for $C_{30}H_{33}N_5O_1$ 0.25H$_2$O: C, 74.43; H, 6.97; N, 14.47.

Found: C, 74.39; H, 6.92; N, 14.34.

FAB HRMS exact mass calc'd for $C_{30}H_{34}N_5O_1$ 480.276336 (MH$^+$), found 480.276866.

EXAMPLE 3

N-Methoxycarbonyl-N-naphth-1-ylmethyl-2(S)-{(1-(4-cyanobenzyl)-1H-imidazol-5-yl)acetyl}amino-3(S)- methyl pentanamine.

To a solution of the product of Example 2 (40 mg, 0.083 mmol) in CH$_2$Cl$_2$ (1 ml) and triethylamine (24 μl, 0.17 mmol) at 0° C. was added methyl chloroformate (39 μl of a 2.1 M solution in CH$_2$Cl$_2$, 0.082 mmol). The reaction was stirred at room temperature for 3 hr, the solvent evaporated in vacuo and the residue purified by preparative HPLC (C-18; 95:5 to 5:95 water:CH$_3$CN containing 0.1% trifluoroacetic acid; gradient elution). Lyophilisation of the collected fractions afforded the title compound as a white solid.

$^1$H NMR(CD$_3$OD, 400 MHz) δ 8.97(1H, m), 8.02-7.76 (5H, m), 7.80-7.20(7H,m), 5.58(2H,s), 5.12(1H,m), 4.20 (1H,m), 3.80-3.45(6H,m), 3.16(1H,m), 1.42(2H,m), 1.08 (1H, m), 0.90-0.80(3H,m), and 0.77(3H, d, J=7.0 Hz) ppm.

FAB Mass spectrum, m/z=538 (M+1).

Anal. calc'd for $C_{32}H_{35}N_5O_3$ 0.25 H$_2$O, 1.85 TFA; C, 56.94; H, 5.00; N, 9.30. Found: C, 56.96; H, 5.02; N, 9.26.

EXAMPLE 4

N-Acetyl-N-naphth-1-ylmethyl-2(S)-{(1-(4-cyanobenzyl)-1H-imidazol-5-yl)acetyl}amino-3(S)- methylpentanamine.

The title compound was prepared using the protocol described in Example 3 using acetyl chloride in place of methylchloroformate.

$^1$H NMR(CD$_3$OD, 400 MHz) δ 8.98(1H, m),8.20-7.76 (6H, m), 7.70-7.20(7H, m), 5.70-5.40(2H, m), 5.09(1H, m), 4.80-4.60(0.5H, m), 4.28(0.5H, m), 4.14(0.5H, m), 3,75(1H, m), 3.65-3.60(1.5H,m), 3.40-3.10(2H,m), 2.22(1.51H, s), 2.02(1.5H, s), 1.45(2H,m), 1.11 (1H, m), 0.87(3H, t, J=7.0 Hz), 0.81(1.5H, d, J=7.0 Hz), 0.75(1.5H, d, J=7.0 Hz) ppm.

FAB Mass spectrum, m/z=522 (M+1).

Anal. calc'd for $C_{32}H_{35}N_5O_2$ 0.05 H$_2$O, 2.35 TFA; C, 55.76; H, 4.78; N, 8.86. Found: C, 55.77; H, 4.78; N, 8.94.

EXAMPLE 5

N-Propionyl-N-naphth-1-ylmethyl-2(S)-{(1-(4-cyanobenzyl)-1H-imidazol-5-yl)acetyl}amino-3(S)- methylpentanamine.

The title compound was prepared using the protocol described in Example 3 using propionyl chloride in place of methylchloroformate.

$^1$H NMR(CD$_3$OD, 400 MHz) δ 8.90(1H, m), 8.20-7.76 (6H, m), 7.70-7.16(7H, m), 5.70-5.40(2H, m), 5.09(1H, m), 4.80-4.60(0.5H, m), 4.27(0.5H, m), 4.14(0.5H, m), 3,82-3.64(1H, m), 3.65-3.60(1.5H,m), 3.42-3.05(1H,m), 2.64-2.20(2H,m), 1.45(2H,m), 1.15(1.5H, t, J=7.2 Hz), 1.20-1.10 (1H,m), 1.03(1.5H, t, J=7.2 Hz), 0.96-0.70((6H,m) ppm.

FAB Mass spectrum, m/z=536 (M+1).

Anal. calc'd for $C_{32}H_{35}N_5O_2$ 0.05H$_2$O, 1.80 TFA; C, 59.26; H, 5.29 N, 9.44. Found: C, 59.26; H, 5.29; N, 9.39.

EXAMPLE 6

N-Methylsulfonyl-N-naphth-1-ylmethyl-2(S)-{(1-(4-cyanobenzyl)-1H-imidazol-5-yl)acetyl}amino-3(S)- methylpentanamine.

The title compound was prepared using the protocol described in Example 3 using methane sulfonyl chloride in place of methylchloroformate.

$^1$H NMR(CD$_3$OD 400 MHz) δ 8.97(1H, m),8.30(1H,m), 7.95-7.90(2H, m), 7.81(2H, d, J=8.2 Hz), 7.60-7.35(8H, m), 5.52(2H, s), 5.02(1H,d, J=14.4 Hz), 4.74(1H,d, J=14.4 Hz), 3.56-3.30(4H, m), 3.18(1H,dd, J=14.6 Hz and 3 Hz), 2.98 (3H,s), 1.26(1H, m), 1.16(1H,m), 0.92(1H,m), 0.69(3H, t, J=7.1 Hz) and 0.61(3H,d, J=7.1 Hz) ppm.

FAB Mass spectrum, m/z=558 (M+1).

Anal. calc'd for $C_{31}H_{35}N_5O_3S$ , 1.90 TFA; C, 53.98; H, 4.80 N, 9.04.

Found: C, 53.96; H, 4.81; N, 9.07.

EXAMPLE 7

N-Ethylsulfonyl-N-naphth-1-ylmethyl-2(S)-{(1-(4-cyanobenzyl)-1H-imidazol-5-yl)acetyl}amino-3(S)- methylpentanamine.

The title compound was prepared using the protocol described in Example 3 using ethane sulfonyl chloride in place of methylchloroformate.

$^1$H NMR(CD$_3$OD 400 MHz) δ 8.97(1H, m),8.27(1H,m), 7.92(2H, m), 7.81(2H, d, J=8.2 Hz), 7.60-7.35(8H, m), 5.55(2H, s), 5.02(1H,d, J=14.4 Hz), 4.76(1H,d, J=14.4 Hz), 3.60-3.35(4H, m), 3.18(1H,dd, J=14.6 Hz and 3 Hz), 3.10 (2H,m), 1.63(3H,t, J=6.5 Hz), 1.30-1.10(2H, m), 0.94(1H, m), 0.71(3H, t, J=7.1 Hz) and 0.61(3H,d, J=7.1 Hz) ppm.

FAB Mass spectrum, m/z=572 (M+1).

Anal. calc'd for $C_{32}H_{37}N_5O_3S$ 0.15 H$_2$O, 1.40 TFA; C, 56.94; H, 5.31 N, 9.54. Found: C, 56.97; H, 5.32; N, 9.54.

EXAMPLE 8

N-Methylaminocarbonyl-N-naphth-1-ylmethyl-2(S)-
{(1-(4-cyanobenzyl)-1H-imidazol-5-yl)
acetyl}amino-3(S)- methylpentanamine.

To a solution of the amine from Example 2 (40 mg, 0.083 mmol) in $CH_2Cl_2$ (1ml) at 0° C. was added methyl isocyanate (20 μl of a 4.24 M solution in $CH_2Cl_2$). The reaction was stirred at room temperature for 2 hr, the solvent evaporated in vacuo and the residue purified by preparative HPLC ( C-18; 95:5 to 5:95 Water:$CH_3CN$ containing 0.1% trifluoroacetic acid; gradient elution). Lyophilisation of the collected fractions afforded the trifluoroacetate salt of the title compound as a white solid.

$^1$H NMR($CD_3OD$ 400 MHz) δ 8.97(1H, m),8.00-7.76 (6H, m), 7.60-7.40(6H,m), 7.28(1H,d, J=7.4 Hz), 5.58(2H, s), 5.05(1H,m), 4.90-4.70(2H,m), 4.30-4.05(1H,m), 3.75-3.45(3H,m), 3.12(1H, dd, J=15.6 and 4.2 Hz), 2.73(3H,s), 1.50-1.35(2H,m), 1.12-1.09(1H,m), 0.90-0.81(3H,m) and 0.78(3H,d, J=6.7 Hz) ppm.

FAB Mass spectrum, m/z=537 (M+1).

Anal. calc'd for $C_{32}H_{36}N_6O_2$ 0.15$H_2O$, 1.60 TFA; C, 58.57 H, 5.29 N, 11.64. Found: C, 58.56; H, 5.28; N, 11.66.

EXAMPLE 9

N-Propyl-N-naphth-1-ylmethyl-2(S)-{(1-(4-cyanobenzyl)-1H-imidazol-5-yl)acetyl}amino-3(S)-methylpentanamine To a slurry of the amine prepared in Example 2 (100.6 mg, 0.21 mmol), crushed 3A molecular sieves (290 mg), and propionaldehyde (15.5 ml, 0.22 mmol) in 1,2 dichloroethane (2 ml) was added sodium triacetoxyborohydride (53.6 mg, 0.253 mmol) at 0° C. The reaction was allowed to warm slowly to RT and stirred for 48 hrs. The reaction was cooled to 0° C. diluted with EtOAc and quenched with sat. aq. $NaHCO_3$ and stirred for 30 min. The organic layer was separated, washed with saturated brine, dried( $MgSO_4$) and purified by preparative HPLC (C-18; 95:5 to 5:95 Water:$CH_3CN$ containing 0.1% trifluoroacetic acid; gradient elution). Lyophilisation of the collected fractions afforded the trifluroacetate salt of the title compound as a white solid. A portion of the product was partitioned between EtOAc and sat aq. $Na_2CO_3$, the organic layer separated and dried ($Na_2SO_4$) and the solvent evaporated in vacuo to afford the corresponding free base as an oil.

$^1$H NMR Free Base ($CD_3OD$ 400 MHz) δ 8.30(1H, d, J=7.5 Hz), 7.83(1H, d, J=7.5 Hz), 7.77(1H, d, J=7.5 Hz), 7.70-7.60(3H,m), 7.50-7.30(4H,m), 7.15(2H, d, J=8.7 Hz), 6.85(1H, s), 5.30(2H,s), 4.02-3.90(3H,m), 3.23(2H,m), 2.56 (1H, dd, J=12.4 and 5.8 Hz), 2.44(2H, t, J=7.4 Hz), 2.36(1H, dd, J=12.4 and 8.9 Hz), 1.56(2H,m), 1.45(1H,m), 1.07(1H, m), 0.90-0.76(1H,m), 0.83(3H,t, J=7.6 Hz), 0.73(3H,d, J=7.6 Hz) and 0.64(3H,t, J=7.6 Hz) ppm.

FAB Mass spectrum, n/z=522 (M+1).

Anal. calc'd for $C_{32}H_{39}N_5O$ 0.15$H_2O$, 2.70 TFA; C, 58.57 H, 5.29 N, 11.64. Found: C, 58.56; H, 5.28; N, 11.66.

EXAMPLE 10

N-3-Chlorobenzyl-N-naphth-1-ylmethyl-2(S)-{(1-(4-cyanobenzyl)-1H-imidazol-5-yl)acetyl}amino-3 (S)- methylpentanamine To a slurry of the amine prepared in Example 2 (45.0 mg, 0.094 mmol), crushed 3A molecular sieves (190 mg), and 3-chlorobenzaldehyde (13 μl, 0.11 mmol) in methanol (2 ml) was added sodium cyanoborohydride (125 μl of a 1 M solution in THF, 0.13 mmol) at room temperature The reaction was stirred at RT for 18 hrs, and 3-chlorobenzaldehyde (26 μl, 0.22 mmol) and sodium cyanoborohydride (200 μl of a 1 M solution in THF, 0.20 mmol) was added. The reaction was stirred an additional 18 hr and then diluted with EtOAc, quenched with sat. aq. $NaHCO_3$ and stirred for 30 min. The organic layer was separated, washed with saturated brine, dried ($Na_2SO_4$) and the solvent evaporated in vacuo. The residue was purified by preparative HPLC (C-18; 95:5 to 5:95 Water: $CH_3CN$ containing 0.1% trifluoroacetic acid; gradient elution). Lyophilisation of the collected fractions afforded the trifluoroacetate salt of the title compound as a white solid. A portion of the product was partitioned between EtOAc and sat aq. $Na_2CO_3$, the organic layer separated, dried ($Na_2SO_4$) and the solvent evaporated in vacuo to afford the corresponding free base as an oil.

$^1$H NMR Free Base ($CD_3OD$ 400 MHz) δ 8.02(1H, d, J=8.3 Hz), 7.81(1H, d, J=8.3 Hz), 7.77(1H, d, J=8.3 Hz), 7.74-7.66(3H,m), 7.46-7.15(10H,m), 6.86(1H, s), 5.37(2H, m), 4.07(1H,m), 3.96 (1H, d, J=13.5 Hz), 3.84 (1H, d, J=13.5 Hz), 3.66 (1H, d, J=13.0 Hz), 3.52 (1H, d, J=13.0 Hz), 3.15(2H,m), 2.56(1H,dd, J=12.6 and 5.7 Hz), 2.37(1H, dd, J=12.6 and 5.7 Hz), 1.39(1H,m), 0.94(1H,m), 0.80(1H, m), 0.72(3H,d, J=7.0 Hz) and 0.61(3H,t, J=7.0 Hz) ppm.

FAB HRMS exact mass calc'd for $C_{37}H_{39}N_5O$ 604.284314 ($MH^+$), found 604.284876

Anal. calc'd for $C_{37}H_{38}N_5OCl$ 0.95$H_2O$, 3.70 TFA; C, 51.12 H, 4.21 N, 6.71. Found: C, 51.12;H,4.18;N, 6.88.

EXAMPLE 11

N-(2-Imidazolylmethyl)-N-naphth-1-ylmethyl-2(S)-
{(1-(4-cyanobenzyl)-1H-imidazol-5-yl)
acetyl}amino-3(S)- methylpentanamine The title compound was prepared using the protocol described in Example 10 using 2-imidazole carboxaldehyde in place of 3-chlorobenzaldehyde.

FAB HRMS exact mass calc'd for $C_{34}H_{38}N_7O$ 560.313784 ($MH^+$), found 560.312362

Anal. calc'd for $C_{37}H_{38}N_5OCl$ 0.35$H_2O$, 3.25 TFA; C, 51.94 H, 4.41 N, 10.47. Found: C, 51.94; H, 4.41; N, 10.80.

EXAMPLE 12

2(RS)-{[1-(Naphth-2-ylmethyl)-1H-imidazol-5-yl)]
acetyl}amino-3-(t-butoxycarbonyl)amino-N-
(naphth-1-ylmethyl)propionamide Step A: Preparation of [1-(Naphth-2-ylmethyl)-1H-imidazol-5-yl)]acetic acid methyl ester A solution of 1-(Triphenylmethyl)-1H-imidazol-4-ylacetic acid methyl ester, the product of Example 1 step B, (4.36 g, 11.4 mmol) and 2-(bromomethyl)naphthalene in $CH_3CN$ (70 ml) was heated at 55° C. for 4 hr. After this time, the reaction was cooled to room temperature and the resulting imidazolium salt (white precipitate) was collected by filtration. The filtrate was concentrated to 30 ml and heated at 55° C. for 18 hr. After this time, the reaction was cooled to room temperature and the resulting white precipitate collected by filtration. The filtrate was concentrated to 10 ml volume and heated at 55° C. for 1 hr. After this time, the reaction was again cooled to room temperature and diluted with ethyl acetate (25 ml). The resulting precipitate was collected by filtration and combined with the previous 2 precipitates in methanol (100 ml) and heated at reflux for 30 min. The solvent was removed in vacuo and the resulting residue was partioned between methylene chloride (200 ml) and sodium bicarbonate (100 ml). The organic layer was evaporated in vacuo and the residue was purified by flash chromatography (SiO$_2$, 0–6% methanol in methylene chloride, gradient elution) to provide the title compound as an off white solid:

$^1$HNMR(CDCl$_3$, 400 MHz) δ 7.82(2H, m), 7.75(1H, m), 7.70(1H, s), 7.49(3H, m), 7.20(1H, d, J=8.4 Hz), 7.06(1H, s), 5.32(2H, s), 3.57(3H, s) and 3.49(2H, s) ppm.

Step B: Preparation of 2-[1-(Naphth-2-ylmethyl)-1H-imidazol-5-yl]acetic acid hydrochloride 2-[1-(Naphth-2-ylmethyl)-1H-imidazol-5-yl]acetic acid methyl ester (0.92 g, 3.28 mmol) was dissolved in 2.5m hydrochloric acid (50 ml) and heated at 55° C. for 3 h. After this time, the solution was evaporated in vacuo to give the title compound as a white solid.

$^1$HNMR(CD$_3$OD, 400 MHz) δ 8.92(1H, s), 7.94(1H, d, J=8.6 Hz), 7.88(2H, m), 7.83(1H, s), 7.54(3H, m), 7.43(1H, d, J=14 Hz), 5.60(2H, s) amd 3.82(2H, s) ppm.

Step C: Preparation of (R,S)-2,3-Diaminopropionic acid methyl ester

A suspension of 2,3-diaminopropionic acid hydrobromide (15.3 g, 82.7 mmol) in methanol (600 ml) was saturated with gaseous hydrogen chloride. The resulting solution was allowed to stand at room temperature for 18 hr. The solvent was evaporated in vacuo to afford the title compound as a pale yellow solid.

$^1$H NMR(d$_6$ DMSO 400 MHz) δ 8.75(6H,s), 4.43(1H, t, J=6.1 Hz), 3.80(3H, s) and 3.34(2H, s) ppm.

Step D: Preparation of 3-(t-Butoxycarbonyl)amino-2-(RS)-aminopropionic acid methyl ester Di-t-butyldicarbonate (16.31 g, 74.7 mmol) in methylene chloride (130 ml) was added dropwise to (RS)-2,3-diamino propionic acid methyl ester (17.42 g, 82.7 mmol) and triethylamine (46 ml, 330 mmol) in methylene chloride (2.61) at −78° C. The reaction was then stirred at 0° C. for 90 min and quenched by addition of 10% aq. KHSO$_4$ (150 ml). The aqueous layer was separated, and the pH adjusted to 10 with sat aq NaHCO$_3$ and 2.5m NaOH. The aqueous solution was extracted with methylene chloride and the combined extracts were dried (Na$_2$SO$_4$), and the solvent evaporated in vacuo. The residue was purified by flash chromatography (SiO$_2$, 2.5%–8% methanol in EtOAc; gradient elution) to afford the title compound as an oil.

$^1$H NMR(CDCl$_3$, 400 MHz) δ 4.98(1H,s), 3.75(3H, s) and 3.58(1H, t), J=6.0 Hz), 3.49(1H, m) and 3.26(1H,m) ppm.

Step E: Preparation of 3-t-Butoxycarbonylamino-2-(RS)-[(Naphth-2-ylmethyl)-1H-imidazol-5-yl] acetylamino-propionic acid methyl ester.

To a solution of 2-[1-(Naphth-2-ylmethyl)-1H-imidazol-5-yl]acetic acid hydrochloride (3.83 g, 12.7 mmol), 3-t-butoxycarbonylamino-2(R,S)- aminopropionic acid methyl ester (3.33 g, 15.3 mmol), HOOBT (2.30 g, 14.1 mmol), and triethylamine (5.80 ml, 42.0 mmol) in DMF (150 ml) at 0° C., was added EDC (2.67 g, 13.9 mmol). The reaction was stirred at room temperature for 18 hrs, diluted with EtOAc and the organic layer washed with sat. aq NaHCO$_3$, brine, dried (Na$_2$SO$_4$), and the solvent evaporated in vacuo. The residue was chromatographed (SiO$_2$, 5% MeOH in CH$_2$Cl$_2$) to afford the title compound as a white solid.

$^1$H NMR(CDCl$_3$, 400 MHz) δ 7.81(1H, d, J=8.5 Hz)), 7.80-7.75(2H, m), 7.60(1H, s), 7.52(1H,s), 7.49(2H,m), 7.24 (1H,d, J=8.5 Hz), 7.06(1H,s), 6.86(1H, br d, J=3 Hz), 5.32(2H,s), 4.74(1H,m), 4.45(1H,m), 3.73(3H,s), 3.52-3.40 (4H,m), and 1.41(9H,s) ppm.

FAB HRMS exact mass calc'd for C$_{25}$H$_{31}$N$_4$O$_5$ 467.229445 (MH$^+$), found 467.229649.

Step F: Preparation of 3-t-Butoxycarbonylamino-2-(RS)-[(Naphth-2-ylmethyl)-1H-imidazol-5-yl] acetylaminopropionic acid.

A solution of the methyl ester prepared in step E (4.80 g, 10.3 mmol) in methanol (100 ml) and 1 M lithium hydroxide (10.4 ml, 10.4 mmol) was stirred at 0° C. for 18 hr. The pH was adjusted to pH 5 by the addition of 1 M HCl and the title compound was collected by filtration and dried in vacuo.

$^1$NMR(CD$_3$OD, 400 MHz) δ 8.15(1H, s), 7.72-7.82(3H, m), 7.70(1H,m), 7.50(2H, m), 7.34(1H,dd, J=8.2 and 1.8 Hz), 7.16(1H,s), 5.49(2H,s), 4.34(1H,m), 3.59(2H,m), 3.48 (1H,dd, J=14.0 and 4.5 Hz), 3.34(1H,m) and 1.40(9H,s) ppm.

FAB Mass spectrum, m/z=453 (M+1).

Step G: Preparation of 2(RS)-{[1-(Naphth-2-ylmethyl)-1H-imidazol-5-yl]acetyl}amino-3-(t-butoxycarbonyl)amino-N-(naphth-1-ylmethyl) propionamide To a solution of the acid prepared in step F (125 mg, 0.276 mmol), 1-naphthylmethylamine (39 μl, 0.28 mmol), HOBT (38.1 mg, 0.28 mmol), and triethylamine (40.0 μl, 0.29 mmol) in DMF (3.0 ml) at 0° C., was added EDC (53.0 mg, 0.28 mmol). The reaction was stirred at room temperature for 4 hrs, diluted with EtOAc and the organic layer washed with sat. aq NaHCO$_3$, brine and dried (Na$_2$SO$_4$). The solvent was evaporated in vacuo to afford the title compound.

$^1$NMR(CDCl$_3$, 400 MHz) δ 7.92(1H,d, J=7.8 Hz), 7.82 (1H,d, J=8.2 Hz), 7.80-7.65(4H,m), 7.60-7.30(9H,m), 7.22 (1H,t, J=5.4 Hz), 7.05(1H,d, J=8.6 Hz), 6.93(1H,s), 5.29 (1H,t, J=5.7 Hz), 5.06(1H,d, J=16.5 Hz), 4.97(1H,d, J=16.5 Hz), 4.83(1H,dd, J=14.8 and 5,8 Hz), 4.76(1H,dd, J=14.8 and 5.3 Hz), 4.38(1H,m), 3.50-3.25(4H,m) and 1.34(9H,s) ppm.

FAB HRMS exact mass calc'd for C$_{35}$H$_{38}$N$_5$O$_4$ 592.292380 (MH$^+$), found 592.293910.

EXAMPLE 13

2(RS)-{[1-(Naphth-2-ylmethyl)-1H-imidazol-5-yl)] acetyl}amino-3-(t-butoxycarbonyl)amino-N-methyl-N-benzyl propionamide The title compound was prepared using the protocol described in Example 12, step G using N-methyl benzylamine in place of 1-naphthylmethylamine.

$^1$NMR(CDCl$_3$ 400 MHz) δ 7.84-7.74(3H,m), 7.62(0.7H, s), 7.58(0.3H,s), 7.52-7.42(3H,m), 7.38-7.26(2H,m), 7.24-7.10(2H,m), 7.07(0.7H,s), 7.01(0.3H,s), 6.67(0.7H,d, J=3.5 Hz), 6.59(0.3H, d, J=3.5 Hz), 5.32(1.4H,s), 5.28(0.6H,s), 5.0-4.85(2H,m) 4.75-4.45(2H,m), 3.52-3.00(4H,m), 2.96 (2.1 H,s), 2.90(0.9H,s),1.42(6.3H, s) and 1.39(2.7H,s) ppm.

FAB Mass spectrum, m/z=556(M+1).

EXAMPLE 14

2(RS)-{[1-(Naphth-2-ylmethyl)-1H-imidazol-5-yl)] acetyl}amino-3-(t-butoxycarbonyl)amino-N-(2-methylbenzyl) propionamide The title compound was prepared using the protocol described in Example 12 step G using 2-methyl benzylamine in place of 1-naphthylmethylamine.

¹NMR(CD₃OD 400 MHz) δ 7.88-7.78(3H,m) 7.76(1H,s), 7.58(1H,s), 7.52-7.45(2H,m), 7.30-7.20(2H,m), 7.17-7.10 (3H,m), 6.95(1H,s), 5.39(2H,m), 4.40(1H,m), 4.40(1H,d, J=15.0 Hz), 4.32(1H,d, J=15.0 Hz), 3.52(2H,s), 3.40-3.20 (2H,m), 2.30(3H,s) and 1.40(9H,s) ppm.

EXAMPLE 15

2(RS)-{[1-(Naphth-2-ylmethyl)-1H-imidazol-5-yl)] acetyl}amino-3-(t-butoxycarbonyl)amino-N-(3-methylbenzyl) propionamide The title compound was prepared using the protocol described in Example 12 step G using 3-methylbenzylamine in place of 1-naphthylmethylamine.

$^1$NMR(CDCl$_3$, 400 MHz) δ 7.85-7.72(3H,m) 7.56(1H,s), 7.52-7.46(2H,m), 7.44(1H,s), 7.28(1H,m), 7.25-7.12(3H, m), 7.12-6.98(3H,m), 6.90(1H,m), 5.26(1H,d, J=16 Hz), 5.18(1H,d, J=16 Hz), 4.30(1H,m), 3.50-3.30(4H,m), 2.37 (3H,s) and 1.42(9H,s) ppm.

FAB Mass spectrum, m/z=556(M+1).

EXAMPLE 16

2(RS)-{[1-(Naphth-2-ylmethyl)-1H-imidazol-5-yl)] acetyl}amino-3-amino-N-(naphth-1-ylmethyl) propionamide hydrochloride.

A solution of the product of Example 12 (174 mg, 0.294 mmol) in CH$_2$Cl$_2$ (10 ml) and trifluoroacetic acid (5 ml) was stirred at room temperature for 3 hrs. The solvent was evaporated in vacuo, methanol (5 ml) was added to the residue and the resulting solution saturated with gaseous HCl. The solvent was evaporated and the title compound was dried in vacuo.

FAB Mass spectrum, m/z=492(M+1).

EXAMPLE 17

2(RS)-{[1-(Naphth-2-ylmethyl)-1H-imidazol-5-yl)] acetyl}amino-3-amino-N-methyl-N-benzyl propionamide hydrochloride The title compound was prepared using the protocol described in Example 16 using the product from Example 13

$^1$NMR(CD$_3$OD 400 MHz) δ 8.83(0.5H,s), 8.73(0.5H,s), 7.96-7.80(3H,m), 7.70(1H,s), 7.60(7.44(3H,m), 7.38-7.12 (6H,m), 5.59(1H,m), 5.38(1H,m), 5.23(0,5H,t, J=5.0 Hz), 5.06(0.5H,t, J=5.0 Hz), 4.74-4.63 (1H,m), 4.50-4.38(1H,m), 3.76(1H,s), 3.60-3.50(0.5H,m), 3.30-3.20(1.5H,m), 3.10-3.00(1H,m), 2.92(1.5H,s), and 2.88(1.5H,s) ppm.

FAB HRMS exact mass calc'd for C$_{27}$H$_{30}$N$_5$O$_2$ 456.239951 (MH$^+$), found 456.239252.

EXAMPLE 18

2(RS)-{[1-(Naphth-2-ylmethyl)-1H-imidazol-5-yl)] acetyl}amino-3-amino-N-(2-methylbenzyl) propionamide hydrochloride The title compound was prepared using the protocol described in the Example 16 using the product of Example 14.

FAB Mass spectrum, m/z=456 (M+1).

EXAMPLE 19

2(RS)-{[1-(Naphth-2-ylmethyl)-1H-imidazol-5-yl)] acetyl}amino-3-amino-N-(3-methylbenzyl) propionamide hydrochloride The title compound was prepared using the protocol described in the Example 16 using the product of Example 15.

FAB Mass spectrum, m/z=456 (M+1).

EXAMPLE 20

2(RS)-{[1-(Naphth-2-ylmethyl)-1H-imidazol-5-yl)] acetyl}amino-3-acetylamino-N-(3-methylbenzyl) propionamide To a solution of the amine from Example 19 (6.48 mg, 0.0116 mmol), and triethylamine (8.53μl, 0.0612 mmol) in CHCl$_3$ (0.165 ml) at 0° C., was added acetyl chloride (116 μl of a 0.1 M solution in CHCl$_3$, 0.0116 mmol). The reaction was vortexed at room temperature, and allowed to stand at room temperature for 18 hrs. The solvent evaporated in vacuo and the residue was purified by preparative HPLC (C-18; 95:5 to 5:95 Water:CH$_3$CN containing 0.1% trifluoroacetic acid; gradient elution), to afford the title compound after lyophilisation.

FAB Mass spectrum, m/z=(M+1).

EXAMPLE 21

2(RS)-{[1-(Naphth-2-ylmethyl)-1H-imidazol-5-yl)] acetyl}amino-3-acetylamino-N-(naphth-1-ylmethyl) propionamide The title compound was prepared using the protocol described in the Example 20 using the amine from Example 16 and acetyl chloride.

$^1$NMR(CDCl$_3$ 400 MHz) δ 8.37(1H,s), 8.15(1H,m), 7.94 (1H,d, J=8 Hz), 7.90-7.70(5H,m), 7.60-7.45(4H, m), 7.40-7.35(2H,m), 7.35-7.25(2H,m), 7.20(1H, s), 7.12(1H,d, J=8.0 Hz), 6.50(1H,m), 5.26(1H,d, J=15 Hz), 5.14(1H,d, J=15 Hz), 4.92(1H,m), 4.79(1H,dd, J=15.0 and 5.0 Hz), 4.37(1H, m), 3.70-3.40(4H,m), and 1.85(3H,s) ppm.

FAB Mass spectrum, m/z=534(M+1).

EXAMPLE 22

2(RS)- [1-(Naphth-2-ylmethyl)-1H-imidazol-5-yl)] acetyl}amino-3-(2-methylpropionyl)amino-N-(naphth-1-ylmethyl)propionamide The title compound was prepared using the protocol described in Example 20 using the amine from Example 16 and 2-methylpropionyl chloride instead of acetyl chloride.

$^1$NMR(CD$_3$OD 400 MHz) δ 8.89(1H,s), 8.60(1H,m), 8.03(1H,d, J=8.4 Hz), 8.00-7.70(6H,m), 7.60-7.46(5H,m), 7.41(1H,dd, J=7.5 and 7.0 Hz), 7.36(1H,dd, J=8.9 and 1.5 Hz), 5.53(2H,m), 5.0-4.70(2H,m), 4.40(1H, t, J=6.0 Hz), 3.71(2H,s), 3.43(2H,m), 2.31(1H, sept, J=6.8 Hz), 1.01(3H, d,J=6.8 Hz), and 0.99(3H,d, J=6.8 Hz) ppm.

FAB HRMS exact mass calc'd for C$_{34}$H$_{36}$N$_5$O$_3$ 4562.281815 (MH$^+$), found 562.281831.

EXAMPLE 23

2(RS)- [1-(Naphth-2-ylmethyl)-1H-imidazol-5-yl)] acetyl}amino-3-(phenylacetyl)amino-N-(naphth-1-ylmethyl)propionamide The title compound was prepared using the protocol described in Example 20 using the amine from Example 16 and phenylacetyl chloride instead of acetyl chloride.

$^1$NMR(CDCl$_3$ 400 MHz) δ 8.32(1H,s), 8.15(1H,d, J=5.7 Hz), 7.92(1H,m), 7.86-7.70(5H,m), 7.60-7.44(5H,m), 7.38 (2H,m), 7.30-7.20(4H,m), 7.13(2H.d, J=6.8 Hz), 7.08(2H, m), 6.58(1H,m), 5.17(1H,d, J=15,4 Hz), 5.07(1H,d, J=15.4 Hz), 4.84(1H,dd, J=15.0 and 5.5 Hz), 4.75(1H,dd, J=15.0 and 5.5 Hz), 4.40(1H,m), 3.60(1H,m), 3.47(1H,m) and 3.45-3.20(4H,m) ppm.

FAB Mass spectrum, m/z=610(M+1).

EXAMPLE 24

2(RS)-{[1-(Naphth-2-ylmethyl)-1H-imidazol-5-yl)]acetyl}amino-3-(phenylacetyl)amino-N-methyl-N-benzyl) propionamide The title compound was prepared using the protocol described in Example 20 using the amine from Example 17 and phenylacetyl chloride instead of acetyl chloride.

$^1$H NMR(CDCl$_3$, 400mHz) δ 8.85(0.5H,s), 8.74(0.5H,s), 8.00-7.80(1H,m), 7.74(1H,s), 7.60-7.45(1H,m), 7.40-7.10 (10 H,m), 5.60(2H,m), 5.40(2H,m), 5.25(0,5H,t, J=5 Hz), 5.10(0.5H,t, J=5.0 Hz), 4.70(1H,dd, J=15 and 5.5 Hz), 4.45(1H,dd, J=15.0 and 7.5 Hz), 3.78(2H,m), 3.30(1H,m), 3.08(1H,m), 2.94(1.5H,s) and 2.88(1.5H,s) ppm.

FAB HRMS exact mass calc'd for $C_{35}H_{36}N_5O_3$ 3574.281815 (MH$^+$), found 574.281831.

EXAMPLE 25

[1-(Naphth-2-ylmethyl)-1H-imidazol-5-yl)]-N-butylacetamide

To a solution of 2-[1-(Naphth-2-ylmethyl)-1H-imidazol-5-yl]acetic acid hydrochloride (89 mg, 0.294 mmol), n-butylamine (30 μl, 0.30 mmol), HOOBT (57 mg, 0.35 mmol), and triethylamine (140 ml, 42.0 mmol) in DMF (4 ml) at 0° C., was added EDC (2.67 g, 13.9 mmol). The reaction was stirred at room temperature for 18 hrs, diluted with EtOAc and the organic layer washed with sat. aq NaHCO$_3$, brine, dried (Na$_2$SO$_4$) and the solvent evaporated in vacuo to afford the title compound as a clear oil.

$^1$H NMR(CDCl$_3$, 400 MHz) δ 7.86-7.74(3H, m),7.65(1H, m), 7.55-7.45(3H, m), 7.22(1H,dd, J=8.6 and 2.0 Hz), 7.04 (1H,s), 5.30(1H,m), 5.25(2H,s), 3.46(2H,s), 2.95(1H,q, J=8 Hz), 1.30-1.10(4H,m) and 0.83(3H,t, J=7.5 Hz) ppm.

FAB HRMS exact mass calc'd for $C_{20}H_{24}N_3O$ 322.191938 (MH$^+$), found 322.191669.

EXAMPLE 26

[1-(Naphth-2-ylmethyl)-1H-imidazol-5-yl)]-N-methyl-N-(3,3-diphenylpropyl)acetamide Step A: Preparation of N-Benzyl-N-3,3-diphenylpropyl amine To a solution of 3,3-diphenylpropylamine (1.01 g, 4.79 mmol), acetic acid (28 ml, 049 mmol), and benzaldehyde (490 μl, 4.80 mmol) in CH$_3$CN (2 ml) was added sodium cyanoborohydride (4.80 ml of a 1 M solution in THF, 4.8 mmol) at 0° C. The reaction was allowed to warm to room temperature and stirred for 18 hrs. The solvent was evaporated in vacuo, quenched with sat. aq. NaHCO$_3$ and extracted with EtOAc. The organic layer was washed with brine, dried (Na$_2$SO$_4$) and the solvent evaporated in vacuo. The residue was dissolved in MeOH (100 ml) and sodium borohydride (182 mg, 5.55 mmol) added and the reaction was stirred for 30 min. The solvent was evaporated and the residue treated with sat. aq. NaHCO$_3$ and extracted with EtOAc. The organic layer was separated, washed with saturated brine, dried (Na$_2$SO$_4$) and the solvent evaporated in vacuo to afford the title compound as an oil.

$^1$H NMR(CDCl$_3$, 400 MHz) δ 7.40-7.00 (15H, m), 4.04 (1H,t, J=7.5 Hz), 3.62(2H,s), 2.62(2H,t, J=7.0 Hz) 2.26(2H, q, J=7.5 Hz) ppm.

Step B: Preparation of N-Benzyl-N-methyl-3,3-diphenylpropylamine

To a solution of N-benzyl-3,3-diphenylpropylamine (1.29 g, 4.30 mmol) and 30% aq. formaldehyde (1.50 ml, 20 mmol) in CH$_3$CN:H$_2$O (2:1, v/v, 40 ml) was added sodium cyanoborohydride (563 mg, 8.96 mmol) at 0° C. The reaction was allowed to warm to room temperature and stirred for 90 min. The organic solvent was evaporated, and the residue diluted with water and extracted with CH$_2$Cl$_2$. The organic extracts were washed with brine, dried (Na$_2$SO$_4$) and the solvent evaporated in vacuo to afford the title compound as an oil.

$^1$H NMR(CDCl$_3$, 400 MHz) δ 7.40-7.00 (15H, m), 4.05 (1H,t, J=7.5 Hz), 3.44(2H,s), 2.38-2.22(4H,m) and 2.16(3H, s) ppm.

Step C: Preparation of N-Methyl-3,3-diphenylpropylamine

A solution of N-benzyl-N-methyl-3,3-diphenylpropylamine (1.03 g, 3.27 mmol) in methanol (35 ml) and aq. HCl (0.27 ml, of a 12.1M aq. solution, 3.3 mmol) was purged with argon and palladium hydroxide (405 mg) added. The flask was evacuated and shaken under an atmosphere of hydrogen (50 psi) for 18 hrs. The hydrogen was replaced by argon and the catalyst removed by filtration. The filtrate was treated with aq. NaOH (100 ml of a 1 M solution) and extracted into Et$_2$O. The organic extracts were dried (Na$_2$SO$_4$) and evaporated in vacuo to afford the title compound as an oil.

$^1$H NMR(CDCl$_3$, 400 MHz) δ 7.32-7.14 (10H, m), 4.05 (1H,t, J=7.5 Hz), 2.54(2H, t, J=7.1 Hz), 2.38(3H,s) and 2.24(2H,m) ppm.

FAB Mass spectrum, m/z=226 (M+1).

Step D: Preparation of [1-(Naphth-2-ylmethyl)-1H-imidazol-5-yl)]-N-methyl-N-3,3-diphenylpropyl acetamide To a solution of 2-[1-(Naphth-2-ylmethyl)-1H-imidazol-5-yl]acetic acid hydrochloride (160.8 mg, 0.531 mmol), N-methyl-3,3-diphenylpropylamine (104 mg, 0.462 mmol) HOOBT (81 mg, 0.50 mmol), and triethylamine (215 ml, 1.54 mmol) in DMF (5 ml) at 0° C., was added EDC (94.3 mg, 0.50 mmol). The reaction was stirred at room temperature for 18 hrs, diluted with EtOAc and the organic layer washed with sat. aq NaHCO$_3$, brine, dried (Na$_2$SO$_4$) and the solvent evaporated in vacuo. The residue was purified by preparative HPLC ( C-18; 95:5 to 5:95 water: CH$_3$CN containing 0.1% trifluoroacetic acid; gradient elution), to afford the title compound after lyophilisation.

$^1$H NMR(CDCl$_3$, 400 MHz) δ 8.45(1H, d, J=11.4 Hz), 7.90-7.82(2H, m), 7.82-7.74(1H,m), 7.64-7.50(3H,m), 7.32-7.16(9.5H,m), 7.09(2H,d, J=7.8 Hz), 6.98(0.5H,s),5.45(1H, s), 5.40(1H,s), 3.90(0.5H,d, J=7.5 Hz), 3.75(0.5H,d, J=7.5 Hz), 3.40(1H,s), 3.37(1H,m), 3.22(1H,dd, J=5.6 and 4.6 Hz), 3.12(1H,s), 2.93(1.5H,s), 2.77(1.5H,s), 2.30(1H,m), and 2.20(1H,m) ppm.

FAB HRMS exact mass calc'd for $C_{32}H_{32}N_3O$ 474.253538 (MH$^+$), found 474.255055.

EXAMPLE 27

2(RS)-{[1-(4-Cyanobenzyl)-1H-imidazol-5-yl]acetyl}amino-3-(t-butoxycarbonyl)amino-N-methyl-N-benzyl propionamide Step A: Preparation of 3-t-Butoxycarbonylamino-2-(RS)-[1-(4-cyanobenzyl)-1H-imidazol-5-yl]acetylamino-propionic acid methyl ester To a solution of [1-(4-cyanobenzyl)-1H-imidazol-5-yl] acetic acid (607 mg, 1.64 mmol), 3-t-Butoxycarbonylamino- 2(RS)-aminopropionic acid methyl ester (352 mg, 1.61 mmol), HOOBT (319 mg, 1.96 mmol), and triethylamine (0.54 ml, 3.87 mmol) in DMF (13 ml) at 0° C., was added EDC (2.67 g, 13.9 mmol). The reaction was stirred at room temperature for 18 hrs, diluted with EtOAc and the organic layer washed with sat. aq NaHCO₃, brine, dried (Na₂SO₄). and the solvent evaporated in vacuo to afford the title compound as a white solid.

¹H NMR(CDCl₃, 400 MHz) δ 7.65(2H, d, J=8.5 Hz), 7.55((1H, s), 7.21(1H, d, J=8.5 Hz), 7.07(1H,s), 5.28(2H,m), 4.78(1H, m), 4.49(1H,m), 3.78(3H,s), 3.60-3.44(3H,m), 3.44(1H,d,J=16.0 Hz), 3.36(1H,d,J=16.0 Hz) and 1.43(9H,s) ppm.

Step B: Preparation of 3-t-Butoxycarbonylamino-2-(RS)-[1-(4-cyanobenzyl)-1H-imidazol-5-yl] acetylamino-propionic acid A solution of the methyl ester from Step A (604 mg, 1.37 mmol) in methanol (14 ml) and 1 M lithium hydroxide (1.40 ml, 1.40 mmol) was stirred at 0° C. for 18 hr. The reaction was quenched by the addition of 1 M HCl (1.40 ml) and the solvent was evaporated in vacuo to afford the title compound and lithium chloride which was used as is.

¹H NMR(CD₃OD 400 MHz) δ 8.03(1H, s), 7.74(2H,d, J=8.4 Hz), 7.35(2H,d, J=8.4 Hz), 7.11(1H,s), 5.41(2H,s), 4.34(1H,m), 3.60-3.45(3H,m), 3.36(1H,m) and 1.41(9H,s) ppm FAB HRMS exact mass calc'd for C₂₁H₂₅N₅O₅ 428.193394 (MH⁺), found 428.193423.

Step C: Preparation of 2(RS)-{[1-(4-Cyanobenzyl)-1H-imidazol-5-yl]acetyl}amino-3-(t-butoxycarbonyl)amino-N-methyl-N-benzyl propionamide To a solution of the acid from Step B (163.5 mg, 0.348 mmol), N-methylbenzylamine (45 μl, 0.29 mmol), HOOBT (58.4 mg, 0.358 mmol), and triethylamine (100.0 μl, 0.29 mmol) in DMF (3.6 ml) at 0° C., was added EDC (55.4 mg, 0.289 mmol). The reaction was stirred at room temperature for 4 hrs, diluted with EtOAc and the organic layer washed with sat. aq NaHCO₃, brine, dried (Na₂SO₄), and the solvent evaporated in vacuo. The residue was chromatographed (SiO₂, 5%–7.5% MeOH in CH₂Cl₂; gradient elution) to afford the title compound as a white solid.

¹H NMR(CD₃OD 400 MHz) δ 8.10-7.70(3H, m), 7.40-7.20(7H, m), 6.97(0.66H,s), 6.91(0.33H,s), 5.42-5.28(2H, m), 5.08(0.33H, m), 4.86(0.66H,m), 4.76-4.42(2H, m), 3.55-3.20(4H,m), 3.08(2H,s), 2.84(1H,s), 1.42(6H,s) and 1.40 (3H, s) ppm.

FAB HRMS exact mass calc'd for C₂₉H₃₄N₆O₄ 531.271979(MH⁺), found 531.270872.

EXAMPLE 28

2(RS)-{[1-(4-Cyanobenzyl)-1H-imidazol-5-yl] acetyl}amino-3-(t-butoxycarbonyl)amino-N-(3-methylbenzyl) propionamide The title compound was prepared using the protocol described in the Example 27 step C using 3-methylbenzylamine in place of N-methylbenzylamine.

¹H NMR(CD₃OD, 400 MHz) δ 7.75(1H, s), 7.68(2H,d, J=8.4 Hz), 7.26(2H,d, J=8.4 Hz), 7.19(1H,t, J=7.7 Hz), 7.12(1H, s), 7.07(2H,t, J=6.0 Hz), 6.95(1H,s), 5.33(2H,m), 4.87(1H,m), 4.38(3H,m), 4.31(1H,d, J=15.2 Hz), 3.47(2H, s), 2.32(3H,s) and 1.42(9H,s) ppm.

FAB HRMS exact mass calc'd for C₂₉H₃₄N₆O₄ 531.271979 (MH⁺), found 531.271895.

EXAMPLE 29

2(RS)-{[1-(4-Cyanobenzyl)-1H-imidazol-5-yl] acetyl}amino-3-(t-butoxycarbonyl) amino-N-(naphth-1-ylmethyl) propionamide The title compound was prepared using the protocol described in Example 27 step C using 1-naphthylmethylamine in place of N-methylbenzylamine.

¹H NMR(CD₃OD, 400 MHz) δ 8.04(1H, d, J=8.5 Hz), 7.89(1H, d, J=7.0 Hz), 7.81(1H,d, J=8.0 Hz), 7.72(1H,s), 7.68(2H, d, J=7.4 Hz), 7.58-7.38 (4H, m), 7.23(2H, d, J=7.4 Hz), 7.07(2H,t, J=6.0 Hz), 6.95(1H,s), 5.28(2H,m), 4.87(2H, m), 4.40(1H, m), 3.47(2H,s), 3.40-3.20(2H,m) and 1.42(9H, s) ppm.

FAB HRMS exact mass calc'd for C₂₉H₃₅N₆O₄ 567.271979 (MH⁺), found 567.269604.

EXAMPLE 30

2(RS)-{[1-(4-Cyanobenzyl)-1H-imidazol-5-yl] acetyl}amino-3-amino-N-methyl-N-benzyl-propionamide A solution of the product from Example 27 (86.3 mg, 0.163 mmol) in EtOAc (5 ml) at 0° C. was saturated with gaseous HCl and stirred for 15 min. The solvent was evaporated and the title compound was dried in vacuo.

¹H NMR(d6 DMSO, 400 MHz) δ 9.20-9.00(2H,m), 8.20 (3H,s), 7.88(1H,d,J=7.5 Hz), 7.65-7.10(6H,m), 5.60-5.40 (2H,m), 5.15-5.00(1H,s), 4.70-4.40(2H, m), 3.80-3.00(4H, m), 2.94(2H,s) and 2.78(1H,s) ppm.

FAB HRMS exact mass calc'd for C₂₄H₂₇N₆O₄ 431.219549 (MH⁺), found 431.218412.

EXAMPLE 31

2(RS)-{[1-(4-Cyanobenzyl)-1H-imidazol-5-yl] acetyl}amino-3-amino-N-(3-methylbenzyl) propionamide The title compound was prepared using the protocol described in Example 30 using the product from Example 28.

¹H NMR(d₆ DMSO, 400 MHz) δ 9.12(1H,m), 8.86(1H, d,J=7.6 Hz), 8.73(1H,t, J=5.7 Hz), 8.20(3H,m), 7.87(2H,d, J=8.7 Hz), 7.60(1H,s), 7.47(2H,d, J=8.7 Hz),7.19(1H,t, J=7.2 Hz), 7.10-7.00(3H,m), 5.53(2H,m), 4.56(1H,m), 4.27 (2H,m), 3.73(2H,s), 3.23(1H,m), 2.90(1H,m) and 2.26(3H,s) ppm.

FAB HRMS exact mass calc'd for C₂₄H₂₇N₆O₂ 431.219549 (MH⁺), found 431.219835.

EXAMPLE 32

2(RS)-{[1-(4-Cyanobenzyl)-1H-imidazol-5-yl] acetyl}amino-3-amino-N-(naphth-1-ylmethyl) propionamide The title compound was prepared using the protocol described in Example 30 using the product from Example 29.

¹H NMR(d₆ DMSO, 400 MHz) δ 9.12(1H,m), 8.92(1H, d,J=7.6 Hz), 8.81(1H,t, J=5.7 Hz), 8.22(3H,m), 8.04(1H,m), 7.92(1H,m), 7.88-7.80(3H, m), 7.58(1H,s), 7.52(2H,m), 7.48-7.38(4H,m), 5.51(2H,m), 4.74(2H,m), 4.57(1H,m), 3.73(2H,s), 3.20(1H,m) and 3.01(1H,m)ppm.

FAB HRMS exact mass calc'd for $C_{27}H_{27}N_6O_2$ 467.219549 MH$^+$), found 467.219920.

EXAMPLE 33

2(RS)-{[1-(4-Cyanobenzyl)-1H-imidazol-5-yl]acetyl}amino-3-(phenylacetyl)amino-N-methyl-N-benzyl) propionamide To a solution of the product from Example 30 (42.5 mg, 84.4 mmol), and triethylamine (58 μl, 420 mmol) in CHCl$_3$ (0.85 ml) at 0° C., was added phenylacetyl chloride (11.2 μl 84.4 mmol). The reaction was vortexed and allowed to stand at room temperature for 18 hrs. The reaction was diluted with EtOAc and the organic layer washed with sat. aq NaHCO$_3$, brine and dried (Na$_2$SO$_4$). The solvent evaporated in vacuo and the residue was purified by preparative HPLC (C-18; 95:5 to 5:95 Water:CH$_3$CN containing 0.1% trifluoroacetic acid; gradient elution), to afford the title compound as a white solid.

$^1$H NMR(CD$_3$OD, 400 MHz) δ 8.95(0.67H,d, J=1.7 Hz,), 8.92(0.33H, d, J=1.7 Hz), 7.76(0.67H, d, J=8.7 Hz), 7.75 (1.33H, d, J=8.7 Hz), 7.51(0.67H, s), 7.44(2H,d, J=8.7 Hz), 7.38-7.20(10.33H,m), 5.55-5.37(2H,m), 5,12(0.33H, dd, J=4.0 and 3.0 Hz),4.98(0.67H, dd, J=4.0 and 3.0 Hz), 4.94-4.66(1H,m), 4.76(0.67H, dd, J=10.4 Hz), 4.28(0.33H, d, J=10.4 Hz), 3.64-3.36(5H,m), 2.98(2H,s), and 2.83(1H,s) ppm.

FAB HRMS exact mass calc'd for $C_{32}H_{33}N_6O_3$ 549.261414 (MH$^+$), found 549.262581.

EXAMPLE 34

2(RS)-{[1-(4-Cyanobenzyl)-1H-imidazol-5-yl]acetyl}amino-3-(acetyl)amino-N-(naphth-1-yl methyl)propionamide To a solution of the product from Example 32 (37.3 mg, 69.1 mmol), and triethylamine (52 μl, 345 mmol) in CHCl$_3$ (0.85 ml) and DMF (0.5 ml) at 0° C., was added acetyl chloride (5.0 μl 69.1 mmol). The reaction was vortexed and allowed to stand at room temperature for 18 hrs. The reaction was diluted with EtOAc and the organic layer washed with sat. aq NaHCO$_3$, brine and dried (Na$_2$SO$_4$). The solvent evaporated in vacuo and the residue was purified by preparative HPLC (C-18; 95:5 to 5:95 Water:CH$_3$CN containing 0.1% trifluoroacetic acid; gradient elution), to afford the title compound as a white solid.

$^1$H NMR(CD$_3$OD, 400 MHz) δ 8.95(1H,d, J=1.0 Hz,), 8.06 (1H, d, J=6.6 Hz), 7.89(1H, d, J=7.0 Hz), 7.89(1H, d, J=7.0 Hz), 7.82(1H, d, J=8.4 Hz), 7.54(2H,d, J=8.4 Hz), 7.60-7.48(5H,m), 7.43(2H,t, J=7.9 Hz), 5.58(2H,m), 4.98-4.70(2H,m), 4.43(1H,dd, J=6.4 and 5.1 Hz), 3.72(1H,d, J=16.0 Hz), 3.65(1H, d, J=16.0 Hz), 3.54(1H, dd, J=13.6 and 4.5 Hz), 3.42(1H, dd, J=13.6 and 6.4 Hz) and 1.86(3H,s) ppm.

FAB HRMS exact mass calc'd for $C_{29}H_{29}N_6O_3$ 509.230114 (MH$^+$), found 509.229190.

EXAMPLE 35

2(RS)-{[1-(4-Cyanobenzyl)-1H-imidazol-5-yl]acetyl}amino-3-(2-methylpropionyl)amino-N-(naphth-1-ylmethyl) propionamide The title compound was prepared using the protocol described in Example 34 using isobutyryl chloride in place of acetyl chloride.

$^1$H NMR(CD$_3$OD, 400 MHz) δ 8.96(1H,d, J=1.0 Hz,), 8.06 (1H, d, J=8.6 Hz), 7.99(1H, d, J=8.6 Hz), 7.82(1H, d, J=7.9 Hz), 7.74(2H, d, J=8.6 Hz), 7.58-7.48(5H,m), 7.43 (2H,t, J=7.9 Hz), 5.52(1H,d, J=15.2 Hz), 5.47(1H,d, J=15.2 Hz), 4.98-4.70(2H,m), 4.44(1H,dd, J=5.8 and 5.0 Hz), 3.70 (1H,d, J=13.9 Hz), 3.66(1H, d, J=13.9 Hz), 3.50(1H, dd, J=13.6 and 3.0 Hz), 3.42(1H, dd, J=13.6 and 6.4 Hz), 2.34(1H,sept, J=6.8 Hz), 1.04(3H,d, J=6.8 Hz) and 1.02(3H, d, J=6.8 Hz) ppm.

FAB HRMS exact mass calc'd for $C_{31}H_{33}N_6O_3$ 537.261414 (MH$^+$), found 537.262247.

EXAMPLE 36

2(RS)-{[1-(4-Cyanobenzyl)-1H-imidazol-5-yl]acetyl}amino -3-(2-methylpropionyl)amino-N-(naphth-1-ylmethyl) propionamide The title compound was prepared using the protocol described in Example 34 using phenylacetyl chloride in place of acetyl chloride.

$^1$H NMR(CD$_3$OD, 400 MHz) δ 8.72(1H,s), 7.94 (1H, d, J=7.4 Hz), 7.79(1H, d, J=7.6 Hz), 7.72(1H, d, J=8.4 Hz), 7.62(2H, d, J=8.3 Hz), 7.48-7.22(7H,m), 7.22-7.08(5H,m), 5.34(1H,d, J=15.7 Hz), 5.28(1H,d, J=15.7 Hz), 4.90-4.60 (2H,m), 4.38(1H,dd, J=5.0 and 4.2 Hz), 3.46(2H,s), 3.40 (2H, m) and 3.34(2H,s) ppm.

FAB HRMS exact mass calc'd for $C_{35}H_{33}N_6O_3$ 585.261414 (MH$^+$), found 585.260592.

EXAMPLE 37

N-[2(S)-([1-(4-Cyanobenzyl)-1H-imidazol-5-yl]acetylamino)-3(S)-methylpentyl]-N-(1-naphthylmethyl)glycine isopropylamide

Step A: Preparation of N-(2(S)-(t-Butoxycarbonylamino)-3(S)-methylpentyl)glycine methyl ester.

Glycine methyl ester hydrochloride (4.41 g, 0.035 mol) was dissolved in 1,2-dichloroethane (50 mL) and DMF (5 mL) and treated with 3A molecular sieves (10 g) and N-t-butoxycarbonyl-isoleucinal (6.3 g, 0.029 mol) with stirring at 0° C. Sodium triacetoxyborohydride (9.27 g, 0.044 mol) was added, and the pH of the mixture was adjusted to 6 with triethylamine (3 ml, 0.022 mol). After stirring for 18 h the mixture was filtered, concentrated and partitioned between EtOAc and water. The aqueous layer was extracted with EtOAc (2×50 mL). The combined organic extracts were washed with aqueous saturated NaHCO$_3$ solution, brine, and dried (Na$_2$SO$_4$). Filtration and evaporation in vacuo afforded a residue which was purified by flash chromatography (SiO$_2$, EtOAc:hexane, 1:3) to give the title compound as an oil.

$^1$H NMR (CDCl$_3$ 400MHz) δ 4.69 (1H, m), 3.72 (3H, s), 3.48–3.62 (1H, m), 3.42 (2H, m), 2.65 (2H, d, J=6 Hz), 1.4–1.6 (2H, m), 1.48 (9H, s), 1.04–1.2 (1H, m), 0.85–0.95 (6H, m)ppm.

Step B: Preparation of N-[2(S)-(t-Butoxycarbonylamino)-3(S)-methylpentyl]-N-(1-naphthylmethyl)glycine methyl ester N-[2(S)-(t-Butoxycarbonylamino)-3(S)-methylpentyl] glycine methyl ester (2.00 g, 6.97 mmol) was dissolved in 1,2-dichloroethane (56 ml) and 3A molecular sieves were added followed by 1-naphthaldehyde (1.89 ml, 13.9 mmol)

and sodium triacetoxyborohydride (6.65 g, 31.4 mmol). The mixture was stirred at ambient temperature for 16 h, filtered and evaporated in vacuo. The residue was partitioned between EtOAc (100 ml) and sat. aq. NaHCO$_3$ (25 ml). The aqueous layer was extracted with EtOAc (3×50 ml). The organic extracts were combined, dried (Na$_2$SO$_4$), filtered, and evaporated in vacuo to afford a residue which was purified by chromatography (SiO$_2$, 15–33% ethyl acetate in hexanes) to afford the title compound as an oil.

$^1$H NMR (CD$_3$OD, 400MHz) δ 8.44-8.38 (1H, d, J=6 Hz), 7.88-7.77 (2H, m,), 7.55-7.35 (4H, m), 6.34-6.27 (1H, m), 4.25 (2H, m), 3.66 (3H, s), 3.40-3.23 (1H, m), 2.95-2.85 (1H, dd, J=6 and 15 Hz), 2.68-2.57 (1H, dd, J=6 and 15 Hz), 1.57-1.46 (1H, m), 1.43 (9H, s), 1.34-1.18 (2H, m), 1.06-0.85 (1H, m) and 0.85-0.71 (6H, m)ppm.

Step C: Preparation of N-[2(S)-(Amino)-3(S)-methylpentyl]-N-(1-naphthylmethyl)glycine methyl ester hydrochloride A solution of N-[2(S)-(t-Butoxycarbonylamino)-3(S)-methylpentyl]-N-(1-naphthylmethyl) glycine methyl ester (5.90 g, 13.8 mmol) in EtOAc (100 ml) was saturated with gaseous hydrogen chloride. The resulting solution was allowed to stand at room temperature for 1 hr. The solvent was evaporated in vacuo to afford the title compound as a white solid.

$^1$H NMR(CD$_3$OD 400 MHz) δ 8.26(1H, d, J=8.6 Hz), 7.92(1H, d, J=7.2 Hz), 7.87(1H, d, J=8.6 Hz), 7.63-7.42(4H, m), 4.34(1H,d, J=12.3 Hz), 4.26(1H,d, J=12.3 Hz), 3.68(3H, s), 3.13(1H, d, J=10.3 Hz), 2.67-2.55(2H,m), 1.46(1H,m), 1.28(2H,m), 1.10-0.90(2H,m), 0.84(3H,d,J=6.8 Hz) and 0.77(3H,t, J=6.8 Hz)ppm.

Step D: Preparation of N-[2(S)-([1-(4-Cyanobenzyl)-1H-imidazol-5- yl]acetylamino)-3(S)-methylpentyl]-N-(1-naphthylmethyl) glycine methyl ester To a solution of 2-[1-(4-cyanobenzyl)-1H-imidazol-5-yl] acetic acid (220 mg,0.533 mmol) and the amine hydrochloride salt from step C (212 mg,0.533 mmol), HOBT (72 mg, 0.533 mmol), and N-methylmorpholine (117 μl, 1.11 mmol) in DMF (2 ml) was added EDC (764 mg, 3.99 mmol). The reaction was stirred at room temperature for 72 hrs, diluted with EtOAc and the organic layer washed with sat. aq NaHCO$_3$, brine, dried (Na$_2$SO$_4$). and evaporated in vacuo. The residue was chromatographed (SiO$_2$, 3–4% MeOH in CH$_2$Cl$_2$, gradient elution) to afford the title compound as a white solid.

$^1$H NMR(CD$_3$OD, 400 MHz) δ 8.30(1H,d, J=8.4 Hz), 7.84(1H,d, J=8.0 Hz), 7.80(1H,t, J=4.5 Hz), 7.68-7.38(3H, m), 7.48-7.32(4H,m), 7.10(2H,d, J=8.0 Hz), 6.87(1H,s), 5.24(1H,d, J=16.7 Hz), 5.18(1H,d,J=16.7 Hz), 4.83(2H,s), 4.27(1H,d, J=12.8 Hz), 4.10(1H,d, J=12.8 Hz), 3.97(1H,m), 3.65(3H,s), 3.40-3.20(2H,m), 2.92(1H,dd, J=13.3 and 4.3 Hz), 2.60(1H,dd, J=13.3 and 10.0 Hz), 1.48(1H,m), 1.25 (1H,m), 0.98(1H,m), 0.78(3H,d, J=6.8 Hz) and 0.77(3H,t, J=7.5 Hz) ppm.

Anal. calc'd for C$_{33}$H$_{37}$N$_5$O$_3$ 1.05H$_2$O, 2.85 TFA C, 51.90; H, 4.72; N, 7.82. Found: C, 51.90; H, 4.70; N, 8.18.

FAB Mass spectrum, m/z=552 (M+1).

Step E: Preparation of N-[2(S)-([1-(4-Cyanobenzyl)-1H-imidazol-5-yl]acetylamino)-3(S)-methylpentyl]-N-(1-naphthylmethyl) glycine A solution of the methyl ester from step D (2.32 g, 4.21 mmol) in MeOH(20 ml) and 1 M lithium hydroxide (4.70 ml, 4.70 mmol) was stirred at RT for 6 hr. The aqueous solution diluted with water (15 ml) and extracted with EtOAc (100 ml), dried (Mg$_2$SO$_4$), and the solvent evaporated in vacuo. The residue was chromatographed (SiO$_2$, 20% MeOH in CH$_2$Cl$_2$) to afford the title compound as a white solid.

$^1$H NMR(CD$_3$OD, 400 MHz) δ 8.33(1H, d,J=8.3 Hz), 7.87(2H,d, J=7.7 Hz), 7.78(1H,s), 7.63(2H,d, J=6.6 Hz), 7.57(1H,d, J=6.4 Hz), 7.50-7.38(4H,m), 7.17(1H,d, J=8.3 Hz), 6.96(1H,s), 5.32(1H,d, J=16.6 Hz), 5.25(1H,d,J=16.6 Hz), 4.64(1H,d, J=13.2 Hz), 4.40(1H,d, J=13.2 Hz), 3.99 (1H,m), 3.60-3.28(4H,m), 3.22(1H,dd, J=13.3 and 3.1 Hz), 2.93(1H,dd, J=13.3 and 10.3 Hz), 1.52(1H,m), 1.29(1H,m), 1.06(1H,m), 0.86-0.76(6H,m) ppm.

Anal. calc'd for C$_{32}$H$_{35}$N$_5$O$_3$ 1.00 H$_2$O, C, 69.17; H, 6.71 N, 12.60. Found: C, 68.95; H, 6.37; N, 12.54.

FAB Mass spectrum, m/z=538 (M+1).

Step F: Preparation of N-[2(S)-([1-(4-Cyanobenzyl)-1H-imidazol-5-yl]acetylamino)-3(S)-methylpentyl]-N-(1-naphthylmethyl)glycine isopropylamide To a solution of the acid from step E (50 mg, 0.093 mmol) and isopropyl amine (212 mg,0.533 mmol), HOBT resin[1] (93 mg, 1.08 mmol/g ; 0.100 mmol), in CH$_2$Cl$_2$ (1.1 ml) was added DCC (23.0 mg, 1.12 mmol). The reaction was stirred at room temperature for 20 min, the resin bound active ester was isolated by filtration and washed with CH$_2$Cl$_2$ (100 ml) and isopropanol:CH2Cl2 (1:1), (50 ml) and dried in vacuo. This resin was added to a solution of isopropylamine (7.0 ml, 0.08 mmol) in CH$_2$Cl$_2$ (0.6 ml) and stirred at room temperature for 20 min. The resin was removed by filtartion, the filtrate evaporated, and the residue purified by chromatography (SiO$_2$, 3% MeOH in CH$_2$Cl$_2$) to afford the title compound as a white solid.

$^1$H NMR(CDCl$_3$, 400 MHz) δ 8.33(1H, m),7.79(1H,m), 7.84(1H,d, J=8.2 Hz), 7.61(2H,d, J=8.4 Hz), 7.50-7.40(4H, m), 7.37(1H,d, 5.9 Hz), 7.05(2H, d, J=8.5 Hz), 6.81(1H, d, J=7.4 Hz), 6.57(1H,s), 5.19(1H,d, J=9.3 Hz), 5.11(2H,m), 4.27(1H,d, J=12.7 Hz), 4.05-3.85(2H,m), 3.71(1 h,d, j=12.9 Hz), 3.32(1H,d, J=13.4 Hz), 3.06(1H, d, J=13.4 Hz), 2.95 (1H,d, j=12.4 Hz), 2.81(1H,d J=12.4 Hz), 2.53(1H, dd, J=13.5 and 3.4 Hz), 2.44(1H,dd, J=13.5 and 9.6 Hz), 1.70-1.60(1H,m), 1.37(1H,m), 1.15(1H,m), 1.05(3H,d, J=6.5 Hz) 1.01(3H,d, J=6.5 Hz), 0.78(3H,t, J=6.2 Hz, 0.71(3H,d, J=6.7 Hz) ppm.

FAB HRMS exact mass calc'd for C$_{35}$H$_{43}$N$_6$O$_2$ 579.344750 (MH$^+$), found 579.343531.

1. Prepared as described by A Berrada, F. Cavelier, R. Jacquier and J. Verducci in *Bulletin de la Societe Chimique de France*. 4, 513-314, 1989.

EXAMPLE 38

N-[2(S)-([1-(4-Cyanobenzyl)-1H-imidazol-5-yl] acetylamino)-3(S)-methylpentyl]-N-(1-naphthylmethyl)glycine piperidinylamide The title compound was prepared using the protocol described in Example 37 step F using piperidine in place of isopropylamine.

$^1$H NMR(CDCl$_3$, 400 MHz) δ 8.11 (1H, d, J=8.0 Hz), 7.82(1H,d, J=7.9 Hz), 7.80-7.74(2H,m), 7.55(2H,d, J=8.2 Hz), 7.48-7.30(5H,m), 7.05(2H,d, J=8.0 Hz), 6.97(1H,s), 5.27(1H,d, J=16.0 Hz), 5.22(1H,d, J=16.0 Hz), 4.28(1H,d, J=13.5 Hz), 4.00(1H,m), 3.90(1H,d, J=13.5 Hz), 3.58(1H, m),3.30(2H,s), 3.16(1H,d, J=15.7 Hz), 3.20(1H,d, J=15.7 Hz), 3.15(1H,m), 3.05(1H,m), 2.76-2.60(2H,m), 1.82(1H,m), 1.70-1.20(8H,m), 1.07(1H,m), 0.88(3H,t, J=7.3 Hz) and 0.76(3H,d,J=6.8 Hz) ppm.

EXAMPLE 39

2(RS)-{[1-(4-Cyanobenzyl)-1H-imidazol-5-yl] acetyl}amino -3-(t-butoxycarbonyl)amino-N-methyl-N-(naphth-1-ylmethyl) propionamide The title compound was prepared using the protocol described in the Example 27 step C using N-methylnaphth-1-ylmethylamine in place of N-methylbenzylamine.

$^1$H NMR(CD$_3$OD, 400 MHz) δ 8.96(0.75H,s), 8.82 (0.25H,s), 8.47(0.75H,d, J=8 Hz), 8.42(0.25H,d, J=8 Hz), 8.07-7.70(5H,m), 7.60-7.20(13H,m), 5.51(1.5H,s), 5.30 (0.5H,s), 5.20-5.00(2H,m), 5.00-4.60(1H,m), 3.73(1H,m), 3.60-3.20(3H,m), 3.09(2.25H,s), 2.99(0.75H,s), 1.40(6.75H,s) and 1.37(2.25H,s) ppm.

FAB Mass spectrum, m/z=581 (M+1),

EXAMPLE 40

N-{1-(4-Cyanobenzyl)-1H-imidazol-5-yl)acetyl}-2 (S){N'-methanesulfonyl-N'-(naphth-1-ylmethyl) aminomethyl}-pyrrolidine Step A: Preparation of 2(S)-Hydroxymethyl-N-trifluoroacetyl pyrrolidine To a solution of L-prolinol (7.02 g, 69.4 mmol) and triethylamine (10.6 ml, 76.1 mmol) in CH$_2$Cl$_2$ (700 ml) at −5° C. was added trifluoroacetic anhydride (9.80 ml, 69.4 mmol) over a period of 4 hr. The solvent was evaporated in vacuo and the residue purified by chromatography(SiO$_2$, 15–20% EtOAc in hexanes, gradient elution). The title compound was obtained as a pale yellow oil.

$^1$H NMR(CDCl$_3$, 400 MHz) δ 4.27(1H,m), 3.84-3.56(4H,m), 3.19(1H, dd, J=7.8 and 3.6 Hz) and 2.20-1.74(4H,m) ppm.

FAB Mass spectrum, m/z=198 (M+1).

Step B: Preparation of 2(S)-Methanesulfonyloxymethyl-N-trifluoroacetyl pyrrolidine To a solution of the product of step A (1.002 g, 5.08 mmol) and triethylamine (0.78 ml, 5.60 mmol) in CH$_2$Cl$_2$ (50 ml) at −25° C. was added methane sulfonyl chloride (0.40 ml, 5.17 mmol) over a period of 5 min and stirring was continued for 1 hr. The solvent was evaporated in vacuo and the residue purified by chromatography(SiO2, 33% EtOAc in hexanes, elution). The title compound was obtained as a colorless oil.

$^1$H NMR(CDCl$_3$, 400 MHz) δ 4.54(1H,dd, J=4.9 and 10.2 Hz), 4.38(1H,m), 4.31(1H,dd, J=3.8 and 10.2 Hz), 3.71(2H,m), 3.01(3H,s), 2.20-1.90(4H,m) ppm.

FAB HRMS exact mass calc'd for C$_8$H$_{13}$NO$_4$SF$_3$ 276.051740(MH$^+$), found 276.051233.

Step C: Preparation of 2(S)-Azidomethylpyrrolidine

In a flask protected by a safety screen, a solution of the product of step B (12.27 g, 0.042 mmol) and lithium azide (2.47 g, 0.051 mmol) in DMF (30 ml) was stirred at 45° C. for 18 hr. The solvent was evaporated in vacuo and the residue triturated with EtOAc (100 ml) and filtered. The filtrate was evaporated in vacuo and the residue dissolved in MeOH (255 ml) which was saturated with gaseous ammonia at 0° C. and then stirred at room temperature for 72 hr. The solvent was removed by distillation in vacuo to afford the title compound as an oil.

$^1$H NMR(CDCl$_3$, 400 MHz) δ 3.40-3.20(3H,m), 3.05-2.85(2H,m), 2.20-1.60(3H,m), 1.50-1.35(1H,m)ppm.

Step D: Preparation of N-{1-(4-Cyanobenzyl)-1H-imidazol-5-yl)acetyl}-2(S)-azidomethyl}-pyrrolidine To a solution of the acid from Example 1 step D (3.00 g, 10.57 mmol), the amine from step B (2.13 g, 11.63 mmol), HOOBT (1.90 g, 11.63 mmol), and triethylamine (1.62 ml, 11.63 mmol) in DMF (20 ml) was added EDC (2.23 g, 11.63 mmol). The reaction was stirred at room temperature for 24 hrs, diluted with EtOAc and the organic layer washed with sat. aq NaHCO$_3$, brine, dried (MgSO$_4$). and evaporated in vacuo. The residue was purified by chromatography (SiO$_2$, 32–4% MeOH in CH$_2$Cl$_2$, gradient elution) to afford the title compound as an oil.

$^1$H NMR(CDCl$_3$, 400 MHz) δ 7.64(2H,d, J=7.0 Hz), 7.52(1H,s), 7.17(2H,d, J=7.0 Hz), 6.97(1H,s), 5.35(2H,m), 4.14(1H,m), 3.69(1H,dd, J=12.1 and5.5 Hz), 3.60-3.20(5H,m), and 2.20-1.80(4H,m) ppm.

Step E: Preparation of N-{1-(4-Cyanobenzyl)-1H-imidazol-5-yl)acetyl -2(S)-aminomethyl}-pyrrolidine A solution of the azide from step D (480 mg, 1.37 mmol) in methanol (20 ml) was purged with argon and 10% palladium on carbon (20 mg) added. The flask was evacuated and stirred under an atmosphere of hydrogen (2 atm) for 3 hrs. The hydrogen was replaced by argon and the catalyst removed by filtration and the solvent evaporated in vacuo to afford the title compound as an oil. A portion of this material was converted to the trifluoroacetate salt.

$^1$H NMR(CD$_3$OD, 400 MHz) Trifluoroacetate salt δ 8.88 (1H,s), 7.74(2H,d, J=8.3 Hz), 7.49(1H,s), 7.45(2H,d, J=8.3 Hz), 5.50(2H,s), 4.18(1H,m), 3.90-3.80(2H,m), 3.60-3.40 (2H,m), 3.15-2.95(2H,m) and 2.20-1.70(4H,m) ppm.

Step F: Preparation of N-{1-(4-Cyanobenzyl)-1H-imidazol-5-yl)acetyl}-2(S) {N'-(naphth-1-ylmethyl) aminomethyl}-pyrrolidine To a slurry of 1-naphthaldehyde (197 μl, 1.63 mmol), crushed 3A molecular sieves (1.0 g), and the amine from step E (421 mg, 1.30 mmol) in 1,2-dichloroethane (10 ml) was added sodium triacetoxyborohydride (345 mg, 1.63 mmol) at 0° C. The reaction was allowed to warm slowly to RT and stirred for 24 hrs. The reaction was cooled to 0° C. and quenched with sat. aq. NaHCO$_3$ and stirred for 30 min. The organic layer was separated, washed with saturated brine, dried (MgSO$_4$) and evaporated in vacuo. The residue was purified by chromatography on a chromatatron (SiO$_2$, 5% MeOH in CH$_2$Cl$_2$) to provide the title compound as an oil.

$^1$HNMR(CDCl$_3$, 400 MHz) δ 8.40-6.70(13H,m), 5.40-5.20(2H,m), 4.30-4.10(2H,m), 3.60-3.40(5H,m),2.95-2.60 (2H,m), 2.40-1.80(4H,m) ppm.

Step G: Preparation of N-{1-(4-Cyanobenzyl)-1H-imidazol-5-yl)acetyl}-2(S)-{N'-methanesulfonyl-N'-(naphth-1-ylmethyl)aminomethyl}-pyrrolidine To a solution of the product of step F (74 mg, 0.16 mmol) in CH$_2$Cl$_2$ (2 ml) and triethylamine (22 μl, 0.16 mmol) at 0° C. was added methanesulfonyl chloride(12.3 μl, 0.16 mmol).

The reaction was stirred at room temperature for 1 hr, quenched with sat aq. NaHCO$_3$ and extracted with CH$_2$Cl$_2$ (2×10 ml). The organic extracts were dried (MgSO$_4$) and the solvent evaporated in vacuo. The residue was purified by preparative HPLC (C-18; 95:5 to 5:95 water:CH$_3$CN containing 0.1% trifluoroacetic acid; gradient elution). Lyophilisation of the collected fractions afforded the title compound as a white solid.

$^1$H NMR(CD$_3$OD, 400 MHz) δ 8.92(1H, m), 8.36(1H, m), 8.00-7.30(11H,m), 5.46(1.2H,s), 5.39(0.8H,s), 5.03(0.6H,d, J=14.5 Hz), 4.90-4.60(1H,m), 4.71(0.4H,d, J=14.5 Hz), 3.80-3.50(2H,m), 3.50-2.70(5H,m), 3.10(1.2H,s), 2.94 (1.8H,s) and 1.80-1.20(4H,m)ppm.

FAB Mass spectrum, m/z=542 (M+1).

Anal. calc'd for C$_{30}$H$_{31}$N$_5$O$_3$ 0.25 H$_2$O, 1.95 TFA; C, 52.98; H, 4.49; N, 9.11. Found: C, 53.00; H, 4.37; N, 9.36.

EXAMPLE 41

N-{(1-(4-Cyanobenzyl)-1H-imidazol-5-yl)acetyl}-2 (S)-{N'-acetyl-N'-naphth-1-ylmethyl-aminomethyl}-pyrrolidine The title compound was prepared using the protocol described in Example 40 step G using acetyl chloride instead of methane sulfonyl chloride.

$^1$H NMR(CD$_3$OD, 400 MHz) δ 9.0-8.8(1H,m), 8.20-7.0 (12H,m), 5.60-4.70(4H,m), 4.60-4.10(1H,m), 4.00-3.00(4H, m) and 2.30-1.80(7H,m)ppm.

FAB Mass spectrum, m/z=506 (M+1).

Anal. calc'd for C$_{31}$H$_{31}$N$_5$O$_2$ 0.05 H$_2$O, 1.80 TFA; C, 58.39; H, 4.66; N, 9.84. Found: C, 58.40; H, 4.67; N, 9.91.

EXAMPLE 42

N-{5-(4-Cyanobenzyl)-1H-imidazol-1-yl)acetyl}-2 (S)-[1(R)-1-(3-chlorophenyl)-1-hydroxy] methylpyrrolidine hydrochloride Step A: N- {t-Butoxycarbonyl}-2(S)-[1-(R,S)-1-(3-chlorophenyl)-1-hydroxy]-methylpyrrolidine To magnesium turnings (753 mg, 30.99 mmol) in diethylether (1 ml) was added a solution of 3-bromochlorobenzene 3.60 ml, 30.88 mmol) in diethylether (25 ml) at a rate so as to maintain a gentle reflux. The reaction was heated at reflux for a further 30 min, allowed to cool to room temperature and diluted with diethyl ether to a total volume of 37 ml.

A solution of N-t-butoxycarbonylprolinal (2.50 g, 11.61 mmol) in diethylether was cooled to 0° C. and 3-chloromagnesium bromide solution (17.0 ml, 14.1 mmol) was added. The reaction was stirred at 0° C. for 10 min and then allowed to warm to room temperature and stirring continued for 30 mins. The solution was cooled to 0° C. and quenched by the addition of a saturated ammonium chloride solution (50 ml). The mixture was extracted with diethyl ether and the combined extracts were washed with brine, dried (MgSO$_4$) and the solvent evaporated in vacuo. The residue was purified by chromatography (SiO$_2$, 10–20% ethylacetate in hexanes, gradient elution) to afford the title compounds as an oil.

$^1$H NMR(CD$_3$OD, 400 MHz) δ 7.50-7.00(4H, m), 5.95 (0.66H, s), 5.55(0.33H, s), 4.85(0.33H, s), 4.50(0.66H, m), 4.30(0.33H, s), 4.06(0.66H, m), 3.70-3.20(2H, m), 2.00-1.60 (13H, m)ppm.

Step B: N-{t-Butoxycarbonyl}-2(S)-[(1(S)-1-(3-chlorophenyl)-1(2-picolinoyloxy)]-methylpyrrolidine and N-{t-Butoxycarbonyl}-2(S)-[(1(R)-1-(3-chlorophenyl)-1(2-picolinoyloxy)]-methylpyrrolidine To a solution of the alcohols from step A (105 mg, 0.337 mmol), triethylamine (0.235 ml, 1.69 mmol), and DMAP (5 mg, 0.04 mmol), in methylene chloride (3.0 ml), was added picolinoyl chloride hydrochloride (90 mg, 0.51 mmol)and the mixture was stirred 1 6 hr. The reaction was diluted with methylene chloride and washed with saturated NaHCO$_3$ solution. The organic extracts were dried, (Na$_2$SO$_4$) and the solvent evaporated in vacuo. The diastereomeric products were separated by chromatography (SiO$_2$, 25% ethylacetate in hexanes). First diastereomer eluted:N-{t-Butoxycarbonyl}-2(S)-[1(R)-1-(3-chlorophenyl)-1-(2-picolinoyloxy)]-methylpyrrolidine.

$^1$H NMR (CD$_3$OD, 400 MHz) δ 8.75(1H, m), 8.26(1H, d, J=0.9 Hz), 8.05(1H, dt, J=6.0, and 1.8 Hz), 7.68(1H, m), 7.60-7.20(4H, m), 6.60(1H, m), 4.29(1H, s), 3.44(1H, m), 3.25(1H, m), 2.30-2.00(2H, m)ppm.

Second diastereomer eluted:

N-{t-Butoxycarbonyl}-2(S)- [1(S)-1-(3-chlorophenyl)-1-picolinoyloxy]-methylpyrrolidine.

$^1$H NMR (CD$_3$OD, 400 MHz) δ 8.72(1H, m), 8.25(1H, m), 8.05(1H, m), 7.64(1H, m), 7.50(1H, m), 7.50-7.20(3H, m), 6.20-6.05(1H, m), 4.39(1H, s), 3.38(1H, q, J=8.2 Hz), 3.12(1H, m) and 2.20-1.30(13H, m)ppm.

Step C: N-{t-Butoxycarbonyl}-2(S)-[1(R)-1-(3-chlorophenyl)-1-hydroxy]methylpyrrolidine To a solution of N-{t-Butoxycarbonyl}-2(S)-[1(R)-1-(3-chlorophenyl)-1-(2-picolinoyloxy)]-methylpyrrolidine (32.7 mg, 0.078 mmol), in THF (2.0 ml) was added lithium hydroxide (0.63 ml of a 1.0 M aqueous solution, 0.63 mmol) at room temperature and the reaction was stirred for 16 hrs. The mixture was diluted with ethylacetate and washed with water and brine, dried (Na$_2$SO$_4$), and the solvents evaporated in vacuo. The residue was purified by chromatography (SiO$_2$, 5% EtOAc in CH$_2$Cl$_2$) to afford the product as a white solid.

$^1$H NMR(CDCl$_3$, 400 MHz) δ 7.50-7.10(4H, m), 5.57 (0.8H, s), 5.15(0.2H, s), 4.85(1H, s), 4.30(0.8H, s), 4.00 (0.2H, s), 3.60(0.2H, s), 3.35(0.8H, s), 2.85(0.8H, s), 2.30 (0.2H, s), 2.10-1.60(4H, s), 1.56(1.8H, s), and 1.52(7.2H, s) ppm.

Step D: N- {t-Butoxycarbonyl}-2(S)-[1(S)-1-(3-chlorophenyl)-1-hydroxyl-methylpyrrolidine The title compound was prepared using the procedure in step C and N-{t-Butoxycarbonyl}-2(S)-[1(S)-1-(3-chlorophenyl)-1-(2-picolinoyloxy)]-methylpyrrolidine.

$^1$H NMR(CDCl$_3$, 400 MHz) δ 7.50-7.10(4H, m), 6.00 (1H, s), 4.50(1H, s), 4.06(1H, m), 3.48(1H, m), 3.36(1H, m) and 1.85-1.40(13H, m) ppm.

Step E: 2(S)-[1(R)-1-(3-chlorophenyl)-1-hydroxy]-methylpyrrolidine

The title compound was prepared by the procedure described in Example 1 step G using the material prepared in step C.

$^1$H NMR (CD$_3$OD, 400 MHz) δ 7.47(1H, m), 7.42-7.30 (3H, m), 5.07(1H, d, J=3.9 Hz), 3.83(1H, m), 3.40-3.20(2H, m), 2.15-1.85(3H, m) and 1.70(1H, m) ppm.

Step F: 1-Trityl-4-(4-cyanobenzyl)-imidazole

To a suspension of activated zinc dust (3.57 g, 54.98 mmol) in THF (50 ml)was added dibromoethane (0.315 ml, 3.60 mmol) and the reaction stirred under argon at 20° C. The suspension was cooled to 0° C. and α-bromo-p-tolunitrile (9.33 g, 47.6 mmol) in THF (100 ml) was added dropwise over a period of 10 min. The reaction was then allowed to stir at 20° C. for 6 hr. Bis(triphenylphosphine) Nickel II chloride (2.40 g, 3.64 mmol) and 5-iodotrityl imidazole (15.95 g, 36.6 mmol) was added in one portion. The resulting mixture was stirred 16 hr at 20° C. and then quenched by addition of saturated $NH_4Cl$ solution (100 ml) and the mixture stirred for 2 hours. Saturated $NaHCO_3$ solution was added to give a pH of 8 and the solution was extracted with EtOAc (2×250 ml), dried ($MgSO_4$) and the solvent evaporated in vacuo. The residue was chromatographed ($SiO_2$, 0–20% $EtOAc/CH_2Cl_2$) to afford the title compound as a white solid.

$^1$H NMR $CDCl_3$ δ (7.54 (2H, d, J=7.9 Hz), 7.38(1H, s), 7.36-7.29 (11H, m), 7.15-7.09(6H, m), 6.58(1H, s) and 3.93(2H, s)ppm.

Step G: 5-(4-Cyanobenzyl)-imidazol-1-yl-methylacetate

To a solution of methyl glycolate (0.545 ml, 7.06 mmol), diisopropylethylamine (1.30 ml, 7.46 mmol), in $CH_2Cl_2$ at −78° C. was added dropwise trifluoromethanesulfonyl anhydride (1.20 ml, 7.13 mmol) and the resulting mixture was stirred at −78° C. for 1 hr. A solution of 1-trityl-4-(4-cyanobenzyl)-imidazole (3.00 g, 7.05 mmol) in $CH_2Cl_2$ (20 ml) was cooled to −78° C. and added dropwise to the above solution. The cooling bath was removed and the reaction was allowed to warm to room temperature and stirred for 3 hours, and then the solvent was evaporated in vacuo. The residue was dissolved in methanol (60 ml), heated at reflux for 30 min, cooled and the solvent evaporated in vacuo. The residue was partitioned between saturated $NaHCO_3$ solution and EtOAc. The organic extracts were dried ($Na_2SO_4$ and the solvent evaporated in vacuo. The residue was purified by chromatography ($SiO_2$, 3 to 10% MeOH in $CH_2Cl_2$, gradient elution) and the title compound was obtained as a white solid.

$^1$H NMR δ $CDCl_3$ (7.61 (2H, d, J=7.9 Hz), 7.53(1H, s), 7.27(2H, d, J=7.9 Hz), 6.89(1H, s), 4.47(2H, s), 3.98(2H, s) and 3.66(3H, s)ppm.

Step H: 5-(4-Cyanobenzyl)-imidazol-1-yl-acetic acid

The title compound was prepared using the procedure described in Example 1 step D using the methyl ester from step G.

$^1$H NMR $CDCl_3$ δ 8.76(1H, s), 7.71 (2H, d, J=8.0 Hz), 7.56(1H, s), 7.45(2H, d, J=8.0 Hz), 7.15(1H, s), 4.72(2H, s) and 4.15(2H, s) ppm.

Step I: N-{5-(4-Cyanobenzyl)-1H-imidazol-1-yl)acetyl}-2(S)-[1 (R)-1-(3-chlorophenyl)-1-hydroxy]methylpyrrolidine-hydrochloride To a solution of the acid from step H (135 mg, 0.476 mmol), the amine hydrochloride salt from step G (101 mg, 0.477 mmol), HOOBT (95 mg, 0.58 mmol), and triethylamine (0.16 ml, 1.15 mmol) in DMF (10 ml) was added EDC (109 mg, 0,569 mmol). The reaction was stirred at room temperature for 48 hrs, diluted with EtOAc and the organic layer washed with sat. aq $NaHCO_3$, brine, dried ($Na_2SO_4$) and evaporated in vacuo. The residue was chromatographed ($SiO_2$, 7% MeOH in $CH_2Cl_2$) to afford the desired amide which was converted to the corresponding hydrochloride salt by treatment with 1equivalent of hydrochloric acid in aqueous acetonitrile and evaporation of the solvents in vacuo.

$^1$H NMR($CD_3OD$, 400 MHz) δ 8.85-8.75(1H, m), 7.90-7.10(9H, m), 5.40-5.00(3H, m), 4.40-4.00(3H, m), 3.60-3.00 (2H, m) and 2.30-1.20(4H, m)ppm.

FAB Mass spectrum, m/z=435 (M+1).

Anal. calc'd for $C_{24}H_{23}N_4O_2Cl$ 1.00 HCl, 0.45 $H_2O$; C, 60.12; H, 5.23; N, 11.68; Found: C, 60.08; H, 5.09; N, 11.77.

EXAMPLE 43

N-{5-(4-Cyanobenzyl)-1H-imidazol-1-yl)acetyl}-2 (S)-[1(S)-1-(3-chlorophenyl)-1-hydroxy]methylpyrrolidine

Step A: 2(S)-[1(S)-1-(3-chlorophenyl)-1-hydroxy]methylpyrrolidine hydrochloride The title compound was prepared by the procedure described in Example 1 step G using the material prepared in Example 42 step D.

$^1$H NMR($CD_3OD$, 400 MHz) δ 7.52(1H, m), 7.50-7.32 (3H, m),4.75(1H, d, J=6.9 Hz), 3.71(1H, q, J=8.0 Hz), 3.40-3.20(2H, m) and 2.20-1.80(4H, m)ppm.

Step B: N-5-(4-Cyanobenzyl)-1H-imidazol-1-yl) acetyl]-2(S)-[1(S)-1-(3-chlorophenyl)-1-hydroxy]methylpyrrolidine The title compound was prepared by the procedure described in Example 42 step I using the amine hydrochloride from step A.

$^1$H NMR($CD_3OD$, 400 MHz) δ 9.00-8.90(1H, m), 7.90-7.10(9H, m), 5.75(1H, d, J=17.0 Hz), 5.30(1H, d, J=17.0 Hz), 5.17(1H, q, J=18 Hz), 4.46(1H, d, J=9.5 Hz), 4.40-4.00 (3H, m), 3.60-3.20(2H, m), 2.20-1.20(4H, m)ppm.

FAB Mass spectrum, m/z=435 (M+1).

Anal. calc'd for $C_{24}H_{23}N_4O_2Cl$ 1.00 HCl, 0.55 $H_2O$; C, 59.89; H, 5.26; N, 11.64. Found: C, 59.86; H, 5.22; N, 12.00.

EXAMPLE 44

N-{5-(4-Cyanobenzyl)-1H-imidazol-1-yl)ethyl}-2 (S)-[1(R)-1-(3-chlorophenyl)-1-hydroxy]methylpyrrolidine

Step A: 1-Hydroxyethyl-5-(4-Cyanobenzyl)-imidazole

A solution of 5-(4-cyanobenzyl)-imidazol-1-yl-methylacetate (0.113 g, 0.472 mmol) in methanol (2 ml) at 0° C. was treated with sodium borohydride (80.7 mg, 2.1 mmol). After 1 hr the reaction was quenched by addition of saturated $NH_4Cl$ solution (2 ml). Saturated $NaHCO_3$ was added and the mixture extracted with ethyl acetate (3×25 ml), dried ($MgSO_4$) and the solvent evaporated in vacuo. The title compound was isolated by chromatography ($SiO_2$, 10% MeOH in $CH_2Cl_2$) as a white solid.

$^1$H NMR $CDCl_3$ δ 7.61 (2H, d, J=7.9 Hz), 7.55(1H, s), 7.27(2H, d, J=7.9 Hz), 6.83(1H, s), 4.05(2H, s), 3.87(2H, t, J=5.1 Hz) and 3.74(2H, t, J=5.1 Hz)ppm.

Step B: 5-(4-Cyanobenzyl)-imidazol-1-yl-ethyl methanesulfonate

A solution of 1-hydroxyethyl-5-(4-Cyanobenzyl)-imidazole (0.532 g, 2.34 mmol) in methylene chloride (70 ml) at 0° C. was treated with Hunigs base (0.489 ml, 2.81 mmol) and methanesulfonyl chloride (0.219 ml, 2.81 mmol). After 2 hrs the reaction was quenched by addition of saturated $NaHCO_3$ solution (50 ml) and the mixture extracted with methylene chloride (50 ml), dried ($MgSO_4$) and the solvent evaporated in vacuo. The title compound was used without furthur purification.

$^1$H NMR CDCl$_3$ δ 7.62 (2H, d, J=7.9 Hz), 7.54(1H, s), 7.29(2H, d, J=7.9 Hz), 6.87(1H, s), 4.25(2H, t), 4.10-4.00 (4H, m), 3.74(2H, t, J=5.1 Hz) and 2.90(3H, s)ppm.

Step C: N-{5-(4-Cyanobenzyl)-1H-imidazol-1-yl) ethyl}-2(S)-[1(R)-1-(3-chlorophenyl)-1-hydroxy] methylpyrrolidine To a solution of 5-(4-cyanobenzyl)-imidazol-1-yl)ethyl methanesulfonate (290 mg, 0.95 mmol) in DMF (10 ml) was added the amine (200 mg, 0.945 mmol) (prepared by treatment of the amine hydrochloride salt obtained in Example 42 step E with 1M sodium hydroxide extraction into EtOAc, drying (Na$_2$SO$_4$), and evaporation of solvent), sodium iodide (710 mg, 4.74 mmol) and Hunig's base (0.330 ml, 1.89 mmol). The mixture was stirred at 55° C. for 12 hrs, and the solvent evaporated in vacuo. The residue was treated with water and 1M NaOH to a pH of 11 and extracted into EtOAc. The organic extracts were dried (Na$_2$SO$_4$), and the solvent evaporated in vacuo. The residue was purified by chromatography (SiO$_2$, 1–2% saturated ammonia in acetonitrile, gradient elution. The residue was converted to the corresponding hydrochloride salt by treatment with 1 equivalent of hydrochloric acid in aqueous acetonitrile and evaporation of the solvents in vacuo.

FAB Mass spectrum, m/z=421(M+1).

Anal. calc'd for C$_{24}$H$_{25}$N$_4$OCl 2.00 HCl, 0.60H$_2$O; C, 57.12 H, 5.63; N, 11.10. Found: C, 57.08; H1 5.71; N, 11.24.

EXAMPLE 45

N-{5-(4-Cyanobenzyl)-1H-imidazol-1-yl)ethyl}-2 (S)- [1 (S)-1-(3-chlorophenyl)-1-hydroxy] methylpyrrolidine The title compound was prepared using the procedure described in Example 44 using the amine hydrochloride from Example 43 step A.

FAB Mass spectrum, m/z=421(M+1).

Anal. calc'd for C$_{24}$H$_{25}$N$_4$OCl 2.00 HCl, 0.20 H$_2$O; C, 57.95; H, 5.55; N, 11.26. Found: C, 57.95; H, 5.37; N, 11.30.

EXAMPLE 46

N-{1-(4-Cyanobenzyl)-1H-imidazol-5-yl)methyl}-2 (S)-[1(R)-1-(3-chlorophenyl)-1-hydroxy] methylpyrrolidine Step A: 1-Triphenylmethyl-4-(hydroxymethyl)-imidazole To a solution of 4-(hydroxymethyl)imidazole hydrochloride (35.0 g, 260 mmol) in dry DMF (250 ml) at room temperature was added triethylamine (90.6 ml, 650 mmol). A white solid precipitated from the solution. Chlorotriphenylmethane (76.1 g, 273 mmol) in of DMF (500 ml) was added dropwise. The reaction mixture was stirred for 20 hrs, poured over ice, filtered, and washed with ice water. The resulting product was slurried with cold dioxane, filtered, and dried in vacuo to provide the titled product as a white solid which was sufficiently pure for use in the next step.

Step B: 1-Triphenylmethyl-4-(acetoxymethyl)-imidazole

The alcohol from Step A (260 mmol, prepared above) was suspended in pyridine (500 ml). Acetic anhydride (74 ml, 780 mmol) was added dropwise, and the reaction was stirred for 48 hrs during which it became homogeneous. The solution was poured into EtOAc, washed sequentially with water, 5% aqueous HCl solution, saturated aqueous NaHCO$_3$, solution, and brine. the organic extracts were dried (Na$_2$SO$_4$), and concentrated in vacuo to provide the product as a white powder, which was sufficiently pure for use in the next reaction.

Step C: 1-(4-Cyanobenzyl)-5-(acetoxymethyl)-imidazole hydrobromide

A solution of the product from Step B (85.8 g, 225 mmol) and 4-cyano benzyl bromide (50.1 g, 232 mmol) in EtOAc (500 ml) was stirred at 60° C. for 20 hrs, during which a pale yellow precipitate formed. The reaction was cooled to room temperature and filtered to provide the solid imidazolium bromide salt. The filtrate was concentrated in vacuo to a volume (200 ml), reheated at 60° C. for 2 hrs, cooled to room temperature, and filtered again. The filtrate was concentrated in vacuo to a volume (100 m), reheated at 60° C. for another 2 hrs, cooled to room temperature, and concentrated in vacuo to provide a pale yellow solid. All of the solid material was combined, dissolved in methanol (500 ml), and warmed to 60° C. After 2 hrs, the solution was concentrated in vacuo to provide a white solid which was triturated with hexane to remove soluble materials. Removal of residual solvents in vacuo provided the titled product hydrobromide as a white solid which was used in the next step without further purification.

Step D: 1-(4-Cyanobenzyl)-5-(hydroxymethyl)-imidazole

To a solution of the acetate from Step C (50.4 g, 150 mmol) in 3:1 THF/water (1.5 1) at 0° C. was added lithium hydroxide monohydrate (18.9 g, 450 mmol). After 1 hr, the reaction was concentrated in vacuo, diluted with EtOAc (3 1), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step E: 1-(4-Cyanobenzyl)-5-(chloromethyl)-imidazole

A solution of 1-(4-Cyanobenzyl)-5-(hydroxymethyl)-imidazole (1.0 g, 4.70 mmol), in thionyl chloride (5 ml), was stirred at 70° C. for 16 hrs. The solvent was evaporated in vacuo and the resulting solid suspended in CH$_2$Cl$_2$, collected by filtration and dried in vacuo. The material was sufficiently pure to be used without furthur purification.

$^1$H NMR CD$_3$OD δ 9.06 (1H, s), 7.83(2H, d, J=8.0 Hz), 7.77(1H, s), 7.55(2H, d, J=8.0 Hz), 5.67(2H, s) and 4.78(2H, s) ppm.

Step F: N-{1-(4-Cyanobenzyl)-1H-imidazol-5-yl) methyl}-2(S)-[1(R)-1-(3-chlorophenyl)-1-hydroxy] methylpyrrolidine A solution of the chloride from step E (127 mg, 0.474 mmol) in DMF (2 ml) was added 2(S)-[1(R)-1-(3-chlorophenyl)-1-hydroxy]methylpyrrolidine (prepared by treatment of the amine hydrochloride salt obtained in Example 42 step E with 1M sodium hydroxide and extraction into EtOAc, drying (Na$_2$SO$_4$) and evaporation of solvent), (100 mg, 0.472 mmol) and Hunig's base (0.20 ml, 1.5 mmol). The mixture was stirred at room temperature for 12 hrs. The reaction was diluted with EtOAc and the pH adjusted to 11 by the addition of 1M NaOH. The organic extracts were dried (Na$_2$SO$_4$), and the solvent evaporated in vacuo. The residue was purified by chromatography (SiO$_2$, eluting with 3% saturated ammonia/acetonitrile). The residue was converted to the corresponding hydrochloride salt by treatment with 2 equivalents of hydrochloric acid in aqueous acetonitrile and evaporation of the solvents in vacuo.

FAB Mass spectrum, m/z=407 (M+1).

Anal. calc'd for C$_{23}$H$_{23}$N$_4$OCl 2.00 HCl, 0.65 H$_2$O; C, 56.51; H, 5.36; N, 11.46. Found: C, 56.57; H, 5.36; N, 11.35.

EXAMPLE 47

N-{1-(4-Cyanobenzyl)-1H-imidazol-5-yl)methyl}-2 (S)-[1(S)-1-(3-chlorophenyl)-1-hydroxy] methylpyrrolidine The title compound was prepared using the procedure described in Example 46 using the amine hydrochloride from Example 43 step A.

FAB Mass spectrum, m/z=407 (M+1).

Anal. calc'd for C$_{23}$H$_{23}$N$_4$OCl 2.00 HCl, 0.65 H$_2$O; C, 56.20; H, 5.39; N, 11.40. Found: C, 56.25; H, 5.33; N, 11.30.

EXAMPLE 48

N-{5-(4-Cyanobenzyl)-1H-imidazol-1-yl)acetyl}-4 (R)-hydroxy-2(S)-[1(R)-1-(3-chlorophenyl)-1-hydroxy]methylpyrrolidine hydochloride The title compound was prepared as in Example 42 steps A-I using 4(R)-t-butyldimethylsiloxy-prolinal.

$^1$H NMR CD$_3$OD δ 8.85 (1H, s), 7.74(2H, d, J=8.3 Hz), 7.50(2H, d, J=8.3 Hz), 7.50-7.20(5H, m), 5.39(1H, m), 5.24(1H, d, J=17.1 Hz), 5.05(1H, d, J=17.1 Hz), 4.55(1H, m), 4.30(1H, m), 3.65(1H, dd, J=11.0 and 4.2 Hz), 3.50(1H, d, J=11.0 Hz), 3.40-3.00(2H, m), 2.14(1H, m) and 1.50(1H, m)ppm.

FAB Mass spectrum, m/z=451 (M+1).

EXAMPLE 49

N-{5-(4-Cyanobenzyl)-1H-imidazol-1-yl)acetyl}-4 (R)-hydroxy-2(S)-[1 (S)-1-(3-chlorophenyl)-1-hydroxy]methylpyrrolidine The title compound was prepared as in Example 43 using 4(R)-hydroxy-2(S)- [1 (S)-1-(3-chlorophenyl)-1-hydroxy] methylpyrrolidine.

Anal. calc'd for C$_{24}$H$_{23}$N$_4$O$_3$CI 1.00 HCl, 0.15 NH$_4$Cl; C, 58.19; H, 5.01; N, 11.73. Found: C, 58.09; H, 5.33; N, 11.97.

EXAMPLE 50

N-{1-(4-Cyanobenzyl)-1H-imidazol-1-ylethyl}-4 (R)-hydroxy-2(S)-[1(R)-1-(3-chlorophenyl)-1-hydroxy]methylpyrrolidine To a solution of 4(R)-hydroxy-2(S)-[1(R)-1-(3-chlorophenyl)-1-hydroxy]methylpyrrolidine (181 mg, 0.79 mmol), Hunigs base (0.138 ml, 0.79 mmol) and 1-(4-cyanobenzyl)-imidazol-5-yl) ethylmethanesulfonate (263 mg, 0.79 mmol) in DMF (1.6 ml) was added sodium iodide (594 mg, 3.96 mmol) and the mixture heated at 55° C. for 16 hrs. The reaction was diluted with EtOAc and the pH adjusted to 12 with 1M NaOH. The organic extract was washed with brine, dried (MgSO$_4$), and the solvent evaporated in vacuo. The residue was chromatographed (SiO$_2$, 2 to 5% NH$_4$OH in acetonitrile, gradient elution) to afford the title compound which was converted to an HCl salt.

Anal. calc'd for C$_{24}$H$_{25}$N$_4$O$_2$Cl 2.00 HCl, 0.85 H$_2$O; C, 54.89; H, 5.51; N, 10.67. Found: C, 54.85; H, 5.43; N, 10.74.

FAB Mass spectrum, m/z=437 (M+1).

EXAMPLE 51

N-{1-(4-Cyanobenzyl)-1H-imidazol-1-ylethyl}-4 (R)-hydroxy-2(S)-[1(S)-1-(3-chlorophenyl)-1-hydroxy]methylpyrrolidine The title compound was prepared according to the procedure described in Example 50 using 4(R)-hydroxy-2(S)-[1(S)-1-(3-chlorophenyl)-1-hydroxy]methylpyrrolidine.

Anal. calc'd for C$_{24}$H$_{25}$N$_4$O$_2$Cl 2.00 HCl, 0.60 H$_2$O, 0.35 EtOAc; C, 55.32; H, 5.67; N, 10.16. Found: C, 55.33; H, 5.75; N, 9.95.

FAB Mass spectrum, m/z=437 (M+1).

EXAMPLE 52

N-[5-(4-Cyanobenzyl)-1H-imidazol-1-ylethyl]-4(R)-hydroxy-2(S)-[1(R)-1-(3-chlorophenyl)-1-hydroxy]methylpyrrolidine The title compound was prepared according to the procedure described in Example 44 step C using 4(R)-hydroxy-2(S)-[1(R)-1-(3-chlorophenyl)-1-hydroxy]methylpyrrolidine.

Anal. calc'd for C$_{24}$H$_{25}$N$_4$O$_2$Cl 2.00 HCl, 0.70 H$_2$O; C, 55.17; H, 5.48; N, 10.72. Found: C, 55.20; H, 5.43; N, 10.63.

FAB Mass spectrum, m/z=437 (M+1).

EXAMPLE 53

N-[5-(4-Cyanobenzyl)-1H-imidazol-1-ylethyl]-4(R)-hydroxy-2(S)-[1(S)-1-(3-chlorophenyl)-1-hydroxy]methylpyrrolidine The title compound was prepared according to the procedure described in Example 52 using 4(R)-hydroxy-2(S)-[1(S)-1-(3-chlorophenyl)-1-hydroxy]methylpyrrolidine Anal. calc'd for C$_{24}$H$_{25}$N$_4$O$_2$Cl 2.00 HCl, 0.95 H$_2$O; C, 54.70; H, 5.53; N, 10.63. Found: C, 54.75; H, 5.45; N, 10.55.

FAB Mass spectrum, m/z=437 (M+1).

EXAMPLE 54

N-[1-(4-Cyanobenzyl)-1H-imidazol-5-ylmethyl]-4 (R)-hydroxy-2(S)-[1(S)-1-(3-chlorophenyl)-1-hydroxy]methylpyrrolidine The title compound was prepared according to the procedure described in Example 46 step F using 4(R)-hydroxy-2(S)-[1(R)-1-(3-chlorophenyl)-1-hydroxy] methylpyrrolidine.

Anal. calc'd for C$_{23}$H$_{23}$N$_4$O$_2$Cl 2.00 HCl, 0.80 H$_2$O; C, 54.14; H, 5.25; N, 10.98. Found: C, 54.09; H, 5.30; N, 11.37.

FAB Mass spectrum, m/z=423 (M+1).

EXAMPLE 55

N-[1-(4-Cyanobenzyl)-1-imidazol-5-ylmethyl]-4(R)-hydroxy-2(S)-[1(R)-1-(3-chlorophenyl)-1-hydroxy]methylpyrrolidine The title compound was prepared according to the procedure described in Example 46 step F using 4(R)-hydroxy-2(S)-[(3-chlorophenyl)-(R)-hydroxymethyl]-pyrollidine.

Anal. calc'd for $C_{23}H_{23}N_4O_2Cl$ 2.00 HCl, 0.80 $H_2O$; C, 54.14; H, 5.25; N, 10.98. Found: C, 54.13; H, 5.40; N, 11.09.
FAB Mass spectrum, m/z=423 (M+1).

EXAMPLE 56

N-{1-(4-Cyanobenzyl)-1H-imidazol-5-yl-methyl-4(R)-hydroxy-2(S)-{N'-acetyl-N'-3-chlorobenzyl}aminomethylpyrrolidine

Step A: 4(R)-Hydroxyproline methyl ester

A suspension of 4(R)-hydroxyproline (35.12 g, 267.8 mmol) in methanol (500 ml) was saturated with gasseous hydrochloric acid. The resulting solution was allowed to stand for 16 hrs and the solvent evaporated in vacuo to afford the title compound as a white solid.

$^1$H NMR $CD_3OD$ δ 4.60 (2H, m), 3.86(3H, s), 3.48(1H, dd, J=3.6 and 12.0 Hz), 3.23(1H, d, J=12.0 Hz), 2.43(1H, m) and 2.21(1H, m) ppm.

Step B: N-t-Butoxycarbonyl-4(R)-hydroxyproline methyl ester

To a solution of 4(R)-hydroxyproline methyl ester (53.5 g, 268 mmol), and triethylamine (75 ml, 540 mmol), in $CH_2Cl_2$ (500 ml), at 0° C., was added a solution of di-t-butyl dicarbonate (58.48, 268 mmol), in $CH_2Cl_2$ (75 ml). The resulting mixture was stirred for 48 hrs at room temperature. The solution was washed with 10% aqueous citric acid solution, saturated $NaHCO_3$ solution, dried ($Na_2SO_4$) and the solvent evaporated in vacuo. The title compound was obtained as a yellow oil and used in the next step without furthur purification.

$^1$H NMR $CD_3OD$ δ 4.40-4.30 (2H, m), 3.75(3H, m), 3.60-3.40(2H, m), 2.30(1H, m), 2.05(1H, m) and 1.55-1.40 (9H, m) ppm.

Step C: N-t-Butoxycarbonyl-4(R)-t-butyldimethylsilyloxy proline methyl ester To a solution of N-t-butoxycarbonyl-4(R)-hydroxy proline methyl ester (65.87 g, 268 mmol), and triethylamine (41 ml, 294 mmol), in $CH_2Cl_2$ (536 ml), at 0° C., was added a solution of t-butyldimethyl silylchloide (42.49 g, 282 mmol), in $CH_2Cl_2$ (86 ml). The resulting mixture was stirred for 16 hrs at room temperature. The solution was washed with 10% aqueous citric acid solution, saturated $NaHCO_3$ solution, dried ($Na_2SO_4$) and the solvent evaporated in vacuo. The title compound was obtained as a yellow oil and used in the next step without furthur purification.

$^1$H NMR $CD_3OD$ δ 4.60-4.40 (2H, m), 3.75(3H, m), 3.60-3.20(2H, m), 2.30-1.90(2H, m), 1.45-1.40(9H, m), 0.90-0.85(9H, m), 0.10-0.00(6H, m) ppm.

Step D: N-t-Butoxycarbonyl-4(R)-t-butyldimethylsilyloxy-2(S)-hydroxymethylpyrrolidine A solution of N-t-butoxycarbonyl-4-(R)-t-butyldimethylsilyloxy proline methyl ester (86.65 g, 241 mmol), in THF (150 ml), was added over 90 minutes to a solution of lithium aluminum hydride (247 ml of a 1 M solution in THF, 247 mmol), under argon, so that the temperature did not exceed 12° C. Stirring was continued for 50 mins and then EtOAc (500 ml) was added cautiously, followed by sodium sulphate decahydrate (34 g), and the resulting mixture stirred for 16 hrs at room temperature. Anhydrous sodium sulphate ($3^4$ g) was added and the mixture stirred an additional 30 min and then filtered. The solids were washed with EtOAc (800 ml), the filtrates combined and the solvent evaporated in vacuo. The title compound was obtained as a colourless oil and used in the next step without further purification.

Step E: N-t-Butoxycarbonyl-4(R)-t-butyldimethylsilyloxy-2(S)-methanesulfonyloxymethylpyrrolidine The title compound was prepared according to the procedure described in Example 40 step B using N-t-butoxycarbonyl-4(R)-t-butyldimethylsilyloxy-2(S)-hydroxymethylpyrrolidine.

FAB Mass spectrum, m/z=410(M+1).

$^1$H NMR $CDCl_3$ δ 4.60-4.00 (4H, m), 3.60-3.30(2H, m), 2.98(3H, s), 2.05-2.00(2H, m), 1.48-1.42(9H, m), 0.90-0.80 (9H, m), 0.10-0.00(6H, m) ppm.

Step F: Preparation of N-t-Butoxycarbonyl-4(R)-t-butyldimethylsilyloxy-2(S)-azidomethylpyrrolidine In a flask protected by a safety screen, a solution of N-t-butoxycarbonyl-4(S)-t-butyldimethylsilyloxy-2(S)-methanesulfonyloxy methyl pyrrolidine(10.40 g, 25.39 mmol) and tetrabutylammonium azide (8.18 g, 28.7 mmol) in toluene (250 ml) was stirred at 80° C. for 5 hr. The reaction was cooled to room temperature and diluted with EtOAc (250 ml), washed with water and brine and dried ($Na_2SO_4$). The solvent was evaporated in vacuo to afford the title compound as a yellow oil which was used in the next step without furthur purification.

$^1$H NMR $CDCl_3$ δ 4.60-3.20 (6H, m), 2.05-1.90(2H, m), 1.47(9H, s), 0.87(9H, s) and 0.10-0.00(6H, m) ppm.

Step G: Preparation of N-t-Butoxycarbonyl-4(R)-t-butyldimethylsilyloxy-2(S)-aminomethylpyrrolidine A solution of N-t-butoxycarbonyl-4(R)-t-butyldimethylsilyloxy-2(S)-azidomethylpyrrolidine (9.06 g, 25.39 mmol) in EtOAc (120 ml) was purged with argon and 10% palladium on carbon (1.05 g) added. The flask was evacuated and stirred under an atmosphere of hydrogen (49 psi) for 16 hrs. The hydrogen was replaced by argon, the catalyst removed by filtration and the solvent evaporated in vacuo. The residue was chromatographed ($SiO_2$, 2.5 to 5% saturated $NH_4OH$ in acetonitrile, gradient elution), to afford the title compound as an oil.

$^1$H NMR($CDCl_3$, 400 MHz) δ 4.40-2.60 (6H, s), 2.05-1.80(2H, m), 1.46(9H, s), 1.36(2H, s), 0.87(9H, s), 0.10-0.00(6H, m)ppm.

Step H: Preparation of N-t-Butoxycarbonyl-4(R)-t-butyldimethylsilyloxy-2(S)-{N'-3-chlorobenzyl}aminomethylpyrrolidine To a slurry of 3-chlorobenzaldehyde (1.2 ml, 10.6 mmol), crushed 3A molecular sieves (9.5 g) and the amine from step G (3.50 g, 10.6 mmol) in methanol (150 ml) was added sodium cyanoborohydride (11.0 ml of a 1M solution in THF, 11.0 mmol) at room temperature. The pH was adjusted to 7 by the addition of glacial acetic acid (0.68 ml, 12 mmol) and the reaction was stirred for 16 hrs. The reaction was filtered and the filtrate evaporated in vacuo. The residue was partitioned between EtOAc and saturated $NaHCO_3$ solution and the organic extract washed with brine, dried ($Na_2SO_4$), and the solvent evaporated in vacuo. The residue was purified by chromatography ($SiO_2$, 2.5% MeOH in $CH_2Cl_2$) to provide the title compound as an oil.

¹HNMR(CDCl₃, 400 MHz) δ 7.40-7.10(4H, m), 4.36(1H, s), 4.15-3.90(2H, m), 3.90-3.30(2H, m), 2.85-2.60(2H, m), 2.05-1.90(2H, m), 1.44(9H, s), 0.87(9H, s) and 0.06(6H, m) ppm.

Step I: Preparation of N-t-Butoxycarbonyl-4(R)-t-butyldimethylsilyloxy-2(S)-{N'-3-chlorobenzyl-N'-acetyl}-aminomethylpyrrolidine To a solution of N-t-butoxycarbonyl-4(R)-t-butyldimethylsilyloxy-2(S)-{N'-3-chlorobenzyl}-aminomethyl pyrrolidine (3.80 g, 8.35 mmol) in CH₂Cl₂ (85 ml) and triethylamine (2.40 ml, 17.0 mmol) at 0° C. was added acetyl chloride (0.60 ml, 8.44 mmol). The reaction was stirred at room temperature for 1 hr, diluted with water and extracted with CH₂Cl₂. The extracts were washed with brine, dried (Na₂SO₄) and the solvent evaporated in vacuo. The residue was purified by chromatography (SiO₂, 10 to 25% EtOAc in CH₂Cl₂, gradient elution).

¹HNMR (CDCl₃, 400 MHz) δ 7.40-7.00(4H, m), 5.10-3,00(8H, m), 2.20-1.70(5H, m), 1.50-1.30(9H, m), 0.87(9H, s) and 0.06(6H, m) ppm.

Step J: Preparation of N-t-Butoxycarbonyl-4(R)-hydroxy-2(S)-{N'-3-chlorobenzyl-N'-acetyl}-aminomethylpyrrolidine To a solution of N-t-butoxycarbonyl-4(R)-t-butyldimethylsilyloxy -2(S)-{N'-3-chlorobenzyl-N'-acetyl}-aminomethylpyrrolidine (4.02 g, 8.09 mmol) in THF (80 ml) at 0° C. was added tetrabutylammonium fluoride (9.00 ml of a 1M solution in THF, 9.00 mmol). The reaction was stirred at 0° C. for 1 hr and then at room temperature for 30 min. The reaction was quenched by the addition of a saturated NH₄Cl solution (50 ml), dilution with EtOAc. The organic extracts were washed with brine, dried (Na₂SO₄) and the solvent evaporated in vacuo. The residue purified by chromatography (SiO₂, 3 to 5% MeOH in CH₂Cl₂, gradient elution) to afford the title compound as a foam.

¹HNMR (CDCl₃, 400 MHz) δ 7.40-7.00(4H, m), 5.00-4,00(4H, m), 4.00-3.10(4H, m), 2.30-1.60(5H, m) and 1.50-1.30(9H, m) ppm.

Step K: 4(R)-hydroxy-2(S)- {N'-3-chlorobenzyl-N'-acetyl}-aminomethylpyrrolidine hydrochloride The title compound was prepared by the procedure described in Example 1 step G using N-t-butoxycarbonyl-4(R)-hydroxy-2(S)-{N'-3-chlorobenzyl-N'-acetyl}-aminomethylpyrrolidine.

¹H NMR(CD₃OD, 400 MHz) δ 7.50-7.15(4H, m), 4.75 (2H, m), 4.52(1H, m), 4.00-3.90(2H, m), 3.45(2H, m), 3.18(1H, brd, J=7.3 Hz), 2.20(3H,s), 2.05(1H, m) and 1.85 (1H, m) ppm.

Step L: 1-(4-Cyanobenzyl)-5-imidazole carboxaldehyde

To a solution of 1-(4-Cyanobenzyl)-5-(hydroxymethyl)-imidazole (21.5 g, 101 mmol) in DMSO (500 ml) at room temperature was added triethylamine (56 ml, 402 mmol), then SO₃-pyridine complex (40.5 g, 254 mmol). After 45 min, the reaction was poured into EtOAc, washed with water and brine, dried (Na₂SO₄), and concentrated in vacuo to provide the aldehyde as a white powder which was sufficiently pure without further purification.

Step M: N-{1-(4-Cyanobenzyl)-1H-imidazol-5-yl-methyl-4(R)-hydroxy-2(S)-{N'-3-chlorobenzyl-N'-acetyl}-aminomethylpyrrolidine To a slurry of 1-(4-Cyanobenzyl)-5-imidazole carboxaldehyde (165 mg, 0.781 mmol), crushed 3A molecular sieves (0.78 g), and the amine hydrochloride from step K (0.235 mg, 0.66 mmol) in methanol (10 ml) was added sodium cyanoborohydride (0.80 ml of a 1M solution in THF, 0.80 mmol) at room temperature. The reaction was stirred for 16 hrs, filtered and the filtrate evaporated in vacuo. The residue was partitioned between EtOAc and saturated NaHCO₃ solution and the organic extract washed with brine, dried (Na₂SO₄), and the solvent evaporated in vacuo. The residue was purified by chromatography (SiO₂, 5% NH₄OH in acetonitrile) to provide the title compound as a foam.

Anal. calc'd for $C_{26}H_{28}N_5O_2Cl$ 1.00 H₂O: C, 62.96; H, 6.10; N, 14.12. Found: C, 62.96; H, 5.78; N, 14.02.

FAB HRMS exact mass calc'd for $C_{26}H_{29}N_5O_2Cl$ 478.200978 (MH⁺), found 478.200698

EXAMPLE 57

N-{1-(4-Cyanobenzyl)-1H-imidazol-5-ylacetyl}-4(R)-hydroxy-2(S)-{N'-acetyl-N'-3-chlorobenzyl}aminomethylpyrrolidine The title compound was prepared using the procedure described in Example 1 stepH, and 4(R)-hydroxy-2(S)-{N'-acetyl-N'-3-chlorobenzyl}-aminomethypyrrolidine hydrochloride.

Anal. calc'd for $C_{27}H_{28}N_5O_3Cl$ 1.0-HCl, 1.15 H₂O: C, 61.57; H, 5.80; N, 13.30. Found: C, 61.60; H, 5.47; N, 13.21.

FAB HRMS exact mass calc'd for $C_{26}H_{29}N_5O_2Cl$ 506.195893 (MH⁺), found 506.197103.

EXAMPLE 58

N{1-(4-Cyanobenzyl)-1H-imidazol-5-yl-methyl-4(R)-hydroxy-2(S)- {N'-acetyl-N'-3-chlorobenzyl}aminomethylpyrrolidine

Step A: N-t-Butoxycarbonyl-4(R)-methoxy-2(S)-{N'-acetyl-N'-3-chlorobenzyl}aminomethylpyrrolidine To a solution of N-t-Butoxycarbonyl-4(S)-hydroxy -2(S)-{N'-acetyl-N' 3-chlorobenzyl}aminomethylpyrrolidine (928 mg, 2.42 mmol) in DMF (12 ml) at 0° C. was added sodium hydride (145 mg of a 60% dispersion in mineral oil, 3.63 mmol). After 15 min methyl iodide (0.30 ml, 4,82 mmol), was added and the reaction stirred at room temperature for 16 hrs. The reaction was quenched with saturated NaHCO₃ solution (2 ml) and extracted with ethyl acetate. The orgainic extract was washed with brine and dried (Na₂SO₄, and the solvent evaporated in vacuo. The residue was purified by chromatography (SiO₂, 25 to 50% EtOAc in CH₂Cl₂, gradient elution) to afford the title compound as a foam.

¹H NMR(CD₃OD, 400 MHz) δ 7.50-7.10(4H, m), 4.90-4.05(4H, m), 3.95(1H, m), 3.90-3.30(3H, m), 3.30(3H, s), 2.10-1.70(5H, s) and 1.60-1.30(9H, m) ppm.

Step B: 4(S)-Methoxy-2(S)-{N'-acetyl-N'-3-chlorobenzyl}-aminomethylpyrrolidine hydrochloride The title compound was prepared by the procedure described in Example 1 step G using N-t-butoxycarbonyl-4(S)-methoxy-2(S)-{N'-acetyl-N'-3-chlorobenzyl}aminomethylpyrrolidine.

¹H NMR(CD₃OD, 400 MHz) δ 7.40(1H, t, J=7.7 Hz), 7.35(1H, d, J=9.2 Hz), 7.29(1H, s), 7.20(1H, d, J=7.7 Hz), 4.73(1H, d, J=17.0 Hz), 4.68(1H, d, J=17.0 Hz), 4.10(1H, m), 3.96(1H, m), 3.81(1H, m), 3.50-3.37(2H, m), 3.32-3.30 (4H, m), 2.30-2.24(1H, m), 2.18(3H, s) and 1.75(1H, m)ppm.

Step C: N{1-(4-Cyanobenzyl)-1H-imidazol-5-yl-methyl-4(R)-hydroxy-2(S)-{N'-acetyl-N'-3-chlorobenzyl} aminomethylpyrrolidine The title compound was prepared by the procedure described in Example 56 step M using 1-(4-Cyanobenzyl)-5-imidazole carboxaldehyde and the amine hydrochloride from step B.

Anal. calc'd for $C_{27}H_{30}N_5O_2Cl$ 2.25HCl, 1.60 $H_2O$: C, 53.79; H, 5.93N, 11.62. Found: C, 53.79; H, 5.92; N, 11.39.

FAB HRMS exact mass calc'd for $C_{27}H_{31}N_5O_2Cl$ 492.216628(MH$^+$), found 492.216101.

EXAMPLE 59

N-{1-(4-Cyanophenethyl)-1H-imidazol-5-yl-methyl-4(R)-hydroxy-2(S)-{N'-acetyl-N'-3-chlorobenzyl}aminomethylpyrrolidine Step A: Preparation of 1-(4-Cyanophenyl)ethyl bromide To a solution of 1-(4-Cyanophenyl)ethanol 1.01 g, 6.84 mmol), in diethyl ether (15 ml) and triphenylphosphine (2.14 g, 8.17 mmol), was added carbon tetrabromide (2.82 g, 8.50 mmol) in dieathylether (20 ml) at room temperature. After 30 min the reaction was filtered through celite and evaporated to dryness. The residue was purified by chromatography (SiO2, 5% EtOAc in hexanes) to afford the title compound as an oil $^1$H NMR(CDCl$_3$, 400 MHz) δ 7.64(2H, d, J=8.2 Hz), 7.53(2H, d, J=8.2 Hz), 5.15(1H, q, J=7.0 Hz) and 2.03(3H, d, J=7.0 Hz) ppm.

Step B: 1-(4-Cyanophenethyl)-1H-imidazol-5-yl-carboxaldehyde

A mixture of 3-tritylimidazol-5yl-carboxaldehyde (805 mg, 2.38 mmol), and the bromide from step A (0.50 g, 2,38 mmol), was heated at 60° C. for 16 hrs in the presense of tetrabutylammonium iodide (89 mg, 0.24 mmol) in acetonitrile (10 ml). The cooled reaction was diluted with EtOAc and washed with saturated aqueous NaHCO$_3$, brine and dried (Na$_2$SO$_4$). The solvent was evaporated in vacuo and the residue chromatographed (SiO$_2$, 5% MeOH in CH$_2$Cl$_2$) to afford the title compound.

Step C: N-{1-(4-Cyanophenethyl)-1H-imidazol-5-yl-methyl-4(R)-hydroxy-2(S)-{N'-acetyl-N'-3-chlorobenzyl}aminomethylpyrrolidine The title compound was prepared by the procedure described in Example 56 step M using 1-(4-Cyanophenethyl)-1H-imidazol-5-yl- carboxaldehyde and 4(R)-methoxy-2(S)-{N'-acetyl-N'-3-chlorobenzyl}aminomethylpyrrolidine hydrochloride.

FAB HRMS exact mass calc'd for $C_{28}H_{33}N_5O_2Cl$ 506.232278 (MH$^+$), found 506.231473.

EXAMPLE 60

N {1-(4-Cyanobenzyl)-1H-imidazol-5-yl-acetyl}-4(R)-methoxy-2(S)-{N'-acetyl-N'-3-chlorobenzyl}aminomethylpyrrolidine The title compound was prepared according to the procedure described in Example 1 step H using 4(R)-methoxy-2(S)-{N'-acetyl-N'-3-chlorobenzyl}aminomethylpyrrolidine hydrochloride.

Anal. calc'd for $C_{28}H_{30}N_5O_2Cl$ 2.00 TFA, 0.50 $H_2O$: C, 50.77; H, 4.39, N, 9.25. Found: C, 50.78; H, 4.38; N, 9.24.

FAB HRMS exact mass calc'd for $C_{28}H_{31}N_5O_2Cl$ 520.211543 (MH$^+$), found 520.211434.

EXAMPLE 61 AND 62

N-{1-(4-Cyanopheneth-1-yl)-1H-imidazol-5-yl-acetyl-4(R)-methoxy-2(S)-{N'-acetyl-N'-3-chlorobenzyl}aminomethylpyrrolidine Step A: Preparation of (R,S)[1-(4-cyanopheneth-1-yl)-1H-imidazol-5-yl]acetic acid The title compound was prepared according to the procedure in Example 1 steps C and D replacing 4 cyanobenzylbromide with 1-(4-cyanophenyl)ethyl bromide.

$^1$H NMR CD$_3$OD δ 8.44 (1H, d, J=0.8 Hz) 7.73(2H,d, J=8.3 Hz), 7.38(2H,d, J=8.3 Hz),7.14(1H,s), 5.73(1H,q, J=7.0 Hz), 3.55(1H,d, J=17.2 Hz), 3.33(1H,d, J=17.2 hz) and 1.92(3H,d, J=7.0 Hz)ppm.

Step B: N-{1-(4-Cyanophen-(R,S)-ethyl)-1H-imidazol-5-yl-acetyl-4(R)-methoxy-2(S)-{N'-acetyl-N'-3-chlorobenzyl}aminomethylpyrrolidine The title compounds was prepared according to the procedure described in Example 1 step H using 4(S)-Methoxy-2(S)-{N'-acetyl-N'-3-chlorobenzyl}aminomethylpyrrolidine hydrochloride and the acids from step A.

Anal. calc'd for $C_{29}H_{32}N_5O_3Cl$ 2.10 TFA, 0.35 $H_2O$: C, 51.14; H, 4.50, N, 8.98. Found: C, 51.15; H, 4.53; N, 8.99.

FAB HRMS exact mass calc'd for $C_{29}H_{33}N_5O_3Cl$ 534.227193 (MH$^+$), found 534.226630. and Anal. calc'd for $C_{29}H_{32}N_5O_3Cl$ 1.90 TFA, 0.25 $H_2O$: C, 52.17; H, 4.59, N, 9.27. Found: C, 52.15; H, 4.61; N, 9.19.

FAB HRMS exact mass calc'd for $C_{29}H_{33}N_5O_3Cl$ 534.227193 (MH$^+$), found 534.228764.

EXAMPLE 63

N{1-(4-Cyanobenzyl)-1H-imidazol-5-yl-ethyl}-4(R)-methoxy-2(S)-{N'-acetyl-N'-3-chlorobenzyl}aminomethylpyrrolidine Step A: Preparation of (1-(4-Cyanobenzyl)-1H-imidazol-5-yl)-ethanol To a stirred solution of the ester from Example 1, step C, (1.50 g, 5.88 mmol), in methanol (20 ml) at 0° C., was added sodium borohydride (1.0 g, 26.3 mmol) portionwise over 5 minutes. The reaction was stirred at 0° C. for 1 hr and then at room temperature for an additional 1 hr. The reaction was quenched by the addition of sat. NH$_4$Cl solution and the methanol was evaporated in vacuo. The residue was partitioned between EtOAc and sat NaHCO$_3$ solution and the organic extracts dried (MgSO$_4$), and evaporated in vacuo. The residue was purified by chromatography (SiO$_2$, 4 to 10% methanol in methylene chloride, gradient elution) to afford the title compound as a solid.

$^1$H NMR CDCl$_3$ δ 7.64(2H, d, J=8.2 Hz), 7.57(1H, s), 7.11(2H, d, J=8.2 Hz), 6.97(1H, s), 5.23(2H, s), 3.79(2H, t, J=6.2 Hz) and 2.66(2H, t, J=6.2 Hz) ppm.

Step B: 1-(4-Cyanobenzyl)-imidazol-5-yl-ethylmethanesulfonate

A solution of (1-(4-Cyanobenzyl)-1H-imidazol-5-yl)-ethanol (0.500 g, 2.20 mmol) in methylene chloride (6.0 ml)

at 0° C. was treated with Hunig's base (0.460 ml, 2.64 mmol) and methane sulfonyl chloride (0.204 ml, 2.64 mmol). After 2 hrs, the reaction was quenched by addition of saturated NaHCO$_3$ solution (50 ml) and the mixture was extracted with methylene chloride (50 ml), dried (MgSO$_4$) and the solvent evaporated in vacuo. The title compound was used without furthur purification.

$^1$H NMR CDCl$_3$ δ 7.69 (1H, s) 7.66(2H, d, J=8.2 Hz), 7.15 (2H, d, J=8.2 Hz), 7.04(1H, s), 5.24(2H, s), 4.31(2H, t, J=6.7 Hz), 2.96(3H, s), and 2.88(2H, t, J=6.6 Hz)ppm.

Step C: N{1-(4-Cyanobenzyl)-1H--imidazol-5-ylethyl}-4(R)-methoxy-2(S)-{N'-acetyl-N'-3-chlorobenzyl}aminomethylpyrrolidine A mixture of 4(R)-methoxy-2(S)- {N'-acetyl-N'-3-chlorobenzyl-aminomethyl}pyrrolidine (135 mg, 0.405 mmol), the mesylate from step B (114 mg, 0.373 mmol), potassium carbonate (140 mg, 1.01 mmol), and sodium iodide (243 mg, 1.62 mmol) in DMF (1.0 ml), were heated at 55° C. for 16 hrs. The cooled mixture was diluted with EtOAc, washed with NaHCO$_3$ solution and brine, dried (Na$_2$SO$_4$) and the solvent evaporated in vacuo. The residue was purified by preparative HPLC (C-18, 95:5 to 5:95 water in acetonitrile containing 0.1% TFA, gradient elution). The title compound was obtained as a white solid after lyophillisation.

Anal. calc'd for C$_{28}$H$_{32}$N$_5$O$_2$Cl 3.15 TFA, 0.45 H$_2$O: C, 47.17; H, 4.16, N, 8.02. Found: C, 47.16; H, 4.19; N, 7.99.

FAB HRMS exact mass calc'd for C$_{28}$H$_{33}$N$_5$O$_2$Cl 506.232278 (MH$^+$), found 506.231017.

EXAMPLE 64

N {1-(4-Cyanobenzyl)-1H-imidazol-5-ylethyl}-2(S)-{N'-acetyl-N'-3-chlorobenzyl}aminomethylpyrrolidine The title compound was prepared by the procedure described in Example 63 using 2(S)-{N'-acetyl-N'-3-chlorobenzyl}aminomethylpyrrolidine Anal. calc'd for C$_{27}$H$_{30}$N$_5$OCl 2.15 HCl, 3.05 H$_2$O: C, 53.22; H, 6.33, N, 11.49. Found: C, 53.23; H, 6.33; N, 11.29.

EXAMPLE 65

N{1-(4-Cyanophenethyl)-1H--imidazol-5-yl-ethyl}-4(R)-methoxy-2(S)-N'-acetyl-N'-3-chlorobenzyl}aminomethylpyrrolidine The title compound was prepared using the procedure described in Example 63 using (R,S)-[1-(4-cyanopheneth-1-yl)-1H-imidazol-5-yl]acetic acid methyl ester in place of 1-(4-cyanobenzyl)-1H-imidazol-5-yl]acetic acid methyl ester.

Anal. calc'd for C$_{29}$H$_{34}$N$_5$O$_2$Cl 3.15 TFA, 0.65 H$_2$O: C, 47.59; H, 4.35; N, 7.86. Found: C, 47.60; H, 4.35; N, 7.83.

FAB HRMS exact mass calc'd for C$_{29}$H$_{35}$N$_5$O$_2$Cl 520.247928 (MH$^+$), found 520.247518.

EXAMPLE 66

N-{1-(4-Cyanobenzyl)-1H-imidazol-5-ylmethyl}-4(R)-benzyloxy-2(S)-{N'-acetyl-N'-3-chlorobenzyl}aminomethylpyrolidine The title compound was prepared as in Example 58 using benzyl bromide in place of methyl iodide.

Anal. calc'd for C$_{33}$H$_{34}$N$_5$O$_2$Cl 2.75 TFA, 0.95 H$_2$O: C, 51.45; H, 4.33; N, 7.79. Found: C, 51.45; H, 4.37; N, 7.70.

FAB HRMS exact mass calc'd for C$_{33}$H$_{35}$N$_5$O$_2$Cl 568.247928 (MH$^+$), found 568.247609.

EXAMPLE 67

N-{1-(4-Cyanobenzyl)-1H-imidazol-5-ylethyl}-4(R)-benzyloxy-2(S)-{N'-acetyl-N'-3-chlorobenzyl}aminomethyl pyrrolidine The title compound was prepared as in Example 63 using 4(R)-benzyloxy-2(S)-{N'-acetyl-N'-3-chlorobenzyl}aminomethyl pyrrolidine Anal. calc'd for C$_{34}$H$_{36}$N$_5$O$_2$Cl 3.00 TFA, 0.85 H$_2$O: C, 51.14; H, 4.37, N, 7.45. Found: C, 51.15; H, 4.42; N, 6.86.

FAB HRMS exact mass calc'd for C$_{34}$H$_{37}$N$_5$O$_2$Cl 582.263579 (MH$^+$), found 582.263900.

EXAMPLE 68

N-{1-(4-Cyanobenzyl)-5-imidazolacetyl}-4(R)-benzyloxy-2(S)- {N'-acetyl-N'-3-chlorobenzyl}aminomethylpyrrolidine The title compound was prepared as in Example 60 using 4(R)-benzyloxy-2(S)-{N'-acetyl-N'-3-chlorobenzyl-aminomethyl}pyrrolidine Anal. calc'd for C$_{34}$H$_{34}$N$_5$O$_3$Cl 1.85 TFA, 0.60 H$_2$O: C, 55.37; H, 4.57; N, 8.56. Found: C, 55.35; H, 4.53; N, 8.57.

FAB HRMS exact mass calc'd for C$_{34}$H$_{35}$N$_5$O$_3$Cl 596.242843 (MH$^+$), found 596.241293.

EXAMPLE 69

N{1-(4-Cyanobenzyl)-5-imidazol-5-ylmethyl}-4(R)-(2-henylbenzyloxy)-2(S)-{N'-acetyl-N'-3-chlorobenzyl}aminomethylpyrrolidine The title compound was prepared as in Example 58 using 2-phenylbenzyl bromide in place of methyl iodide.

Anal. calc'd for C$_{39}$H$_{38}$N$_5$O$_2$Cl 2.50 TFA, 0.10 H$_2$O: C, 56.76; H, 4.41; N, 7.52. Found: C, 56.78; H, 4.27; N, 7.16.

FAB HRMS exact mass calc'd for C$_{39}$H$_{39}$N$_5$O$_2$Cl 644.279229 (MH$^+$), found 644.279744.

EXAMPLE 70

N-{1-(4-Cyanobenzyl)-1H-imidazol-5-ylmethyl}-4(R)-(4-chlorobenzyloxy)-2(S)- {N'-acetyl-N'-3-chlorobenzyl}aminomethylpyrrolidine The title compound was prepared as in Example 58 using 4-chlorobenzyl bromide in place of methyl iodide.

Anal. calc'd for C$_{33}$H$_{33}$N$_5$O$_2$Cl$_2$ 3.15 TFA: C, 49.08; H, 3.79; N, 7.28. Found: C, 49.10; H, 3.67; N, 7.31.

FAB HRMS exact mass calc'd for C$_{33}$H$_{34}$N$_5$O$_2$Cl$_2$ 602.208956 (MH$^+$), found 602.208118.

EXAMPLE 71

N{1-(4-Cyanobenzyl)-5-imidazolemethyl}-4(R)-(4-cyanobenzyloxy)-2(S)-{N'-acetyl-N'-3-chlorobenzyl}aminomethylpyrrolidine The title compound was prepared as in Example 58 using 4-cyanobenzyl bromide in place of methyl iodide.

Anal. calc'd for C$_{34}$H$_{33}$N$_6$O$_2$Cl 2.85 TFA: C, 51.94; H, 3.94; N, 9.15. Found: C, 51.93; H, 3.83; N, 9.16.

FAB HRMS exact mass calc'd for C$_{34}$H$_{34}$N$_6$O$_2$Cl 593.243177 (MH$^+$), found 593.243346.

EXAMPLE 72

N{1-(4-Cyanobenzyl)-5-imidazol-5-ylmethyl}-4(R)-(3-pyridylmethoxy)-2(S)-{N'-acetyl-N'-3-chlorobenzyl}aminomethylpyrrolidine The title compound was prepared as in Example 58 using 3-picolyl chloride in place of methyl iodide.

Anal. calc'd for $C_{32}H_{33}N_6O_2Cl$ 4.45 TFA: C, 45.22; H, 3.58; N, 7.74. Found: C, 45.20; H, 3.56; N, 7.86.

FAB HRMS exact mass calc'd for $C_{32}H_{34}N_6O_2Cl$ 569.243177(MH$^+$), found 569.243177.

EXAMPLE 73

N{1-(4-Cyanobenzyl)-1H-imidazol-5-ylmethyl}-4(R)-(phenoxy)-2(S)-{N'-acetyl-N'-3-chlorobenzyl}aminomethylpyrrolidine The title compound was prepared as in Example 58 using diphenyliodonium chloride in place of methyl iodide.

Anal. calc'd for $C_{32}H_{32}N_5O_2Cl$ 2.75 TFA, 0.35 $H_2O$: C, 51.54; H, 4.09; N, 8.01. Found: C, 51.55; H, 4.12; N, 7.75.

FAB HRMS exact mass calc'd for $C_{32}H_{33}N_5O_2Cl$ 554.232278 (MH$^+$), found 554.232523.

EXAMPLE 74

N-{1-(4-Cyanobenzyl)-1H-imidazol-5-ylmethyl}-4(R)-(2-methylacetyloxy)-2(S)-{N'-acetyl-N'-3-chlorobenzyl}aminomethylpyrrolidine The title compound was prepared as in Example 58 using 2-bromo methylacetate in place of methyl iodide.

FAB HRMS exact mass calc'd for $C_{29}H_{33}N_5O_4Cl$ 550.222108 MH$^+$), found 550.221829.

EXAMPLE 75

N-{1-(4-Cyanobenzyl)-1H-imidazol-5-ylmethyl}-4(R)-(acetyloxy)-2(S)-{N-acetyl-N'-3-chlorobenzyl}aminomethylpyrrolidine To a solution of N-{1-(4-Cyanobenzyl)-1H-imidazol-5-ylmethyl}-4(R)-(2-methylacetyloxy)-2(S)- {N'-acetyl-N'-3-chlorobenzyl-aminomethyl}pyrrolidine (43 mg, 0.055 mmol) in THF (0.5 ml) was added lithium hydroxide (0.221 ml, 0.221 mmol) and the solution stirred at room temperature for 16 hrs. The reaction was quenched by the addition of trifluoroacetic acid (0.013 ml) and the solvents evaporated in vacuo. The residue was purified by preparative HPLC (C-18, 95 to 5% water in acetonitrile containing 0.1% TFA, gradient elution), to afford the title compound.

Anal. calc'd for $C_{28}H_{30}N_5O_4Cl$ 2.95 TFA, 1.15 $H_2O$: C, 45.59; H, 3.98; N, 7.84. Found: C, 45.59; H, 4.02; N, 7.83.

EXAMPLE 76

N-{1-(4-Cyanobenzyl)-1H-imidazol-5-ylacetyl}-4(R)-(2-methylacetyloxy)-2(S)-{N'-acetyl-N'-3-chlorobenzyl}aminomethylpyrrolidine The title compound was prepared as in Example 60 using 2-bromo methylacetate in place of methyl iodide.

FAB HRMS exact mass calc'd for $C_{30}H_{33}N_5O_5Cl$ 578.217022 (MH$^+$), found 578.216687.

EXAMPLE 77

N-{1-(4-Cyanobenzyl)-1H-imidazol-5-ylacetyl}-4(R)-(acetyloxy)-2(S)-{N'-3-chlorobenzyl-N'-acetyl}aminomethylpyrrolidine To a solution of N-{1-(4-Cyanobenzyl)-1H-imidazol-5-ylacetyl}-4(R)-(2-methylacetyloxy)-2(S)- {N'-acetyl-N'-3-chlorobenzyl}-aminomethylpyrrolidine (38 mg, 0.055 mmol) in THF (0.5 ml) was added lithium hydroxide (0.164 ml, 0.164 mmol) and the solution stirred at room temperature for 16 hrs. The reaction was quenched by the addition of trifluoroacetic acid (0.013 ml) and the solvents evaporated in vacuo. The residue was purified by preparative HPLC (C-18, 95 to 5% water in acetonitrile containing 0.1% TFA, gradient elution) to afford the title compound.

Anal. calc'd for $C_{29}H_{30}N_5O_5Cl$ 1.50 TFA, 1.15 $H_2O$: C, 50.85; H, 4.51; N, 9.27. Found: C, 50.84; H, 4.54; N, 9.18.

EXAMPLE 78

N{1-(4-Cyanobenzyl)-1H-imidazol-5-ylmethyl}-4(S)-(phenoxy)-2(S)-{N'-acetyl-N'-3-chlorobenzyl}aminomethylpyrrolidine Step A: Preparation of N-t-Butoxycarbonyl-4(S)-phenoxy-2(S)-{N'-acetyl-N'-3-chlorobenzyl}aminomethylpyrrolidine To a solution of N-t-butoxycarbonyl-4(S)-hydroxy-2(S)-{N'-acetyl-N'-3-chlorobenzyl}aminomethylpyrrolidine (200 mg, 0.522 mmol, prepared in step J Example 56), phenol (49.1 mg, 0.522 mmol) and triphenylphosphine (137.3 mg, 0.524 mmol), in THF (13.0 ml), at room temperature was added diethylazodicarboxylate (0.083 ml, 0.53 mmol) and the mixtured stirred for 16 hrs. The solvent was evaporated in vacuo and the residue purified by chromatography (SiO$_2$, 50% EtOAc in hexanes) to afford the title compound as an oil.

$^1$H NMR CD$_3$OD d 7.50-6.70 (9H, m), 5.10-5.00 (1H, m), 4.80-4.20(3H, m), 4.00-3.20(4H, m), 2.40-2.00(5H, m) and 1.46(9H,s) ppm.

Step B: 4(S)-Phenoxy-2(S)-{N'-acetyl-N'-3-chlorobenzyl}-aminomethylpyrrolidine

The title compound was prepared by the procedure described in Example 1 step G using N-t-butoxycarbonyl-4(S)-phenoxy-2(S)-{N'-acetyl-N'-3-chlorobenzyl}aminomethylpyrrolidine $^1$H NMR(CD$_3$OD, 400 MHz) δ 7.50-6.90 (9H, m), 5.18 (1H, m), 4.70(2H, m), 4.10-4.00(1H, m), 3.94(1H, m), 3.63(1H, d, J=12.8 Hz), 3.54(1H, dd, J=12.8 and 5.3 Hz), 3.40(1H, dd, J=3.5 and 14.9 Hz), 2.60(1H, m), 2.20(3H, s) and 2.00(1H, m) ppm.

Step C: 1-(4-Cyanobenzyl)-5-imidazolemethyl-4(R)-(phenoxy)-2(S)-{N'-3-chlorobenzyl-N'-acetyl}aminomethyl pyrrolidine The title compound was prepared as in Example 73 using 4(S)-(phenoxy)-2(S)- {N' acetyl-N'-3-chlorobenzyl}-aminomethylpyrrolidine Anal. calc'd for $C_{32}H_{32}N_5O_2Cl$ 2.70 TFA, 0.10 $H_2O$: C, 52.01; H, 4.07; N, 8.11. Found: C, 52.03; H, 4.10; N, 7.96.

FAB HRMS exact mass calc'd for $C_{32}H_{33}N_5O_2Cl$ 554.232278 (MH$^+$), found 554.231721.

EXAMPLE 79

N{1-(4-Cyanobenzyl)-5-imidazolethyl}-4(S)-(phenoxy)-2(S)-{N'-acetyl-N'-3-chlorobenzyl}aminomethylpyrrolidine The title compound was prepared as in Example 63 using 4(S)-(2-phenylbenzyloxy)-2(S)-{N'-acetyl-N'-3-chlorobenzyl}-aminomethylpyrrolidine Anal. calc'd for $C_{33}H_{34}N_5O_2Cl$ 2.00 HCl, 0.55 $H_2O$: C, 60.89; H, 5.74; N, 10.76. Found: C, 60.90; H, 5.86; N, 11.06. FAB MS 567 (M+1).

EXAMPLE 80

N{1-(4-Cyanobenzyl)-1H-imidazol-5-ylethyl}-4(S)-fluoro-2(S)-{N'-acetyl-N'-3-chlorobenzyl}aminomethylpyrrolidine Step A: N-t-Butoxycarbonyl-4(S)-fluoro -2(S)-{N'-acetyl-N'-3-chlorobenzyl}aminomethylpyrrolidine To a solution of N-t-butoxycarbonyl-4(S)-hydroxy-2(S)-{N'-acetyl-N'-3-chlorobenzyl}aminomethylpyrrolidine (2.11 g, 5.51 mmol, prepared in step J Example 56, and diethylaminosulfur trifluoride (0.90 ml, 6.81 mmol), in $CH_2Cl_2$ (120 ml), at 0° C. was stirred for 1 hr. Methanol (20 ml) was added and after 30 min the reaction was diluted with $CH_2Cl_2$ and washed with saturated aqueous $NaHCO_3$ solution, dried ($Na_2SO_4$), and the solvent evaporated in vacuo. The residue purified by chromatography ($SiO_2$, 1.5 to 2.5% MeOH in $CH_2Cl_2$ gradient elution) to afford the title compound as an oil.

Step B: Preparation of 4(S)-fluoro-2(S)-{N'-acetyl-N'-3-chlorobenzyl}aminomethylpyrrolidine The title compound was prepared by the procedure described in Example 1 step G using N-t-butoxycarbonyl-4(S)-fluoro-2(S)-{N'-acetyl-N'-3-chlorobenzyl}aminomethylpyrrolidine.

Step C: N{1-(4-Cyanobenzyl)-1H-imidazol-5-ylethyl-4(S)-(fluoro)-2(S)-{N'-acetyl-N'-3-chlorobenzyl}aminomethyl pyrrolidine The title compound was prepared as in Example 63 using 4(S)-fluoro-2(S)-{N'-acetyl-N'-3-chlorobenzyl}aminomethylpyrrolidine.

Anal. calc'd for $C_{27}H_{329}N_5OClF$ 2.90 TFA: C, 47.77; H, 3.90;N, 8.49. Found: C, 47.80; H, 3.91; N, 8.46.

FAB MS 494 (M+1)

EXAMPLE 81

N{1-(4-Cyanobenzyl)-1H-imidazol-5-ylethyl-4(R)-(2-phenylbenzyloxy)-2(S)-{N'-acetyl-N'-3-chlorobenzyl}aminomethylpyrrolidine The title compound was prepared as in Example 63 using 4(R)-(2-phenylbenzyloxy)-2(S)-{N'-acetyl-N'-3-chlorobenzyl}aminomethylpyrrolidine Anal. calc'd for $C_{40}H_{40}N_5O_2Cl$ 3.15 TFA: C, 54.56; H, 4.29; N, 6.87. Found: C, 54.56; H, 4.03; N, 6.93.

FAB HRMS exact mass calc'd for $C_{40}H_{41}N_5O_2Cl$ 658.294879 (MH$^+$), found 658.294834.

EXAMPLE 82

N{1-(4-Cyanobenzyl)-1H-imidazol-5-ylethyl}-4(R)-(4-chlorobenzyloxy)-2(S)-{N'-acetyl-N'-3-chlorobenzyl}aminomethylpyrrolidine The title compound was prepared as in Example 63 using 4(R)-(4-chlorobenzyloxy)-2(S)-{N'-acetyl-N'-3-chlorobenzyl}aminomethylpyrrolidine Anal. calc'd for $C_{34}H_{35}N_5O_2Cl_2$ 3.20 TFA, 0.15 $H_2O$: C, 49.31; H, 3.94; N, 7.12. Found: C, 49.31; H, 3.72; N, 7.26.

FAB HRMS exact mass calc'd for $C_{34}H_{36}N_5O_2Cl_2$ 616.224606 (MH$^+$), found 616.223491.

EXAMPLE 83

N{1-(4-Cyanobenzyl)-1H-imidazol-5-ylethyl}-4(R)-(4-cyanobenzyloxy)-2(S)-{N'-acetyl-N'-3-chlorobenzyl}aminomethylpyrrolidine The title compound was prepared as in Example 63 using 4(R)-(4-cyanobenzyloxy)-2(S)-{N'-acetyl-N'-3-chlorobenzyl}aminomethylpyrrolidine Anal. calc'd for $C_{35}H_{35}N_6O_2Cl$ 3.10 TFA, 0.10 $H_2O$: C, 51.42; H, 4.01; N, 8.73. Found: C, 51.44; H, 3.90; N, 8.51.

FAB HRMS exact mass calc'd for $C_{35}H_{36}N_6O_2Cl_2$ 607.258827 (MH$^+$), found 607.259832.

EXAMPLE 84

N{1-(4-Cyanobenzyl)-1H-imidazol-5-ylethyl}-4(R)-(3-pyridylmethoxy)-2(S)-{N'-acetyl-N'-3-chlorobenzyl}aminomethylpyrrolidine The title compound was prepared as in Example 63 using 4(R)-(3-pyridylmethoxy)-2(S)-{N'-acetyl-N'-3-chlorobenzyl}aminomethyl-pyrrolidine.

Anal. calc'd for $C_{33}H_{35}N_6O_2Cl$ 3.95 HCl, 1.10 EtOAc: C, 54.51; H, 5.84; N, 10.20. Found: C, 54.55; H, 6.07; N, 10.22.

FAB HRMS exact mass calc'd for $C_{33}H_{36}N_6O_2Cl$ 583.258827 (MH$^+$), found 583.259083.

EXAMPLE 85

N-{1-(4-Cyanobenzyl)-1H-imidazol-5-ylacetyl}-2(S)-{N'-acetyl-N'-3-cyanobenzyl}aminomethylpyrrolidine Step A: Preparation of N-{1-(4-Cyanobenzyl)-1H-imidazol-5-ylacetyl}-2(S)-{N'-3-cyanobenzyl}aminomethylpyrrolidine To a slurry of 3-cyanobenzaldehyde (40.5 mg, 0.309 mmol), crushed 3A molecular sieves (505 mg), and N-{1-(4-cyanobenzyl)-1H-imidazol-5-yl)acetyl}-2(S)-aminomethyl}-pyrrolidine from Example 40 step E (100.9 mg, 0.312 mmol), and potassium acetate (51 mg, o.54 mmol) in methanol (5 ml) was added sodium cyanoborohydride (0.31 ml of a 1M solution in THF, 0.31 mmol) at room temperature. The reaction was stirred for 24 hrs, diluted with EtOAc and filtered. The filtrate was washed with saturated aqueous $NaHCO_3$, dried ($Na_2SO_4$) and evaporated in vacuo. The residue was purified by chromatography on a chromatatron ($SiO_2$, 5% $NH_4OH$ in acetonitrile) to provide the title compound as an oil.

$^1$HNMR(CDCl$_3$, 400 MHz) d 7.80-6.80(10H, m), 5.45-5.30(2H, m), 4.25-3.80(3H, m), 3.60-3.30(4H, m), 2.95-2.50 (2H, m) and 2.20-1.80(4H, m) ppm.

Step B: N-{1-(4-Cyanobenzyl)-1H-imidazol-5-ylacetyl}-2(S)-{N'-acetyl-N'-3-cyanobenzyl}aminomethylpyrrolidine The title compound was prepared using the protocol described in Example 40 step G using acetyl chloride instead of methane sulfonyl chloride.

Anal. calc'd for $C_{28}H_{28}N_6O_2$ 0.25$H_2O$, 1.50 TFA; C, 56.75; H, 4.61; N, 12.81. Found: C, 56.74; H, 4.62; N, 12.72.

FAB HRMS exact mass calc'd for $C_{28}H_{29}N_6O_2$ 481.235199 (MH$^+$), found 481.235799.

EXAMPLE 86

N-{1-(4-Cyanobenzyl)-1H-imidazol-5-yl)acetyl}-2 (S)-{N'-acetyl-N'-3-methoxybenzyl}aminomethylpyrrolidine.

The title compound was prepared using the protocol described in Example 85 using 3-methoxybenzaldehyde.

Anal. calc'd for $C_{28}H_{31}N_5O_3$ 0.35 $H_2O$, 1.50 TFA; C, 56.17; H, 5.05; N, 10.56. Found: C, 56.18; H, 5.06; N, 10.90.

FAB HRMS exact mass calc'd for $C_{28}H_{32}N_5O_3$ 486.250515 (MH+), found 486.250698.

EXAMPLE 87

N-{1-(4-Cyanobenzyl)-1H-imidazol-5-yl)acetyl}-2 (S)-{N'-acetyl-N'-3-trifluoromethylbenzyl}aminomethylpyrrolidine The title compound was prepared using the protocol described in Example 85 using 3-trifluoromethylbenzaldehyde.

Anal. calc'd for $C_{28}H_{28}N_5O_2F_3$ 0.45 $H_2O$, 2.20 TFA; C, 49.73; H, 4.01; N, 8.95. Found: C, 49.75; H, 3.99; N, 9.17.

FAB HRMS exact mass calc'd for $C_{28}H_{29}N_5O_2F_3$ 524.227335 (MH+), found 524.226844.

EXAMPLE 88

N-{1-(4-Cyanobenzyl)-1H-imidazol-5-yl)acetyl}-2 (S)-{N'-acetyl-N'-2-methoxybenzyl}aminomethylpyrrolidine The title compound was prepared using the protocol described in Example 85 using 2-methoxybenzaldehyde.

Anal. calc'd for $C_{28}H_{31}N_5O_3$ 0.50 $H_2O$, 2.15 TFA; C, 52.45; H, 4.65; N, 9.47. Found: C, 52.45; H, 4.67; N, 9.58.

FAB HRMS exact mass calc'd for $C_{28}H_{32}N_5O_3$ 486.250515 (MH+), found 486.249829.

EXAMPLE 89

N-{1-(4-Cyanobenzyl)-1H-imidazol-5-yl)acetyl}-2 (S)-{N'-acetyl-N'-2-trifluoromethylbenzyl}aminomethylpyrrolidine The title compound was prepared using the protocol described in Example 85 using 2-trifluoromethylbenzaldehyde.

Anal. calc'd for $C_{28}H_{28}N_5O_2F_3$ 0.40 $H_2O$, 2.05 TFA; C, 50.43; H, 4.07; N, 9.16. Found: C, 50.43; H, 4.07; N, 9.24.

FAB HRMS exact mass calc'd for $C_{28}H_{29}N_5O_2F_3$ 524.227335 (MH+), found 524.227352.

EXAMPLE 90

N-{1-(4-Cyanobenzyl)-1H-imidazol-5-yl)acetyl}-2 (S)-{N'-acetyl-N'-(2,2-diphenylethyl)}aminomethylpyrrolidine The title compound was prepared using the protocol described in Example 85 using diphenylacetaldehyde.

Anal. calc'd for $C_{34}H_{35}N_5O_2$ 0.40 $H_2O$, 1.60 TFA; C, 60.76; H, 5.13; N, 9.52. Found: C, 60.76; H, 5.11; N, 9.54.

EXAMPLE 91

N-{1-(4-Cyanobenzyl)-1H-imidazol-5-yl)acetyl}-2 (S)-{N'-acetyl-N'-diphenylmethyl}aminomethylpyrrolidine Step A: N-{1-(4-Cyanobenzyl)-1H-imidazol-5-yl) acetyl}-2(S)-{N'-diphenylmethyl}aminomethylpyrrolidine A solution of N-{1-(4-Cyanobenzyl)-1H-imidazol-5-yl)acetyl}-2(S)-aminomethyl-pyrrolidine (0.175 mg, 0.544 mmol), triethylamine (0.055 ml, 0.544 mmol) and benzhydrylbromide (0.134 mg, 0.544 mmol) in DMF (2.0 ml) were stirred at room temperature for 24 hrs. The reaction was quenched with saturated NaHCO₃ solution and extracted with EtOAc. The organic extracts were washed with brine, dried (MgSO₄), and evaporated in vacuo. The residue was purified by chromatography (SiO₂, 5% NH₄OH in acetonitrile) to afford the title compound as an oil.

Step B: N-{1-(4-Cyanobenzyl)-1H-imidazol-5-yl) acetyl}-2(S)-{N'-acetyl-N'-diphenylmethyl}aminomethylpyrrolidine The title compound was prepared using the protocol described in Example 41 using the material from step A.

Anal. calc'd for $C_{33}H_{33}N_5O_2$ 1.00 $H_2O$, 3.30 TFA; C, 51.37; H, 4.17; N, 7.56. Found: C, 51.36; H, 4.16; N, 7.85.

FAB HRMS exact mass calc'd for $C_{33}H_{34}N_5O_2$ 532.271251 (MH+), found 532.272495.

EXAMPLE 92

N-{1-(4-Cyanobenzyl)-1H-imidazol-5-yl)acetyl}-2 (S)-{N'-acetyl-N'-2-chlorobenzyl}aminomethylpyrrolidine The title compound was prepared using the protocol described in Example 85 using 2-chlorobenzaldehyde.

Anal. calc'd for $C_{27}H_{28}N_5O_2Cl$ 1.00 $H_2O$, 1.50 TFA; C, 53.06; H, 4.68; N, 10.31. Found: C, 53.04; H, 4.66; N, 10.32.

EXAMPLE 93 AND 94

N-{2(R)-Methyl-2-(1-(4-Cyanobenzyl)-1H-imidazol-5-yl))acetyl}-2(S)-{N'-acetyl-N'-3-chlorobenzyl}aminomethylpyrrolidine and N-{2(S)-Methyl-2-(1-(4-Cyanobenzyl)-1H-imidazol-5-yl)) acetyl}-2(S)-{N'-acetyl-N'-3-chlorobenzyl}aminomethylpyrrolidine Step A: 2(R,S)-Methyl-2-{1-(Triphenylmethyl)-1H-imidazol-4-yl}-acetic acid methyl ester A solution of 1-(triphenylmethyl)-1H-imidazol-4-ylacetic acid methyl ester (1.01 g, 2.63 mmol) in THF (25 ml) was cooled to −78° C. Lithium hexamethyldisilazide (2.76 ml of a 1 M solution in THF, 2.76 mmol) was added dropwise and the reaction stirred 30 min at −78° C. Methyl iodide (0.164 ml, 2.76 mmol) was added and the reaction stirred a furthur 1 hr at −78° C. and then at −20° C. for 4 hrs. The reaction was quenched with water (10 ml) and saturated NaHCO₃ solutuon (10 ml) and extracted with EtOAc. The organic extracts were dried (MgSO₄) and the solvent evaporated in vacuo. Chromatography of the residue (SiO₂, 2 to 3% MeOH in CH₂Cl₂, gradient elotion) afforded the product.

¹H NMR CDCl₃, δ 7.40-7.00(16H, m), 6.71(1H, s), 3.77(1H, q, J=7.1 Hz), 3.69(3H, s) and 1.47(3H, d, J=7.1 Hz) ppm.

Step B: 2(R,S)-Methyl-2-(1-(4-cyanobenzyl)-1H-imidazol-5-yl)-acetic acid

The title compound was prepared according to the procedure described in Example 1 steps C and D using the material from step A.

¹H NMR CDCl₃, δ 8.15(1H, s), 7.75(2H, d, J=8.2 Hz), 7.35(2H, d, J=8.2 Hz), 7.15(1H, s), 5.44(2H, m), 3.50(1H, q, J=7.1 Hz) and 1.45(3H, d, J=7.1 Hz) ppm.

Step C: N-2(R)-Methyl-2-(1-(4-Cyanobenzyl)-1H-imidazol-5-yl))acetyl}-2(S)-{N'-acetyl-N'-3-chlorobenzyl-aminomethyl}-pyrrolidine and N-{2 (S)-Methyl-2-(1-(4-Cyanobenzyl)-1H-imidazol-5-yl))acetyl}-2(S)-{N'-acetyl-N'-3-chlorobenzyl}aminomethylpyrrolidine The title compounds were prepared as an inseparable mixture using the protocol described in Example 85 using 2(R,S)-methyl-2-(1-(4-cyanobenzyl)-1H-imidazol-5-yl)-acetic acid.

97

Anal. calc'd for $C_{28}H_{30}N_5O_2Cl$ 0.55 $H_2O$, 0.30 EtOAc, 1.55 HCl; C, 59.86; H, 5.98; N, 11.95. Found: C, 59.82; H, 5.99; N, 11.95.

Anal. calc'd for $C_{28}H_{30}N_5O_2Cl$ 0.35 $H_2O$, 0.25 EtOAc, 1.45 HCl; C, 59.52; H, 5.88; N, 11.97. Found: C, 59.52; H, 5.88; N, 11.90.

EXAMPLE 95

N-{1-(4-Cyanobenzyl)-1H-imidazol-5-yl)acetyl}-2(S)-{N'-acetyl-N'-3-chlorobenzyl}aminomethylpyrrolidine The title compound was prepared using the protocol described in Example 85 using 3-chlorobenzaldehyde.

Anal. calc'd for $C_{27}H_{28}N_5O_2Cl$ 0.95 $H_2O$, 1.50 TFA; C, 53.13; H, 4.67; N, 10.33. Found: C, 53.09; H, 4.65; N, 10.36.

EXAMPLE 96

N{1-(4-Cyanobenzyl)-1H-imidazol-5-yl)acetyl}-2(S)-{N'-acetyl-N'-4-chlorobenzyl}aminomethylpyrrolidine The title compound was prepared using the protocol described in Example 85 using 4-chlorobenzaldehyde.

Anal. calc'd for $C_{27}H_{28}N_5O_2Cl$ 1.05 $H_2O$, 1.55 TFA; C, 52.73; H, 4.65; N, 10.47. Found: C, 52.71; H, 4.65; N, 10.47.

EXAMPLE 97

N{1-(4-Cyanobenzyl)-1H-imidazol-5-yl)acetyl}-2(S)-{N'-acetyl-N'-2,3-dichlorobenzyl}aminomethylpyrrolidine The title compound was prepared using the protocol described in Example 85 using 2,3-dichlorobenzaldehyde.

Anal. calc'd for $C_{27}H_{27}N_5O_2Cl_2$ 0.20 $H_2O$, 1.65 TFA; C, 50.82 H, 4.09; N, 9.78. Found: C, 50.82; H, 4.12; N, 9.80.

EXAMPLE 98

N-[1-(4-Cyanobenzyl)-1H-imidazol-5-yl]acetyl-4(R)-benzyloxy-2(S)-{N'-acetyl-N'-naphth-1-ylmethyl}aminomethylpyrrolidine Step A: N-t-Butoxycarbonyl-4(R)-benzyloxyproline naphth-1-ylmethylamide The title compound was prepared using the procedure in Example 1 step H using N-t-butoxycarbonyl-4(R)- benzyloxyproline and naphth-1-ylmethylamine.

Step B: N-t-Butoxycarbonyl-4(R)-benzyloxy-2(S)-{N'-naphth-1-ylmethyl}aminomethylpyrrolidine To a solution of N-t-butoxycarbonyl-4(R)-benzyloxy proline naphth-1-ylmethylamide (1.20 g, 2.606 mmol), in THF (34 ml) at −35° C. was added borane (5.20 ml of a 1M solution in THF, 5.2 mmol). The reaction was allowed to warm to room temperature and stirred for 16 hrs. The reaction was quenched with methanol (30 ml) and the solvent evaporated in vacuo. The residue was chromatographed ($SiO_2$, 50% EtOAc in hexanes), to afford the title compound as an oil.

FAB MS 446 (M+1).

Step C: N-t-Butoxycarbonyl-4(R-benzyloxy-2(S)-{N'-acetyl-N'-naphth-1-ylmethyl}aminomethylpyrrolidine The title compound was prepared using the protocol described in Example 40 step G using acetyl chloride.

98

$^1$HNMR (CDCl$_3$, 400 MHz) d 8.10-7.00(12H, m), 5.70-2.90(13H, m), 2.40-2.00(2H, m) and 1.45(9H, s)ppm.

FAB MS 489(M+1).

Step D: 4(R)-Benzyloxy-2(S)-{N'-acetyl-N'-naphth-1-ylmethyl}-aminomethylpyrrolidine hydrochloride The title compound was prepared using the protocol described in Example 1 step G and the compound prepared in step C.

$^1$HNMR(CD$_3$OD, 400 MHz) δ 8.00(1H, d, J=8.6 Hz), 7.94(1H, d, J=7.1 Hz), 7.87(1H, d, J=8.2 Hz), 7.70-7.40(3H, m), 7.40-7.20(6H, m), 5.24(11H, d, J=17.6 Hz), 5.16(11H, d, J=17.6 Hz), 4.50(11H, d, J=11.7 Hz), 4.47(1H, d, J=11.7 Hz), 4.31(1H, t, J=4.5 Hz), 4.05(1H, m), 3.90(1H, m), 3.60-3.30(3H, m), 2.12(1H, m), 2.20(3H, s) and 1.89(1H, m) ppm.

FAB MS 389 (M+1).

Step E: Preparation of N-[1-(4-cyanobenzyl)-1H-imidazol-5-yl]acetyl-4(R)-benzyloxy-2(S)-{N'-acetyl-N -naphth-1-ylmethyl}aminomethylpyrrolidine The title compound was prepared using the protocol described in Example 1 step H and the compound prepared in step D.

Anal. calc'd for $C_{38}H_{37}N_5O_3$ 0.15 $H_2O$, 1.95 TFA; C, 60.14; H, 4.73; N, 8.37. Found: C, 60.16; H, 4.76; N, 8.31.

FAB HRMS exact mass calc'd for $C_{38}H_{38}N_5O_3$ 612.297465 (MH$^+$), found 612.298079.

EXAMPLE 99

N-[1-(4-Cyanobenzyl)-1H-imidazol-5-yl]acetyl-4(R)-benzyloxy-proline naphth-1-ylmethylamide The title compound was prepared using the protocol described in Example 1 step H and 4(R)-benzyloxy proline naphth-1-ylmethylamide.

Anal. calc'd for $C_{36}H_{33}N_5O_3$ 0.60 $H_2O$, 1.50 TFA; C, 61.19; H, 4.70; N,9.15. Found: C,61.21;H,4.67;N,9.21.

FAB HRMS exact mass calc'd for $C_{36}H_{34}N_5O_3$ 584.266165 (MH$^+$), found 584.267734.

EXAMPLE 100

N-[1-(4-Cyanobenzyl)-1H-imidazol-5-yl]acetylproline naphth-1-ylmethylamide

The title compound was prepared using the protocol described in Example 99 and proline naphth-1-ylmethylamide Anal. calc'd for $C_{29}H_{27}N_5O_2$ 0.65 $H_2O$, 1.00 TFA; C, 61.72; H, 4.90; N, 11.61. Found: C, 61.70; H, 5.05; N, 11.58.

FAB HRMS exact mass calc'd for $C_{29}H_{28}N_5O_2$ 478.224300 (MH$^+$), found 478.224053.

EXAMPLE 101

N-{1-(4-cyanobenzyl)-1H-imidazol-5-yl)acetyl-4(R)-methoxy-2(S)-{N'-acetyl-N'-5,6,7,8-tetrahydronaphth-1-ylmethyl}aminomethylpyrrolidine Step A: N-t-Butoxycarbonyl-4(R)-hydroxy-2(S)-(N'-acetyl-N'-5,6,7,8-tetrahydronaphth-1-ylmethyl}aminomethyl-pyrrolidine The title compound was prepared using the protocol described in Example 56 step G and N-t-butoxycarbonyl-4

(R)-benzyloxy-2(S)-{N'-acetyl-N'-naphth-1-ylmethyl}aminomethylpyrrolidine from Example 98, Step C.

FAB MS 403 (M+1).

Step B: N-t-Butoxycarbonyl-4(R)-methoxy-2(S)-{N'-acetyl-N'-5,6,7,8-tetrahydronaphth-1-ylmethyl}aminomethylpyrrolidine The title compound was prepared using the protocol described in Example 58 step A using N-t-butoxycarbonyl-4(S)-hydroxy-2(S)-{N'-acetyl-N'-5,6,7,8-tetrahydronaphthylmethyl}-aminomethylpyrrolidine from Step A.

Step C: 4(S)-Methoxy-2(S)-{N'-acetyl-N'-tetrahydronaphth-1-ylmethyl}aminomethylpyrrolidine hydrochloride The title compound was prepared using the protocol described in Example 1 step G.

Step D: N-{1-(4-Cyanobenzyl)-1H-imidazol-5-yl)acetyl-4(R)-methoxy-2(S)-{N'-acetyl-N'-5,6,7,8-tetrahydronaphth-1-ylmethyl}aminomethylpyrrolidine The title compound was prepared using the protocol described in Example 1 step H.

Anal. calc'd for $C_{32}H_{37}N_5O_3$ 0.40 $H_2O$, 2.25 TFA; C, 54.57; H, 5.02; N, 8.72. Found: C, 54.57; H, 5.02; N, 8.82.

FAB HRMS exact mass calc'd for $C_{32}H_{38}N_5O_3$ 540.297465 (MH$^+$), found 540.296505.

EXAMPLE 102

N-{1-(4-cyanobenzyl)-1H-imidazol-5-yl)acetyl-4(R)-benzyloxy-2(S)-{N'-acetyl-N'-5,56,7,8-tetrahydronaphth-1-ylmethyl}aminomethyl-pyrrolidine The title compound was prepared using the protocol described in Example 101 using benzyl bromide in place of methyl iodide.

Anal. calc'd for $C_{38}H_{41}N_5O_3$ 0.40 $H_2O$, 2.05 TFA; C, 59.02; H, 5.16; N, 8.17. Found: C, 59.01; H, 5.15; N, 8.22.

FAB HRMS exact mass calc'd for $C_{38}H_{42}N_5O_3$ 616.328766 (MH$^+$), found 616.327514.

EXAMPLE 103

1-(4-Cyanobenzyl)-1H-imidazol-5-ylmethyl-2(S)-{N'-acetyl-N'-3-chlorobenzyl}aminomethylpyrrolidine The title compound was prepared using the protocol described in Example 56 step M and 2(S)-{N'-acetyl-N'-3-chlorobenzyl}amino-methylpyrrolidine.

Anal. calc'd for $C_{26}H_{28}N_5OCl$ 0.50 $H_2O$, 2.65 TFA; C, 48.96; H, 4.22; N, 8.98. Found: C, 48.96; H, 4.20; N, 8.81.

FAB HRMS exact mass calc'd for $C_{26}H_{29}N_5OCl$ 462.206064 (MH$^+$), found 462.206270.

EXAMPLE 104

N-Allyloxycarbonyl-2(S)-{(1-(4-Cyanobenzyl)-1H-imidazol-5-yl)acetyl}amino-3(S)-methyl-pentanamine

Step A: 2(S)-N-t-Butoxycarbonylamino-3(S)-methyl-pentanamine

The title compound was prepared using the procedure described in Example 40 steps B, C and E using 2(S)-N-t-butoxycarbonylamino-3(S)-methyl-pentanol in place of 2(S)-N-t-butoxycarbonylhydroxymethyl pyrrolidine.

$^1$H NMR(CDCl$_3$, 400 MHz) δ 4.55(1H, s), 3.60-3.40(3H, m), 2.83(1H, m), 2.62(1H, m), 1.60(1H, m), 1.45(9H, s) and 1.30-0.80(8H, m) ppm.

Step B: N-Allyloxycarbonyl-2(S)-N-t-butoxycarbonylamino-3(S)-methyl-pentanamine A solution of 2(S)-N-t-butoxycarbonylamino-3(S)-methyl-pentanamine (1.921 g, 8.88 mmol), triethylamine (2.50 ml, 18.0 mmol) in $CH_2Cl_2$ (90 ml) was treated with allylchloroformate (1.45 ml, 8.88 mmol) at 0° C. and the reaction allowed to warm to room temperature and stirred for 16 hrs. The solvent was evaporated in vacuo and the residue chromatographed (SiO$_2$, 15–20% EtOAc in hexanes to afford the title compound as an oil.

$^1$HNMR(CDCl$_3$, 400 MHz) δ 5.92(1H, m), 5.30(1H, d, J=17.5 Hz), 5.22(1H, d, J=10.0 Hz), 5.10(1H, s), 4.60-4.50 (3H, m), 3.58(1H, s), 3.40-3.20(2H, m), 1.60(1H, m), 1.45 (9H,s) and 1.25-0.90(8H, m) ppm.

Step C: N-Allyloxycarbonyl-2(S)-amino-3(S)-methyl-pentanamine hydrochloride

The title compound was prepared by the procedure described in Example 1 step G.

$^1$HNMR(CD$_3$OD, 400 MHz) δ 5.95(1H,m), 5.35(1H, d, J=17.5 Hz), 5.22(1H, d, J=10.0 Hz), 4.60(2H, s), 3.60-3.10 (3H, m), 1.78(1H, m), 1.60(1H, m) and 1.25(1H,m) and 1.10-0.90(6H, m) ppm.

Step D: N-Allyloxycarbonyl-2(S)-{(1-(4-Cyanobenzyl)-1H-imidazol-5-yl)acetyl}amino-3(S)-methyl-pentanamine The title compound was prepared by the procedure described in Example 1 step G using N-Allyloxycarbonyl-2(S)-amino-3(S)-methyl-pentanamine hydrochloride.

Anal. calc'd for $C_{23}H_{29}N_5O$ 0.25 $H_2O$; C, 64.54; H, 6.95; N, 16.36. Found: C, 64.56; H, 6.86; N, 16.04.

FAB HRMS exact mass calc'd for $C_{23}H_{30}N_5O$ 424.234865 (MH$^+$), found 424.234627.

EXAMPLE 105

2(S)-{(1-(4-Cyanobenzyl)-1H-imidazol-5-yl)acetyl}amino-3(S)-methyl-N-(naphth-2-ylsulfonyl)-pentanamine

Step A: 2(S)-{(1-(4-cyanobenzyl)-1H-imidazol-5-yl)acetyl}amino-3(S)-methyl-pentanamine To a solution of N-allyloxycarbonyl-2(S)-{(1-(4-cyanobenzyl)-1H-imidazol-5-yl)acetyl}amino-3 (S)-methyl-pentanamine (2.372 g, 5.60 mmol) and 5,5-dimethyl-1,3-cyclohexanedione (6.21 g, 44.3 mmol) in THF (70 ml) was added (tetrakistriphenylphosphine) palladium (O) (1.12 g, 0.969 mmol) and the reaction was stirred in the dark for 2 hrs. The solvent was evaporated in vacuo and the residue partitioned between Et$_2$O and 1M aqueous HCl. The aqueous layer was treated with Na$_2$CO$_3$ solution until pH 10 and extracted with EtOAc. The organic extracts were washed with brine, dried (Na$_2$SO$_4$), and the solvent evaporated in vacuo. The residue was chromatographed (SiO$_2$, 3% NH$_4$OH in acetonitrile) to afford an enamine. The title compound was obtained by treating the enamine with bromine water following the procedure of Halpern *Aust. J. Chem.* 17 1964, 1282.

FAB HRMS exact mass calc'd for $C_{19}H_{26}N_5O$ 340.213736 (MH$^+$), found 340.213895.

Step B: 2(S)-{(1-(4-cyanobenzyl)-1H-imidazol-5-yl)acetylamino}-3(S)-methyl-N-(naphth-2-ylsulfonyl)-pentanamine The title compound was prepared using the protocol described in Example 40 step G using naphth-2-ylsulfonyl chloride instead of methane sulfonyl chloride.

Anal. calc'd for $C_{29}H_{31}N_5O_3S$ 0.30 $H_2O$, 1.65 TFA; C, 53.64; H, 4.63; N, 9.68. Found: C, 53.62; H, 4.67; N, 9.69.

FAB HRMS exact mass calc'd for $C_{29}H_{32}N_5O_3S$ 530.222587 (MH$^+$), found 530.224351.

EXAMPLE 106

2(S)-[1-(4-Cyanobenzyl)-1H-imidazol-5-yl]acetyl}amino-3(S)-methyl-N-(naphth-1-ylsulfonyl)-pentanamine The title compound was prepared using the protocol described in Example Example 105 using naphth-1-ylsulfonyl chloride.

Anal. calc'd for $C_{29}H_{31}N_5O_3S$ 0.40 $H_2O$, 1.40 TFA; C, 54.84; H, 4.80; N, 10.06. Found: C, 54.87; H, 4.81; N, 10.08.

FAB HRMS exact mass calc'd for $C_{29}H_{32}N_5O_3S$ 530.222587 (MH$^+$), found 530.221441.

EXAMPLE 107

N-Acetyl-N-2-chlorobenzyl-2(S)-{(1-(4-cyanobenzyl)-1H-imidazol-5-yl)acetyl}amino-3(S)-methyl-pentanamine Step A: N-2-chlorobenzyl-2(S)-{1-(4-Cyanobenzyl)-1H-imidazol-5-yl)acetyl}amino-3(S)-methyl-pentanamine The title compound was prepared using the protocol described in Example 10 step G using 2-chlorobenzaldehyde and the amine from Example 105 step A.

FAB MS 464 (M+1).

Step B: N-Acetyl-N-2-chlorobenzyl-2(S)-{(1-(4-cyanobenzyl)-1H-imidazol-5-yl)acetyl}amino-3(S)-methyl-pentanamine The title compound was prepared using the protocol described in Example 41 using the amine from step A.

FAB HRMS exact mass calc'd for $C_{28}H_{33}N_5O_2Cl$ 506.232278 (MH$^+$), found 506.233741.

EXAMPLE 108

N-Acetyl-N-3-chlorobenzyl-2(S)-{(1-(4-cyanobenzyl)-1H-imidazol-5-yl)acetyl}amino-3(S)-methyl-pentanamine Step A: N-3-Chlorobenzyl-2(S)-{(1-(4-cyanobenzyl)-1H-imidazol-5-yl)acetyl}amino-3(S)-methyl-pentanamine The title compound was prepared using the protocol described in Example 10 step G using 3-chlorobenzaldehyde and the amine from Example 105 step A.

FAB MS 464 (M+1)

Step B: N-Acetyl-N-3-chlorobenzyl-2(S)-{(1-(4-cyanobenzyl)-1H-imidazol-5-yl)acetyl}amino-3(S)-methyl-pentanamine The title compound was prepared using the protocol described in Example 41 using the amine from step A.

FAB HRMS exact mass calc'd for $C_{28}H_{33}N_5O_2Cl$ 506.232278 (MH$^+$), found 506.231892.

EXAMPLE 109

N-Acetyl-N-4-chlorobenzyl-2(S)-{(1-(4-cyanobenzyl)-1H-imidazol-5-yl)acetyl}amino-3(S)-methyl-pentanamine Step A: N-4-Chlorobenzyl-2(S)-{(1-(4-Cyanobenzyl)-1H-imidazol-5-yl)acetyl}amino-3(S)-methyl-pentanamine The title compound was prepared using the protocol described in Example 10 step G using 4-chlorobenzaldehyde and the amine from Example 105 step A.

FAB MS 464 (M+1)

Step B: N-Acetyl-N-4-chlorobenzyl-2(S)-{(1-(4-Cyanobenzyl)-1H-imidazol-5-yl)acetyl}amino-3(S)-methyl-pentanamine The title compound was prepared using the protocol described in Example 41 using the amine from step A.

Anal. calc'd for $C_{28}H_{32}N_5O_2Cl$ 1.00 $H_2O$, 1.95 TFA; C, 51.33; H, 4.85; N, 9.38. Found: C, 51.34; H, 4.84; N, 9.28.

FAB HRMS exact mass calc'd for $C_{28}H_{33}N_5O_2Cl$ 506.232278 (MH$^+$), found 506.232238.

EXAMPLE 110

N-Acetyl-N-2,3-dichlorobenzyl-2(S)-{(1-(4-cyanobenzyl)-1H-imidazol-5-yl)acetyl}amino-3(S )-methyl-pentanamine Step A: N-2,3-Dichlorobenzyl-2(S)-{(1-(4-Cyanobenzyl)-1H-imidazol-5-yl)acetyl}amino-3(S)-methyl-pentanamine The title compound was prepared using the protocol described in Example 10 step G using 2,3-dichlorobenzaldehyde and the amine from Example 105 step A.

FAB MS 498 (M+1).

Step B: N-Acetyl-N-3-chlorobenzyl-2(S)-{(1-(4-Cyanobenzyl)-1H-imidazol-5-yl)acetyl}amino-3(S )-methyl-pentanamine The title compound was prepared using the protocol described in Example 41 using the amine from step A.

Anal. calc'd for $C_{28}H_{31}N_5O_2Cl_2$ 0.30 $H_2O$, 1.85 TFA; C, 50.31; H, 4.45; N, 9.25. Found: C, 50.32; H, 4.47; N, 9.43.

FAB HRMS exact mass calc'd for $C_{28}H_{32}N_5O_2Cl_2$ 540.193327 (MH$^+$), found 540.193425.

EXAMPLE 111

N-Allyloxycarbonyl-N-naphth-1-ylmethyl-2(S)-{2(R,S)-methyl-2-(1-(4-cyanobenzyl)-1H-imidazol-5-yl)acetyl}amino-3(S)-methyl-pentanamine The title compound was prepared according to the procedures described in Example 1 using 2(R,S)-methyl-2-{(1-(4-cyanobenzyl)-1H-imidazol-5-yl}acetic acid.

Anal. calc'd for $C_{35}H_{39}N_5O_3$ 0.05 $H_2O$, 1.45 TFA; C, 61.19; H, 5.49; N, 9.41. Found: C, 61.15; H, 5.50; N, 9.58.

EXAMPLE 112

N-t-Butoxycarbonylaminoacetyl-N-naphth-1-ylmethyl-2(S)-{1-(4-cyanobenzyl)-1H-imidazol-5-ylacetyl}amino-3(S )-methylpentanamine The title compound was prepared using the protocol described in Example 1 step H using N-t-butoxycarbonyl glycine and N-naphth-1-ylmethyl-2(S)-{(1-(4-cyanobenzyl)-1H-imidazol-5-ylacetyl}amino-3(S)-methyl pentanamine from Example 2.

FAB HRMS exact mass calc'd for $C_{37}H_{45}N_6O_4$ 630.350229 (MH$^+$), found 637.350834.

EXAMPLE 113

N-Aminoacetyl-N-naphth-1-ylmethyl-2(S)-{1-(4-cyanobenzyl)-1H-imidazol-5-ylacetyl}amino-3(S)-methylpentanamine The title compound was prepared using the protocol described in Example 1 step G using N-t-butoxycarbonylaminoacetyl-N-naphth-1-ylmethyl-2(S)-{1-(4-cyanobenzyl)-1H-imidazol-5-ylacetyl}amino-3(S)-methylpentanamine.

Anal. calc'd for $C_{32}H_{36}N_6O_2$ 3.10 HCl; C, 59.16; H, 6.07; N, 12.94. Found: C, 59.09; H, 6.27; N, 12.85.

FAB HRMS exact mass calc'd for $C_{32}H_{37}N_6O_2$ 537.297800 (MH$^+$), found 537.297766.

EXAMPLE 114

N-{5-(4-Cyanobenzyl)-1H-imidazol-1-yl)ethyl}-2(S)-{N'-acetyl-N'-3-chlorobenzyl}aminomethylpyrrolidine The title compound was prepared using the protocol described in Example 44 using 2(S)-{N'-acetyl-N'-3-chlorobenzyl}aminomethyl-pyrrolidine.

Anal. calc'd for $C_{27}H_{30}N_5OCl$ 2.00 HCl, 0.70 H$_2$O; C, 57.75; H, 6.00; N, 12.47. Found: C, 57.75; H, 6.04; N, 12.20.

EXAMPLE 115

N-{5-(4-Cyanobenzyl)-1H-imidazol-1-yl)ethoxycarbonyl}-2(S)-{N'-acetyl-N'-3-chlorobenzyl}aminomethylpyrrolidine The title compound was prepared using the protocol described in Example 44 using 2(S)-{N'-acetyl-N'-3-chlorobenzyl}aminomethyl-pyrrolidine Anal. calc'd for $C_{28}H_{30}N_5O_3Cl$ 2.10 HCl, 0.60 EtOAc; C, 56.22; H, 5.73; N, 10.78. Found: C, 56.20; H, 5.48; N, 10.75.

EXAMPLE 116

N-{5-(4-Cyanobenzyl)-1H-imidazol-1-ylacetyl}-2(S)-{N'-acetyl-N'-3-chlorobenzyl}aminomethylpyrrolidine The title compound was prepared using the procedure described in Example 42 using 2(S)-{N'-acetyl-N'-3-chlorobenzyl}aminomethylpyrrolidine Anal. calc'd for $C_{27}H_{28}N_5O_2Cl$ 1,00 HCl, 1.50 H$_2$O, 0.16 EtOAc; C, 60.22; H, 6.06; N, 12.77. Found: C, 60.21; H, 5.82; N, 12.48.

EXAMPLE 117

N{1-(4-Cyanobenzyl)-1H-imidazol-5-yl)ethyl}-2(S)-{N'-acetyl-N'-3-chlorophenyl}aminomethylpyrrolidine Step A: N-t-Butoxycarbonyl-2(S)-{N'-acetylaminomethyl}-pyrrolidine The title compound was prepared using the procedure described in Example 41 using N-t-butoxycarbonyl-2(S)-aminomethylpyrrolidine.

Step B: N-t-Butoxycarbonyl-2(S)- {N'-acetyl-N'-3-chlorophenyl}-aminomethylpyrrolidine To a solution of N-t-butoxycarbonyl-2(S)-{N'-acetyl}aminomethylpyrrolidine (1.55 g, 6.40 mmol) and triethylamine (1.34 ml, 9.60 mmol) in CH$_2$Cl$_2$ (50 ml) was added tri-(3-chlorophenyl)bismuth (6.86 g, 12.62 mmol) and copper II acetate (1.74 g, 9.60 mmol). The reaction was stirred at room temperature for 16 hrs, silica gel (75 g) was added and the mixture filtered. The solid was washed with 5% MeOH in CH$_2$Cl$_2$. The filtrate was evaporated in vacuo and the residue purified by chromatography (SiO$_2$, 10–100% EtOAc in hexanes, gradient elution) to afford the title compound as an oil.

$^1$H NMR (CDCl$_3$, 400 MHz) δ 7.60-7.20(4H, m), 4.25 (1H, m), 3.90(1H, m), 3.80(1H, m), 3.50-3.20(2H, m), 2.20-1.80(7H, m) and 1.50-1.10(9H, m)ppm.

Step C: 2(S)-{N'-Acetyl-N'-3-chlorophenyl}aminomethyl-pyrrolidine hydrochloride

The title compound was prepared using the procedure described in Example 1 step G and the material prepared in step B.

$^1$H NMR (CDCl$_3$,400 MHz) δ 7.54-7.46(3H, m), 7.35-7.30(1H, m), 4.30(1H, m), 3.75-3.65(2H,m), 3.48-3.38(2H, m), 2.20-2.02(3H,m), 1.92(3H, s), 1.78-1.66(1H, m) ppm.

Step D: N-{1-(4-Cyanobenzyl)-1H-imidazol-5-yl)ethyl}-2(S)-{N'-acetyl-N'-3-chlorophenyl}aminomethylpyrrolidine The title compound was prepared using the procedure described in Example 63 using 2(S)-{N'-acetyl-N'-3-chlorophenyl}aminomethylpyrrolidine.

FAB HRMS exact mass calc'd for $C_{26}H_{29}N_5OCl$ 462.206064 (MH$^+$), found 462.207329.

EXAMPLE 118

N-{1-(4-Cyanobenzyl)-1H-imidazol-5-yl)methyl}-2(S)-{N'-acetyl-N'-3-chlorophenyl}aminomethylpyrrolidine hydrochloride The title compound was prepared using the procedure described in Example 56 using 2(S)-{N'-acetyl-N'-3-chlorophenyl}aminomethyl-pyrrolidine.

Anal. calc'd for $C_{25}H_{26}N_5OCl$ 2.40 HCl, 1.40H$_2$O; C, 53.56; H, 5.61; N 12.49. Found: C, 53.60; H, 5.60; N, 12.36.

EXAMPLE 119

N-{1-(4-Cyanobenzyl)-1H-imidazol-5-yl)acetyl}-2(S)-{N'-acetyl-N'-3-chlorophenyl}aminomethylpyrrolidine The title compound was prepared using the procedure described in Example 1 step H using 2(S)-{N'-acetyl-N'-3-chlorophenyl}aminomethyl-pyrrolidine.

Anal. calc'd for $C_{26}H_{26}N_5OCl$ 1.30 HCl, 0.50 H$_2$O; C, 58.66; H, 5.36; N 13.15. Found: C, 58.66; H, 5.37; N, 13.06.

EXAMPLE 120

N-[1-(3-[1H-Imidazol-4-yl]propionyl)-pyrrolidin-2(S)-ylmethyl]-(N-2-methylbenzyl)glycine N'-(3-chlorophenyl)amide Step A: 2-Methylbenzylglycine methyl ester hydrochloride To a solution of 2-methylbenzyl alcohol (100 g, 0.82 mol) and diisopropylethylamine (171 mL, 0.98 mol) in CH$_2$Cl$_2$ (400 mL) at −5° C. was added dropwise methanesulfonyl chloride (74 mL, 0.95 mmol) with stirring under argon. After 1 hr at −5° and 3 hr at 20° C., this solution was added dropwise simultaneously with diisopropylethylamine (428 mL, 2.46 mol) to a slurry of glycine methyl ester hydrochloride (308.8 g, 2.45 mol) in DMF (400 mL) at 0° C. The reaction mixture was allowed to warm to ambient temperature for overnight, then treated slowly with satd NaHCO$_3$ solution (1 L) and EtOAc (1 L). The layers were separated, the aqueous washed with EtOAc, and the organics combined, washed with satd NaHCO$_3$ solution, brine, and dried (MgSO$_4$). This solution was filtered, cooled to 0° C., and HCl was bubbled into the solution to precipitate the title compound. $^1$H NMR (CDCl$_3$) δ 7.61 (d, 1H, J=7 Hz), 7.7–7.8 (m, 3H), 4.31 (s, 2H), 3.77 (s, 3H), 3.65 (s, 2H), 2.46 (s, 3H).

Step B: N-[(t-Butyloxycarbonyl)-pyrrolidin-2(S)-ylmethyl]-(N-2-methylbenzyl)-glycine methyl ester 2-Methylbenzylglycine methyl ester hydrochloride (36.7 g, 0.16 mol) and N-[(tert-Butyloxy)carbonyl-prolinal (Pettit et al., J. Org. Chem. (1994) 59, [21] 6287–95) (31.6 g, 0.159 mol) were dissolved in CH$_2$Cl$_2$ (500 mL), treated with 3A molecular sieves (20 g) and stirred for 18 hrs at room temperature under argon. The reaction mixture was filtered, quenched with aq satd NaHCO$_3$ (5 mL) and concentrated and the residue was extracted with EtOAc 3×200 mL). The extracts were combined, washed with aq satd NaHCO$_3$ solution, brine, and dried (MgSO$_4$). Filtration and concentration the title compound as a yellow oil which was used without further purification.

Step C: N-[(t-Butyloxycarbonyl)-pyrrolidin-2(S)-ylmethyl]-(N-2-methylbenzyl)-glycine N-[(t-Butyloxycarbonyl)-pyrrolidin-2(S)-ylmethyl]-(N-2-methylbenzyl)-glycine methyl ester (41.85 g, 0.111 mol) was dissolved in CH$_3$OH (300 mL) at 0° C. and treated with 2 N NaOH solution (111 mL, 0.222 mol) and allowed to stir at ambient temperature for 3 hr. 1 N HCl (235 mL, 0.235 mol) was added, the CH$_3$OH was removed on a rotary evaporator, and the residue was extracted with EtOAc (2×1.5 L), washed with brine, and dried (MgSO$_4$). Filtration and concentration to dryness gave the title compound as a white solid. $^1$H NMR (CD$_3$OD ) δ 7.56 (d, 1H, J=7.5 Hz), 7.15–7.36 (m, 3H), 4.70 (d, 1H, J=13 Hz), 4.27 (d, 1H, J=13 Hz), 4.1–4.2 (m, 1H), 3.73 (d, 1H, J=16 Hz), 3.59 (d, 1H, J=16 Hz), 3.15–3.5 (m, 4H), 2.49 (s, 3H), 2.1–2.2 (m, 1H), 1.7–1.9 (m, 2H), 1.6–1.7 (m, 1H), 1.46 (s, 9 h).

Step D: N-[(t-Butyloxycarbonyl)-pyrrolidin-2(S)-ylmethyl]-(N-2-methylbenzyl)-glycine N'-3-chlorophenyl)amide N-[(t-Butyloxycarbonyl)-pyrrolidin-2(S)-ylmethyl]-(N-2-methylbenzyl)-glycine (5.4 g, 0.115 mol), 3-chloroaniline (2.4 mL, 0.227 mol), HOOBT (3.65 g, 0.224 mol), and EDC (4.28 g, 0.223 mol) were dissolved in DMF (20 mL) at ambient temperature and the pH was adjusted with Et$_3$N (3.10 mL, 0.222 mol). After stirring overnight, the mixture was concentrated to remove the DMF, and the residue partitioned between EtOAc and H$_2$O. The aqueous layer was extracted with EtOAc, the organics combined, washed with H$_2$O, brine, and dried (MgSO$_4$), then filtered and concentrated to give the title compound as a yellow oil.

Step E: Pyrrolidin-2(S)-ylmethyl-(N-2-methylbenzyl)- glycine N'-(3-chlorophenyl) amide hydrochloride N-[(t-Butyloxycarbonyl)-pyrrolidin-2(S)-ylmethyl]-(N-2-methylbenzyl)- glycine N'-(3-chlorophenyl) amide (2.56 g, 5.42 mmol) was dissolved in EtOAc (125 mL), cooled to 0° C., and HCl gas was bubbled into the solution for 10 min followed by stirring under argon for 3 hr. Argon was bubbled into the solution and the solvent was removed in vacuo to give the title compound as a white amorphous solid.

Step F: N-[1-(3-[1H-Imidazol-4-yl]propionyl)-pyrrolidin-2(S) ylmethyl]-(N-2-methylbenzyl) glycine N'-(3-chlorophenyl) amide hydrochloride Pyrrolidin-2(S)-ylmethyl]-(N-2-methylbenzyl)- glycine N'(3-chlorophenyl) amide hydrochloride (0.26 g, 0.58 mmol), 1H-imidazol-4-yl]propionic acid hydrochloride (0.26 g, 1.5 mmol), EDC (0.22 g, 1.1 mmol), HOOBT (0.19 g, 1.2 mmol) were dissolved in DMF (19 mL) at 25° C., the pH of the mixture adjusted to 8 with Et$_3$N (0.485 mL, 3.48 mmol). After stirring for 18 h, the reaction mixture was partitioned between EtOAc and satd NaHCO$_3$ solution, the organic layer separated, washed with brine, dried (MgSO$_4$), filtered, and concentrated to dryness to give the title compound after preparative RP HPLC (Vydac column, 0.1% TFA/CH$_3$CN: 0.1% TFA/H$_2$O, 95:5 to 5:95 gradient), lyophilization, and conversion to its HCl salt.

Anal. calcd for $C_{27}H_{32}N_5O_2Cl.2$ HCl.1.6 H$_2$O: C, 54.43; H, 6.29; N, 11.76; found: C, 54.44; H, 6.48; N, 11.56.

FAB MS 494 (M+1).

EXAMPLE 121

1-[1-(4-Cyanobenzyl)-1H-imidazol-5-ylacetyl] pyrrolidin-2(S)-ylmethyl]-(N-2-methylbenzyl)-glycine N'-(3-chlorophenylmethyl) amide hydrochloride 1-(4-Cyanobenzyl)-1H-imidazol-5-ylacetic acid (0.14 g, 0.494 mmol), pyrrolidin-2(S)-ylmethyl]-(N-2-methylbenzyl)-glycine N'-(3-chlorophenyl) amide hydrochloride (Example 120, Step E) (0.109 g, 0.245 mmol), EDC (0.09 g, 0.469 mmol), HOOBT (0.08 g, 0.49 mmol) were dissolved in DMF (5 mL) at 25° C., the pH of the mixture adjusted to 8 with Et$_3$N (0.205 mL, 1.47 mmol). After stirring for 18 h, the reaction mixture was partitioned between EtOAc and satd NaHCO$_3$ solution, the organic layer separated, washed with brine, dried (MgSO$_4$), filtered, and concentrated to dryness to give the title compound after preparative RP HPLC (Vydac column, 0.1% TFA/CH$_3$CN: 0.1% TFA/H$_2$O, 95:5 to 5:95 gradient), lyophilization, and conversion to its HCl salt.

Anal. calcd for $C_{34}H_{35}N_6O_2Cl.2.1$ HCl.0.95 H$_2$O: C, 59.30; H, 5.71; N, 12.20; Found: C, 59.34; H, 5.71; N, 11.85.

FAB MS 595 (M+1).

EXAMPLE 122

N-[1-(3-[1H-Imidazol-4-yl]propionyl)-pyrrolidin-2 (S)-ylmethyl]-(N-2-methylbenzyl)-glycine N'-methyl-N'-(3-chlorophenyl) amide Step A: N-[(t-Butyloxycarbonyl)-pyrrolidin-2(S)-ylmethyl]-(N-2-methylbenzyl)-glycine N'-methyl-N'-3-chlorophenyl) amide N-[(t-Butyloxycarbonyl)-pyrrolidin-2(S)-ylmethyl]-(N-2-methylbenzyl)- glycine-N-3-chlorophenyl) amide (Example 120, Step D) (3.97 g, 8.41 mmol) was dissolved in dry THF (40 mL) with stirring at 0° C. under Ar, treated with NaH (60% dispersion in mineral oil, 0.68 g, 17 mmol), and after 15 min treated with iodomethane (2.10 mL, 33.7 mmol). The reaction mixture was stirred at 25° C. for 4 h, then evaporated to dryness and partitioned between EtOAc and aq satd NaHCO$_3$ solution. The organic layer was separated, washed with brine, dried (MgSO$_4$), filtered, and concentrated to dryness to give the title compound as a white solid. FAB MS 486 (M+1).

Step B: Pyrrolidin-2(S)-ylmethyl]-(N-2-methylbenzyl)-glycine N'-methyl-N'-(3-chlorophenyl) amide hydrochloride N-[(t-Butyloxycarbonyl)-pyrrolidin-2(S)-ylmethyl]-(N-2-methylbenzyl)- glycine N'-methyl-N'-(3-chlorophenyl) amide (3.75 g, 7.17 mmol) was dissolved in EtOAc (125 mL), cooled to 0° C., and HCl gas was bubbled into the solution for 10 min followed by stirring under argon for 3 hr. Argon was bubbled into the solution and the solvent was removed in vacuo to give the title compound as a white amorphous solid which was used without further purification.

Step C: N-[1-(3-[1H-Imidazol-4-yl]propionyl)-pyrrolidin-2(S)-y lmethyl]-(N-2-methylbenzyl) glycine N'-methyl-N'-(3-chlorophenyl) amide hydrochloride Pyrrolidin-2(S)-ylmethyl]-(N-2-methylbenzyl)- glycine-N-methyl-N-(3-chlorophenyl) amide hydrochloride (0.43 g, 0.94 mmol), 1H-imidazol-4-yl]propionic acid hydrochloride (0.33 g, 1.9 mmol), EDC (0.36 g, 1.9 mmol), HOOBT (0.31 g, 1.9 mmol) were dissolved in DMF (20 mL) at 25° C., the pH of the mixture adjusted to 8 with Et$_3$N (0.917 mL, 6.58 mmol). After stirring for 72 h, the reaction mixture was partitioned between EtOAc and satd NaHCO$_3$ solution, the organic layer separated, washed with brine, dried (MgSO$_4$), filtered, and concentrated to dryness to give the title compound after preparative RP HPLC (Vydac column, 0.1% TFA/CH$_3$CN: 0.1% TFA/H20, 95:5 to 5:95 gradient), lyophilization, and conversion to its HCl salt.

Anal. calcd for C$_{28}$H$_{34}$N$_5$O$_2$Cl.2 HCl.0.5 H$_2$O: C, 57.00; H, 6.32; N, 11.87; Found: C, 56.98; H, 6.57; N, 11.51.

FAB MS 508 (M+1).

EXAMPLE 123

1- [1-(4-Cyanobenzyl)-1H-imidazol-5-ylacetyl] pyrrolidin-2(S)-ylmethyl]-(N-2-methylbenzyl)-glycine N'-methyl-N'-(3-chlorophenylmethyl) amide hydrochloride 1-(4-Cyanobenzyl)-1H-imidazol-5-ylacetic acid (0.14 g, 0.494 mmol), pyrrolidin-2(S)-ylmethyl]-(N-2-methylbenzyl)- glycine N'-methyl-N'-3-chlorophenyl) amide hydrochloride (Example 122, Step B) (0.107 g, 0.232 mmol), EDC (0.09 g, 0.469 mmol), HOOBT (0.08 g, 0.49 mmol) were dissolved in DMF (5 mL) at 25° C., the pH of the mixture adjusted to 8 with Et$_3$N (0.194 mL, 1.39 mmol). After stirring for 18 h, the reaction mixture was partitioned between EtOAc and satd NaHCO$_3$ solution, the organic layer separated, washed with brine, dried (MgSO$_4$), filtered, and concentrated to dryness to give the title compound after preparative RP HPLC (Vydac column, 0.1% TFA/CH$_3$CN: 0.1% TFA/H$_2$O, 95:5 to 5:95 gradient), lyophilization, and conversion to its HCl salt.

Anal. calcd for C$_{35}$H$_{37}$N$_6$O$_2$Cl.2.15 HCl.1.25 H$_2$O: C, 59.22; H, 5.91; N, 11.84; Found: C, 59.22; H, 5.92; N, 11.67.

FAB MS 609 (M+1).

EXAMPLE 124

(S)-2-[(1-(4-cyanobenzyl)-5-imidazolylmethyl) amino]1-[N-(2,3-dimethylphenyl)acetamido]hexane hydrochloride Step A: 1-Triphenylmethyl-4-(hydroxymethyl) imidazole To a solution of 4-(hydroxymethyl)imidazole hydrochloride (35 g) in 250 mL of dry DMF at room temperature was added triethylamine (90.6 mL). A white solid precipitated from the solution. Chlorotriphenylmethane (76.1 g) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: 1-Triphenylmethyl-4-(acetoxymethyl) imidazole

Alcohol from Step A was suspended in 500 mL of pyridine. Acetic anhydride (74 mL) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next step.

Step C: 1-(4-Cyanobenzyl)-5-(acetoxymethyl) imidazole hydrobromide

A solution of the product from Step B and α-bromo-p-tolunitrile (50.1 g) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: 1-(4-Cyanobenzyl)-5-(hydroxymethyl) imidazole

To a solution of the acetate from Step C (50.4 g) in 1.5 L of 3:1 THF/water at 0° C. was added lithium hydroxide monohydrate (18.9 g). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step E: 1-(4-Cyanobenzyl)-5-imidazolecarboxaldehyde

To a solution of the alcohol from Step D (21.5 g) in 500 mL of DMSO at room temperature was added triethylamine (56 mL), then SO$_3$-pyridine complex (40.5 g). After 45 minutes, the reaction was poured into 2.5 L of EtOAc, washed with water (4×1 L) and brine, dried (Na$_2$SO$_4$), filtered, and concentrated in vacuo to provide the titled aldehyde as a white powder which was sufficiently pure for use in the next step without further purification.

Step F: N-Methoxy-N-methyl-2(S)-(t-butoxycarbonylamino)-hexanamide

3(S)-Butoxycarbonylaminohexanoic acid (24.6 g, 0.106 mol), N,O-dimethylhydroxylamine hydrochloride (15.5 g, 0.15 mol), EDC hydrochloride (22.3 g, 0.117 mol) and HOBT (14.3 g, 0.106 mol) were stirred in dry, degassed DMF (300 mL) at 20° C. under nitrogen. N-Methylmorpholine was added to obtain pH 7. The reaction was stirred overnight, the DMF distilled under high vacuum, and the residue partitioned between ethyl acetate and 2% potassium hydrogen sulfate. The organic phase was washed with saturated sodium bicarbonate, water, and saturated brine, and dried with magnesium sulfate. The solvent was removed in vacuo to give the title compound.

Step G: 2(S)-(tert-Butoxycarbonylamino)hexanal

A mechanically stirred suspension of lithium aluminum hydride (5.00 g, 0.131 mol) in ether (250 mL) was cooled to −45° C. under nitrogen. A solution of the product from Step A (28.3 g, 0.103 mol) in ether (125 mL) was added, maintaining the temperature below −35° C. When the addition was complete, the reaction was warmed to 5° C., then recooled to −45° C. A solution of potassium hydrogen sulfate (27.3 g, 0.200 mol) in water was slowly added, maintaining the temperature below −5° C. After quenching, the reaction was stirred at room temperature for 1 h. The mixture was filtered through Celite, the ether evaporated, and the remainder partitioned between ethyl acetate and 2% potassium hydrogen sulfate. After washing with saturated brine, drying over magnesium sulfate and solvent removal, the title compound was obtained.

Step H: N-(2,3-Dimethylphenyl)-2(S)-(tert butoxycarbonylamino)hexanamine 2,3-Dimethylaniline (8.32 mL, 68.3 mmol) was dissolved in dichloroethane under nitrogen. Acetic acid was added to obtain pH 5, and sodium triacetoxyborohydride (17.2 g, 80.8 mmol) and crushed molecular sieves (4 g) were added. A solution of the product from Step B (13.3 g, 62.1 mmol) in dichloroethane (80 mL) was added slowly dropwise at 20° C. The reaction was stirred overnight, then quenched with saturated sodium bicarbonate solution. The aqueous layer was removed, the organic phase washed with saturated brine and dried over magnesium sulfate. Crystallization from hexane gave the title compound.

Step I: 2(S)-(tert-Butoxycarbonylamino)-1-[N-(2,3-dimethylphenyl)acetamido]hexane To a solution of the product of Step H (500 mg, 1.56 mmol) and triethylamine (0.240 mL, 1.72 mmol) in 10 mL of dichloromethane at 0° C. was added acetyl chloride (0.122 mL, 1.72 mmol). After 20 min, the solution was warmed to room temperature, then stirred another 2 hours. The reaction was poured into CH2Cl2, washed with 10% citric acid and brine, dried ($Na_2SO_4$), filtered, and concentrated in vacuo to provide the titled product.

Step J: (S)-2-[(1-(4-Cyanobenzyl)-5-imidazolylmethyl)amino]-1-[(2,3-dimethylphenyl) amino]hexane Through a solution of the product from Step 1 (533 mg, 1.47 mmol) in 20 mL of EtOAc at 0° C. was bubbled HCl gas. The saturated solution was warmed to room temperature and stirred for 40 minutes, then concentrated in vacuo. To a solution of this amine salt in 6 mL of 1:1 MeOH/THF at 0° C. was added the aldehyde from Step E (325 mg, 1.54 mmol) and 0.05 mL of acetic acid. After one hour, sodium cyanoborohydride was added (97 mg, 1.54 mmol), and the solution was allowed to warm to room temperature overnight. After ~16 hours, the reaction was poured into EtOAc, washed with sat. aq. $NaHCO_3$ and brine, dried ($Na_2SO_4$), filtered, and concentrated in vacuo. The resulting product was purified by silica gel chromatography (1–2% MeOH/$CHCl_3$). A portion of this was taken up in EtOAc/$Et_2O$ and treated with excess HCl gas, then stripped to provide the titled compound.

FAB mass spectrum m/e 458 (M+1).

Analysis calculated for $C_{28}H_{35}N_5O \cdot 2.0$ HCl: C, 63.39; H, 7.03; N, 13.20; Found: C, 63.03; H, 6.97; N, 12.92.

EXAMPLE 125

(S)-2-[N-(1-(4-cyanobenzyl)-5-imidazolylmethyl)-N-(methyl)amino]-1-[N-(2,3-dimethylphenyl) acetamido]hexane hydrochloride To a solution of the product from Step J of Example 124 (186 mg, 0.41 mmol) and formaldehyde (0.158 mL, 37% in $H_2O$, 2.1 mmol) in 2 mL of acetonitrile was added sodium cyanoborohydride (41 mg, 0.66 mmol). The pH of the solution was adjusted to 5–7 by dropwise addition of AcOH. After 4 hours, another portion of sodium cyanoborohydride was added (30 mg), and the reaction was stirred overnight. The reaction was poured into EtOAc, washed with sat. aq. $NaHCO_3$ and brine, dried ($Na_2SO_4$), filtered, and concentrated in vacuo. The resulting product was purified by silica gel chromatography (EtOAc, then 10% MeOH/$CHCl_3$). A portion of this was taken up in EtOAc/$Et_2O$ and treated with excess HCl gas, then stripped to provide the titled compound.

FAB mass spectrum m/e 472 (M+1).

Analysis calculated for $C_{29}H_{37}N_5O \cdot 2.0$ HCl: C, 58.50; H, 6.88; N, 11.62; Found: C, 58.53; H, 7.52; N, 11.53.

EXAMPLE 126

N-[1-(4-cyanobenzyl)-5-imidazolylmethyl]-N'-(3-chlorophenyl)ethylenediamine hydrochloride Step A: N-(2-aminoethyl)-3-chloroaniline hydrochloride To a solution of 3-chloroaniline (30 mL) in 500 mL of dichloromethane at 0° C. was added dropwise a solution of 4 N HCl in 1,4-dioxane (80 mL). The solution was warmed to room temperature, then concentrated to dryness in vacuo to provide a white powder. A mixture of this powder with 2-oxazolidinone (24.6 g) was heated under nitrogen atmosphere at 160° C. for 10 hours, during which the solids melted, and gas evolution was observed. The reaction was allowed to cool, forming the titled compound as a pale brown solid.

Step B: N-[1-(4-cyanobenzyl)-5-imidazolylmethyl]-N'-(3-chlorophenyl)ethylenediamine The amine hydrochloride from Step A (978 mg) was partitioned between dilute aqueous $NaHCO_3$ solution and methylene chloride. The aqueous layer was washed with three portions of $CH_2Cl_2$, and the combined organics were dried ($Na_2SO_4$), filtered, and concentrated in vacuo to provide the free amine. To a solution of the amine in 11 mL of 1,2-dichloroethane at 0° C. was added 4 Å powdered molecular sieves (2 g), followed by sodium triacetoxyborohydride (3.04 g). The aldehyde from Step E of Example 1 (1.21 g) was added, and the reaction was stirred at 0° C. After 15 hours, , the reaction was poured into EtOAc, washed with sat. aq. NaHCO$_3$, and the aqueous layer was extracted with EtOAc. The combined organics were washed with brine, dried (Na$_2$SO$_4$), filtered, and concentrated in vacuo. The resulting product was taken up in 60 mL of 5:1 benzene:CH$_2$Cl$_2$, and propylamine (10 mL) was added. The reaction was stirred for 12 hours, then concentrated in vacuo, and purified by silica gel chromatography (5% MeOH/CHCl$_3$) to provide the titled compound as a white foam. A portion of this was taken up in CH$_2$Cl$_2$ and treated with excess HCl/Et$_2$O, then stripped to provide the titled compound.

FAB mass spectrum m/e 366 (M+1).

Analysis calculated for C$_{20}$H$_{20}$N$_5$Cl.2.70 HCl: C, 51.77; H, 4.93; N, 15.09; Found: C, 51.81; H, 4.96; N, 13.43.

EXAMPLE 127

1-(4-Cyanobenzyl)-5-[N-(3-phenylpropyl) aminomethyl]imidazole hydrochloride

The titled compound was prepared from from the aldehyde product from Step E of Example 124 and 3-phenylpropylamine using the procedure described in Step B of Example 126.

FAB mass spectrum m/e 331 (M+1).

Analysis calculated for C$_{21}$H$_{22}$N$_4$.2.10 HCl.0.80 H$_2$O: C, 59.86; H, 6.15; N, 13.30; Found: C, 59.97; H, 6.18; N, 13.09.

EXAMPLE 128

(S)-2-[(1-(4-Cyanobenzyl)-5-imidazolylmethyl) amino]-N-(benzyloxycarbonyl)-N-(3-chlorobenzyl)-4-(methanesulfonyl)butanamine hydrochloride Step A: (S)-2-(tert-Butoxycarbonylamino)-N-methoxy-N-methyl-4-(methylthio)butanamide L-N-Boc-methionine (30.0 g, 0.120 mol), N,O-dimethylhydroxylamine hydrochloride (14.1 g, 0.144 mol), EDC hydrochloride (27.7 g, 0.144 mol) and HOBT (19.5 g, 0.144 mol) were stirred in dry DMF (300 mL) at 20° C. under nitrogen. More N,O-dimethylhydroxylamine hydrochloride (2.3 g, 23 mmol) was added to obtain pH 7–8. The reaction was stirred overnight, the DMF distilled to half the original volume under high vacuum, and the residue partitioned between ethyl acetate and sat. NaHCO$_3$ soln. The organic phase was washed with saturated sodium bicarbonate, water, 10% citric acid, and brine, and dried with sodium sulfate. The solvent was removed in vacuo to give the titled compound.

Step: B: (S)-2-(tert-Butoxycarbonylamino)-N-methoxy-N-methyl-4-(methanesulfonyl)butanamide To solution of the product from Step A (23.1 g, 79.2 mmol) in methanol (300 mL) at 0° C. was added a suspension of magnesium monoperoxyphthalate (117 g, 238 mmol) in 500 mL MeOH. The reaction was allowed to warm to room temperature. After 16 hours, the reaction was quenched at 0° C. by the addition of 2 N Na$_2$S$_2$O$_3$ soln. The solution was poured into EtOAc and sat NaHCO$_3$ solution, and the organic layer was washed with brine, dried (Na$_2$SO$_4$), filtered, and concentrated in vacuo to provide the crude titled compound.

Step C: (S)-2-(tert-Butoxycarbonylamino)-4-(methanesulfonyl)butanal

A suspension of lithium aluminum hydride (5.15 g, 0.136 mol) in ether (290 mL) was stirred at room temperature for one hour. The solution was cooled to –75° C. under nitrogen, and a solution of the product from Step B (23.9 g, 73.6 mol) in THF (60 mL) was added over ca. 30 min, maintaining the temperature below –40° C. When the addition was complete, the reaction was warmed to –15° C., then recooled to –35° C. A solution of potassium hydrogen sulfate (19.4 g) in 77 mL water was slowly added. The mixture was warmed to room temperature, and stirred for one hour. The solution was filtered through a pad of celite, washed with 10% HCl solution, sat. NaHCO$_3$ solution and brine, dried (Na$_2$SO$_4$), filtered, and concentrated in vacuo to provide the titled aldehyde.

Step D: (S)-2-(tert-butoxycarbonylamino)-N-(3-chlorobenzyl)-4-(methanesulfonyl)butanamine To a solution of 3-chlorobenzylamine (0.628 mL, 5.14 mmol) and crushed molecular sieves (1.5 g) in dichloroethane (10 mL) under nitrogen at 0° C. was added sodium triacetoxyborohydride (2.73 g, 12.9 mmol), followed the product from Step C (2.73 g, 5.14 mmol). The reaction was stirred overnight, allowing it to warm to room temperature. The solution was poured into EtOAc and sat NaHCO$_3$ solution, and the organic layer was washed with brine, dried (Na$_2$SO$_4$), filtered, and concentrated in vacuo to provide the crude product which was purified by silica gel chromatography (2.5–5% MeOH/CHCl$_3$) to obtain the titled compound as a white foam.

Step E: (S)-2-(tert-Butoxycarbonylamino)-N-(benzyloxycarbonyl)-N-(3-chlorobenzyl)-4-(methanesulfonyl)butanamine To a solution of the amine from Step D (754 mg, 1.93 mmol) and triethylamine (0.403 mL, 2.89 mmol) in 5 mL of dichloromethane at 0° C. was added benzylchloroformate (0.303 mL, 2.12 mmol). After 2 hours, the solution was poured into EtOAc and sat NH$_4$Cl solution, and the organic layer was washed with sat. NaHCO$_3$ soln. and brine, dried (Na$_2$SO$_4$), filtered, and concentrated in vacuo to provide the crude product which was purified by silica gel chromatography (30–40% EtOAc/hexane) to obtain the titled compound as a white foam.

Step F: (S)-2-[(1-(4-cyanobenzyl)-5-imidazolylmethyl)amino]-N-(benzyloxycarbonyl)-N-(3-chlorobenzyl)-4-(methanesulfonyl)butanamine To a solution of the product from Step E (360 mg, 0.686 mmol) in 6 mL of dichloromethane was added at room temperature dropwise 3 mL of trifluoroacetic acid. After 30 minutes, the solution was concentrated in vacuo. The resulting product was reconcentrated from benzene three times to remove excess trifluoroacetic acid. To a solution of the amine salt in 4.2 mL of 1,2-dichloroethane at 0° C. was added 4 Å powdered molecular sieves, followed by sodium triacetoxyborohydride (363 mg, 1.71 mmol). The aldehyde from Step E of Example 1 (159 mg, 0.754 mmol) was added at 0° C., followed by N-methylmorpholine (0.076 mL, 0.69 mmol). The reaction was stirred overnight, allowing it to warm to room temperature. The solution was poured into EtOAc, washed with sat. aq. NaHCO$_3$ and brine, dried (Na$_2$SO$_4$), filtered, and concentrated in vacuo. The resulting product was purified by silica gel chromatography (50–75% acetone/hexane) to provide the desired product. A portion of this was taken up in CH$_2$Cl$_2$ and treated with excess HCl/Et$_2$O, then stripped to provide the titled compound.

FAB mass spectrum m/e 620 (M+1).

Analysis calculated for C$_{32}$H$_{34}$N$_5$O$_4$SCl.2.0 HCl.0.30 H$_2$O C, 55.03; H, 5.28; N, 10.03; Found: C, 55.00; H, 5.42; N, 9.99.

EXAMPLE 129

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in Examples 1–128 were tested for inhibitory activity against human FPTase by the assay described above and were found to have IC$_{50}$ of <50 μM.

EXAMPLE 130

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_{2/1}$ mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

EXAMPLE 131

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits Ras farnesyl-transferase having the Formula I:

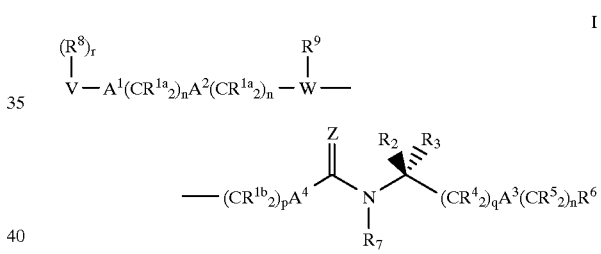

wherein:

R$^{1a}$ is independently selected from:
 a) hydrogen,
 b) aryl, heterocycle, C$_3$–C$_{10}$ cycloalkyl, C$_2$–C$_{20}$ alkenyl, C$_2$–C$_{20}$ alkynyl, R$^{10}$O-, R$^{11}$S(O)$_m$-, R$^{10}$C(O)NR$^{10}$-, CN, NO$_2$, (R$^{10}$)$_2$N-C(NR$^{10}$)-, R$^{10}$C(O)-, R$^{10}$OC(O)-, N$_3$, -N(R$^{10}$)$_2$, or R$^{11}$OC(O)NR$^{10}$-,
 c) C$_1$–C$_6$ alkyl unsubstituted or substituted by aryl, heterocyclic, C$_3$–C$_{10}$ cycloalkyl, C$_2$–C$_{20}$ alkenyl, C$_2$–C$_{20}$ alkynyl, R$^{10}$O-, R$^{11}$S(O)$_m$-, R$^{10}$C(O)NR$^{10}$-, CN, (R$^{10}$)$_2$N-C(NR$^{10}$)-, R$^{10}$C(O)-, R$^{10}$OC(O)-, N$_3$, -N(R$^{10}$)$_2$, or R$^{11}$OC(O)-NR$^{10}$-;

R$^{1b}$ is independently selected from:
 a) hydrogen,
 b) substituted or unsubstituted aryl, substituted or unsubstituted heterocycle, C$_3$–C$_{10}$ cycloalkyl, C$_2$–C$_{20}$ alkenyl, C$_2$–C$_{20}$ alkynyl, R$^{10}$O-, R$^{11}$S(O)$_m$-, CN, NO$_2$, (R$^{10}$)$_2$N-C(NR$^{10}$)-, R$^{10}$C(O)-, R$^{10}$OC(O)-, N$_3$ or -N(R$^{10}$)$_2$,
 c) C$_1$–C$_6$ alkyl unsubstituted or substituted by substituted or unsubstituted aryl, substituted or unsubstituted heterocyclic, C$_3$–C$_{10}$ cycloalkyl, C$_2$–C$_{20}$ alkenyl, C$_2$–C$_{20}$ alkynyl, R$^{10}$O-, R$^{11}$S(O)$_m$-, CN, (R$^{10}$)$_2$N-C(NR$^{10}$)-, R$^{10}$C(O)-, R$^{10}$OC(O)-, N$_3$ or -N(R$^{10}$)$_2$;

R² or R³ are combined with R⁷ to form a ring such that

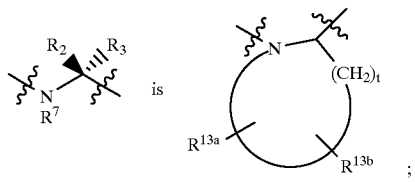

R⁴ and R⁵ are independently selected from:
a) hydrogen,
b) C₁–C₆ alkyl unsubstituted or substituted by C₂–C₂₀ alkenyl, R¹⁰O-, R¹¹S(O)ₘ-, R¹⁰C(O)NR¹⁰-, CN, N₃, (R¹⁰)₂N-C(NR¹⁰)-, R¹⁰C(O)-, -N(R¹⁰)₂, or R¹¹OC(O)NR¹⁰-,
c) unsubstituted or substituted aryl, unsubstituted or substituted heterocycle, C₃–C₁₀ cycloalkyl, C₂–C₂₀ alkenyl, halogen, R¹⁰O-, R¹¹S(O)ₘ-, R¹⁰C(O)NR¹⁰-, CN, NO₂, (R¹⁰)₂N-C(NR¹⁰)-, R¹⁰C(O)-, N₃, -N(R¹⁰)₂, or R¹¹OC(O)NR¹⁰-, and
d) C₁–C₆ alkyl substituted with an unsubstituted or substituted group selected from aryl, heterocyclic and C₃–C₁₀ cycloalkyl;

R¹³ᵃ and R¹³ᵇ are independently selected from:
a) hydrogen,
b) C₁–C₆ alkyl unsubstituted or substituted by C₂–C₂₀ alkenyl, R¹⁰O-, R¹¹S(O)ₘ-, R¹⁰C(O)NR¹⁰-, CN, N₃, (R¹⁰)₂N-C(NR¹⁰)-, R¹⁰C(O)-, -N(R¹⁰)₂, or R¹¹OC(O)NR¹⁰-,
c) unsubstituted or substituted aryl, unsubstituted or substituted heterocycle, C₃–C₁₀ cycloalkyl, C₂–C₂₀ alkenyl, halogen, R¹⁴O-, R¹¹S(O)ₘ-, R¹⁰C(O)NR¹⁰-, CN, NO₂, (R¹⁰)₂N-C(NR¹⁰)-, R¹⁰C(O)-, N₃, -N(R¹⁰)₂, or R¹¹OC(O)NR¹⁰-, and
d) C₁–C₆ alkyl substituted with an unsubstituted or substituted group selected from aryl, heterocyclic and C₃–C₁₀ cycloalkyl;

R⁶ is selected from:
a) hydrogen,
b) substituted or unsubstituted aryl, substituted or unsubstituted heterocycle, C₃–C₁₀ cycloalkyl, C₂–C₂₀ alkenyl, C₂–C₂₀ alkynyl, C₁–C₂₀ perfluoroalkyl, allyloxy, F, Cl, Br, R¹⁰O-, R¹¹S(O)ₘ-, R¹⁰C(O)NR¹⁰-, CN, NO₂, R¹⁰₂N-C(NR¹⁰)-, R¹⁰C(O)-, N₃, -N(R¹⁰)₂, (R¹²)₂NC(O)- or R¹¹OC(O)NR¹⁰-, and
c) C₁–C₆ alkyl unsubstituted or substituted by substituted or unsubstituted aryl, substituted or unsubstituted heterocycle, C₃–C₁₀ cycloalkyl, C₂–C₂₀ alkenyl, C₂–C₂₀ alkynyl, C₂–C₂₀ perfluoroalkyl, F, Cl, Br, R¹⁰O-, R¹¹S(O)ₘ-, R¹⁰C(O)NH-, CN, H₂N-C(NH)-, R¹⁰C(O)-, N₃, -N(R¹⁰)₂, or R¹⁰OC(O)NH-;

R⁷ is independently selected from
a) hydrogen,
b) unsubstituted or substituted aryl,
c) unsubstituted or substituted heterocycle,
d) unsubstituted or substituted C₃–C₁₀ cycloalkyl, and
e) C₁–C₆ alkyl substituted with hydrogen or an unsubstituted or substituted group selected from aryl, heterocycle and C₃–C₁₀ cycloalkyl;

R⁸ is selected from:
a) hydrogen,
b) substituted or unsubstituted aryl, substituted or unsubstituted heterocycle, C₃–C₁₀ cycloalkyl, C₂–C₂₀ alkenyl, C₂–C₂₀ alkynyl, C₁–C₂₀ perfluoroalkyl, allyloxy, F, Cl, Br, R¹⁰O-, R¹¹S(O)ₘ-, R¹⁰C(O)NR¹⁰-, -S(O)₂NR¹⁰₂, CN, NO₂, R¹⁰₂N-C(NR¹⁰)-, R¹⁰C(O)-, R¹⁰OC(O)-, N₃, -N(R¹⁰)₂, or R¹¹OC(O)NR¹⁰-, and
c) C₁–C₆ alkyl unsubstituted or substituted by substituted or unsubstituted aryl, substituted or unsubstituted heterocycle, C₃–C₁₀ cycloalkyl, C₂–C₂₀ alkenyl, C₂–C₂₀ alkynyl, C₂–C₂₀ perfluoroalkyl, F, Cl, Br, R¹⁰O-, R¹¹S(O)ₘ-, R¹⁰C(O)NH-, CN, H₂N-C(NH)-, R¹⁰C(O)-, R¹⁰OC(O)-, N₃, -N(R¹⁰)₂, or R¹⁰OC(O)NH-;

R⁹ is selected from:
a) hydrogen,
b) C₂–C₂₀ alkenyl, C₂–C₂₀ alkynyl, C₂–C₂₀ perfluoroalkyl, F, Cl, Br, R¹⁰O-, R¹¹S(O)ₘ-, R¹⁰C(O)NR¹⁰-, CN, NO₂, (R¹⁰)₂N-C-(NR¹⁰)-, R¹⁰C(O)-, R¹⁰OC(O)-, N₃, -N(R¹⁰)₂, or R¹¹OC(O)NR¹⁰-, and
c) C₁–C₆ alkyl unsubstituted or substituted by C₂–C₂₀ perfluoroalkyl, F, Cl, Br, R¹⁰O-, R¹¹S(O)ₘ-, R¹⁰C(O)NR¹⁰-, CN, (R¹⁰)₂N-C(NR¹⁰)-, R¹⁰C(O)-, R¹⁰OC(O)-, N₃, -N(R¹⁰)₂, or R¹¹OC(O)NR¹⁰-;

R¹⁰ is independently selected from hydrogen, C₁–C₆ alkyl, benzyl and aryl;

R¹¹ is independently selected from C₁–C₆ alkyl and aryl;

R¹² is independently selected from hydrogen, C₁–C₆ alkyl and aryl, or (R¹²)₂ forms -(CH₂)ₛ-;

R¹⁴ is independently selected from hydrogen, C₁–C₆ alkyl, C₁–C₆ alkyl substituted with CO₂R¹⁰, C₁–C₆ alkyl substituted with aryl, C₁–C₆ alkyl substituted with substituted aryl, C₁–C₆ alkyl substituted with heterocycle, C₁–C₆ alkyl substituted with substituted heterocycle, aryl and substituted aryl;

A¹, A² and A³ are independently selected from: a bond, -CH=CH-, -C≡C-, -C(O)-, -C(O)NR⁷-, -NR⁷C(O)-, O, -N(R⁷)-, -S(O)₂N(R⁷)-, -N(R⁷)S(O)₂-, or S(O)ₘ;

A⁴ is selected from: a bond, O, -N(R⁷)- or S,

V is selected from:
a) hydrogen,
b) heterocycle,
c) aryl,
d) C₁–C₂₀ alkyl wherein from 0 to 4 carbon atoms are replaced with a heteroatom selected from O, S, and N, and
e) C₂–C₂₀ alkenyl, provided that V is not hydrogen if A¹ is S(O)ₘ and V is not hydrogen if A¹ is a bond, n is 0 and A² is S(O)ₘ;

W is a heterocycle;

Z is independently R¹ᵃ₂ or O;

| | |
|---|---|
| m is | 0, 1 or 2; |
| n is | 0, 1, 2, 3, or 4; |
| p is | 0, 1, 2, 3, or 4; |
| q is | 0, 1, 2, 3, or 4; |
| r is | 0 to 5, provided that r is 0 when V is hydrogen; |
| s is | 4 or 5; and |
| t is | 3, 4 or 5; | or a pharmaceutically acceptable salt thereof.

2. The compound according to claim 1 of the formula I:

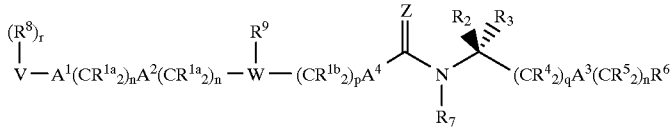

wherein:
$R^{1a}$ is independently selected from: hydrogen or $C_1$–$C_6$ alkyl;
$R^{1b}$ is independently selected from:
  a) hydrogen,
  b) substituted or unsubstituted aryl, substituted or unsubstituted heterocycle, $C_3$–$C_{10}$ cycloalkyl, $R^{10}O$-, -$N(R^{10})_2$ or $C_2$–$C_6$ alkenyl, and
  c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_6$ alkenyl, $R^{10}O$-, or -$N(R^{10})_2$;
$R^2$ or $R^3$ are combined with $R^7$ to form a ring such that:

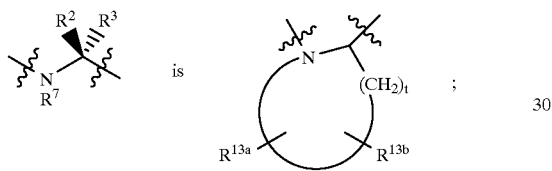

$R^4$ and $R^5$ are independently selected from:
  a) hydrogen,
  b) $C_1$–$C_6$ alkyl unsubstituted or substituted by $C_2$–$C_6$ alkenyl, $R^{10}O$-, $R^{11}S(O)_m$-, $R^{10}C(O)NR^{10}$-, CN, $N_3$, $(R^{10})_2N$-$C(NR^{10})$-, $R^{10}C(O)$-, -$N(R^{10})_2$, or $R^{11}OC(O)NR^{10}$-,
  c) substituted or unsubstituted aryl, substituted or unsubstituted heterocycle, $C_3$–$C_{10}$ cycloalkyl, $C_2$–$C_6$ alkenyl, halogen, $R^{10}O$-, $R^{11}S(O)_m$-, $R^{10}C(O)NR^{10}$-, CN, $NO_2$, $(R^{10})_2N$-$(NR^{10})$-, $R^{10}C(O)$-, $N_3$, -$N(R^{10})_2$, or $R^{11}OC(O)NR^{10}$-, and
  d) $C_1$–$C_6$ alkyl substituted with an unsubstituted or substituted group selected from aryl, heterocyclic and $C_3$–$C_{10}$ cycloalkyl;
$R^{13a}$ and $R^{13b}$ are independently selected from:
  a) hydrogen,
  b) $C_1$–$C_6$ alkyl unsubstituted or substituted by $C_2$–$C_6$ alkenyl, $R^{10}O$-, $R^{11}S(O)_m$-, $R^{10}C(O)NR^{10}$-, CN, $N_3$, $(R^{10})_2N$-$C(NR^{10})$-, $R^{10}C(O)$-, -$N(R^{10})_2$, or $R^{11}OC(O)NR^{10}$-,
  c) substituted or unsubstituted aryl, substituted or unsubstituted heterocycle, $C_3$–$C_{10}$ cycloalkyl, $C_2$–$C_6$ alkenyl, halogen, $R^{14}O$-, $R^{11}S(O)_m$-, $R^{10}C(O)NR^{10}$-, CN, $NO_2$, $(R^{10})_2N$-$(NR^{10})$-, $R^{10}C(O)$-, $N_3$, -$N(R^{10})_2$, or $R^{11}OC(O)NR^{10}$-, and
  d) $C_1$–$C_6$ alkyl substituted with an unsubstituted or substituted group selected from aryl, heterocyclic and $C_3$–$C_{10}$ cycloalkyl;
$R^6$ is independently selected from:
  a) hydrogen,
  b) substituted or unsubstituted aryl, substituted or unsubstituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$-, allyloxy, $R^{10}C(O)NR^{10}$-, CN, $NO_2$, $(R^{10})_2N$-$C(NR^{10})$-, $R^{10}C(O)$-, -$N(R^{10})_2$, $(R^{12})_2NC(O)$- or $R^{11}OC(O)NR^{10}$-, and
  c) $C_1$–$C_6$ alkyl substituted by $C_1$–$C_6$ perfluoroalkyl, $R^{10}O$-, $R^{10}C(O)NR^{10}$-, $(R^{10})_2N$-$C(NR^{10})$-, $R^{10}C(O)$-, -$N(R^{10})_2$, or $R^{11}OC(O)NR^{10}$-;
$R^7$ is independently selected from
  a) hydrogen,
  b) unsubstituted or substituted aryl,
  c) unsubstituted or substituted heterocycle,
  d) unsubstituted or substituted $C_3$–$C_{10}$ cycloalkyl, and
  e) $C_1$–$C_6$ alkyl substituted with hydrogen or an unsubstituted or substituted group selected from aryl, heterocycle and $C_3$–$C_{10}$ cycloalkyl;
  wherein heterocycle is selected from pyrrolidinyl, imidazolyl, pyridinyl, thiazolyl, pyridonyl, indolyl, quinolinyl, isoquinolinyl, and thienyl;
$R^8$ is selected from:
  a) hydrogen,
  b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$-, $R^{10}C(O)NR^{10}$-, CN, $NO_2$, $(R^{10})_2N$-$C(NR^{10})$-, $R^{10}C(O)$-, $R^{10}OC(O)$-, -$N(R^{10})_2$, or $R^{11}OC(O)NR^{10}$-, and
  c) $C_1$–$C_6$ alkyl substituted by $C_1$–$C_6$ perfluoroalkyl, $R^{10}O$-, $R^{10}C(O)NR^{10}$-, $(R^{10})_2N$-$C(NR^{10})$-, $R^{10}C(O)$-, $R^{10}C(O)$-, -$N(R^{10})_2$, or $R^{11}OC(O)NR^{10}$-;
$R^9$ is selected from:
  a) hydrogen,
  b) $C_2$–$C_6$ alkenyl, $C_2$–$C_6$ alkynyl, $C_1$–$C_6$ perfluoroalkyl, F, Cl, $R^{10}O$-, $R^{11}S(O)_m$-, $R^{10}C(O)NR^{10}$-, CN, $NO_2$, $(R^{10})_2N$-$C(NR^{10})$-, $R^{10}C(O)$-, $R^{10}OC(O)$-, -$N(R^{10})_2$, or $R^{11}OC(O)NR^{10}$-, and
  c) $C_1$–$C_6$ alkyl unsubstituted or substituted by $C_1$–$C_6$ perfluoroalkyl, F, Cl, $R^{10}O$-, $R^{11}S(O)_m$-, $R^{10}C(O)NR^{10}$-, CN, $(R^{10})_2N$-$C(NR^{10})$-, $R^{10}C(O)$-, $R^{10}OC(O)$-, -$N(R^{10})_2$, or $R^{11}OC(O)NR^{10}$-;
$R^{10}$ is independently selected from hydrogen, $C_1$-$C_6$ alkyl, benzyl and aryl;
$R^{11}$ is independently selected from $C_1$–$C_6$ alkyl and aryl;
$R^{12}$ is independently selected from hydrogen, $C_1$–$C_6$ alkyl and aryl, or $(R^{12})_2$ forms -$(CH_2)_s$-;
$R^{14}$ is independently selected from hydrogen, $C_1$–$C_6$ alkyl, $C_1$–$C_6$ alkyl substituted with $CO_2R^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;
$A^1$, $A^2$ and $A^3$ are independently selected from: a bond, -CH=CH-, -C≡C-, -C(O)-, -C(O)NR$^7$-, -NR$^7$C(O)-, -S(O)$_2$NR$^7$-, -NR$^7$S(O)$_2$-, O, -N(R$^7$)-, or S(O)$_m$;
$A^4$ is selected from: a bond, O, -N(R$^7$)- or S;
V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl, c) aryl,
d) $C_1-C_{20}$ alkyl wherein from 0 to 4 carbon atoms are replaced with a heteroatom selected from O, S, and N, and
e) $C_2-C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, oxazolyl, isoxazolyl, indolyl, quinolinyl, or isoquinolinyl;

Z is independently $R^{1a}{}_2$ or O;

| | |
|---|---|
| m is | 0, 1 or 2; |
| n is | 0, 1, 2, 3 or 4; |
| p is | 0, 1, 2, 3 or 4; |
| q is | 0, 1, 2, 3 or 4; |
| r is | 0 to 5, provided that r is 0 when V is hydrogen; and |
| t is | 3, 4 or 5; | or a pharmaceutically acceptable salt thereof.

3. The compound according to claim 1 of the formula I:

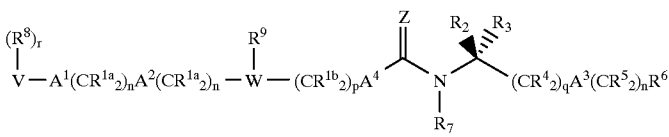

I wherein:
$R^{1a}$ is independently selected from: hydrogen or $C_1-C_6$ alkyl;
$R^{1b}$ is independently selected from:
a) hydrogen,
b) substituted or unsubstituted aryl, substituted or unsubstituted heterocycle, $C_3-C_{10}$ cycloalkyl, $R^{10}O-$ or $C_2-C_6$ alkenyl,
c) $C_1-C_6$ alkyl unsubstituted or substituted by aryl, heterocycle, $C_3-C_{10}$ cycloalkyl, $C_2-C_6$ alkenyl, $R^{10}O-$, or $-N(R^{10})_2$;

$R^2$ or $R^3$ are combined with $R^7$ to form a ring such that:

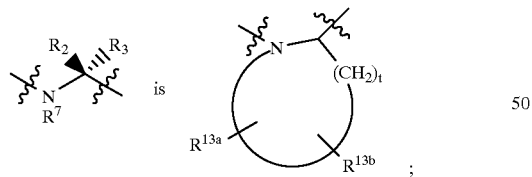

$R^4$ and $R^5$ are independently selected from:
a) hydrogen,
b) $C_1-C_6$ alkyl unsubstituted or substituted by $C_2-C_6$ alkenyl, $R^{10}O-$, $R^{11}S(O)_m-$, $R^{10}C(O)NR^{10}-$, CN, $N_3$, $(R^{10})_2N-C(NR^{10})-$, $R^{10}C(O)-$, $-N(R^{10})_2$, or $R^{11}OC(O)NR^{10}-$,
c) substituted or unsubstituted aryl, substituted or unsubstituted heterocycle, $C_3-C_{10}$ cycloalkyl, $C_2-C_6$ alkenyl, fluoro, chloro, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $N_3$, $-N(R^{10})_2$, or $R^{11}OC(O)NR^{10}-$, and
d) $C_1-C_6$ alkyl substituted with an unsubstituted or substituted group selected from substituted or unsubstituted aryl, substituted or unsubstituted heterocyclic and $C_3-C_{10}$ cycloalkyl;

$R^{13a}$ and $R^{13b}$ are independently selected from:
a) hydrogen,
b) $C_1-C_6$ alkyl unsubstituted or substituted by $C_2-C_6$ alkenyl, $R^{10}O-$, $R^{11}S(O)_m-$, $R^{10}C(O)NR^{10}-$, CN, $N_3$, $(R^{10})_2N-C(NR^{10})-$, $R^{10}C(O)-$, $-N(R^{10})_2$, or $R^{11}OC(O)NR^{10}-$,
c) substituted or unsubstituted aryl, substituted or unsubstituted heterocycle, $C_3-C_{10}$ cycloalkyl, $C_2-C_6$ alkenyl, fluoro, chloro, $R^{14}O-$, $R^{11}S(O)_m-$, $R^{10}C(O)NR^{10}-$, CN, $NO_2$, $(R^{10})_2N-C(NR^{10})-$, $R^{10}C(O)-$, $N_3$, $-N(R^{10})_2$, or $R^{11}OC(O)NR^{10}-$, and
d) $C_1-C_6$ alkyl substituted with an unsubstituted or substituted group selected from substituted or unsubstituted aryl, substituted or unsubstituted heterocyclic and $C_3-C_{10}$ cycloalkyl;

$R^6$ is independently selected from:
a) hydrogen,
b) substituted or unsubstituted aryl, substituted or unsubstituted heterocycle, $C_1-C_6$ alkyl, $C_2-C_6$ alkenyl, $C_2-C_6$ alkynyl, $C_1-C_6$ perfluoroalkyl, F, Cl, $R^{10}O-$, allyloxy, $R^{10}C(O)NR^{10}-$, CN, $NO_2$, $(R^{10})_2N-C(NR^{10})-$, $R^{10}C(O)-$, $-N(R^{10})_2$, $(R^{12})_2NC(O)-$ or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^7$ is independently selected from
a) hydrogen,
b) unsubstituted or substituted aryl,
c) unsubstituted or substituted heterocycle,
d) unsubstituted or substituted cycloalkyl, and
e) $C_1-C_6$ alkyl substituted with hydrogen or an unsubstituted or substituted group selected from aryl, heterocycle and cycloalkyl;

wherein heterocycle is selected from pyrrolidinyl, imidazolyl, pyridinyl, thiazolyl, pyridonyl, indolyl, quinolinyl, isoquinolinyl, and thienyl;

$R^8$ is selected from:
a) hydrogen,
b) $C_1-C_6$ alkyl, $C_2-C_6$ alkenyl, $C_2-C_6$ alkynyl, $C_1-C_6$ perfluoroalkyl, F, Cl, $R^{10}O-$, $R^{10}C(O)NR^{10}-$, CN, $NO_2$, $(R^{10})_2N-C(NR^{10})-$, $R^{10}C(O)-$, $R^{10}OC(O)-$, $-N(R^{10})_2$, or $R^{11}OC(O)NR^{10}-$, and
c) $C_1-C_6$ alkyl substituted by $C_1-C_6$ perfluoroalkyl, $R^{10}O-$, $R^{10}C(O)NR^{10}-$, $(R^{10})_2N-C(NR^{10})-$, $R^{10}C(O)-$, $R^{10}OC(O)-$, $-N(R^{10})_2$, or $R^{11}OC(O)NR^{10}-$;

$R^9$ is selected from:
a) hydrogen,
b) $C_2-C_6$ alkenyl, $C_2-C_6$ alkynyl, $C_1-C_6$ perfluoroalkyl, F, Cl, $R^{10}O-$, $R^{11}S(O)_m-$, $R^{10}C(O)NR^{10}-$, CN, $NO_2$, $(R^{10})_2N-C(NR^{10})-$, $R^{10}C(O)-$, $R^{10}OC(O)-$, $N(R^{10})_2$, or $R^{11}OC(O)NR^{10}-$, and
c) $C_1-C_6$ alkyl unsubstituted or substituted by $C_1-C_6$ perfluoroalkyl, F, Cl, $R^{10}O-$, $R^{11}S(O)_m-$, $R^{10}C(O)NR^{10}-$, CN, $(R^{10})_2N-C(NR^{10})-$, $R^{10}C(O)-$, $R^{10}OC(O)-$, $-N(R^{10})_2$, or $R^{11}OC(O)NR^{10}-$;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl and aryl, or $(R^{12})_2$ forms -$(CH_2)_s$-;

$R^{14}$ is independently selected from hydrogen, $C_1$–$C_6$ alkyl, $C_1$–$C_6$ alkyl substituted with $CO_2R^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;

$A^1$ and $A^2$ are independently selected from: a bond, -CH=CH-, -C≡C-, -C(O)-, -C(O)NR$^7$-, -NR$^7$C(O)-, -S(O)$_2$NR$^7$-, -NR$^7$S(O)$_2$-, O, -N(R$^7$)-, or S(O)$_m$;

$A^4$ is selected from: a bond, O, -N(R$^7$)- or S;

$A^3$ is selected from: a bond, -C(O)NR$^7$-, -NR$^7$C(O)-, -S(O)$_2$NR$^7$-, -NR$^7$S(O)$_2$- or -N(R$^7$)-;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and
provided that V is not hydrogen if $A^1$ is S(O)$_m$ and V is not hydrogen if $A^1$ is a bond, n is 0 and $A^2$ is S(O)$_m$;

W is a heterocycle selected from pyrrolidinyl, imidazolyl, pyridinyl, thiazolyl, pyridonyl, 2-oxopiperidinyl, indolyl, quinolinyl, or isoquinolinyl;

Z is independently $R^{1a}{}_2$ or O;

| | |
|---|---|
| m is | 0, 1 or 2; |
| n is | 0, 1, 2, 3 or 4; |
| p is | 0, 1, 2, 3 or 4; |
| q is | 0 or 1; |
| r is | 0 to 5, provided that r is 0 when V is hydrogen; and |
| t is | 3, 4 or 5; | or a pharmaceutically acceptable salt thereof.

4. The compound according to claim 1 of the formula Ia:

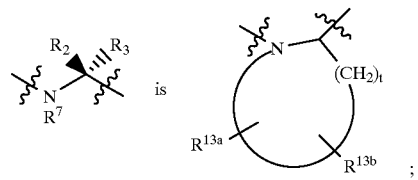

$R^2$ or $R^3$ are combined with $R^7$ to form a ring such that:

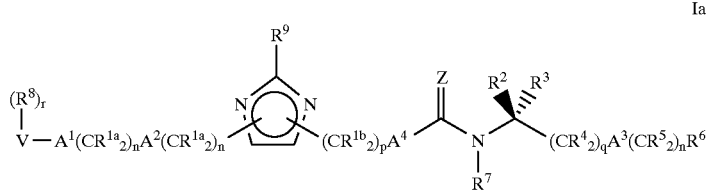

$R^4$ and $R^5$ are independently selected from:
a) hydrogen,
b) $C_1$–$C_6$ alkyl unsubstituted or substituted by $C_2$–$C_6$ alkenyl, $R^{10}$O-, $R^{11}$S(O)$_m$-, $R^{10}$C(O)NR$^{10}$-, CN, $N_3$, $(R^{10})_2$N-C(NR$^{10}$)-, $R^{10}$C(O)-, -N(R$^{10}$)$_2$, or $R^{11}$OC(O)NR$^{10}$-,
c) substituted or unsubstituted aryl, substituted or unsubstituted heterocycle, $C_3$–$C_{10}$ cycloalkyl, $C_2$–$C_6$ alkenyl, fluoro, chloro, $R^{10}$O-, $R^{11}$S(O)-, $R^{10}$C(O)NR$^{10}$-, CN, NO$_2$, $(R^{10})_2$N-C(NR$^{10}$)-, $R^{10}$C(O)-, $N_3$, -N(R$^{10}$)$_2$, or $R^{11}$OC(O)NR$^{10}$-, and
d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^{13a}$ and $R^{13b}$ are independently selected from:
a) hydrogen,
b) $C_1$–$C_6$ alkyl unsubstituted or substituted by $C_2$–$C_6$ alkenyl, $R^{10}$O-, $R^{11}$S(O)$_m$-, $R^{10}$C(O)NR$^{10}$-, CN, $N_3$, $(R^{10})_2$N-C(NR$^{10}$)-, $R^{10}$C(O)-, -N(R$^{10}$)$_2$, or $R^{11}$OC(O)NR$^{10}$-,
c) substituted or unsubstituted aryl, substituted or unsubstituted heterocycle, $C_3$–$C_{10}$ cycloalkyl, $C_2$–$C_6$ alkenyl, fluoro, chloro, $R^{14}$O-, $R^{11}$S(O)$_m$-, $R^{10}$C(O)NR$^{10}$-, CN, NO$_2$, $(R^{10})_2$N-C(NR$^{10}$)-, $R^{10}$C(O)-, $N_3$, -N(R$^{10}$)$_2$, or $R^{11}$OC(O)NR$^{10}$-, and
d) $C_1$–$C_6$ alkyl substituted with an unsubstituted or substituted group selected from substituted or unsubstituted aryl, substituted or unsubstituted heterocyclic and $C_3$–$C_{10}$ cycloalkyl;

$R^6$ is independently selected from:
a) hydrogen,
b) substituted or unsubstituted aryl, substituted or unsubstituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}$O-, allyloxy, $R^{10}$C(O)NR$^{10}$-, CN, NO$_2$, $(R^{10})_2$N-C(NR$^{10}$)-, $R^{10}$C(O)-, -N(R$^{10}$)$_2$, $(R^{12})_2$NC(O)- or $R^{11}$OC(O)NR$^{10}$-, and
c) $C_1$–$C_6$ alkyl substituted by $C_1$–$C_6$ perfluoroalkyl, $R^{10}$O-, $R^{10}$C(O)NR$^{10}$-, $(R^{10})_2$N-C(NR$^{10}$)-, $R^{10}$C(O)-, -N(R$^{10}$)$_2$, or $R^{11}$OC(O)NR$^{10}$-;

$R^7$ is independently selected from
a) hydrogen,
b) unsubstituted or substituted aryl,
c) unsubstituted or substituted heterocycle, Ia wherein:
$R^{1a}$ is independently selected from: hydrogen or $C_1$–$C_6$ alkyl;

$R^{1b}$ is independently selected from:
a) hydrogen,
b) substituted or unsubstituted aryl, substituted or unsubstituted heterocycle, $C_3$–$C_{10}$ cycloalkyl, $R^{10}$O- or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}$O-, or -N(R$^{10}$)$_2$;

d) unsubstituted or substituted cycloalkyl, and
e) $C_1$–$C_6$ alkyl substituted with hydrogen or an unsubstituted or substituted group selected from aryl, heterocycle and cycloalkyl;
wherein heterocycle is selected from pyrrolidinyl, imidazolyl, pyridinyl, thiazolyl, pyridonyl, indolyl, quinolinyl, isoquinolinyl, and thienyl;

$R^8$ is selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}$O-, $R^{10}$C(O)$NR^{10}$-, CN, $NO_2$, $(R^{10})_2$N-C($NR^{10}$)-, $R^{10}$C(O)-, $R^{10}$OC(O)-, $-N(R^{10})_2$, or $R^{11}$OC(O)$NR^{10}$-, and
c) $C_1$–$C_6$ alkyl substituted by $C_1$–$C_6$ perfluoroalkyl, $R^{10}$O-, $R^{10}$C(O)$NR^{10}$-, $(R^{10})_2$N-C($NR^{10}$)-, $R^{10}$C(O)-, $R^{10}$OC(O)-, $-N(R^{10})_2$, or $R^{11}$OC(O)$NR^{10}$-;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}$O-, $R^{11}$S(O)$_m$-, $R^{10}$C(O)$NR^{10}$-, CN, $NO_2$, $(R^{10})_2$N-C($NR^{10}$)-, $R^{10}$C(O)-, $R^{10}$OC(O)-, $-N(R^{10})_2$, or $R^{11}$OC(O)$NR^{10}$-, and
c) $C_1$–$C_6$ alkyl unsubstituted or substituted by $C_1$–$C_6$ perfluoroalkyl, F, Cl, $R^{10}$O-, $R^{11}$S(O)$_m$-, $R^{10}$C(O)$NR^{10}$-, CN, $(R^{10})_2$N-C($NR^{10}$)-, $R^{10}$C(O)-, $R^{10}$OC(O)-, $-N(R^{10})_2$, or $R^{11}$OC(O)$NR^{10}$-;

$R^{10}$ is independently selected from hydrogen, $C_1$–$C_6$ alkyl, benzyl and aryl;

$R^{11}$ is independently selected from $C_1$–$C_6$ alkyl and aryl;

$R^{12}$ is independently selected from hydrogen, $C_1$–$C_6$ alkyl and aryl, or $(R^{12})_2$ forms $-(CH_2)_s-$;

$R^{14}$ is independently selected from hydrogen, $C_1$–$C_6$ alkyl, $C_1$–$C_6$ alkyl substituted with $CO_2R^{10}$, $C_1$–$C_6$ alkyl substituted with aryl, $C_1$–$C_6$ alkyl substituted with substituted aryl, $C_1$–$C_6$ alkyl substituted with heterocycle, $C_1$–$C_6$ alkyl substituted with substituted heterocycle, aryl and substituted aryl;

$A^1$ and $A^2$ are independently selected from: a bond, -CH=CH-, -C≡C-, -C(O)-, -C(O)$NR^7$-, -$NR^7$C(O)-, -S(O)$_2NR^7$-, -$NR^7$S(O)$_2$-, O, -N($R^7$)-, or S(O)$_m$;

$A^4$ is selected from: a bond, O, -N($R^7$)- or S;

$A^3$ is selected from: a bond, -C(O)$NR^7$-, -$NR^7$C(O)-, -S(O)$_2NR^7$-, -$NR^7$S(O)$_2$- or -N($R^7$)-;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and
provided that V is not hydrogen if $A^1$ is S(O)$_m$ and V is not hydrogen if $A^1$ is a bond, n is 0 and $A^2$ is S(O)$_m$;

Z is independently $R^{1a}_2$ or O;

| | |
|---|---|
| m is | 0, 1 or 2; |
| n is | 0, 1, 2, 3 or 4; |
| p is | 0, 1, 2, 3 or 4; |
| q is | 0 or 1; |
| r is | 0 to 5, provided that r is 0 when V is hydrogen; and |
| t is | 3, 4 or 5; | or a pharmaceutically acceptable salt thereof.

5. A compound which inhibits farnesyl-protein transferase which is:

N-{1-(4-Cyanobenzyl)-1H-imidazol-5-yl)acetyl}-2(S){N'-methanesulfonyl-N'-(naphth-1-ylmethyl)aminomethyl}-pyrrolidine N-{1-(4-Cyanobenzyl)-1H-imidazol-5-yl)acetyl}-2(S)-{N'-acetyl-N'-naphth-1-ylmethyl-aminomethyl}-pyrrolidine N-5-(4-Cyanobenzyl)-1H-imidazol-1-yl)acetyl}-2(S)-[1(R)-1-(3-chlorophenyl)-1-hydroxy]methylpyrrolidine N-{5-(4-Cyanobenzyl)-1H-imidazol-1-yl)acetyl}-2(S)-[1(S)-1-(3-chlorophenyl)-1-hydroxy]methylpyrrolidine N-{5-(4-Cyanobenzyl)-1H-imidazol-1-yl)ethyl}-2(S)-[1(R)-1-(3-chlorophenyl)-1-hydroxy]methylpyrrolidine N-{5-(4-Cyanobenzyl)-1H-imidazol-1-yl)ethyl}-2(S)-[1(S)-1-(3-chlorophenyl)-1-hydroxy]methylpyrrolidine N-{1-(4-Cyanobenzyl)-1H-imidazol-5-yl)methyl}-2(S)-[1(R)-1-(3-chlorophenyl)-1-hydroxy]methylpyrrolidine N{1-(4-Cyanobenzyl)-1H-imidazol-5-yl)methyl}-2(S)-[1(S)-1-(3-chlorophenyl)-1-hydroxy]methylpyrrolidine N-{5-(4-Cyanobenzyl)-1H-imidazol-1-yl)acetyl}-4(R)-hydroxy-2(S)-[1 (R)-1-(3-chlorophenyl)-1-hydroxy]methylpyrrolidine N-{5-(4-Cyanobenzyl)-1H-imidazol-1-yl)acetyl}-4(R)-hydroxy-2(S)-[1 (S)-1-(3-chlorophenyl)-1-hydroxy]methylpyrrolidine N-{1-(4-Cyanobenzyl)-1H-imidazol-1-ylethyl}-4(R)-hydroxy-2(S)-[1(R)-1-(3-chlorophenyl)-1-hydroxy]methylpyrrolidine N-[1-(4-Cyanobenzyl)-1H-imidazol-1-ylethyl}-4(R)-hydroxy-2(S)-[1(S)-1-(3-chlorophenyl)-1-hydroxy]methylpyrrolidine N-[5-(4-Cyanobenzyl)-1H-imidazol-1-ylethyl]-4(R)-hydroxy-2(S)-[1(R)-1-(3-chlorophenyl)-1-hydroxy]methylpyrrolidine N-[5-(4-Cyanobenzyl)-1H-imidazol-1-ylethyl]-4(R)-hydroxy-2(S)-[1(S)-1-(3-chlorophenyl)-1-hydroxy]methylpyrrolidine N-[1-(4-Cyanobenzyl)-1-imidazol-5-ylmethyl]-4(R)-hydroxy-2(S)-[1(R)-1-(3-chlorophenyl)-1-hydroxy]methylpyrrolidine N-{1-(4-Cyanobenzyl)-1H-imidazol-5-yl-methyl-4(R)-hydroxy-2(S)-{N'-acetyl-N'-3-chlorobenzyl}aminomethylpyrrolidine N-{1-(4-Cyanobenzyl)-1H-imidazol-5-ylacetyl}-4(R)-hydroxy-2(S)-{N'-acetyl-N'-3-chlorobenzyl}aminomethylpyrrolidine N-{1-(4-Cyanobenzyl)-1H-imidazol-5-yl-methyl-4(R)-hydroxy-2(S)-{N'-acetyl-N'-3-chlorobenzyl}aminomethylpyrrolidine N-{1-(4-Cyanophenethyl)-1H-imidazol-5-yl-methyl-4(R)-hydroxy-2(S)-{N'-acetyl-N'-3-chlorobenzyl}aminomethylpyrrolidine N-{1-(4-Cyanobenzyl)-1H-imidazol-5-yl-acetyl}-4(R)-methoxy-2(S)-{N'-acetyl-N'-3-chlorobenzyl}aminomethylpyrrolidine N-{1-(4-Cyanopheneth-1-yl)-1H-imidazol-5-yl-acetyl-4(R)-methoxy-2(S)-{N'-acetyl-N'-3-chlorobenzyl}aminomethylpyrrolidine N-{1-(4-Cyanobenzyl)-1H--imidazol-5-yl-ethyl}-4(R)-methoxy-2(S)-{N'-acetyl-N'-3-chlorobenzyl}aminomethylpyrrolidine N-{1-(4-Cyanobenzyl)-1H-imidazol-5-ylethyl}-2(S)-{N'-acetyl-N'-3-chlorobenzyl-aminomethyl}pyrrolidine N-{1-(4-Cyanophenethyl)- 1H-imidazol-5-yl-ethyl}-4(R)-methoxy-2(S)-{N'-acetyl-N'-3-chlorobenzyl}aminomethyl pyrrolidine N{1-(4-Cyanobenzyl)-1H-imidazol-5-ylmethyl}-4(R)-benzyloxy-2(S)-{N'-acetyl-N'-3-chlorobenzyl}aminomethylpyrrolidine N-{1-(4-Cyanobenzyl)-1H-imidazol-5-ylethyl}-4(R)-benzyloxy-2(S)-{N'-acetyl-N'-3-chlorobenzyl}aminomethyl pyrrolidine N-{1-(4-Cyanobenzyl)-5-imidazolacetyl}-4(R)-benzyloxy-2(S)-{N'-acetyl-N'-3-chlorobenzyl}aminomethylpyrrolidine N-{1-(4-Cyanobenzyl)-5-imidazol-5-ylmethyl}-4(R)-(2-phenylbenzyloxy)-2(S)-{N'-acetyl-N'-3-chlorobenzyl}aminomethylpyrrolidine N{1-(4-Cyanobenzyl)-1H-imidazol-5-ylmethyl}-4(R)-(4-chlorobenzyloxy)-2(S)-{N'-acetyl-N'-3-chlorobenzyl}aminomethylpyrrolidine N{1-(4-Cyanobenzyl)-5-imidazolemethyl}-4(R)-(4-cyanobenzyloxy)-2(S)-{N'-acetyl-N'-3-chlorobenzyl}aminomethylpyrrolidine N-{1-(4-Cyanobenzyl)-5-imidazol-5-ylmethyl}-4(R)-(3-pyridylmethoxy)-2(S)-{N'-acetyl-N'-3-chlorobenzyl}aminomethylpyrrolidine N-{1-(4-Cyanobenzyl)-1H-imidazol-5-ylmethyl}-4(R)-(phenoxy)-2(S)-{N'-acetyl-N'-3-chlorobenzyl}aminomethylpyrrolidine N-{1-(4-Cyanobenzyl)-1H-imidazol-5-ylmethyl}-4(R)-(2-methylacetyloxy)-2(S)-{N'-acetyl-N'-3-chlorobenzyl}aminomethylpyrrolidine N{1-(4-Cyanobenzyl)-1H-imidazol-5-ylmethyl}-4(R)-(acetyloxy)-2(S)-{N'-acetyl-N'-3-chlorobenzyl}aminomethylpyrrolidine N-{1-(4-Cyanobenzyl)-1H-imidazol-5-ylacetyl}-4(R)-(2-methylacetyloxy)-2(S)-{N'-acetyl-N'-3-chlorobenzyl}aminomethylpyrrolidine N-{1-(4-Cyanobenzyl)-1H-imidazol-5-ylacetyl}-4(R)-(acetyloxy)-2(S)-{N'-3-chlorobenzyl-N'-acetyl}aminomethylpyrrolidine N-{1-(4-Cyanobenzyl)-1H-imidazol-5-ylmethyl}-4(S)-(phenoxy)-2(S)-{N'-acetyl-N'-3-chlorobenzyl}aminomethylpyrrolidine N-{1-(4-Cyanobenzyl)-5-imidazolethyl}-4(S)-(phenoxy)-2(S)-{N'-acetyl-N'-3-chlorobenzyl}aminomethylpyrrolidine N-{1-(4-Cyanobenzyl)-1H-imidazol-5-ylethyl}-4(S)-fluoro-2(S)-{N'-acetyl-N'-3-chlorobenzyl}aminomethylpyrrolidine N-{1-(4-Cyanobenzyl)-1H-imidazol-5ylethyl-4(R)-(2-phenylbenzyloxy)-2(S)-{N'-acetyl-N'-3-chlorobenzyl}aminomethylpyrrolidine N-{1-(4-Cyanobenzyl)-1H-imidazol-5-ylethyl}-4(R)-(4-chlorobenzyloxy)-2(S)-{N'-acetyl-N'-3-chlorobenzyl}aminomethylpyrrolidine N-{1-(4-Cyanobenzyl)-1H-imidazol-5-ylethyl}-4(R)-(4-cyanobenzyloxy)-2(S)-{N'-acetyl-N'-3-chlorobenzyl}aminomethylpyrrolidine N-{1-(4-Cyanobenzyl)-1H-imidazol-5-ylethyl}-4(R)-(3-pyridylmethoxy)-2(S)-{N'-acetyl-N'-3-chlorobenzyl}aminomethyl-pyrrolidine N-{1-(4-Cyanobenzyl)-1H-imidazol-5-ylacetyl}-2(S)-{N'-acetyl-N'-3-cyanobenzyl}aminomethylpyrrolidine N-{1-(4-Cyanobenzyl)-1H-imidazol-5-yl)acetyl}-2(S)-{N'-acetyl-N'-3-methoxybenzyl}aminomethylpyrrolidine.

N-{1-(4-Cyanobenzyl)-1H-imidazol-5-yl)acetyl}-2(S)-{N'-acetyl-N'-3-trifluoromethylbenzyl}aminomethylpyrrolidine N-{1-(4-Cyanobenzyl)-1H-imidazol-5-yl)acetyl}-2(S)-{N'-acetyl-N'-2-methoxybenzyl}aminomethylpyrrolidine N-{1-(4-Cyanobenzyl)-1H-imidazol-5-yl)acetyl}-2(S)-{N'-acetyl-N'-2-trifluoromethylbenzyl}aminomethylpyrrolidine N-{1-(4-Cyanobenzyl)-1H-imidazol-5-yl)acetyl}-2(S)-{N'-acetyl-N'-(2,2-diphenylethyl)}aminomethylpyrrolidine N{1-(4-Cyanobenzyl)-1H-imidazol-5-yl)acetyl}-2(S)-{N'-acetyl-N'-diphenylmethyl}aminomethylpyrrolidine N-{1-(4-Cyanobenzyl)-1H-imidazol-5-yl)acetyl}-2(S)-{N'-acetyl-N'-2-chlorobenzyl}aminomethylpyrrolidine N-{2(R)-Methyl-2-(1-(4-Cyanobenzyl)-1H-imidazol-5-yl))acetyl}-2(S)-{N'-acetyl-N'-3-chlorobenzyl}aminomethylpyrrolidine N-{2(S)-Methyl-2-(1-(4-Cyanobenzyl)-1H-imidazol-5-yl))acetyl}-2(S)-{N'-acetyl-N'-3-chlorobenzyl}aminomethylpyrrolidine N-{1-(4-Cyanobenzyl)-1H-imidazol-5-yl)acetyl}-2(S)-{N'-acetyl-N'-3-chlorobenzyl}aminomethylpyrrolidine N-{1-(4-Cyanobenzyl)-1H-imidazol-5-yl)acetyl}-2(S)-{N'-acetyl-N'-4-chlorobenzyl}aminomethylpyrrolidine N-{1-(4-Cyanobenzyl)-1H-imidazol-5-yl)acetyl}-2(S)-{N'-acetyl-N'-2,3-dichlorobenzyl}aminomethylpyrrolidine N-{1-(4-Cyanobenzyl)-1H-imidazol-5-yl}acetyl-4(R)-benzyloxy-2(S)-{N'-acetyl-N'-naphth-1-ylmethyl}aminomethylpyrrolidine N-{1-(4-Cyanobenzyl)-1H-imidazol-5-yl}acetyl-4(R)-benzyloxy-proline naphth-1-ylmethylamide N-{1-(4-Cyanobenzyl)-1H-imidazol-5-yl}acetylproline naphth-1-ylmethylamide N-{1-(4-cyanobenzyl)-1H-imidazol-5-yl)acetyl-4(R)-methoxy-2(S)-{N'-acetyl-N'-5,6,7,8-tetrahydronaphth-1-ylmethyl}aminomethylpyrrolidine N-1-(4-cyanobenzyl)-1H-imidazol-5-yl)acetyl-4(R)-benzyloxy-2(S)-{N'-acetyl-N'-5,56,7,8-tetrahydronaphth-1-ylmethyl}aminomethyl-pyrrolidine 1-(4-Cyanobenzyl)-1H-imidazol-5-ylmethyl-2(S)-{N'-acetyl-N'-3-chlorobenzyl}aminomethylpyrrolidine N-{5-(4-Cyanobenzyl)-1H-imidazol-1-yl)ethyl}-2(S)-{N'-acetyl-N'-3-chlorobenzyl}aminomethylpyrrolidine N-{5-(4-Cyanobenzyl)-1H-imidazol-1-yl)ethoxycarbonyl}-2(S)-{N'-acetyl-N'-3-chlorobenzyl}aminomethylpyrrolidine N-{5-(4-Cyanobenzyl)-1H-imidazol-1-ylacetyl}-2(S)-{N'-acetyl-N'-3-chlorobenzyl}aminomethylpyrrolidine N-{1-(4-Cyanobenzyl)-1H-imidazol-5-yl)ethyl}-2(S)-{N'-acetyl-N'-3-chlorophenyl}aminomethylpyrrolidine N-{1-(4-Cyanobenzyl)-1H-imidazol-5-yl)methyl}-2(S)-{N'-acetyl-N'-3-chlorophenyl}aminomethylpyrrolidine hydrochloride N-{1-(4-Cyanobenzyl)-1H-imidazol-5-yl)acetyl}-2(S)-
{N'-acetyl-N'-3-chlorophenyl}aminomethylpyrrolidine N-{1-(3-[1H-Imidazol-4-yl]propionyl)-pyrrolidin-2(S)-
ylmethyl}-(N-2-methylbenzyl)glycine N'-(3-
chlorophenyl)amide 1-[1-(4-Cyanobenzyl)-1H-imidazol-5-ylacetyl]
pyrrolidin-2(S)-ylmethyl]-(N-2-methylbenzyl)-glycine
N'-(3-chlorophenylmethyl) amide N-{1-(3-[1H-Imidazol-4-yl]propionyl)-pyrrolidin-2(S)-
ylmethyl}-(N-2-methylbenzyl)-glycine N'-methyl-N'-
(3-chlorophenyl) amide or 1-[1-(4-Cyanobenzyl)-1H-imidazol-5-ylacetyl]
pyrrolidin-2(S)-ylmethyl]-(N-2-methylbenzyl)-glycine
N'-methyl-N'-(3-chlorophenylmethyl) amide or a pharmaceutically acceptable salt or optical isomer thereof.

6. The compound according to claim 5 which inhibits farnesyl-protein transferase which is:

N-{1-(4-cyanobenzyl)-1H-imidazol-5-yl)acetyl}-2(S)-
{N'-acetyl-N'-naphthylmethyl-aminomethyl}-
pyrrolidine

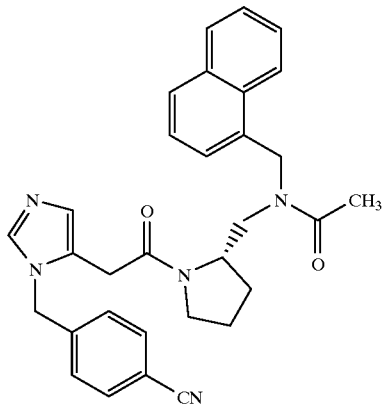

or a pharmaceutically acceptable salt thereof.

7. The compound according to claim 5 which inhibits farnesyl-protein transferase which is:

N-{5-(4-Cyanobenzyl)-1H-imidazol-1-yl)ethyl}-2(S)-[1
(R)-1-(3-chlorophenyl)-1-hydroxy]methylpyrrolidine

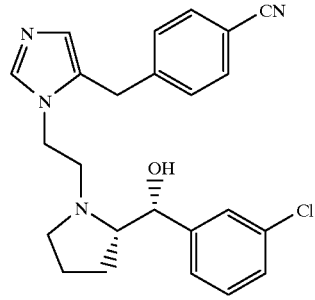

or a pharmaceutically acceptable salt or optical isomer thereof.

8. The compound according to claim 5 which inhibits farnesyl-protein transferase which is:

N-{1-(4-Cyanobenzyl)-1H-imidazol-1-ylethyl}-4(R)-
hydroxy-2(S)-[1(R)-1-(3-chlorophenyl)-1-hydroxy]
methylpyrrolidine

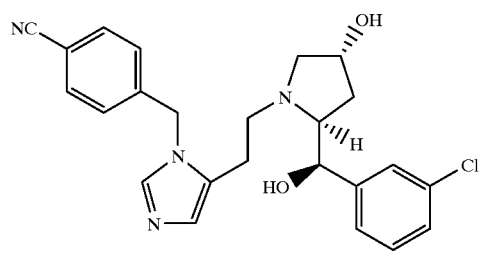

or a pharmaceutically acceptable salt or optical isomer thereof.

9. The compound according to claim 5 which inhibits farnesyl-protein transferase which is:

N-[5-(4-Cyanobenzyl)-1H-imidazol-1-ylethyl]-4(R)-
hydroxy-2(S)-[1(R)-1-(3-chlorophenyl)-1-hydroxy]
methylpyrrolidine

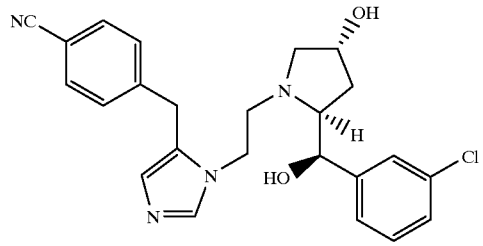

or a pharmaceutically acceptable salt or optical isomer thereof.

10. The compound according to claim 5 which inhibits farnesyl-protein transferase which is:

N {1-(4-Cyanobenzyl)-1H-imidazol-5-ylethyl}-2(S)-{N'-
acetyl-N'-3-chlorobenzyl}aminomethylpyrrolidine

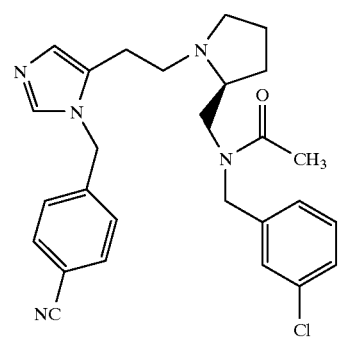

or a pharmaceutically acceptable salt or optical isomer thereof.

11. The compound according to claim 5 which inhibits farnesyl-protein transferase which is:

N-{1-(4-Cyanobenzyl)-1H-imidazol-5-yl)methyl}-2(S)-
{N'-acetyl-N'-3-chlorophenyl}aminomethylpyrrolidine

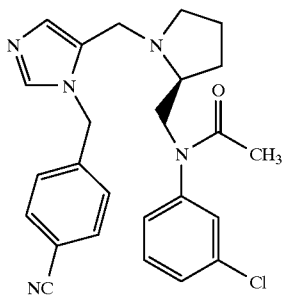

or a pharmaceutically acceptable salt or optical isomer thereof.

12. The compound according to claim 5 which inhibits farnesyl-protein transferase which is:

N-{5-(4-Cyanobenzyl)-1H-imidazol-1-yl)ethyl}-2(S)-{N'-acetyl-N'-3-chlorobenzyl}aminomethylpyrrolidine

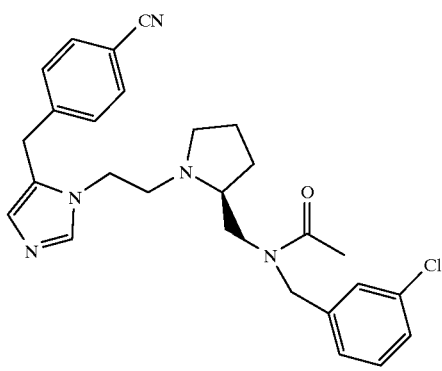

or a pharmaceutically acceptable salt or optical isomer thereof.

13. A pharmaceutical composition comprising a pharmaceutical carrier, and dispersed therein, a therapeutically effective amount of a compound of claim 1.

14. A pharmaceutical composition comprising a pharmaceutical carrier, and dispersed therein, a therapeutically effective amount of a compound of claim 2.

15. A pharmaceutical composition comprising a pharmaceutical carrier, and dispersed therein, a therapeutically effective amount of a compound of claim 5.

16. A method for inhibiting farnesylation of Ras protein which comprises administering to a mammal in need thereof a therapeutically effective amount of the composition of claim 13.

17. A method for inhibiting farnesylation of Ras protein which comprises administering to a mammal in need thereof a therapeutically effective amount of the composition of claim 14.

18. A method for inhibiting farnesylation of Ras protein which comprises administering to a mammal in need thereof a therapeutically effective amount of the composition of claim 15.

19. A method for treating cancer which comprises administering to a mammal in need thereof a therapeutically effective amount of a composition of claim 13.

20. A method for treating cancer which comprises administering to a mammal in need thereof a therapeutically effective amount of a composition of claim 14.

21. A method for treating cancer which comprises administering to a mammal in need thereof a therapeutically effective amount of a composition of claim 15.

22. A method for treating or preventing a disease or condition in a mammal, the disease or condition which is selected from:

a) a benign proliferative disorder component of NF-1;
b) infection of hepatitis delta and related viruses;
c) restenosis;
d) polycystic kidney disease; and
e) fungal infections;

which comprises administering to a mammal in need thereof a therapeutically effective amount of a composition of claim 13.

* * * * *

UNITED STATES PATENT AND TRADEMARK OFFICE
CERTIFICATE OF CORRECTION

PATENT NO. : 5,972,984
DATED : October 26, 1999
INVENTOR(S) : Neville J. Anthony, et al.

It is certified that error appears in the above-identified patent and that said Letters Patent is hereby corrected as shown below:

On the cover page, in box [75] an inventor's name should read as follows:

-- Christopher J. Dinsmore -- .

At claim 1, column 114, at lines 31-41, the structure should be:

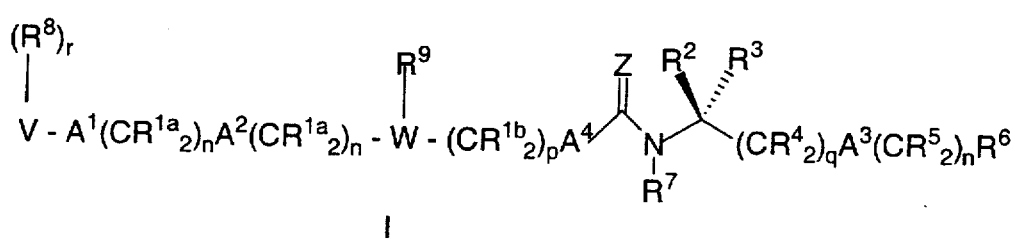

At claim 1, column 115, at lines 2-10, the structures should be:

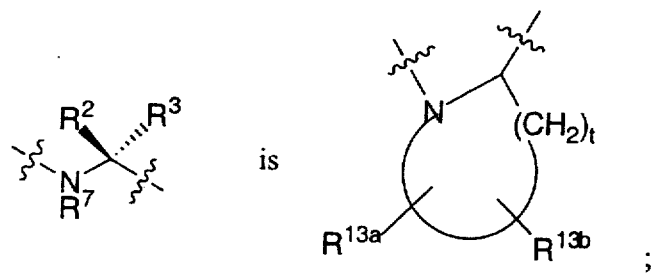

UNITED STATES PATENT AND TRADEMARK OFFICE
CERTIFICATE OF CORRECTION

PATENT NO. : 5,972,984
DATED : October 26, 1999
INVENTOR(S) : Neville J. Anthony, et al.

It is certified that error appears in the above-identified patent and that said Letters Patent is hereby corrected as shown below:

At claim 2, column 117, at lines 3-10, the structure should be:

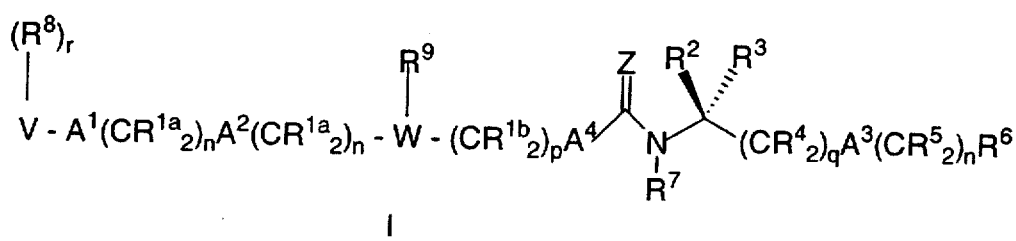

At claim 3, column 119, at lines 24-33, the structures should be:

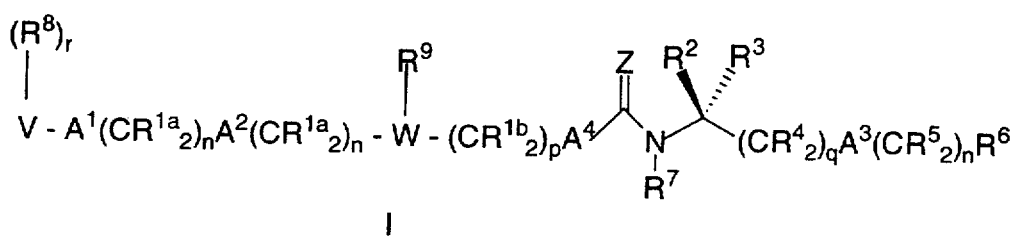

UNITED STATES PATENT AND TRADEMARK OFFICE
CERTIFICATE OF CORRECTION

PATENT NO. : 5,972,984
DATED : October 26, 1999
INVENTOR(S) : Neville J. Anthony, et al.

It is certified that error appears in the above-identified patent and that said Letters Patent is hereby corrected as shown below:

At claim 3, column 120, line 63, should be:

-- $R^{10}OC(O)$-, $-N(R^{10})_2$, or $R^{11}OC(O)NR^{10}$-, and -- .

At claim 3, column 121, line 18 should be:

-- $-S(O)_2NR^7$-, $-NR^7S(O)_2$- or $-N(R^7)$-; -- .

At claim 4, column 122, line 20 should be:

-- $C_2-C_6$ alkenyl, fluoro, chloro, $R^{10}O$-, $R^{11}S(O)_m$-, -- .

At claim 4, column 123, line 40 should be:

-- $-CH=CH$-, $-C\equiv C$-, $-C(O)$-, $-C(O)NR^7$-, $-NR^7C(O)$-, -- .

Signed and Sealed this

First Day of August, 2000

Attest:

Q. TODD DICKINSON

*Attesting Officer*     *Director of Patents and Trademarks*